(12) United States Patent
Lu et al.

(10) Patent No.: US 10,925,481 B2
(45) Date of Patent: Feb. 23, 2021

(54) SYSTEMS AND METHODS FOR MEASURING VISUAL FUNCTION MAPS

(71) Applicant: Ohio State Innovation Foundation, Columbus, OH (US)

(72) Inventors: Zhong-Lin Lu, Dublin, OH (US); Pengjing Xu, Columbus, OH (US); Luis Lesmes, San Diego, CA (US); Deyue Yu, Columbus, OH (US)

(73) Assignees: Ohio State Innovation Foundation, Columbus, OH (US); Adaptive Sensory Technology, Inc., San Diego, CA (US)

( * ) Notice: Subject to any disclaimer, the term of this patent is extended or adjusted under 35 U.S.C. 154(b) by 182 days.

(21) Appl. No.: 16/290,654

(22) Filed: Mar. 1, 2019

(65) Prior Publication Data
US 2019/0269315 A1   Sep. 5, 2019

Related U.S. Application Data

(60) Provisional application No. 62/637,653, filed on Mar. 2, 2018.

(51) Int. Cl.
| | |
|---|---|
| *A61B 3/00* | (2006.01) |
| *A61B 3/113* | (2006.01) |
| *A61B 3/06* | (2006.01) |
| *G06N 20/00* | (2019.01) |
| *G06N 7/00* | (2006.01) |

(52) U.S. Cl.
CPC .......... *A61B 3/0025* (2013.01); *A61B 3/063* (2013.01); *A61B 3/113* (2013.01); *G06N 7/005* (2013.01); *G06N 20/00* (2019.01)

(58) Field of Classification Search
CPC ....... A61B 3/0025; A61B 3/113; A61B 3/063; A61B 3/024; G06N 20/00; G06N 7/005

USPC ......................................... 351/200, 205, 209
See application file for complete search history.

(56) References Cited

U.S. PATENT DOCUMENTS

| | | | | |
|---|---|---|---|---|
| 7,788,075 B2 * | 8/2010 | DeYoe | .................... | G06T 11/00 703/11 |
| 8,337,019 B2 * | 12/2012 | Murray | .................. | A61B 3/024 351/209 |
| 10,339,464 B2 * | 7/2019 | Martin | ................... | G16B 40/20 |

(Continued)

FOREIGN PATENT DOCUMENTS

WO      1999027842 A1    6/1999

OTHER PUBLICATIONS

International Search Report and Written Opinion in International Application No. PCT/US2019/020388, dated May 16, 2019 (7 pages).

*Primary Examiner* — Tuyen Tra
(74) *Attorney, Agent, or Firm* — Benesch, Friedlander, Coplan & Aronoff LLP

(57) ABSTRACT

A system can include a non-transitory memory to store machine readable instructions and data, and a processor to access the non-transitory memory and execute the machine-readable instructions. The machine-readable instruction can include a global module that can be programmed to generate a visual field map (VFM) model that can include a set of visual function map parameters for an entire visual field for a subject. The global module can be programmed to update the set of visual function map parameters corresponding to updating a shape of the VFM based on subject response data generated during each administration of a vision test to a subject.

25 Claims, 98 Drawing Sheets

(56) References Cited

U.S. PATENT DOCUMENTS

2006/0058619 A1  3/2006  DeYoe et al.
2007/0121070 A1  5/2007  Alster et al.
2010/0149488 A1  6/2010  Lo et al.
2011/0190657 A1  8/2011  Zhou et al.
2013/0176534 A1  7/2013  Frankfort et al.
2014/0333898 A1  11/2014  Boate et al.

* cited by examiner

SYSTEMS AND METHODS FOR MEASURING VISUAL FUNCTION MAPS

CROSS-REFERENCE TO RELATED APPLICATIONS

This patent application claims the benefit of U.S. Provisional Patent Application No. 62/637,653, filed on Mar. 2, 2018, the entire contents of which is incorporated by reference in its entirety.

GOVERNMENT SPONSORSHIP

This invention was made with government support under grant numbers EY021553 and EY025658 awarded by the National Institutes of Health. The government has certain rights in the invention.

TECHNICAL FIELD

This disclosure generally relates to systems and methods for measuring visual function maps.

BACKGROUND

Visual field mapping is a psychophysical method used for measuring visual function over a visual field. Currently, visual field mapping devices exist for measuring light sensitivity at retinal locations across a subject's visual field. These devices can be configured to generate a visual field map (VFM) characterizing the subject's light sensitivity over the visual field. A visual field broadly refers to an area in which a stimulus can be visually detected by a subject. VFMs are commonly used for diagnosing visual dysfunction caused by a particular medical condition, such as glaucoma, age-related macular degeneration (AMD), diabetes, stroke, pituitary disease, brain tumors or other neurological conditions.

SUMMARY

In an example, a system can include a non-transitory memory to store machine readable instructions and data, and a processor to access the non-transitory memory and execute the machine-readable instructions. The machine-readable instruction can include a global module that can be programmed to generate a visual field map (VFM) model that can include a set of visual function map parameters for an entire visual field for a subject. The global module can be programmed to update the set of visual function map parameters corresponding to updating a shape of the VFM based on subject response data generated during each administration of a vision test to a subject. The machine readable instruction can include a switch module that can be programmed to evaluate a performance of the global module and make a determination as to whether to switch to a local module, and upon switching, calculate independent parameters for each retinal location of the visual field based on the set of visual function map parameters in the global module The machine readable instruction can include a local module that can be programmed to update the independent parameters based on the subject response data generated during subsequent administration of the vision test to the subject to provide an assessment of visual function at each retinal location of the visual field for the subject.

The Summary is provided merely for purposes of summarizing some example embodiments to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments.

BRIEF DESCRIPTION OF THE DRAWINGS

FIGS. 7A-6P illustrate exemplary estimated light sensitivity VFMs for subject 2 generated by a method, for example, as depicted in FIG. 3, and a YN method for measuring visual function maps.

FIGS. 8A-6P illustrate exemplary estimated light sensitivity VFMs for subject 3 generated by a method, for example, as depicted in FIG. 3, and a YN method for measuring visual function maps.

FIGS. 9A-6P illustrate exemplary estimated light sensitivity VFMs for subject 4 generated by a method, for example, as depicted in FIG. 3, and a YN method for measuring visual function maps.

FIGS. 10A-6P illustrate exemplary estimated light sensitivity VFMs for subject 5 generated by a method, for example, as depicted in FIG. 3, and a YN method for measuring visual function maps.

FIGS. 11A-6P illustrate exemplary estimated light sensitivity VFMs for subject 6 generated by a method, for example, as depicted in FIG. 3, and a YN method for measuring visual function maps.

DETAILED DESCRIPTION

Figure 1:
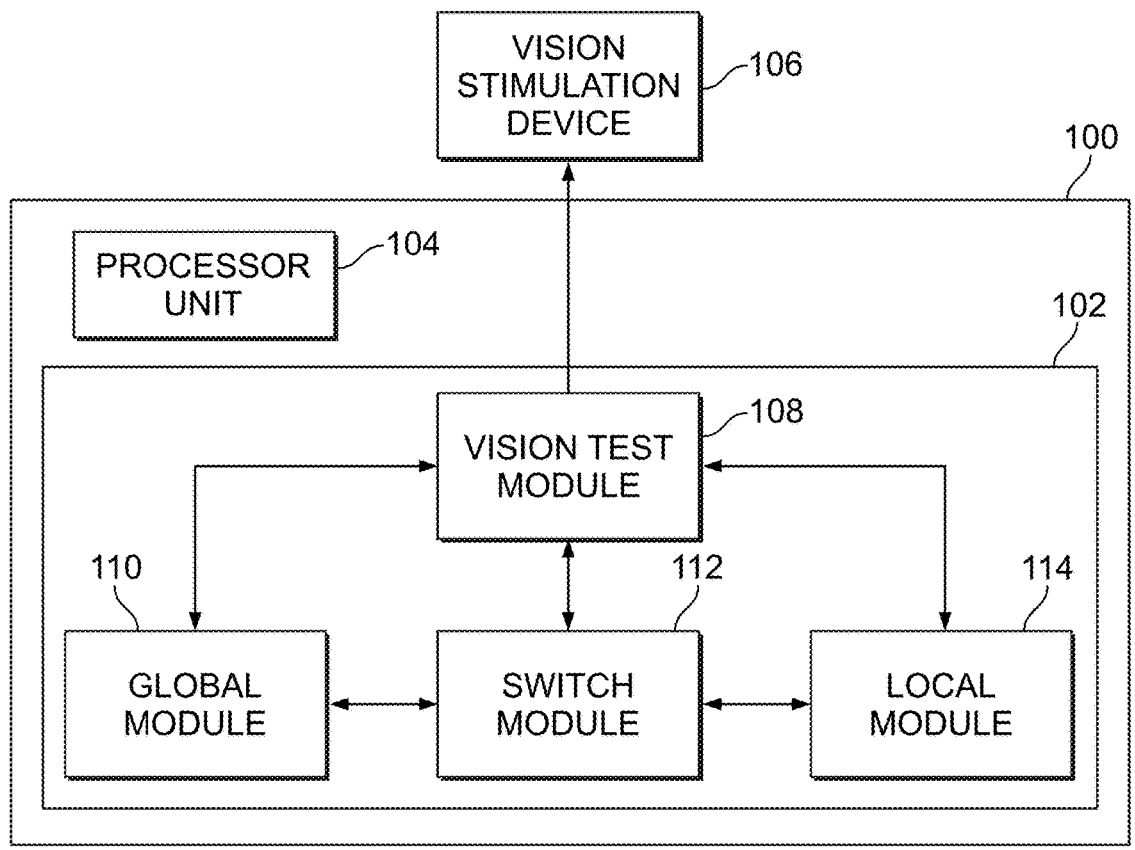
FIG. 1 depicts an example of a system for measuring visual function maps.

The present disclosure relates to systems, methods, and/or products generally referred to as systems and methods, for measuring visual function maps (VFMs). The systems and methods can improve on existing visual field mapping devices which are limited to measuring visual function at only a single visual field (VF) location. As such, existing devices provide a limited characterization of visual function. For example, existing devices for evaluating central and peripheral vision (e.g., for low vision) are limited to measuring visual acuity, contrast sensitivity, and reading performance at only a single retinal location, not the VFM for the subject which requires measurements in all retinal locations of the visual field. Even further, existing visual field mapping devices for measuring light sensitivity are inefficient and lack robustness in mapping visual functions. For example, mapping a subject's sensitivity to light is standard for evaluating the subject for visual dysfunction, such as glaucoma. However, the frequency of performing visual field assessment for diseases, such as glaucoma, using these devices is often not uniform across eye-care practitioners, and a variability of the static parametric thresholds (measured with repeated tests) generally increases with distance from fixation (eccentricity), even within a single test session. In addition to being imprecise, obtaining a complete and precise measure of the visual field for the subject is substantially time-consuming (e.g., could take hours).

The systems and methods described herein provide a measure of visual function map for a subject that is more accurate, precise and efficient in contrast to existing devices used for measuring visual function maps. The systems and methods described herein can quantitatively assess a perceptual system. In some examples, the perceptual system can include a visual system or an artificial visual system. The visual system can include at least an eye, an artificial eye, or an electronic eye. The systems and methods described herein can be used to evaluate a performance of the visual system. The evaluation can include a measurement of visual field performance of the visual system. Thus, according to the systems and methods described herein a visual field for the subject can be quantified to generate a VFM.

In some examples, according to the systems, methods and/or products described herein, the VFM can be evaluated for dysfunctions. For example, the VFM can be evaluated to detect a dysfunction in central or peripheral vision. The dysfunction in the central and/or peripheral vision can be caused by glaucoma, a stroke, a pituitary disease, a brain tumor, scotoma, or other visual or neurological deficits. In some examples, the systems and methods described herein can be configured to evaluate the VFM to assess the dysfunction (e.g., disease progression), and/or determine a medical treatment for said dysfunction.

Examples are described herein for mapping light sensitivity and contrast sensitivity. However, the examples described herein should not be construed and/or limited to only light and contrast sensitivity mapping. The systems and methods described herein are equally as applicable to visual function mapping, including, but not limited to, visual acuity, contrast sensitivity function (CSF), color, stereo vision, temporary frequency, motion sensitivity, reading speed, and crowding. The visual function maps can have a plurality of different function forms as described herein, such as, for example, an ellipsoid function, a cone function, a hyperboloid function, a hyperbolic paraboloid function, or other surface functions. As such, the systems and methods described herein can generate a plurality of VFMs characterizing different visual functions. The advantages and technical improvements that the systems and methods described herein have over existing visual field mapping devices will become more readily apparent and better appreciated by the examples described herein.

FIG. 1 depicts an example of a system 100 for measuring visual function maps. The system 100 can be configured to generate a VFM. The VFM can include a plurality of VF locations corresponding to retinal locations in a visual field of a subject. The VFM can include visual data for each VF location characterizing a visual function of a corresponding retinal location in the visual field. For example, the visual field data for a given VF location can include a score representative of a visual performance of the corresponding retinal location in the visual field. The VFM can quantify each retinal location in response to physical stimuli. As such, the VFM can represent sensations and/or perceptions at each retinal location produced by the subject in response to the physical stimuli.

The system 100 can be configured to generate a plurality of different VFMs according to a particular visual function that is being measured. The system 100 can be configured to generate each VFM based on a given visual field test (also referred to herein, as a "vision test"). The system 100 can be configured to administer the vision test to the subject. As such, each VFM can provide a measure of a performance for a given visual function across retinal locations in the visual field. The given visual function can include, but not limited to, light sensitivity, contrast sensitivity, visual acuity, contrast sensitivity function, color sensitivity, stereo vision, temporary frequency sensitivity, motion sensitivity, reading speed, and crowding. In an example, the system 100 can be configured to measure light sensitivity at each retinal location in the visual field based on the vision test. The system 100 can be configured to generate a light sensitivity VFM based on the measured light sensitivity at each retinal location in the visual field. The system 100 can be configured to evaluate the light sensitivity VFM to detect a dysfunction in vision in the subject. In some examples, the light sensitivity VFM can be evaluated for glaucoma in the subject. In another example, the system 100 can be configured to measure contrast sensitivity at each retinal location in the visual field based on the vision test. The system 100 can be configured to generate a contrast sensitivity VFM based on the measured contrast sensitivity at each retinal location in the visual field. The system 100 can be configured to evaluate the contrast sensitivity VFM to detect a dysfunction in vision in the subject. In some examples, the contrast sensitivity VFM can be evaluated for AMD in the subject.

The system 100 can include memory 102. The memory 102 can include executable machine-readable instructions. The system 100 can further include a processing unit 104 that can be configured to access the memory 102 and execute the machine-readable instructions stored therein. In some examples, the processing unit 104 can include a graphic processing unit (GPU). The GPU can include a CUDA-Enabled GPU, such as a Nvidia® GeForce 1080 video card, or the like. The system 100 can be configured to process more visual field data associated with measuring visual function maps in contrast to currently available VFM devices. Existing VFM devices cannot effectively process the required amount of visual field data efficiently in a timely manner, and furthermore fail to provide an accurate and precise VFM for the subject. By using the GPU, the system 100 can be configured to generate VFMs in a more efficient manner, with more accuracy and precision according to the methods described herein in contrast to existing VFM devices. As such, the system 100 includes technological advantages over existing VFM devices. Thus, the system 100 improves an underlying technology for measuring visual function maps according to the methods described herein. In the present example, although the components (e.g., modules) of the system 100 are illustrated as being implemented on the same system, in other examples, the different components could be distributed across different systems and communicate, for example, over a network. In some examples, the memory 102 can be part of the processing unit 104. In some examples, part or all of the memory 102 and/or the processing unit 104 can be implemented in a private and/or public cloud environment.

The memory 102 can further include vision test data (not shown in FIG. 1). The vision test data can include vision test parameters for the vision test. The vision test can be administered by the system 100 to the subject to provide a measure of a subject's vision, including their central vision, and/or peripheral (side) vision. The vision test parameters can be user-definable, and can be stored in the memory 102 as vision test parameter data. As described herein, one or more of the vision test parameters can be continuously updated based on performance data from the subject in response to the vision test. The performance data (or subject response data) can include, but not limited to, response accuracy, response time, pointing, and/or eye movement data for the subject. The performance data can be generated based on a user input from the subject during each vision test. Thus, the vision test parameters can be updated for a future vision test based on the user input from a prior vision test. Thus, the vision test can be dynamically adjusted following each administration of the vision test to the subject.

The system 100 can further include a vision stimulation device 106 and a vision test module 108. The visual stimulation device 106 can include a display (not shown in FIG. 1). The vision test module 108 can be programmed to control the administration of the vision test to the subject based on the vision test data. Each vision test can be administrated sequentially, over a given period of time, or between medical treatments. The vision test module 108 can be programmed to control the vision stimulation device 106 to administer the vision test to the subject based on the vision test parameters. For examples, in mapping light sensitivity, the vision test parameters can include a luminance parameter, a size and/or shape parameter, a location parameter, and a duration parameter.

Each administration of the vision test can include positioning the subject relative to the vision stimulation device 106 and presenting a stimulus at a particular location on the display for a given period of time. For examples, in mapping light sensitivity, each vision test can include presenting a stimulus (e.g., a light target) with a luminance defined by the luminance parameter at a given location on the display based on the location parameter. The light at the given location on the display can be presented for a given amount of time according to the duration parameter. The vision test can be administered to the subject in a computerized manner based on the vision test parameters by the visual stimulation device 106.

During each administration of the vision test, the subject can provide one or more responses based on a stimulus (e.g., a light target). The one or more responses can include information characterizing the stimulus and/or information related to the stimulus. For example, the subject can be presented with a light target at the given location and queried as to whether the subject is able to detect the light at the given location. The subject can provide the one or more responses via an input device (not shown in FIG. 1) during the vision test. The input device can include an audio input device, such as a microphone, or the like. As such, the subject can verbally acknowledge detection of the light (e.g., with a "Yes"), or verbally acknowledge not detecting the light (e.g., with a "No"). Additionally, or alternatively, the input device can include a keyboard, a mouse, a pointing device, an eye tracker or the like. In this example, the subject can provide the acknowledgement of detecting and not detecting the light using, for example, the keyboard.

The input device can be configured to generate the performance data based on the one or more responses provided by the subject during the vision test. The response data can be stored in the memory 102 (not shown in FIG. 1), for example, by the processor 104. In some examples, the system 100 can include an eye tracking unit (not shown in FIG. 1) to record the subject's eye movement during the vision test. The eye tracking unit can be configured to generate eye movement data characterizing the subject's eye movement as a response to the stimulus during the vision test. The eye movement data can be stored as part of the response data in the memory 102. The eye tracking unit can be configured to provide a fixation location, a fixation duration, a fixation stability, a saccade amplitude, a saccade direction, a number of saccades, a saccade accuracy of the eye movement control, and information on fixational eye movements (e.g. microsaccade and/or drift) from the subject during the vision test.

The system can further include a global module 110. The global module 110 can be programmed to update the vision test parameters for a subsequent vision test based on the response data associated with a prior vision test administered to the subject. The global module 110 can be programmed to generate vision test parameter update data based on a selected parameter in a parameter space, as described herein. The global module 110 can be programmed to be in communication with the vision test module 108. The vision test module 108 can be programmed to receive the vision test parameter update data. The vision test module 108 can be programmed to update the vision test parameters for the subsequent vision test based on the vision test parameter update data. For examples, in mapping light sensitivity, the vision test module 108 can be programmed to update the luminance parameter, the size parameter, the shape parameter, the location parameter, and/or the duration parameter for the subsequent vision test.

The global module 110 can be programmed to generate a VFM model. The VFM model can characterize an overall visual function map of the visual field (e.g., a shape) for the subject. The VFM model can include a visual function measure for each retinal location of the visual field. Each visual function can characterize a visual performance (e.g., visual function) of a corresponding retinal location of the visual field. In some examples, the visual function map can be characterized by a parametric function (e.g., exponential, parabolic, two lines, Gaussian, polynomial, or the like). The global module 110 can be programmed to retrieve baseline response data (not shown in FIG. 1). The baseline response data can be stored in the memory 102. The baseline response data can characterize a prior measured visual performance of retinal locations of the visual field for a set of subjects. The set of subject(s) can have a normal (or healthy) measured visual function at a given retinal location of the visual field. A healthy subject can correspond to a human that does not have a deficit or a pathology in any one or more of motor, sensory and cognitive functions associated with visual function. Healthy subjects can be stratified by age and other demographic factors. The set of subject(s) can also be subjects with a particular type(s) and degree(s) of vision related disease(s).

The global module 110 can be programmed to generate an initial VFM model to provide an initial characterization of the overall visual function map of the subject. As such, each visual function map can provide an initial visual performance for each retinal location of the visual field. The global module 110 can be programmed to update the visual function map for all retinal locations of the visual field based on the response data generated in response to the vision test. Thus, the global module 110 can be programmed to update iteratively the VFM model characterizing the overall visual function map of the visual field.

The global module 110 can be programmed to generate a visual function map for all retinal locations in the visual field with a set of visual function parameters. In an example, each visual function map can correspond to a titled elliptic paraboloid function (TEPF). In some examples, the set of visual function map parameters can include (1) a central gain (e.g., sensitivity at a fovea), EPZ, (2) a bandwidth (latus rectum) in a horizontal direction, EPA, which can describe the visual function map's full-width at half-maximum (e.g., in octaves) in the horizontal direction of the visual field, (3) a bandwidth in a vertical direction, EPB, (4) a tilted level in the horizontal direction, SLA, (5) the tilted level in the vertical direction, SLB, and (6) a decision criterion (e.g., in a Yes/No) task in light detection).

In the example of mapping light sensitivity, the global module 110 can be programmed such that a height of the TEPF, $\tau(x,y)$, can define a light sensitivity (1/threshold) at a fixed d'=1.0 level at retinal location (x,y):

$$\tau(x, y) = EPZ - \left(\frac{x}{EPA}\right)^2 - \left(\frac{y}{EPB}\right)^2 + SLA * x + SLB * y. \quad (1)$$

A d' psychometric function for each retinal location (x,y), that is, perceptual sensitivity for a given stimulus intensity s, can be modeled by the global module 110 as:

$$d'(s, x, y) = \frac{\beta(s * \tau(x, y))^\gamma}{\sqrt{(s * \tau(x, y))^{2\gamma} + (\beta^2 - 1)}}, \quad (2)$$

where s is an intensity of a stimulus, $\gamma$ is a steepness of the d' psychometric function, and $\beta$ is an asymptote of the psychometric function. The psychometric function can be approximately linear over low to medium stimulus intensity and saturate at high intensities. In some examples, $\gamma$ and $\beta$ can be fixed. For example, $\gamma=2.1$ and $\beta=5.0$ can be fixed.

In a Yes/No detection task at a retinal location (x,y), a probability of reporting target presence ("Yes") by the subject can be determined according to a perceptual sensitivity and decision criterion, which can be modeled by the global module 110 as:

$$P(s,x,y) = \int_{-\infty}^{+\infty} \phi(t-(d'(s,x,y)-\lambda(x,y))\Phi(t)dt, \quad (3)$$

where ( ) is a probability density function of a standard normal distribution friction, $\Phi$( ) is a cumulative probability density function of standard normal distribution function, d'(s, x, y) is a d' value associated with a stimulus with signal intensity s at the retina location (x,y), and $\lambda(x,y)$ is a decision criterion at the retina location (x,y).

The global module 110 can be programmed to use a single $\lambda$ across all the retinal locations. As described herein, a local module 114 can be programmed to use an independent $\lambda(x,y)$ at each retinal location. The global module 110 can be programmed to generate a likelihood function for each retinal location of the visual field. The likelihood function can completely describe a probability of detecting light across all retinal locations and at all light levels. In an example, the likelihood function can be represented by the global module 110 as:

$$P'(s, x, y) = \frac{1}{2}\varepsilon + (1-\varepsilon)P(s, x, y), \quad (4)$$

where P(s,x,y) is the psychometric function, $\varepsilon$ is a lapse rate, (x,y) is a given retinal location, and s is a stimulus parameter for a given vision test.

In some examples, the global module 110 can be programmed to use a fixed lapse rate $\varepsilon$ for the subject in Equation (4). In some examples, the global module 110 can be programmed with the fixed lapse rate of 0.03. Alternatively, the lapse rate can be estimated from subject's response.

In the example of mapping contrast sensitivity, a 10-alternative forced-choice letter identification task and the associated likelihood function are used.

Initially, the global module 110 can be programmed to establish the set of visual function map parameters of the visual function for all retinal locations of the visual field based on the baseline response data. The global module 110 can be programmed to update the set of visual function map parameters for all retinal locations of the visual field based on the response data following each administration of the vision test. The global module 110 can be programmed to refine the visual function map for all retinal locations of the visual field following each vision test by the subject. As such, a more accurate estimate of visual function map for the subject can be provided by the global module 110 following each subsequent vision test.

The global module 110 can be programmed to update the set of visual function map parameters for all retinal locations of the visual field based on the response data generated during each vision test according to a Bayesian inference. The global module 110 can be programmed to update a joint probability distribution for all the visual function map parameters based on the response data generated during each administration of the vision test. The global module 110 can be programmed to characterize each visual function map parameter by a probability density function to represent a relative likelihood that a value of a given visual function parameter would equal that sample. In an example, the prior of each of the probability density functions can be one of a uniform density function, a hyperbolic probability density function, and a combination thereof.

Additionally, or alternatively, the global module 110 can be programmed to characterize all visual function map parameters by a n-dimensional joint probability distribution in a parameter space, wherein n is an integer equal to a number of visual function parameters. The global module 110 can be programmed to define a broad joint prior distribution $p_0(\theta)$ in the n-dimensional parameter space. The parameter space can represent all possible variations of the visual function at a given retinal location of the visual field. For example, in mapping light sensitivity, a probability density function, $p(\vec{\theta})$, where $\vec{\theta} = (EPZ, EPA, EPB, SLA, SLB, \lambda)$, can be defined over a six-dimensional parameter space of the TEPF and a decision criterion. The global module 110 can be programmed to generate an initial prior probability distribution, $p_{t=0}(\vec{\theta})$, for all visual function map parameters prior to any response data collection (e.g., vision test t=0).

The global module 110 can be programmed to inform the prior according to a plurality of methods: (1) Structure-based prior: Structural imaging such as fundus images or OCT SLO (OSLO) can be used to localize scotoma(s), anatomic fovea and preferred retinal locus (PRLs) and inform the prior; (2) Prior derived from statistical or machine learning: Statistical and/or machine learning algorithms can be used to classify patients and derive informative priors for different types of patients: (3) Prior derived from the hierarchical adaptive approach: A hierarchical Bayes extension of the method described herein can provide a judicious way to exploit two complementary schemes of inference (with past and future data) to achieve even greater accuracy and efficiency in information gain. In this approach, each incoming subject is assigned into several possible patient categories with probabilities. Each category of patients has its own learned prior. The hierarchical approach can simultaneously update the probabilities of patient classification and the VFM throughout the testing process, and update the priors of the categories after testing each new subject; and (4) Priors informed by other VFMs. For each new VFM (e.g., VFM of contrast sensitivity), one can priors informed by the results from a previous VFM (e.g., VFM of light sensitivity).

The global module 110 can be programmed to update a prior probability distribution for all visual function map parameters for all retinal locations across the visual field after each vision test. The global module 110 can be programmed to update the prior probability distribution to a posterior probability distribution based on the response data generated during each vision test according to a Bayes rule. For example, the global module 110 can be programmed to update a prior probability distribution $p_t(\vec{\theta})$ in a t-th vision test to a posterior probability distribution $p_t(\vec{\theta}|s,r_t)$ with the subject's response $r_t$ (e.g., Yes or No, or stimulus identity) to a vision test with a stimulus, s, according to the Bayes rule:

$$P_t(\vec{\theta}|s, r_t) = \frac{P(r_t|\vec{\theta}, s) P_t(\vec{\theta})}{P_t(r_t|s)}, \quad (5)$$

where $\theta$ represents the set of visual function map parameters of a given visual function, $p_t(\vec{\theta})$ is a prior probability distribution function of $\vec{\theta}$.

The probability of a response $r_t$ at a given stimulus condition s, $p_t(r_t|s)$, can be estimated by the global module 110 by weighting an empirical response probability by the prior:

$$P_t(r_t|s) = \Sigma_{\vec{\theta}}[P(r_t|\vec{\theta},s) P_t(\vec{\theta})], \quad (6)$$

where $p(r_t|s, \vec{\theta})$ is a likelihood of observing response $r_t$ given $\vec{\theta}$ and stimulus s.

The posterior $p_t(\vec{\theta}|s, r_t)$ following the t-th vision test can serve as the prior $p_{t+1}(\vec{\theta})$ in the subsequent vision test:

$$P_{t+1}(\vec{\theta}) = P_t(\vec{\theta}|s,r_t). \quad (7)$$

The global module 110 can be programmed to estimate the visual function map parameters of the given visual function after each vision test based on the marginal posterior distributions. The global module 110 can be programmed to determine a stimulus parameter for each administration of the vision test. The global module 110 can be programmed to generate vision test parameter update data based on the stimulus parameter. In some examples, the vision test parameter update data can include the stimulus parameter. The stimulus parameter can correspond to one or more of the plurality of vision test parameters of the vision test. For example, in mapping light sensitivity, the stimulus parameter can include a luminance value, a size and/or shape value, a duration value, and/or a location value. Thus, the stimulus parameter can include one of the luminance parameter, the size parameter, the shape parameter, the duration parameter, the location parameter, and combinations thereof.

The vision test module 108 can be programmed to generate a stimulus space that can include a plurality of stimulus parameters characterizing all possible stimulus locations (x, y) and stimulus intensities. In other examples, the global module 110 can be programmed to generate the stimulus space. The global module 110 can be programmed to select a stimulus parameter among the plurality of stimulus parameters that can maximize an expected information gain about the set of visual function map parameters of the visual function for each retinal location in the visual field. The global module 110 can be programmed to select the stimulus parameter from the parameter space for each administration of the vision test based on the prior probability distribution of the visual function map parameters. The global module 110 can be programmed to update the posterior probability distribution for all visual function map parameters based on the response data generated during each administration of the vision test. With the prior probability distribution and the stimulus space, the probability of detecting or identifying any stimulus in the visual field for all possible observers can be computed by the global module 110 according to Equation (4).

To determine the stimulus parameter for a t-th vision test, the global module 110 can be programmed to predict the observer's response to every possible stimulus parameter in the t-th vision test based on current estimated posterior probability density functions for the set of visual function map parameters. The global module 110 can be programmed to compute an expected posterior distribution for the set of visual function map parameters for each possible stimulus parameter. The global module 110 can be programmed to identify the stimulus parameter from the stimulus space having the least expected entropy among the plurality of stimulus parameters for the t-th vision test. This can be equivalent to optimizing the expected information gain, quantified as the entropy change between the prior and the posterior probability density functions for the set of visual function map parameters for all retinal locations in the visual field. In an example, the stimulus parameters utilized in a subsequent vision test can be randomly selected from among the plurality of stimulus parameters in the stimulus space, for example with a top 10% of an expected information gain.

In an example, the global module 110 can be programmed to perform a one-step ahead search for minimum entropy in the stimulus space. The global module 110 can be programmed to select an optimal stimulus parameter for the subsequent vision test administration that would lead to the minimum expected entropy. The global module 110 can be programmed to compute the subject's response probability $P_{t+1}(r|s)$ in every possible stimulus condition in the subsequent vision test administration based on the current prior probability distribution, the expected posterior probability distributions for all possible stimuli parameters, and the expected entropy for each possible stimulus parameter.

The global module 110 can be programmed to define entropy of the posterior probability distribution as:

$$H_{t+1}(s,r) = -\Sigma_{\vec{\theta}} P_{t+1}(\vec{\theta}|s,r) * \log(P_{t+1}(\vec{\theta}|s,r)), \quad (8)$$

where r represents observer's response (Yes or No, or stimulus identity) to a vision test with signal intensity s.

Alternatively, the global module 110 can be programmed to define entropy of the posterior probability distribution of a subset of visual function map parameters or weighted sums of a full or subset of visual function map parameters.

The expected entropy after the vision test with the signal intensity of stimulus, s, can be calculated by the global module 110 as a weighted sum of posterior entropy:

$$E[H_{t+1}(s,r)] = \Sigma_r H_{t+1}(s,r) * P_{t+1}(r|s), \quad (9)$$

The stimulus parameter with the minimum expected entropy can be selected for the next vision test by the global module 110 according to:

$$s_{t+1} = \operatorname*{argmin}_{s} E[H_{t+1}(s)]. \quad (10)$$

This is equivalent to maximizing the expected information gain, quantified as the entropy change between the prior and posterior. Accordingly, the global module 110 can be programmed to compute an expected information gain, computed as difference between the entropy of the prior probability distribution and the expected posterior probability distribution for each potential stimulus parameter before each vision test administration.

According to the Bayesian update and optimal stimulus parameter selection, the global module 110 can be programmed to update the joint posterior distribution of the set visual function map parameters for all retinal locations based on the subject's response during each vision test administration. For example, together with a decision criterion and a slope of the psychometric function, the global module 110 can be programmed to predict a probability of detecting a light at each retinal location in the visual field of the subject. The global module 110 can be programmed to generate a score for each retinal location of the visual field characterizing a performance of visual function at a given retinal location. For example, in mapping, light sensitivity, the score for each retinal location can represent a perceptual sensitivity (1/threshold) at a fixed d' level at the given retinal location.

The system 100 can further include a switch module 1112. The switch module 112 can be programmed to evaluate a rate of information gain by the global module 110 relative to an information gain criterion. The switch module 112 can be programmed to generate a prior probability distribution on measures of visual function at each retinal location based on the posterior probability distribution for the set of visual function parameters generated by the global module 110. For example, in mapping light sensitivity, the prior probability distribution can be over both perceptual sensitivity and decision criterion at each retinal location of the visual field of the subject.

The switch module 112 can be programmed to compute a total expected information gain (TEI) in the global module from a top 10% potential stimuli. With an increasing number of vision test administrations, the TEI can be expected to gradually decrease from an initial value as the system 100 learns more about the set of visual function map parameters of each visual function for all retinal locations in the visual field. As the learning saturates over a plurality of vision test administrations, the trend of TEI may reverse—that is, the TEI in a vision test t+1 may be higher than that a previous vision test. The switch module 112 can be programmed to compare the TEI in the vision test t+1 with an average TEI of three previous vision tests, t−2, t−1, and t to determine whether a local module 114 should be activated. The switch module 112 can be programmed to activate the local module 114 corresponding to "switching" the local module 114 based on a result of the comparison. For example, the switch module 112 can be programmed to activate the local module 114 when the TEI in vision test t+1 is less than the average TEI of three previous vision tests, t−2, t−1, and t.

In some examples, the switch module 112 can be programmed to evaluate the rate of information gain in the global module 110 and determine to activate the local module 114 when the rate of information gain is lower than a criterion value. Alternatively, the switch module 112 can be programmed to evaluate the potential information gains from the global module and local module, the convergence of parameters of visual function in the global module, or a fixed trial number for pre-diagnosed eye diseases, and base on the evaluation to make a determination as to whether to activate the local module 114.

The switch module 112 can be programmed to generate a prior distribution of visual function measure for each retinal location in the visual field in response to activating the local module 114 based on the posterior of the set of visual parameters in the global module. For example, the switch module 112 can be programmed to sample the posterior distribution from the global module to generate the prior distribution for each retinal location. The local module 114 can be configured to calculate independent parameters at each retinal location of the visual field. For example, in mapping light sensitivity, τ(x,y) according to equation (2) is no longer described according to equation (1), but rather can be independent for each retinal location. In addition, the decision criterion λ(x,y) can be independent for each retinal location. As such, each retinal location can be associated with independent parameters and therefore independent priors and posteriors distributions. As described herein, the initial priors for the local module 114 can be generated by the switch module 112. Although the parameters are independent across retinal locations, optimal stimulus parameter selection can be based on the total expected entropy across all the retinal locations. The local module 114 can be programmed to evaluate the expected entropy from all retinal locations in the visual field to select the test location, stimulus intensity, the size, the shape, and/or duration (e.g., stimulus parameter in the stimulus space).

The local module 114 can be programmed to assess the visual function at each retinal location of the visual field according to an adaptive procedure. In some examples, the adaptive procedure can include a Bayesian adaptive procedure. The local module 114 can be programmed to determine an order and stimulus of the vision test based on the relative information gain across locations. For example, in mapping light sensitivity, a Bayesian Yes/No (Bayesian YN) method can be used as the adaptive procedure. The Bayesian YN method can be used to assess visual function at each retinal location and the expected information gain across all retinal locations and stimulus intensity levels to determine the optimal stimulus for each vision test. For example, in mapping contrast sensitivity, a Bayesian forced-choice (Bayesian FC) method can be used as the adaptive procedure. The Bayesian FC method can be used to assess visual function at each retinal location and the expected information gain across all retinal locations and stimulus contrast levels to determine the optimal stimulus for each vision test. The local module 114 can be programmed to terminate evaluating the visual function for each retinal location of the visual field according to the adaptive procedure after a given number of vision test administrations. Alternatively, the local module 114 can be programmed to terminate after achieving a defined object (e.g., after reaching a criterion level of precision for the visual function parameters of visual function or perceptual sensitivity across all retina locations, or reaching a time limit).

The system 100 described herein can select the optimal test stimulus parameter based on maximum expected information gain, equivalent to the minimum expected entropy, in each vision test. In some examples, the system 100 can be configured with other metrics for information gain, such as fisher information, mutual information, or measures of the variability of the posterior distribution, can be used. Moreover, stimulus selection can be implemented by the system 100 with other methods beyond the one step ahead strategy, such as a multiple step-ahead search based on a dynamic programming strategy, or "region growing" techniques used in Humphrey and Octopus perimeters. In some examples, an exhaustive search algorithm can be used. In other examples, methods such as Markov chain Monte Carlo (MCMC) can be used to search the stimulus space. The system 100 can further include a printer (not shown in FIG. 1). The printer can be configured to provide a detailed printout of the subject's visual field, which can be used in ophthalmic diagnostics. The hybrid Bayesian adaptive test framework described herein significantly reduces the testing time for estimating basic visual functions for individuals, and thus improving diagnosis and treatments of dysfunction, including, but not limited to, age-related macular degeneration (AMD), glaucoma, diabetic retinopathy, retinitis pigmentosa, or other neurological conditions.

The system 100 can be configured to provide a measure of visual function at each retinal location in the visual field of the subject. Perimetry widely used in clinical vision is limited to providing only a light sensitivity VFM. Other visual functions (e.g., visual acuity) are typically measured only in one single spatial location, either at a fovea or a preferred retinal locus (PRL). However, vision tests at a single retinal location cannot fully represent typical usage of residual vision in ophthalmic patients' everyday activities. To obtain a more comprehensive assessment of residual vision in patients, other visual function maps, including but not limited to visual acuity, contrast sensitivity function, binocular vision, color vision, temporal frequency, motion sensitivity, reading speed, and crowding maps are required. Indeed, existing technologies cannot effectively and/or efficiently generate VFMs as tremendous amount of data collection is required. That is, existing apparatuses cannot provide a level of accuracy and precision as the system 100 described herein since existing apparatuses use less efficient testing strategies and cannot process large amounts of test data. Traditional adaptive procedures have been developed to estimate threshold and in a few applications a slope of a psychometric function for only a single stimulus condition at a time. Although the measurement of individual thresholds can be utilized, these conventional methods do not take advantage of the relationship across conditions, and the demand of data collection is multiplied by the number of conditions.

The systems and methods described herein efficiently address the major technical challenges in mapping visual functions associated with existing VFM devices. For example, the systems and methods described herein can provide accurate, precise, efficient visual field mapping of light sensitivity and contrast sensitivity. The technical techniques described herein can be applied to map visual functions including, but not limited to, light sensitivity, visual acuity, contrast sensitivity function, color sensitivity, binocular vision, reading speed, and crowding. Clinical assessment of all these VFMs can provide comprehensive evaluations of residual visual functions for monitoring vision loss, evaluating therapeutic interventions, and developing effective rehabilitation for ophthalmic patients. Furthermore, the systems and methods described herein can be used to identify core metrics of functional vision. By measuring performance in a battery of everyday visual tasks on a large group of subjects, the subject's performance can be modeled in everyday visual tasks with the candidate metrics provided by the techniques herein (e.g., light sensitivity, contrast sensitivity, acuity) and identify the core metrics. The core metrics can be used to assess visual deficits, and provide a thorough assessment of residual vision in the subject.

The systems and methods described herein include Bayesian adaptive processes to estimate sensitivity thresholds in Yes/No detection tasks. These adaptive processes apply the SDT framework to directly estimate sensitivity thresholds. By directly assessing sensitivity and decision parameters, the Bayesian YN method resolves the criterion dependence of Yes/No thresholds that has largely prevented wide spread application in psychophysical applications. The systems and methods described herein also include Bayesian adaptive processes to estimate sensitivity thresholds in forced-choice tasks. These adaptive processes apply the SDT framework to directly estimate sensitivity thresholds. By directly assessing sensitivity and decision parameters, the Bayesian FC method can also treat criterion dependence issues in forced-choice tasks.

The systems and methods described herein can be configured to combine a global and local framework to measure visual function maps based on Bayesian adaptive techniques. This framework reduces testing time and costs for estimating basic visual functions for normal and visually-impaired individuals, while improving a quality and precision of measuring visual functions of the subject. As such, the systems and methods described herein include a hybrid Bayesian adaptive test framework, which combines a global approach for preliminary assessment of the VFM's shape, and an approach for assessing the individual visual field locations.

Moreover, the systems and methods described herein can integrate the Bayesian YN method developed for measuring light sensitivity at a single location to measure light sensitivity across the visual field. The efficiency of the systems and methods described herein can be validated by comparing independent measures of light sensitivity at multiple spatial locations using the Bayesian YN method at each single location, and measures obtained using the techniques described herein in both computer simulation and psychophysical evaluations.

The systems and methods described herein can integrate the Bayesian FC method developed for measuring contrast sensitivity at a single location to measure contrast sensitivity across the visual field. The efficiency of the systems and methods described herein can be validated by comparing independent measures of contrast sensitivity at multiple spatial locations using the Bayesian FC method at each single location, and measures obtained using the techniques described herein in both computer simulation and psychophysical evaluations.

The techniques herein can be applied to map other critical visual functions with not only the Bayesian YN and Bayesian FC methods, but other alternative tasks and methods used in assessing visual functions such as letter identification in acuity tests.

Other visual tasks, including visual acuity, contrast sensitivity function, color, stereo vision, temporary frequency, motion sensitivity, reading speed, and crowding maps, can be adapted to practice in the systems and methods described herein. Letters or stimuli composed of letters can be used in measuring functional vision metrics, such as visual acuity, contrast sensitivity function, color, reading speed, and crowding maps. For example, more response alternatives in letter tasks can reduce the guessing rate and increase the slope of the psychometric function and therefore increase information gain in each vision test and enhance the efficiency of the adaptive procedures. Additionally, or alternatively, letters contain a broad band of spatial frequencies along all orientations compared to gratings. In a contrast sensitivity function procedure, Sloan letters are bandpass filtered with a 1-octave bandwidth. In contrast sensitivity function, stereo vision and temporary frequency, motion tasks, static or moving gratings can also be used as visual stimuli. Furthermore, the systems and methods described herein can be extended to binocular VFM. Moreover, although the systems and methods described use the Bayesian YN and Bayesian FC methods with respect to the local module 114, the Bayesian YN and Bayesian FC method can be replaced with other methods, such as a staircase method, or another alternative method for threshold assessment. Additionally, the systems and methods described herein can be integrated with a fundus camera and/or OCT SLO (OSLO) system to provide both structural and functional assessment of visual field. For example, eye tracking can be integrated into the system 100 to monitor fixation stability and to measure the subjects' responses to the stimuli in tasks.

Figure 2:
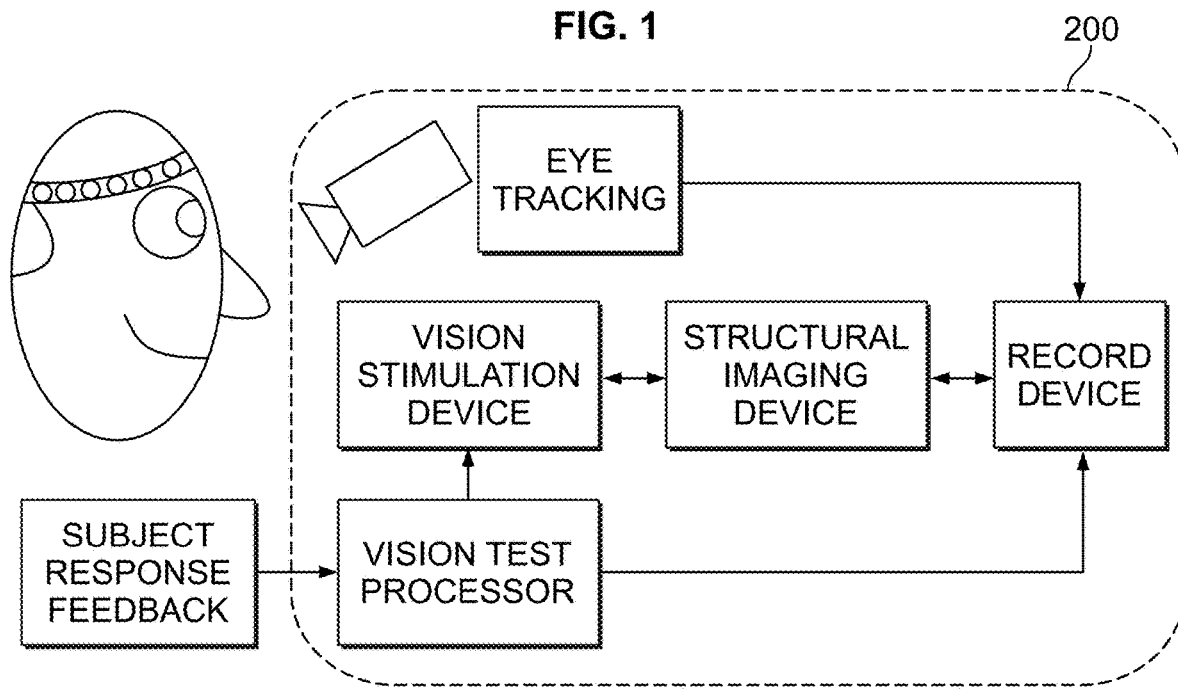
FIG. 2 depicts an exemplary environment for implementing another system for measuring visual function maps.

FIG. 2 depicts an exemplary environment for implementing a system 200 for measuring visual function. In some examples, the system 200 can correspond to the system 100, as depicted in FIG. 1. In other examples, the system 200 can correspond to a portion of the system 100, and thus can include some of the components of the system 100. According to the methods described herein the system 200 can be configured to administer a vision test to provide a measure of visual function performance for the subject.

Figure 3:
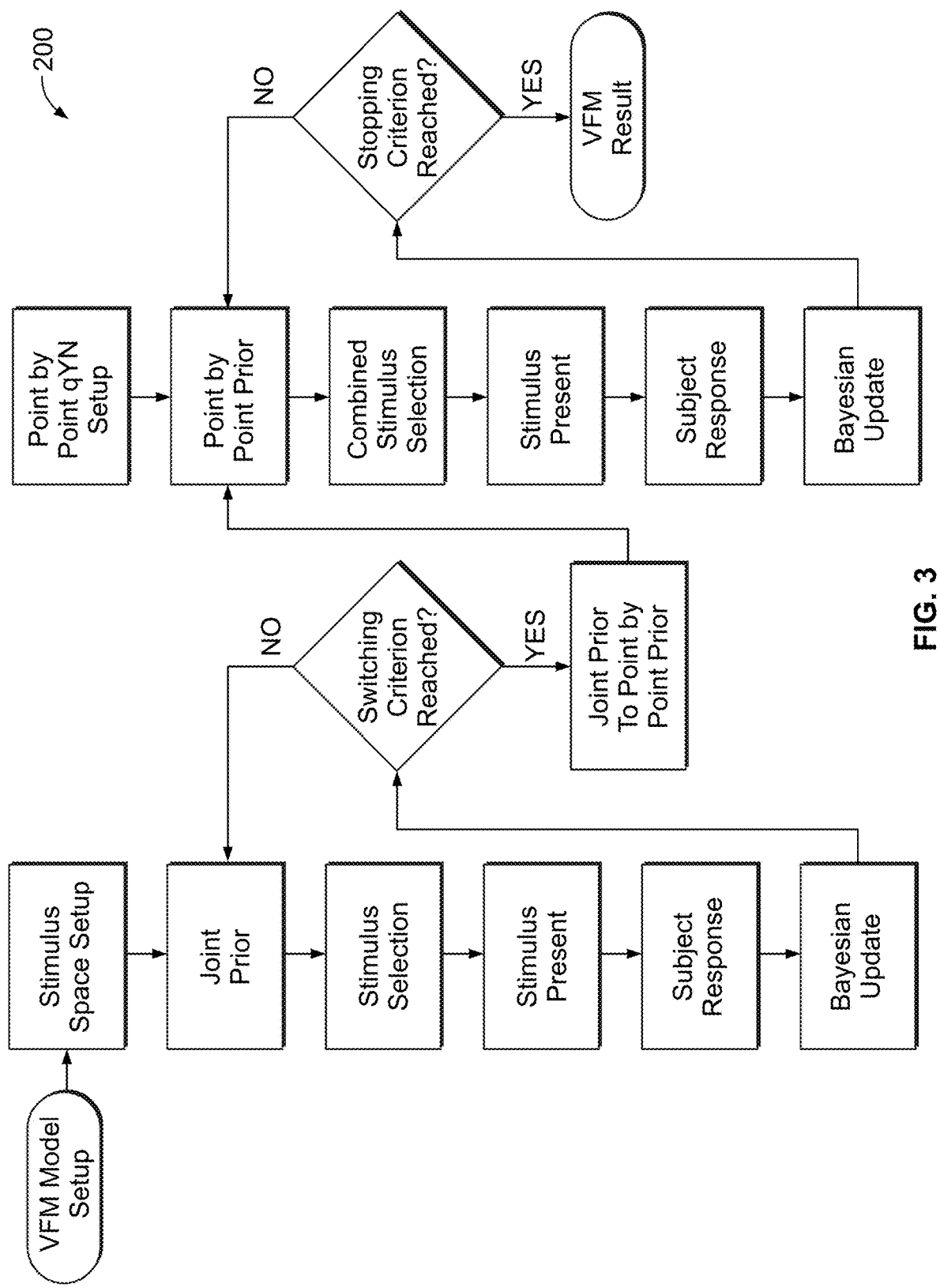
FIG. 3 depicts an example of a flow diagram illustrating a method for measuring visual function maps.

In view of the foregoing structural and functional features described above, a method that can be implemented will be better appreciated with reference to FIG. 3. While, for purposes of simplicity of explanation, the method of FIG. 3 is shown and described as executing serially, it is to be understood and appreciated that such method is not limited by the illustrated order, as some aspects could, in other examples, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource of a system, for example, the system 100, as shown in FIG. 1, or the system 200, as shown in FIG. 2. As such, the method 300 can be implemented by the system 100, as depicted in FIG. 1, or the system 200, as depicted in FIG. 2.

Accordingly, the systems and methods described herein provide a measure of visual function map that is more accurate, precise and efficient in contrast to existing VFM devices for measuring visual function. At least some of the advantages and improvements that the systems and methods described herein have over existing VFM devices for measuring visual function maps will be better appreciated by the foregoing simulation and experimental evaluations.

Implementation One: Light Sensitivity Mapping

In the first set of simulation and experimental evaluations, 100 VF locations (60×60 deg) were sampled, and a performance of the method described herein for measuring visual function map was compared to a known method for measuring visual function, which evaluated each location independently.

Simulation Evaluation

To evaluate a performance of the method described herein for measuring visual function maps, the method described herein and a known method for measuring visual function maps was simulated. The known method was a Bayesian YN method. A normal observer was simulated and cued to report a presence or absence of a luminance target at one of 100 retinal locations for the simulation according to the method described herein and the Bayesian YN method. The parameters of the simulated observer were defined to approximate an observer in a psychophysical evaluation, as described herein. Six parameters were defined and included an $EPA=81.0$ (degree/$\sqrt{dB}$), $EPB=41.1$ (degree/$\sqrt{dB}$), $EPZ=24.3$ (dB), $SLA=0.020$ (dB/degree), $SLB=0.032$ (dB/ degree), and λ=1.20. The blind spot of simulated OS eye is on [−15 (degree), −3 (degree)].

The parameter space for the simulation included 20 linearly spaced EPA values (e.g., from 69.0 to 93.0 degree/√dB), 20 linearly spaced EPB values (e.g., from 33.6 to 51.6 degree/√dB), 32 linearly spaced EPZ values (e.g., from 16.3 to 25.0 dB), 15 linearly spaced SLA values (eg., from −0.2 to 0.2 dB/degree), 15 linearly spaced SLB values (e.g., from −0.17 to 0.23 dB/degree) and 20 linearly spaced λ values (e.g., from 0.4 to 2.1). A broad parameter space was used to substantially mitigate effects of extreme values, which can bias toward a center of the parameter space when the observer's true parameter values are near the boundary of the parameter space. A visual function map model was generated to characterize visual function for the simulation. The visual function map model included the six parameters. Each of the six-parameters corresponded to a probability distribution. In the simulation, prior probability distributions for the six-parameters for a psychophysical validation were used. Each prior was defined by a hyperbolic secant (sech) function.

For each prior parameter, $\theta_i$, for i=1, 2, 3, 4, 5, 6, for the simulation, a mode of a marginal prior, $p(\theta_i)$, was defined according to a best guess for that parameter, $\theta_{i,\ guess}$, and a width was defined according to a confidence value associated with the best guess, $\theta_{i,\ confidence}$:

$$P(\theta_i) = \operatorname{sech}(\theta_{i,confidence} \times (\theta_i - \theta_{i,guess})), \quad (11)$$

Where:

$$\operatorname{sech}(z) = \frac{2}{e^z + e^{-z}}. \quad (12)$$

For the simulation, the priors were defined to be a log-symmetric around $\theta_{i,guess}$, whose values for the respective parameters were: EPA=71.4 (degree/√dB), EPB=46.1 (degree/√dB) EPZ=24.5 (dB), SLA=0.019 (dB/degree), SLB=0.048 (dB/degree), and λ=1.16. For $\theta_{confidence}$ of each parameter, the value was set to 0.67 for EPA, 1.26 for EPB, 1.93 for EPZ, 3.13 for SLA, 3.03 for SLB, and 2.68 for λ. The joint prior was defined as a normalized product of the marginal priors. The stimulus space included a 10×10 grid of retina locations [60 (degree)×60 (degree)] and linearly spaced luminance values (e.g., from 10.2 dB to 25.0 dB). In the simulation, the linearly spaced luminance values included 60 values that were associated with a global module and 120 luminance values that were associated with a local module.

A performance of the method described herein was evaluated relative to the Bayesian YN method for mapping the visual function. The method described herein was based on the global module, the switch module and local module. The Bayesian YN method was based only on the local module. Each of the methods were compared over a plurality of repeated simulations (e.g., 1,000 repeated simulations) over a plurality of tests (e.g., 1,200 tests) for the simulated subject. In the simulation, an initial prior associated with the Bayesian YN method was generated based on a prior of the global module associated with the method described herein.

Accuracy can be defined as a measure of how much estimates deviate from a truth on average. The root mean squared error (RMSE) of the estimated sensitivities across all 100 VF locations after the i-th trial can be calculated as:

$$RMSE_i = \sqrt{\frac{\sum_k \sum_j (\tau_{ijk} - \tau_k^{true})^2}{J \times K}}, \quad (13)$$

where $\tau_{ijk}$ is the estimated sensitivity (1/threshold) at the k-th VF location after i trials obtained in the j-th simulation, and $\tau_k^{true}$ is the true sensitivity of that location. An average absolute bias of an estimated threshold of every location after the i-th trial was calculated as:

$$\text{average absolute } bias_i = \frac{\sum_k \left| \sum_j (\tau_{ijk} - \tau_k^{true}) \right|}{J \times K}, \quad (14)$$

Precision can be defined as an inverse of a variability of the estimates. In the simulation, two techniques were used to assess the precision of the methods. The first technique was based on a standard deviation of repeated measures:

$$SD_i = \sqrt{\frac{\sum_k \sum_j (\tau_{ijk} - \operatorname{mean}(\tau_{ijk}))^2}{J \times K}}. \quad (15)$$

The second technique was based on a half width of a credible interval (HWCI) of a posterior distribution of an estimated threshold for retina locations. The HWCI can refer to a shortest interval that represents a given portion of a distribution. The 68.2% credible interval can represent a range within which an actual value lies with a 68.2% probability, whereas a confidence interval, the most popular index of precision, can represent an interval that can include a true value of a parameter for 68.2% of unlimited repetitions. The HWCI of the posterior distribution can correspond to a proper index of precision that can be obtained with a single application of the methods described herein.

Figure 4A:
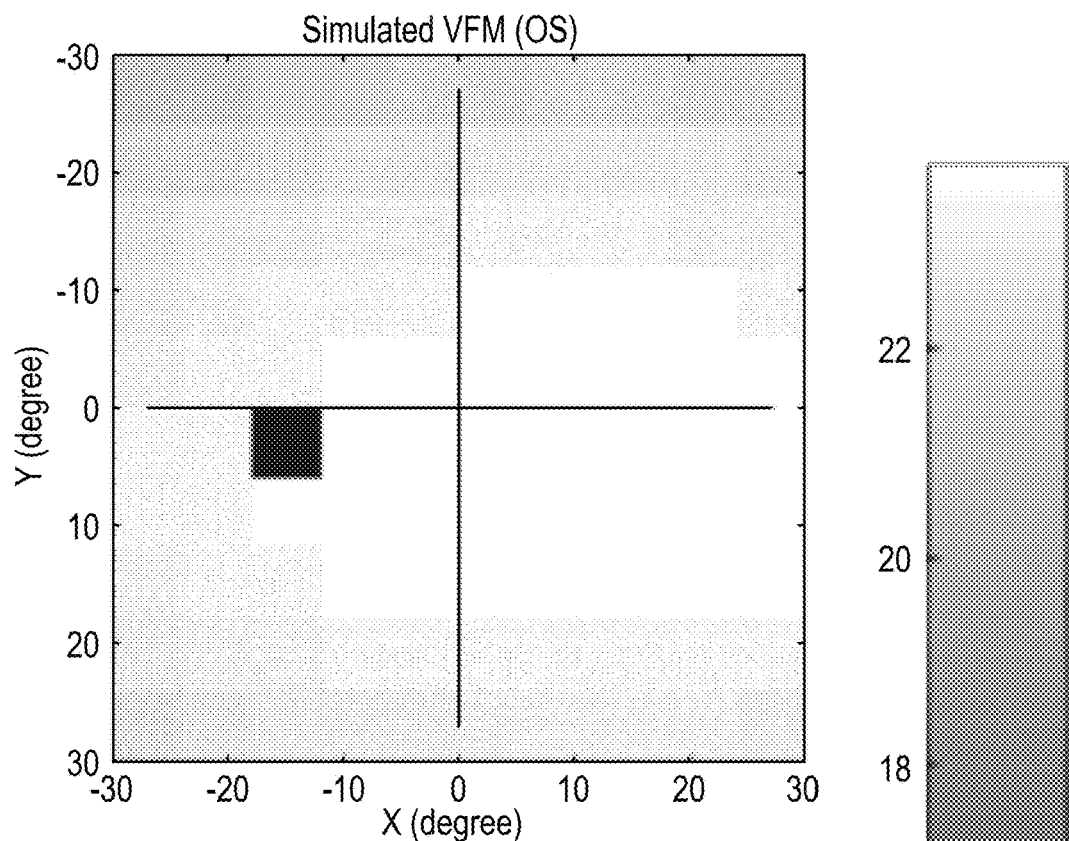
FIGS. 4A-Q illustrate exemplary estimated light sensitivity visual field maps (VFMs) generated by simulations of a method, for example, as depicted in FIG. 3, and a Yes/No (YN) method for measuring visual function maps.
Figure 4B:
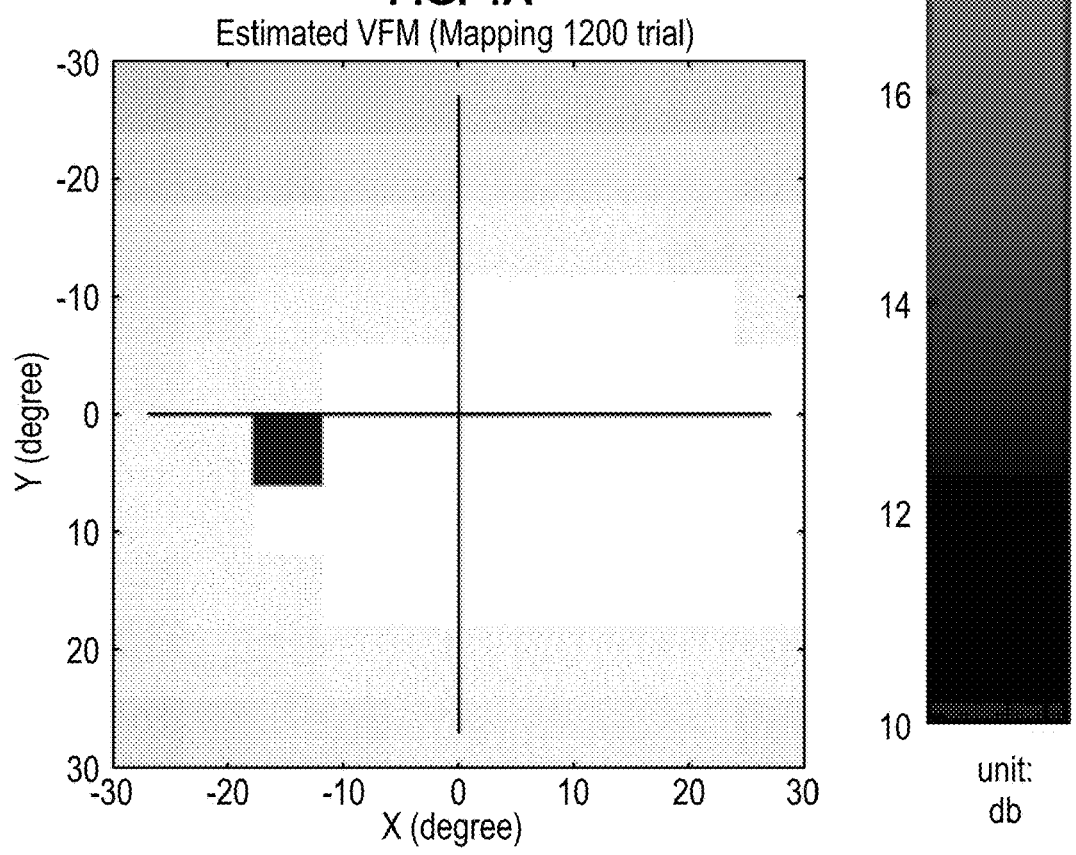
Figure 4C:
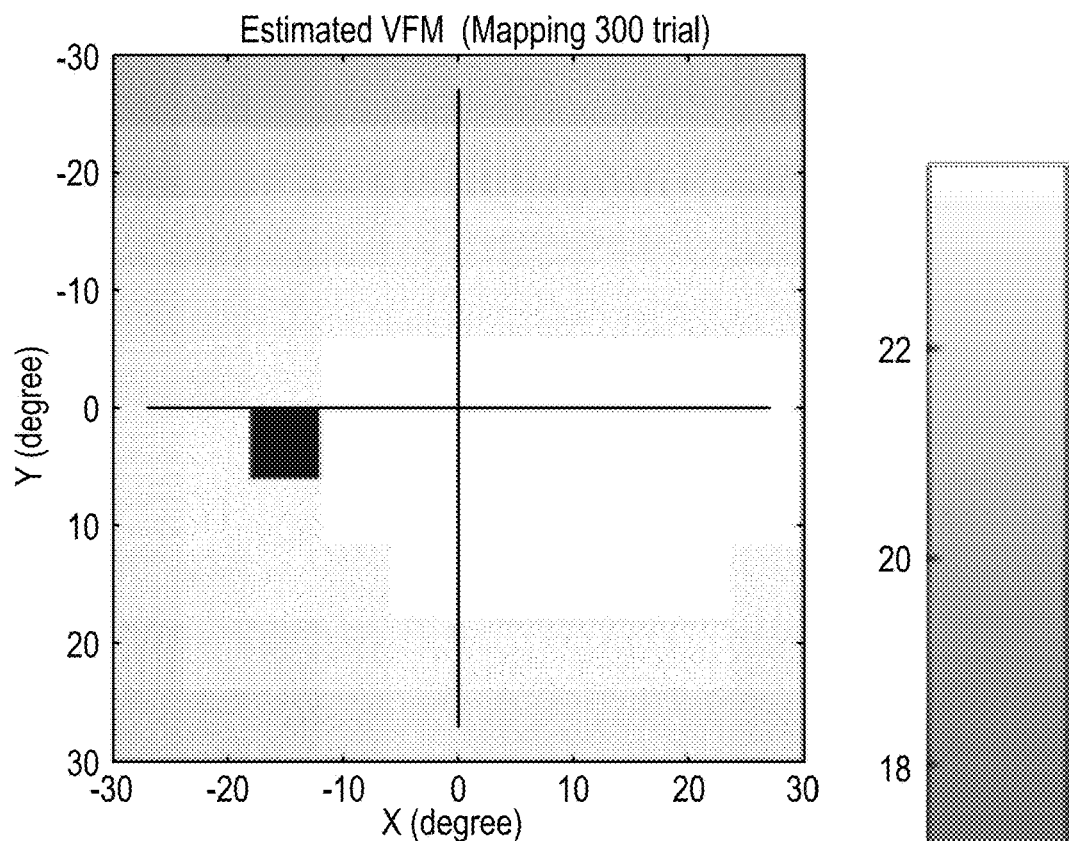
Figure 4D:
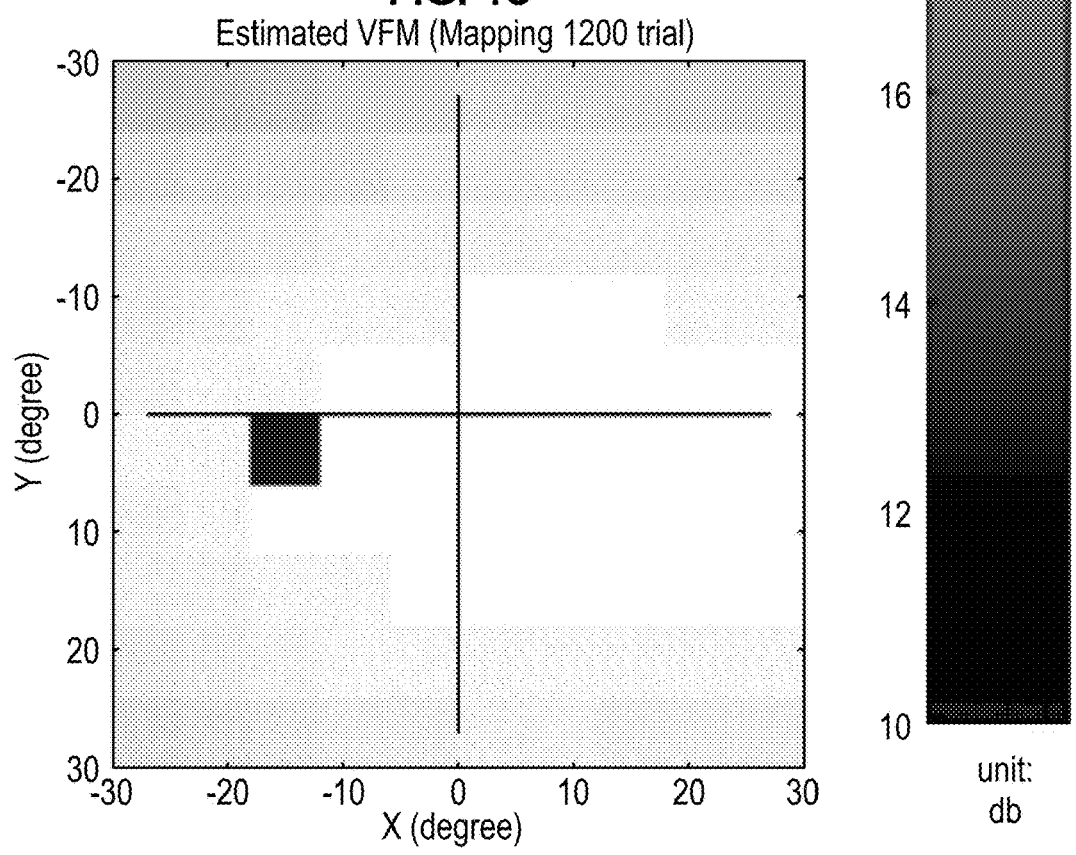
Figure 4E:
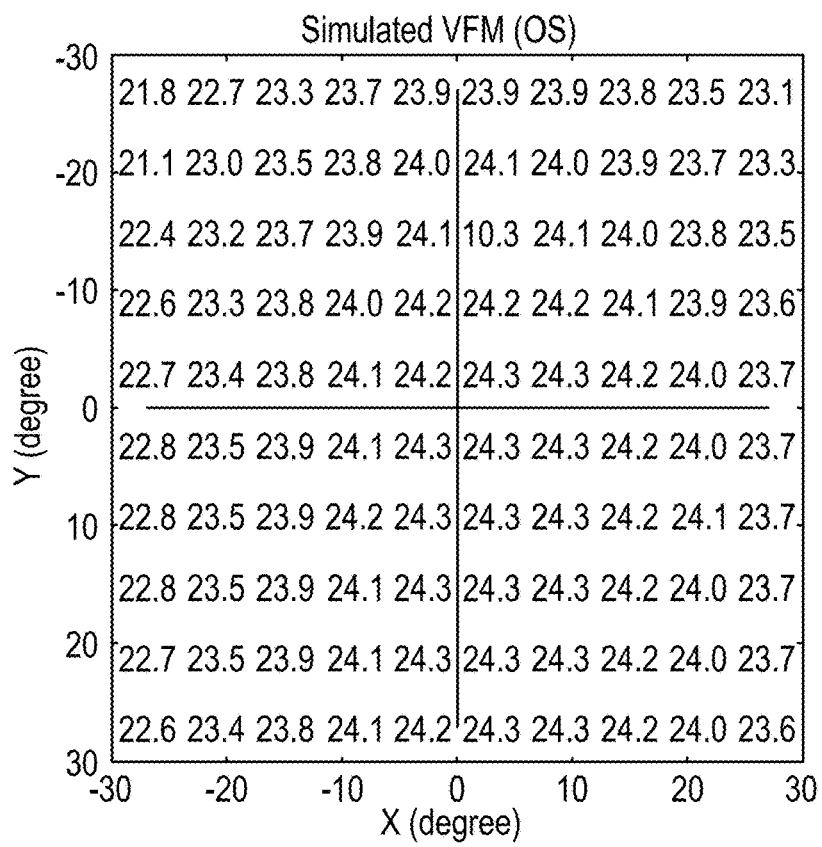
Figure 4F:
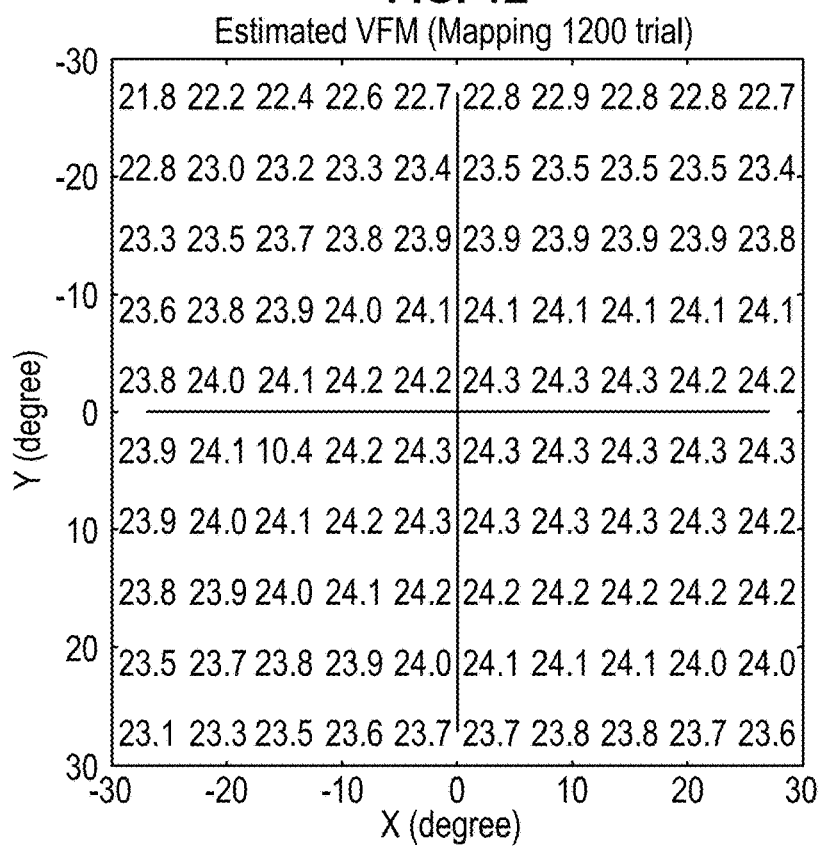
Figure 4G:
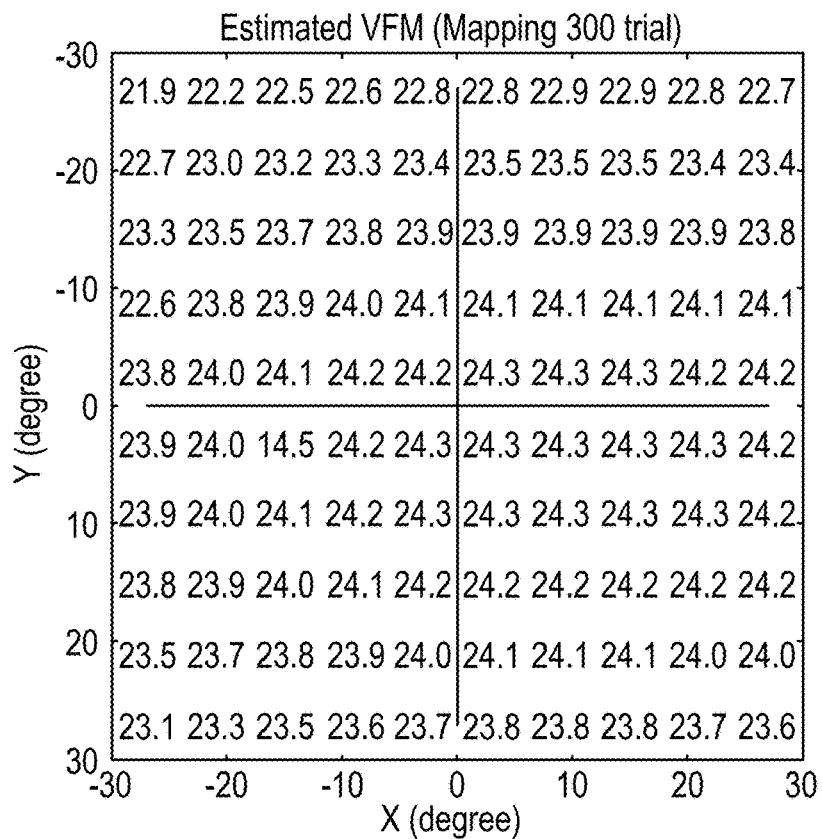
Figure 4H:
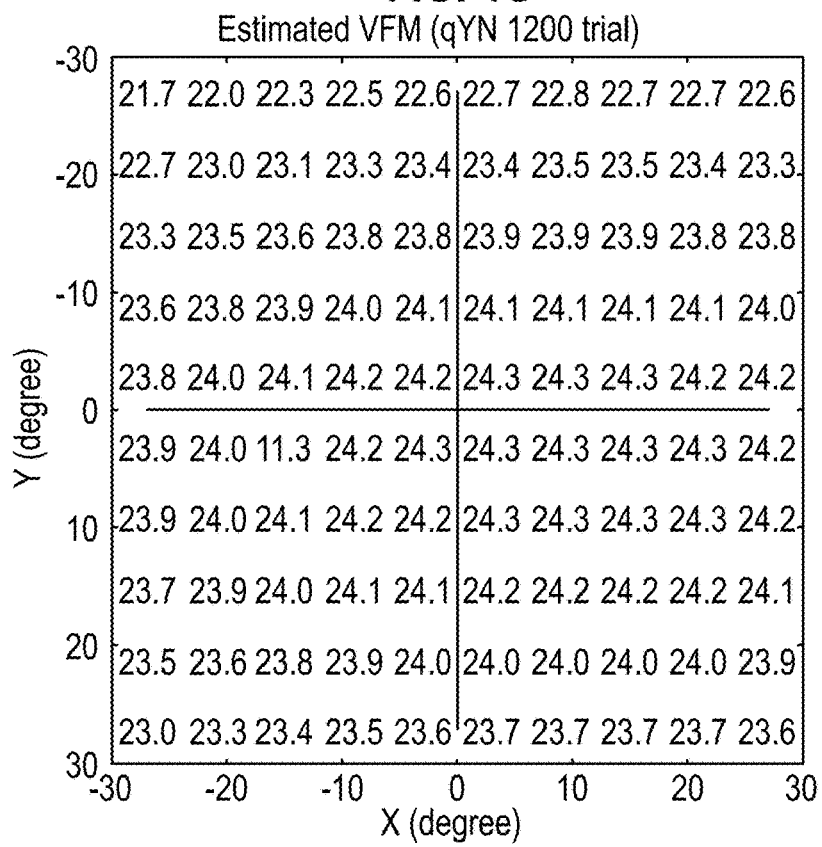
Figure 4I:
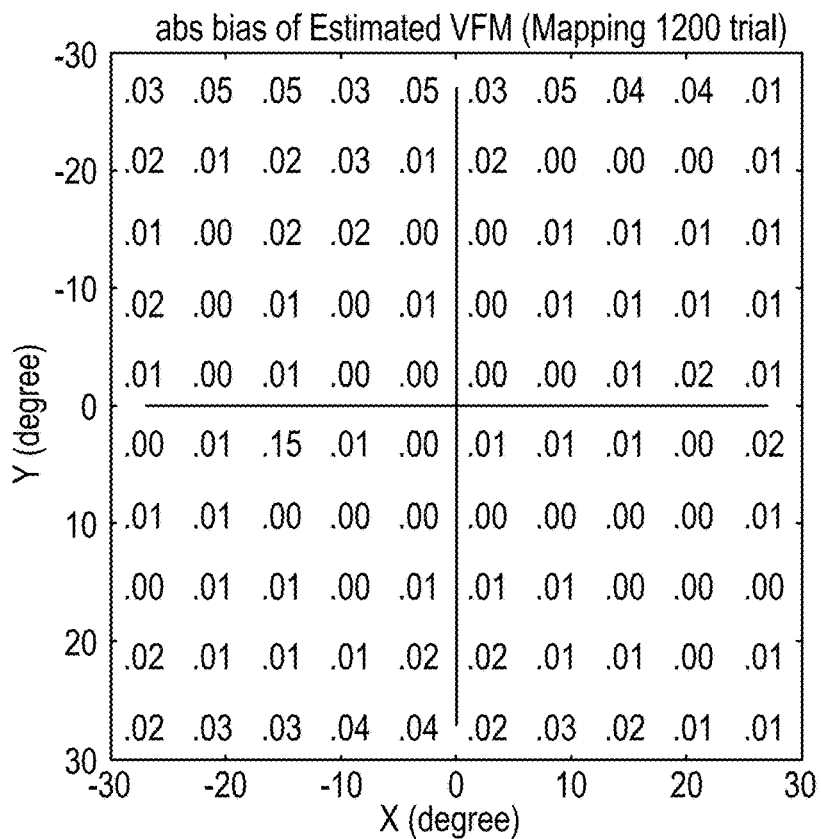
Figure 4J:
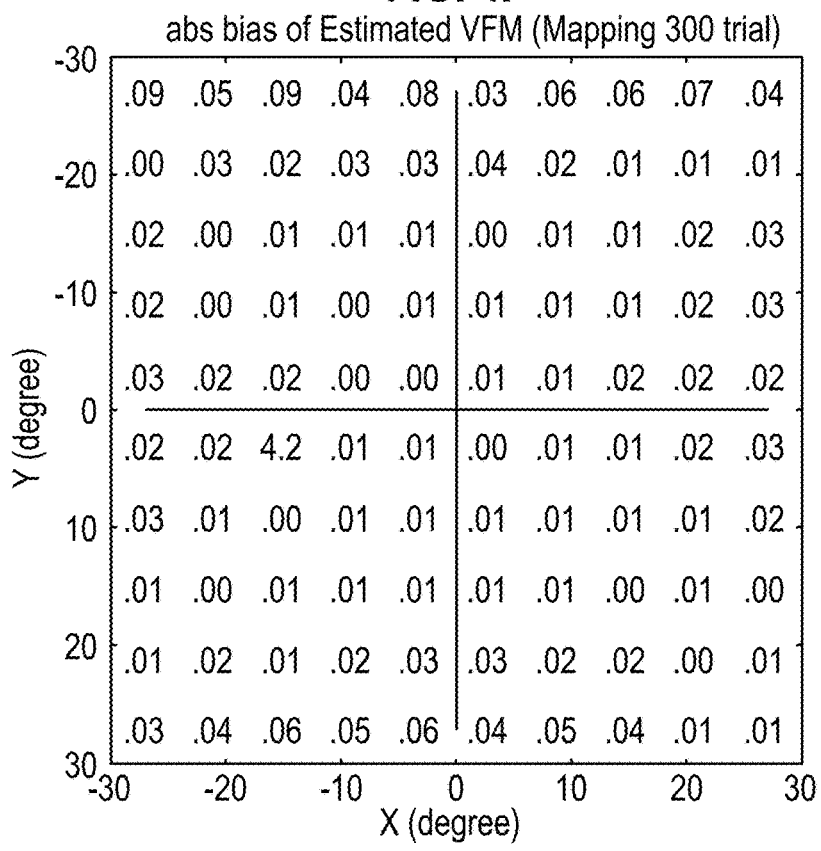
Figure 4K:
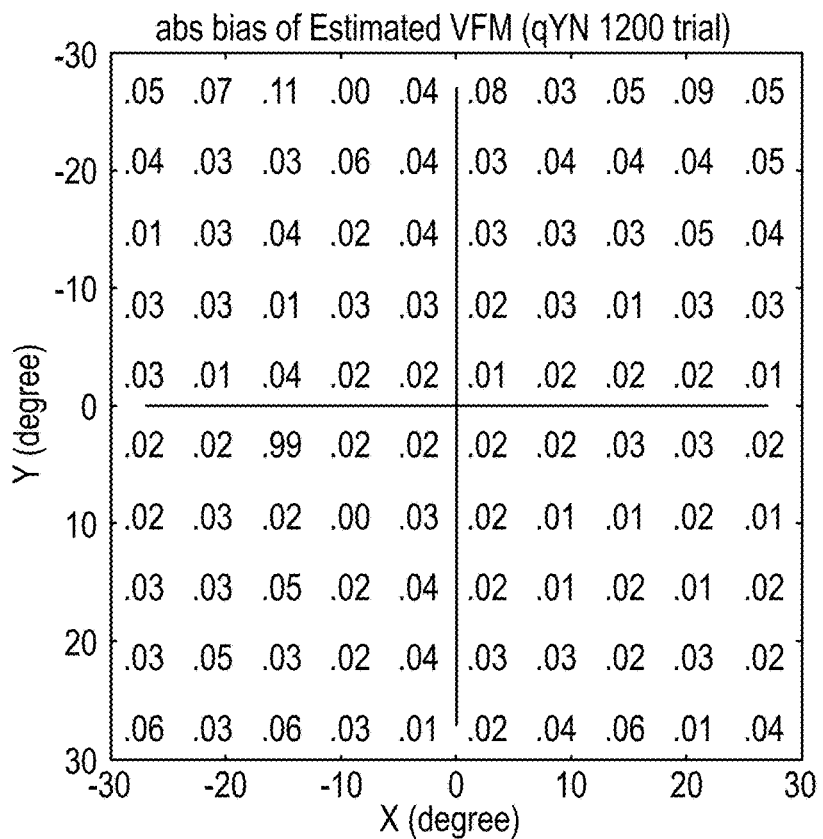
Figure 4L:
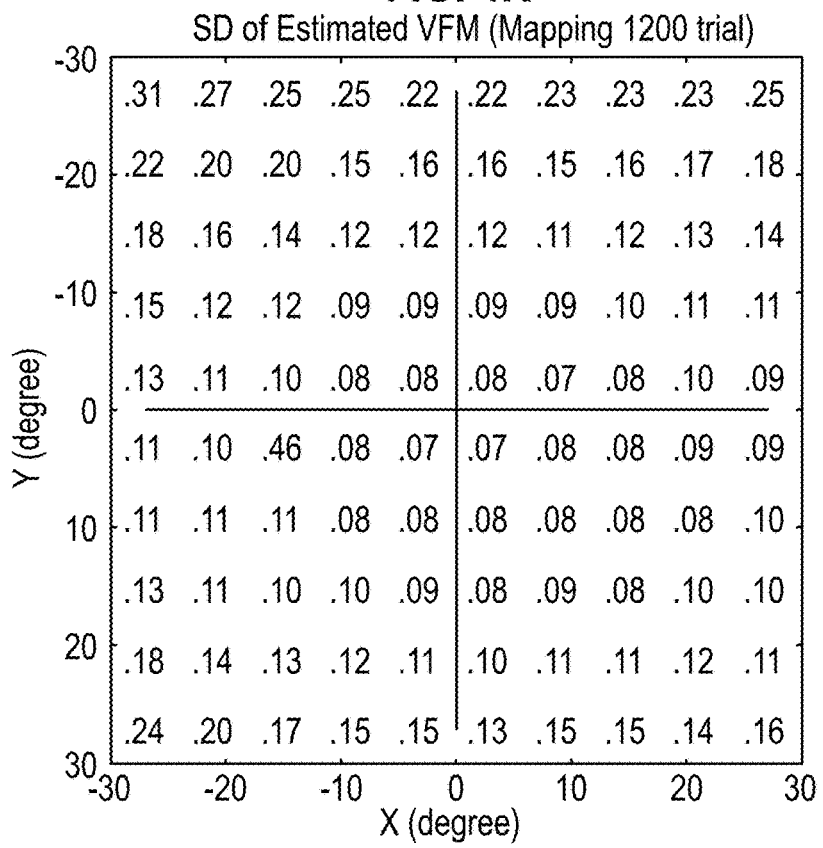
Figure 4M:
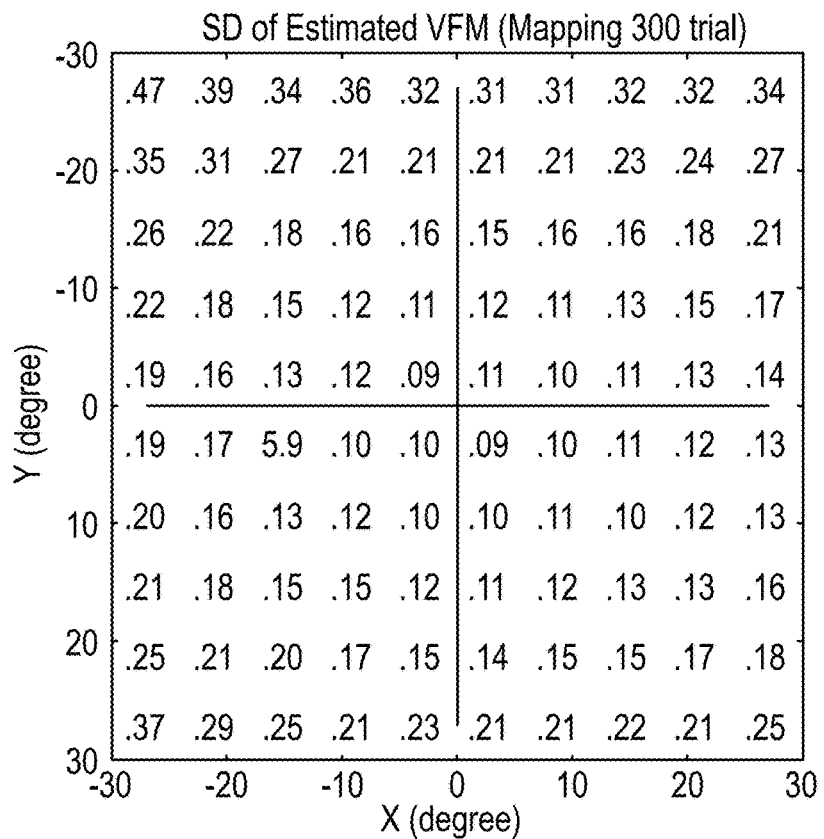
Figure 4N:
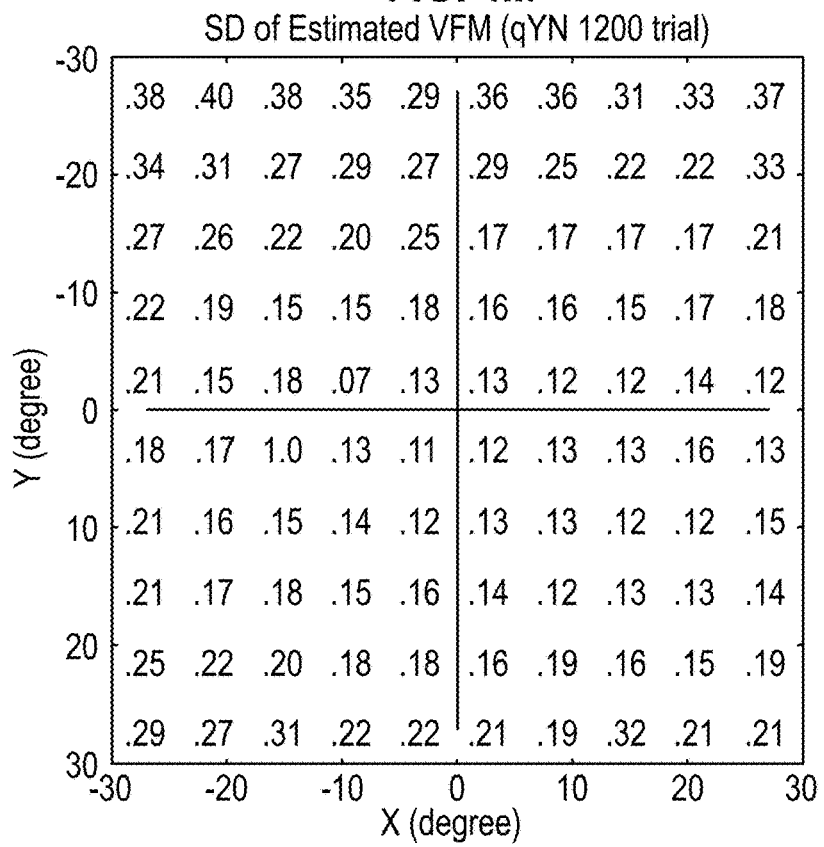
Figure 4O:
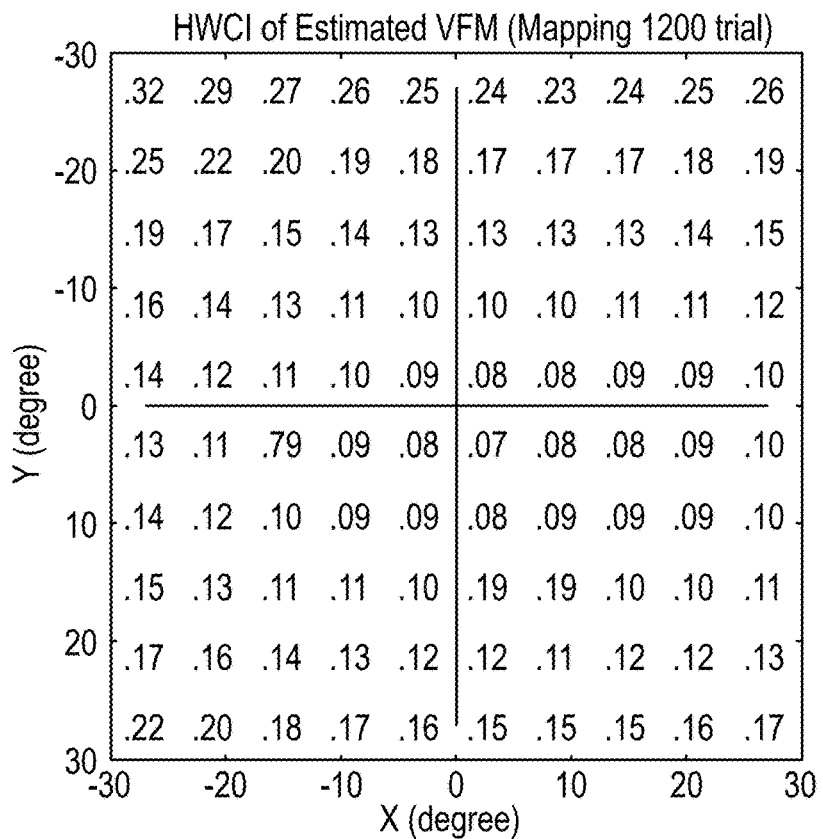
Figure 4P:
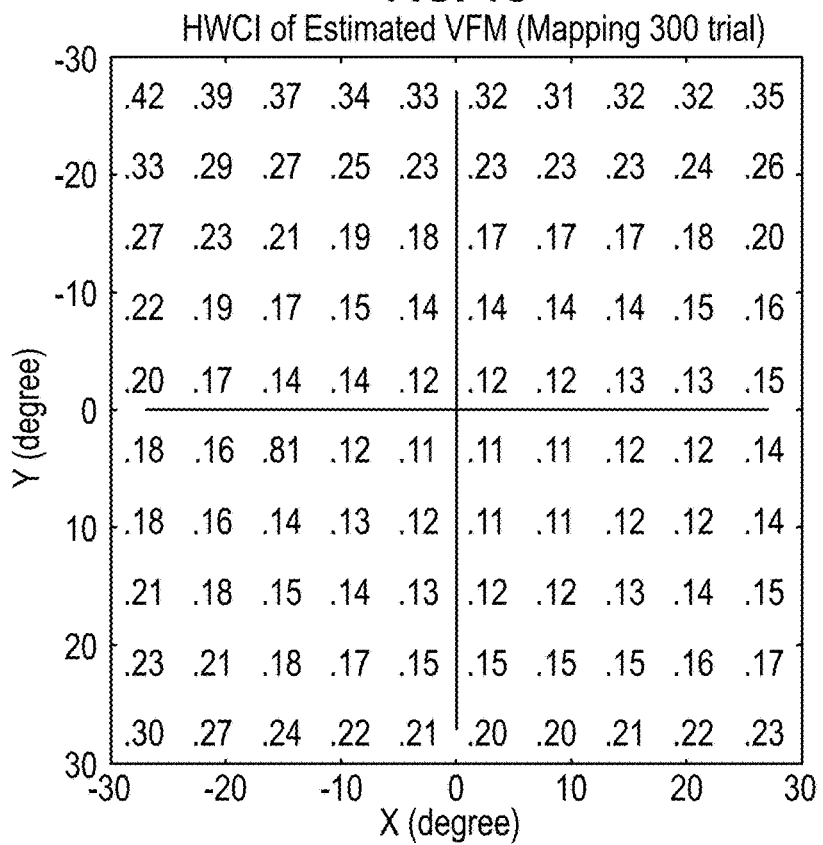
Figure 4Q:
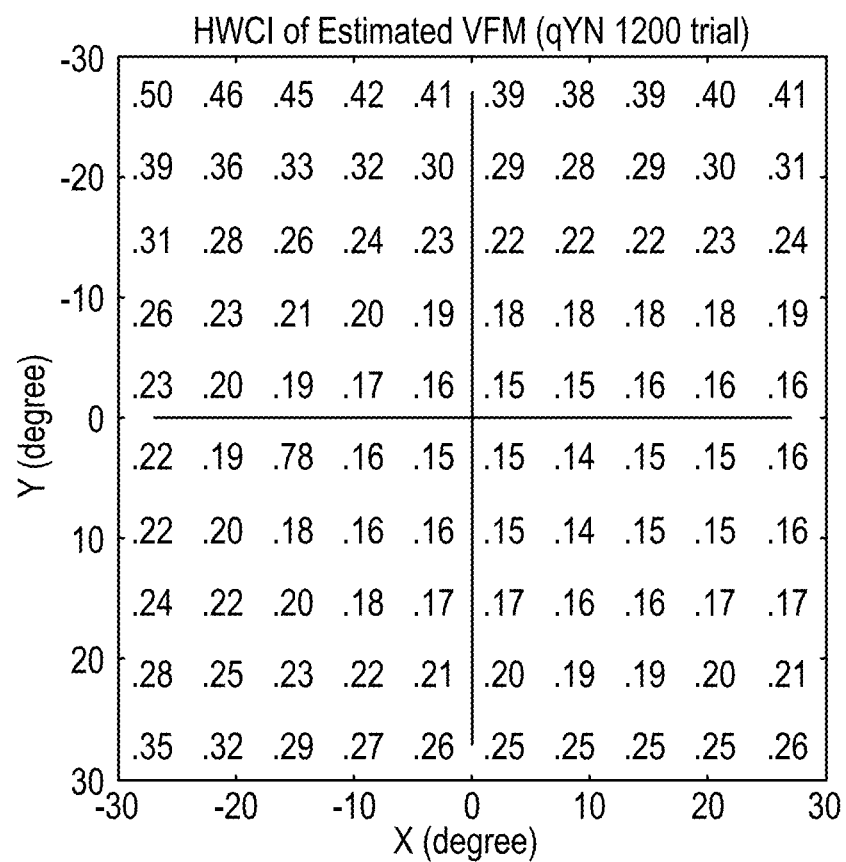

FIGS. 4A-Q illustrate exemplary estimated light sensitivity VFMs for the simulated subject generated by simulations of the method described herein and the Bayesian YN method for measuring visual function map. The VFM for the simulated observer is presented in a first column. The estimated results obtained with the method described herein after 1200 tests and 300 tests are presented in a second column and third column. The estimated results obtained with the Bayesian YN method are presented in a fourth column. The VFM estimates are presented in a first row with a corresponding color-map and a second row with numerical values in each respective column. The absolute bias, standard deviation and 68.2% HWCI of the VFM estimates are presented in the third, fourth and fifth rows.

Figure 5A:
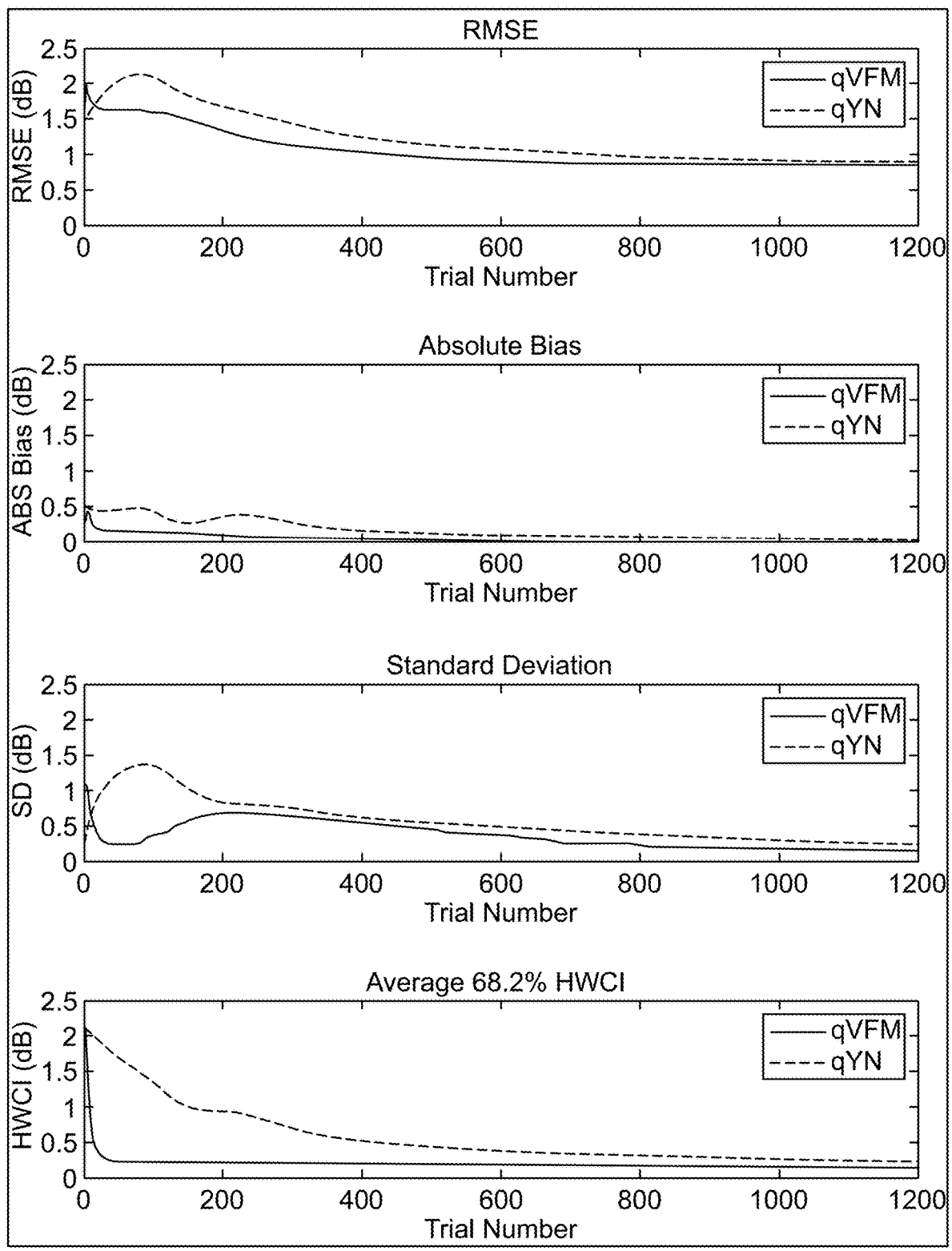
FIG. 5A illustrates an exemplary average root mean squared error (RMSE), are average absolute bias, a standard deviation (SD), and a half width of a credible interval (HWCI) based on simulations of a method, for example, as depicted in FIG. 3, and a YN method for measuring visual function maps.

FIG. 5A illustrate an exemplary average RMSE, age average absolute bias, a standard deviation, and a 68.2% HWCI based on simulations of the method described herein and the Bayesian YN method for measuring visual function maps. The average RMSE of the estimated sensitivities across all 100 retina locations started at 1.41 dB in both the method described herein and the Bayesian YN method. The average RMSE decreased to 0.76 dB in the method described herein and 1.15 dB in the Bayesian YN method alter the first 300 tests, and to 0.15 dB in the method described herein and 0.26 dB the Bayesian YN method in the end of 1200 tests.

The average absolute bias of the estimated sensitivities across all 100 retina locations started at 0.28 dB in both the method described herein and the Bayesian YN method. The average absolute bias decreased to 0.06 dB in the method described and 0.28 dB in the Bayesian YN method after the first 300 tests, and to 0.01 dB in the method described herein and 0.04 dB in the Bayesian YN method in the end of 1200 tests. The SD was 0.63 dB in the method described herein and 0.75 dB in the Bayesian YN method after 300 tests and decreased to 0.15 dB in the method described herein and 0.24 dB in the Bayesian YN method after 1200 tests. The 68.2% HWCI correspondingly decreased with the trial number in all conditions and provided better precision in the method described herein. The 68.2% HWCI started at 2.12 dB in the method described herein and the Bayesian YN method, decreased to 0.20 dB in the method described herein and 0.69 dB in the Bayesian YN method alter the first 300 tests and to 0.15 dB in the method described herein and 0.24 dB in Bayesian YN method after 1200 tests.

Figure 5B:
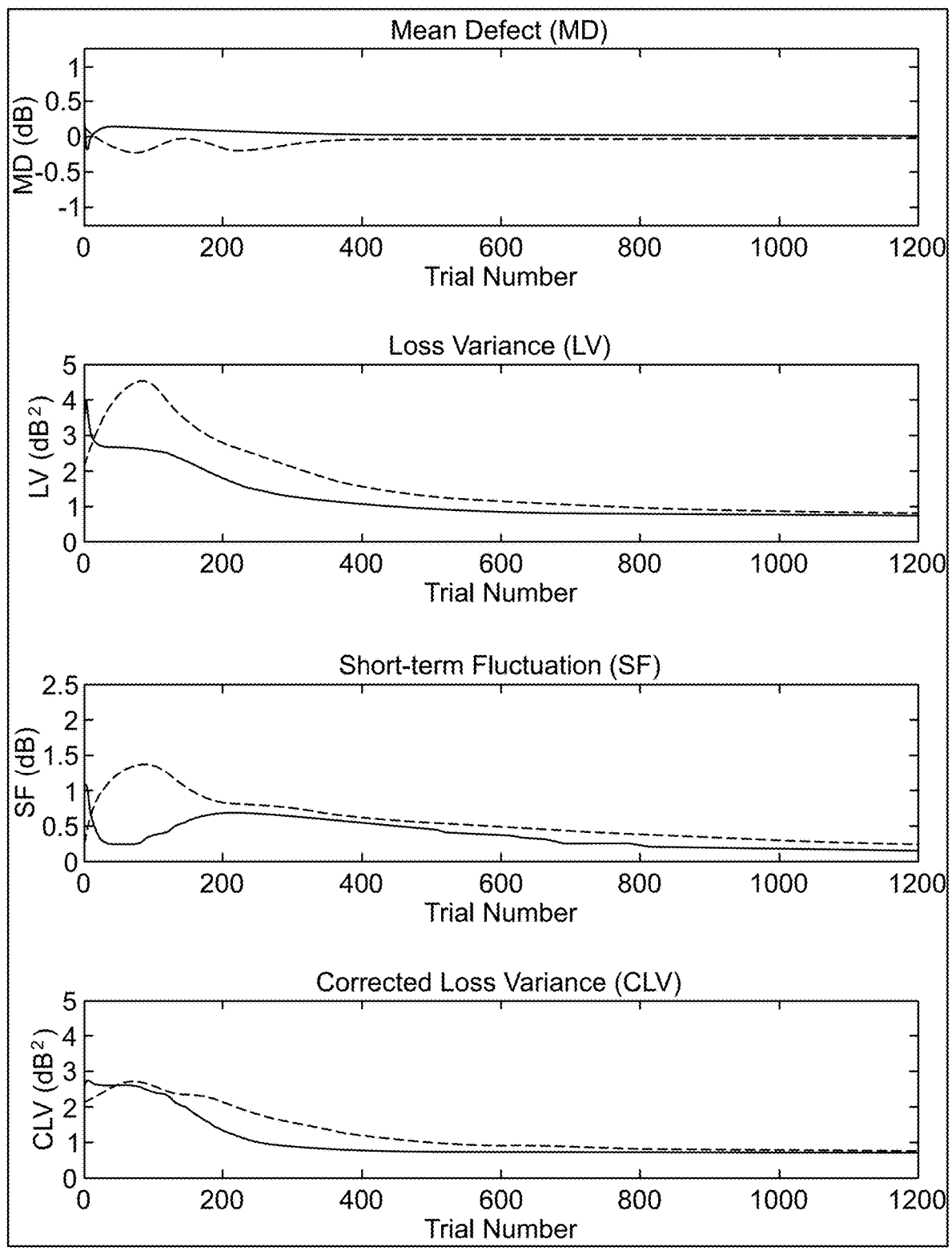
FIG. 5B illustrate an exemplary mean defect (MD), a loss variance (LV), a short-term fluctuation (SF), a corrected loss variance (CLV) based on simulations of a method, for example, as depicted in FIG. 3, and a Bayesian YN method for measuring visual function maps.
Figure 6A:
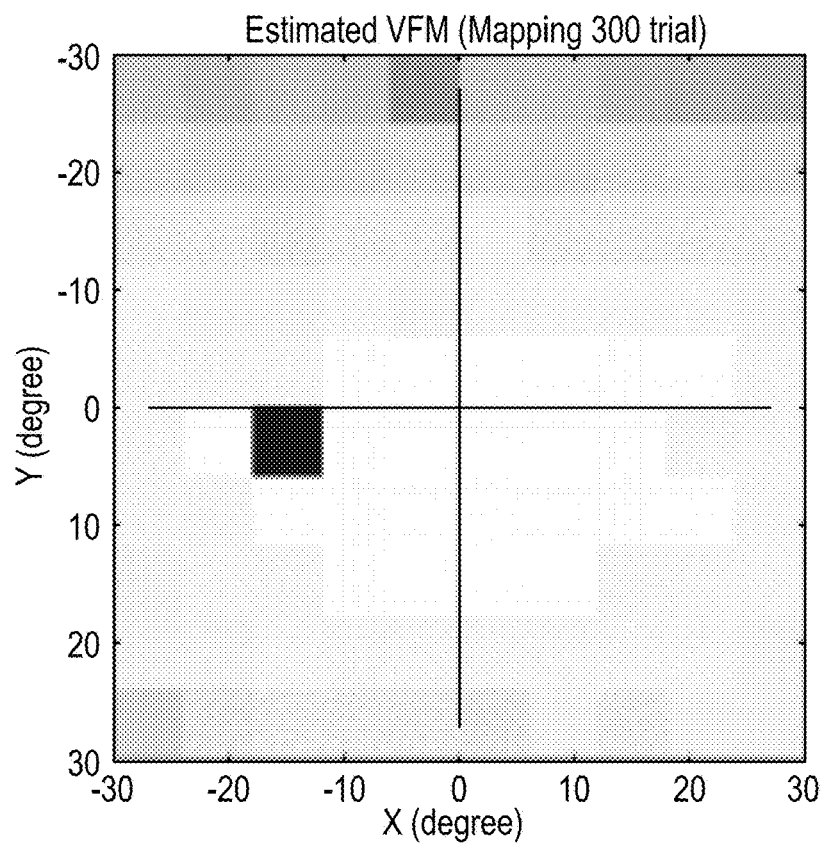
FIGS. 6A-6P illustrate exemplary estimated light sensitivity VFMs for subject 1 generated by a method, for example, as depicted in FIG. 3, and a YN method for measuring visual function maps.
Figure 6B:
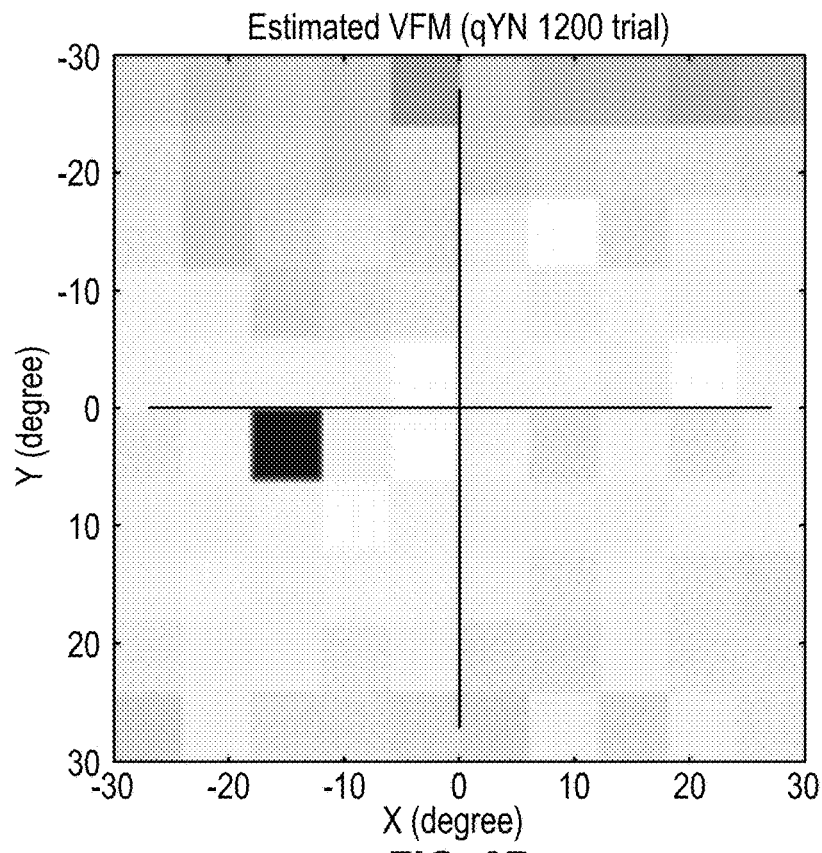
Figure 6C:
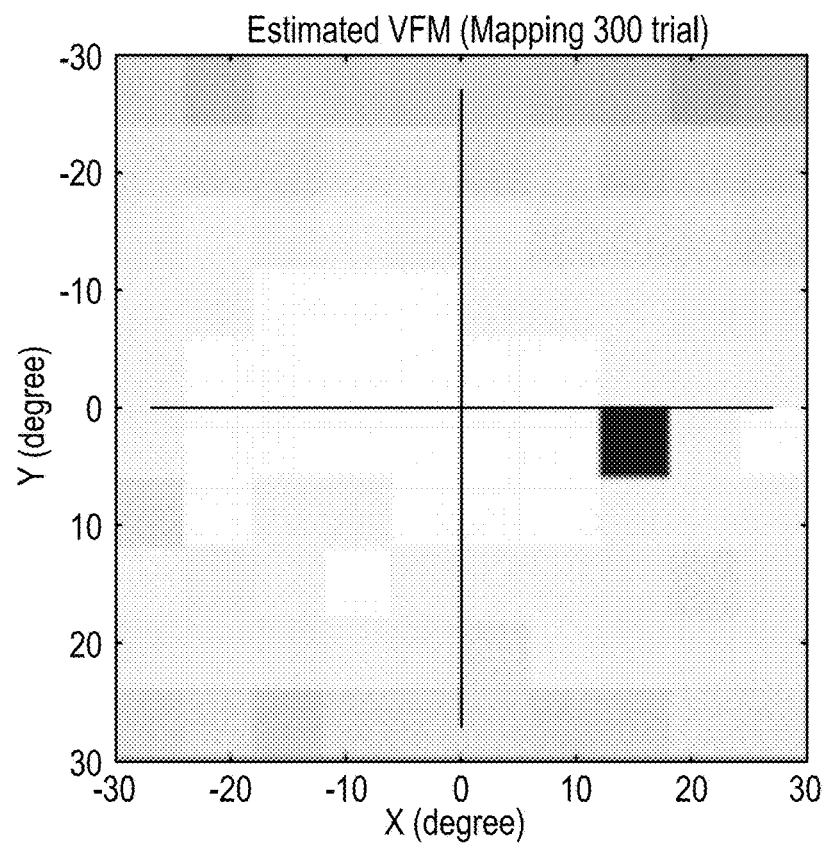
Figure 6D:
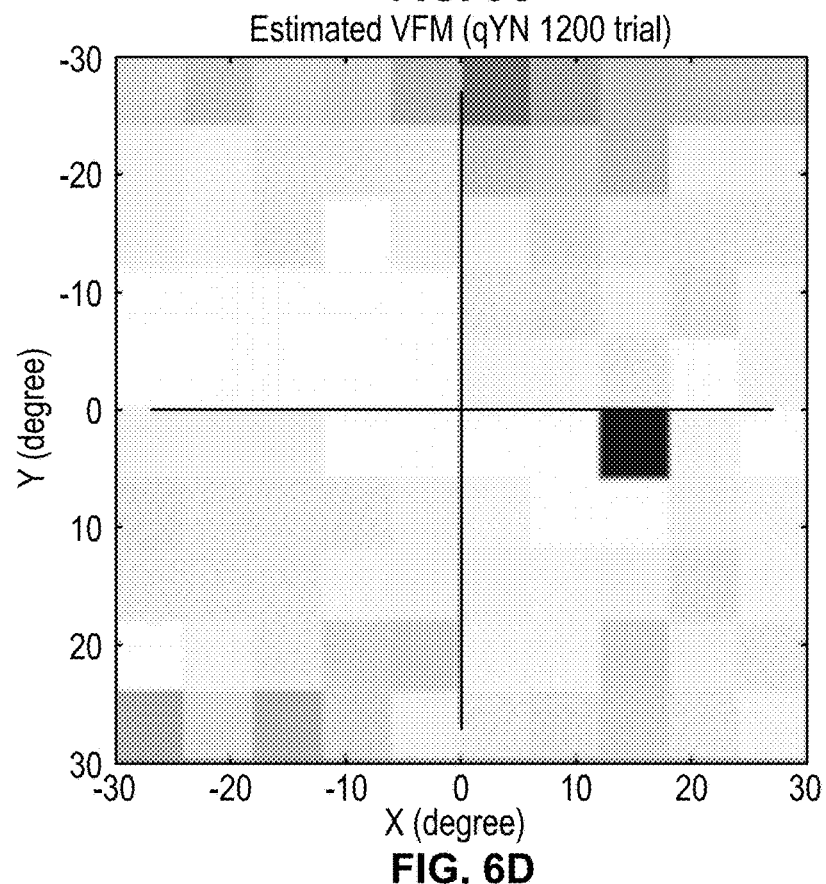
Figure 6E:
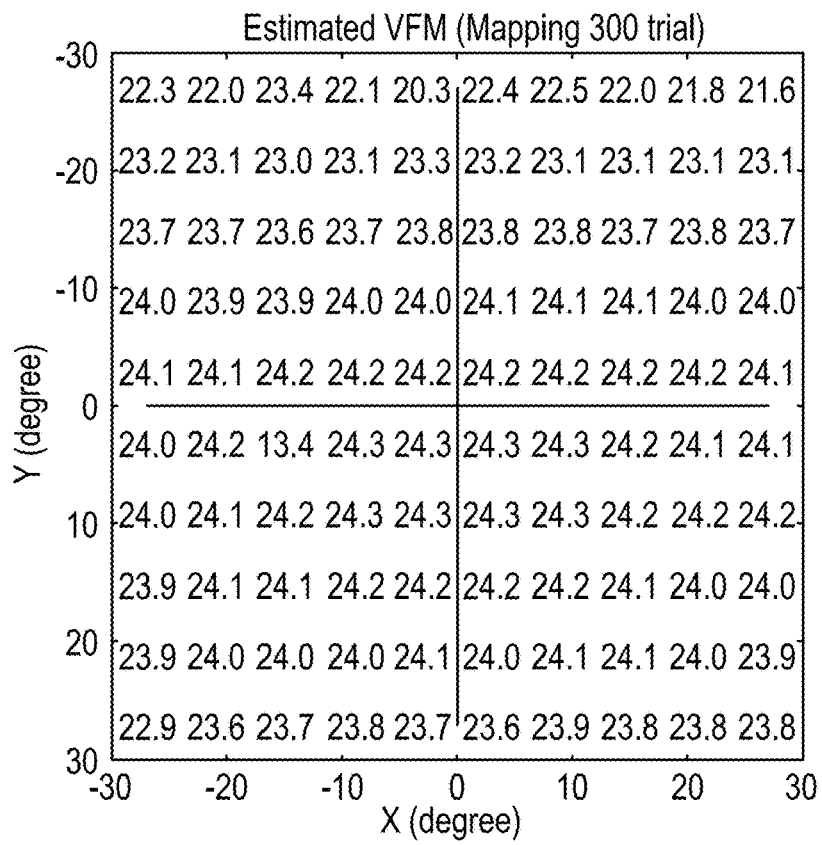
Figure 6F:
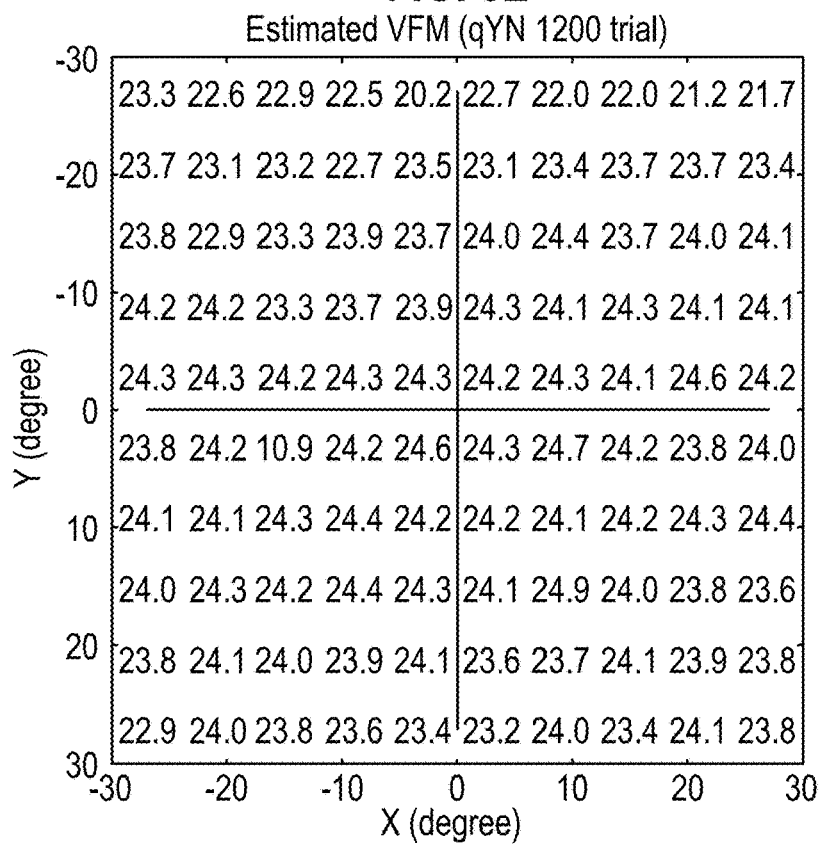
Figure 6G:
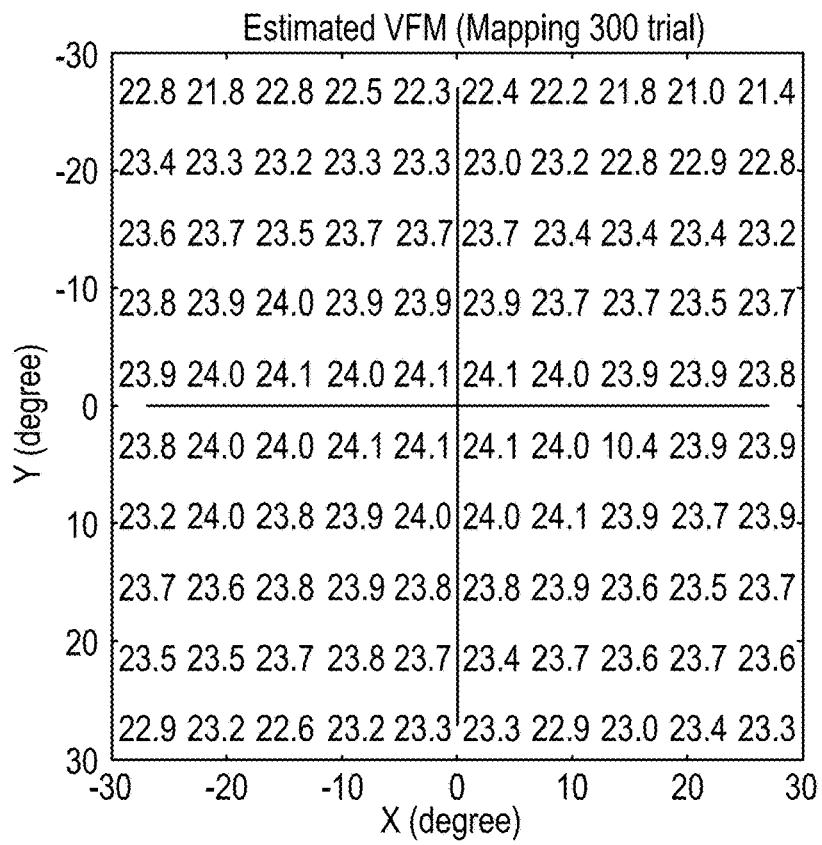
Figure 6H:
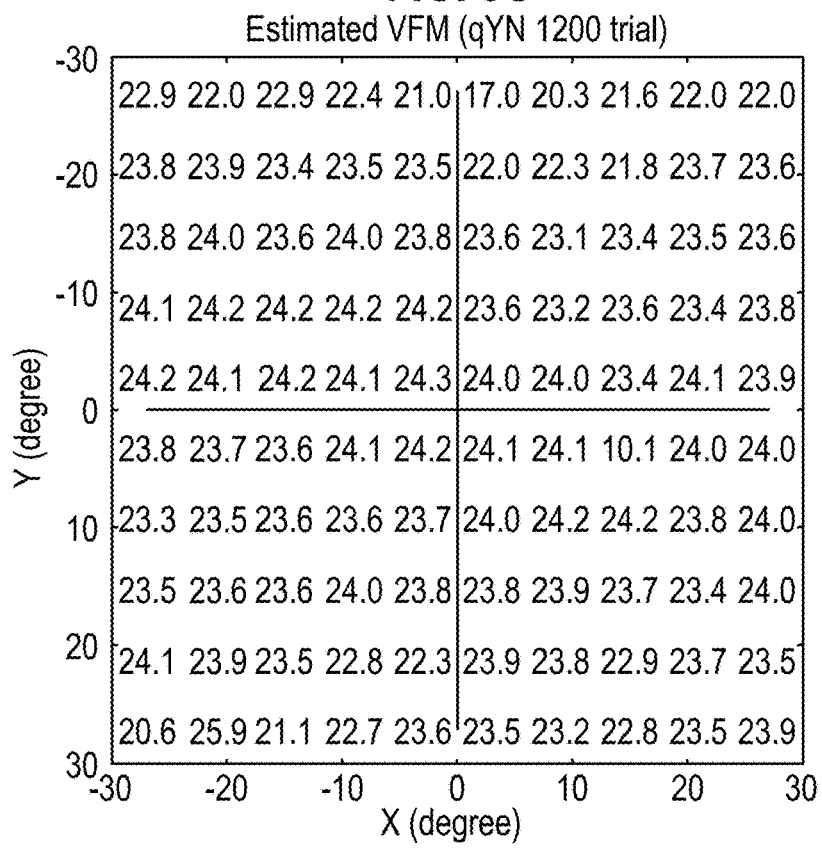
Figure 6I:
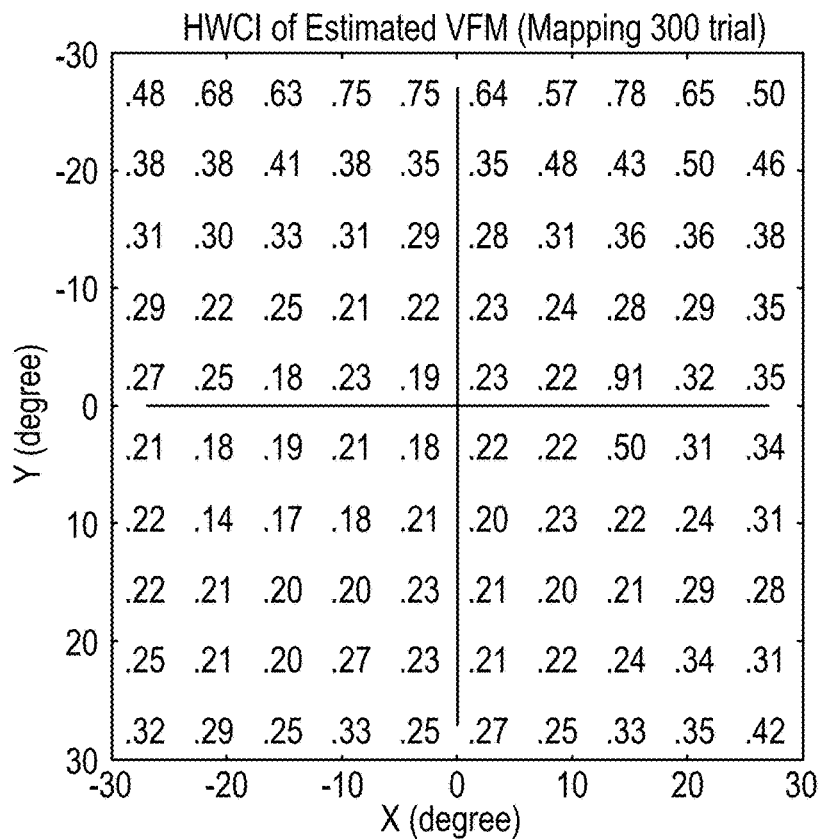
Figure 6J:
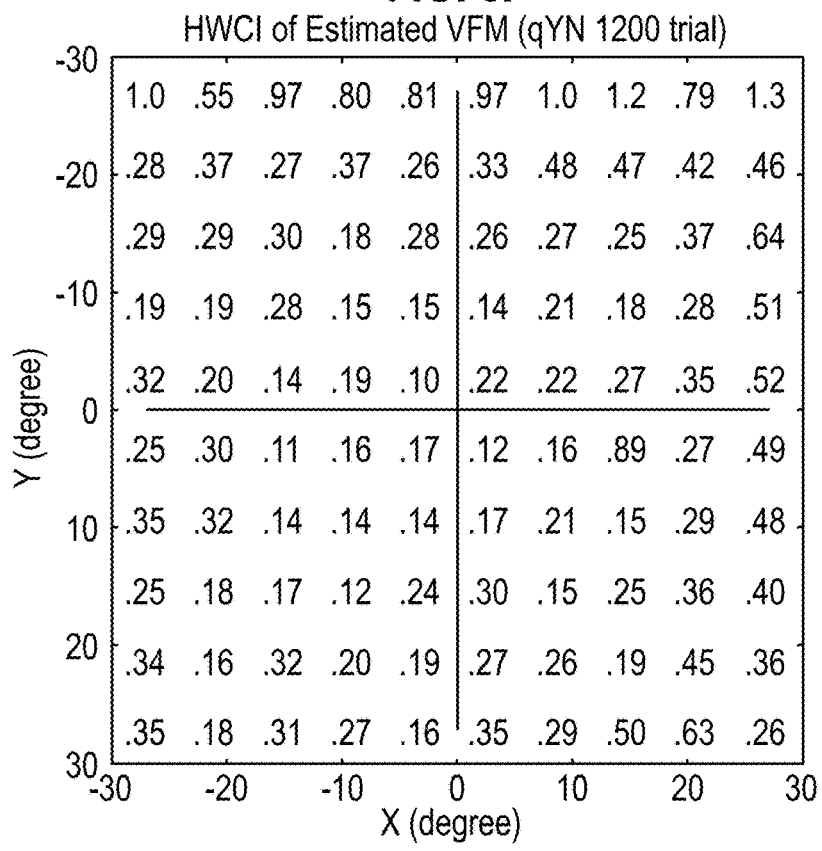
Figure 6K:
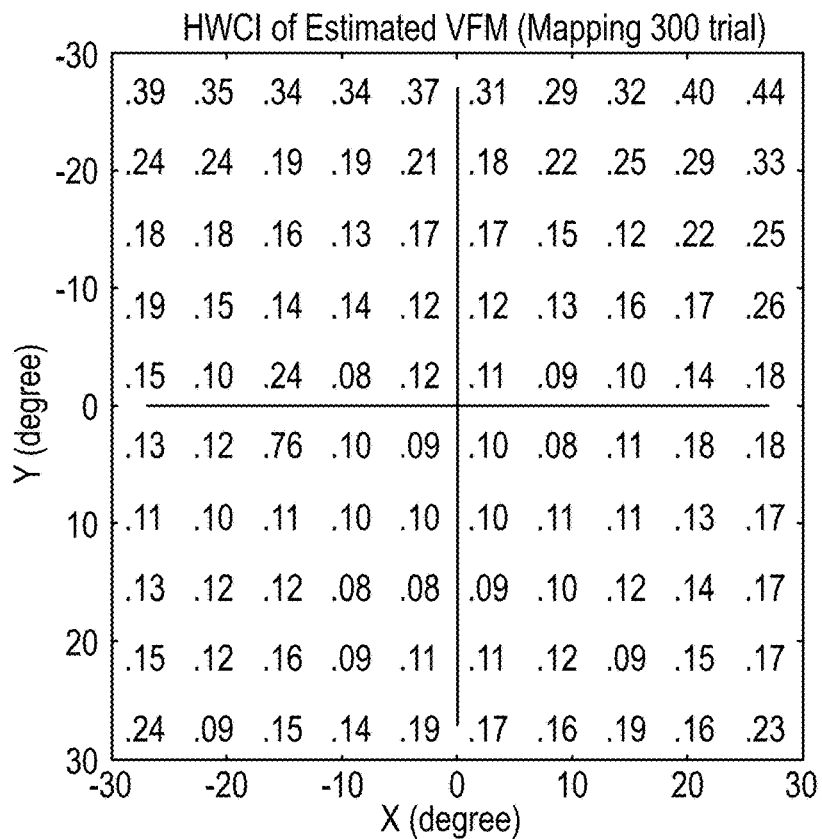
Figure 6L:
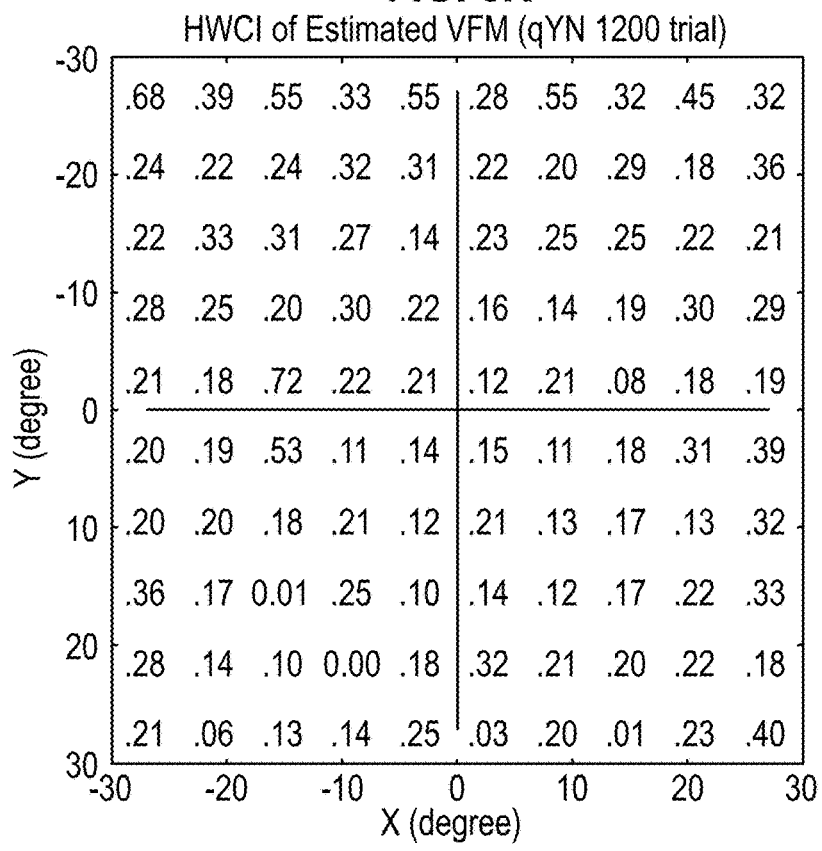
Figure 6M:
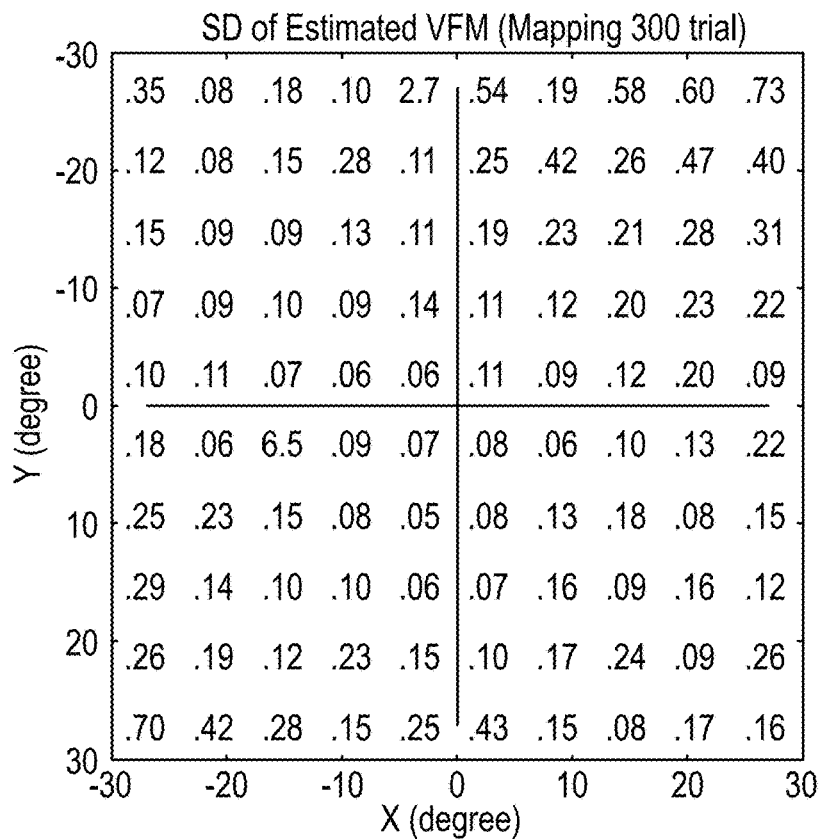
Figure 6N:
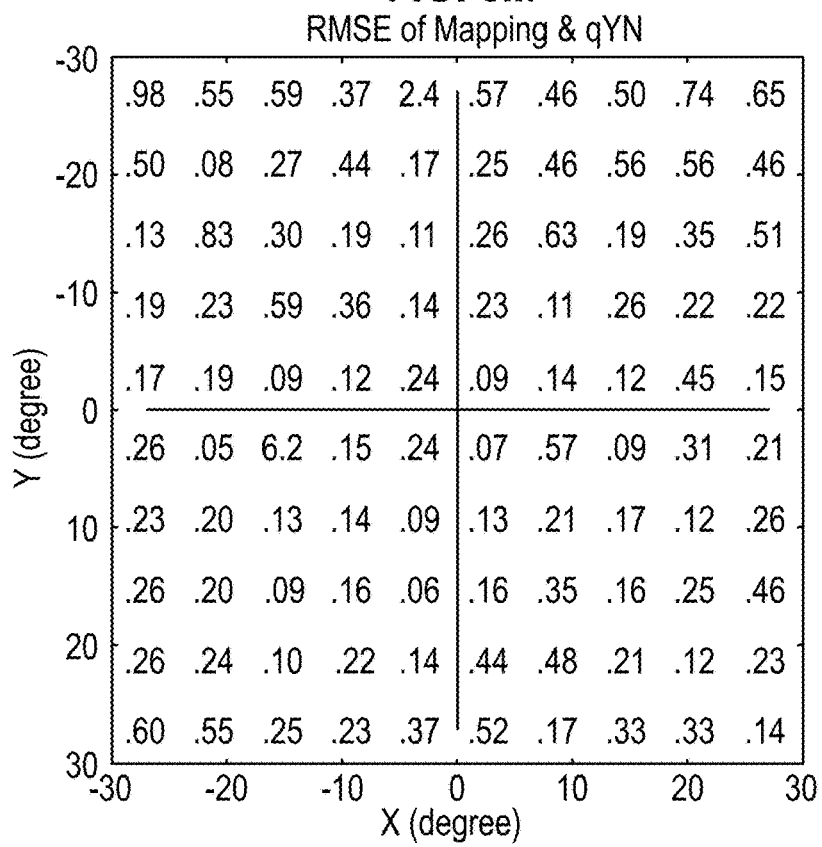
Figure 6O:
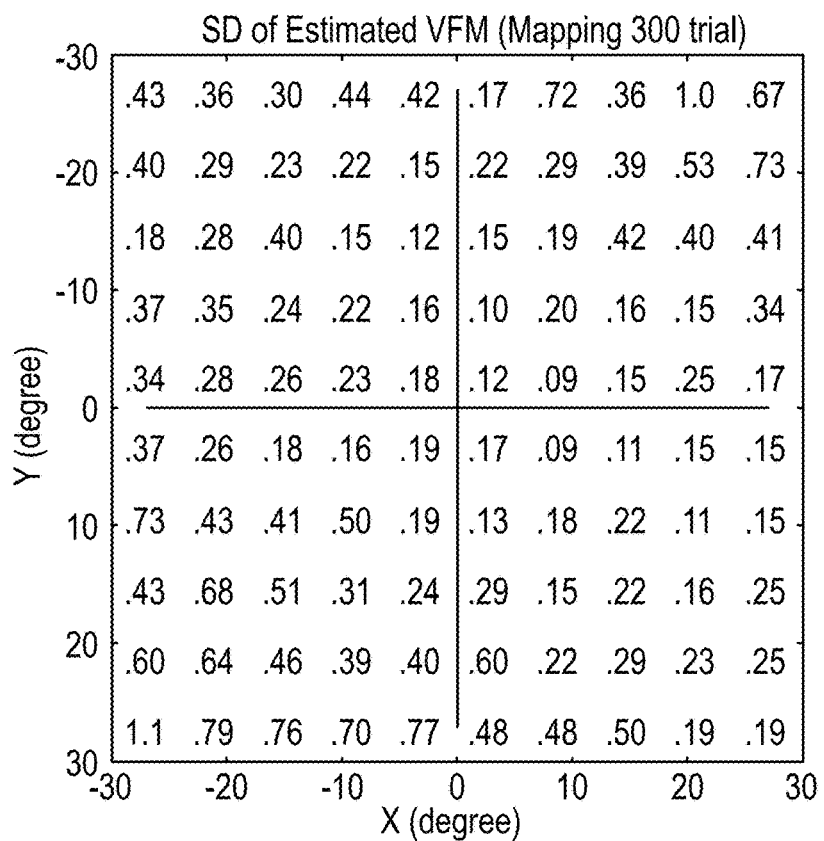
Figure 6P:
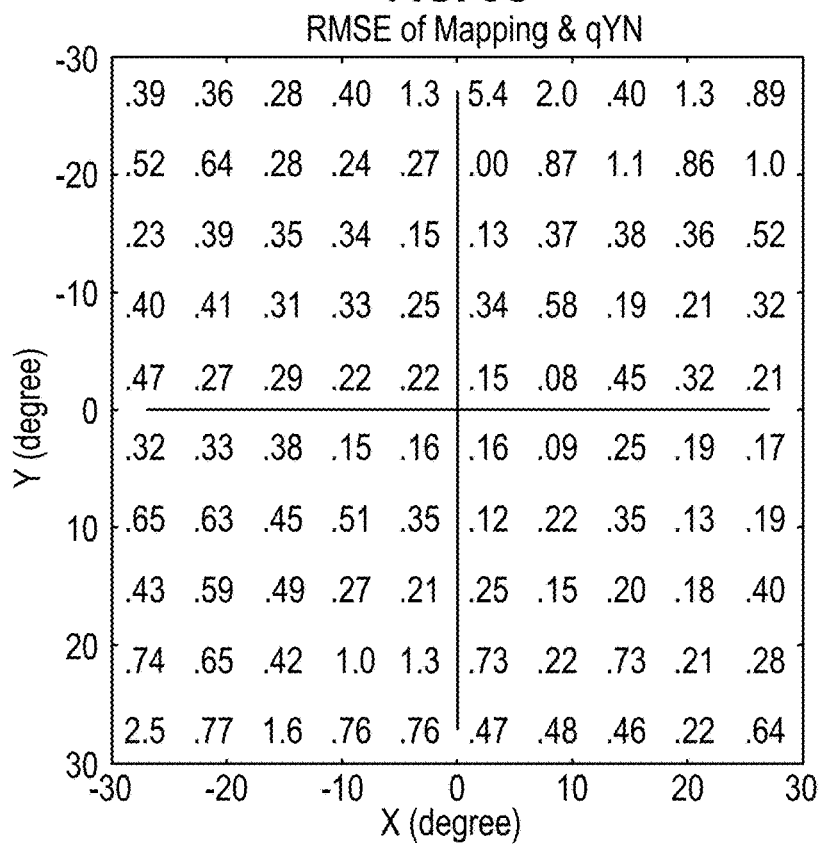
Figure 7A:
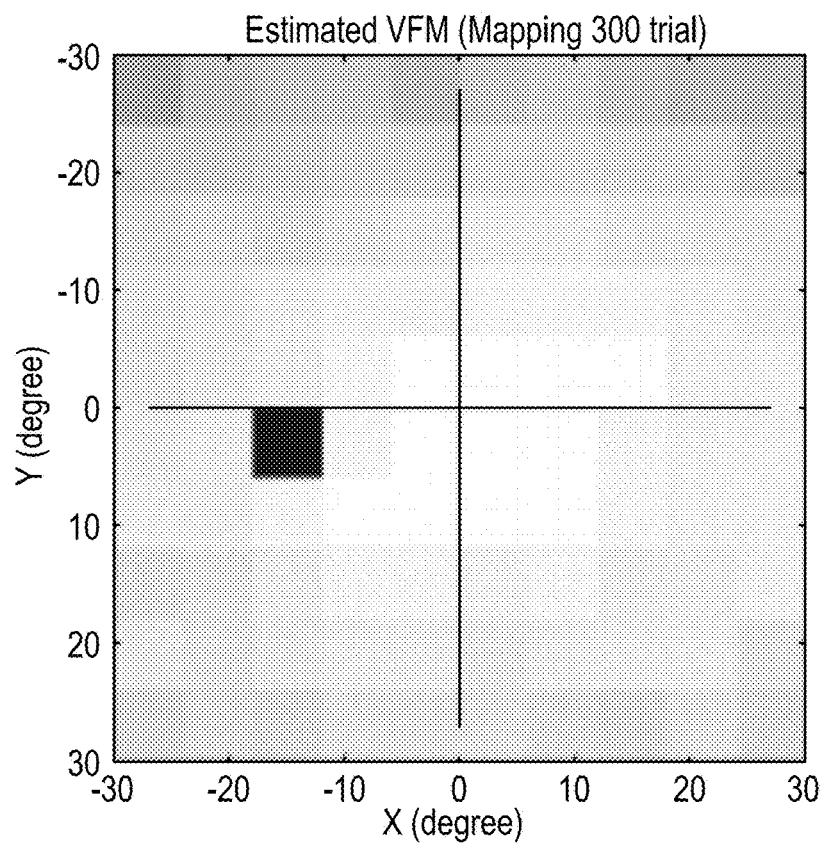
Figure 7B:
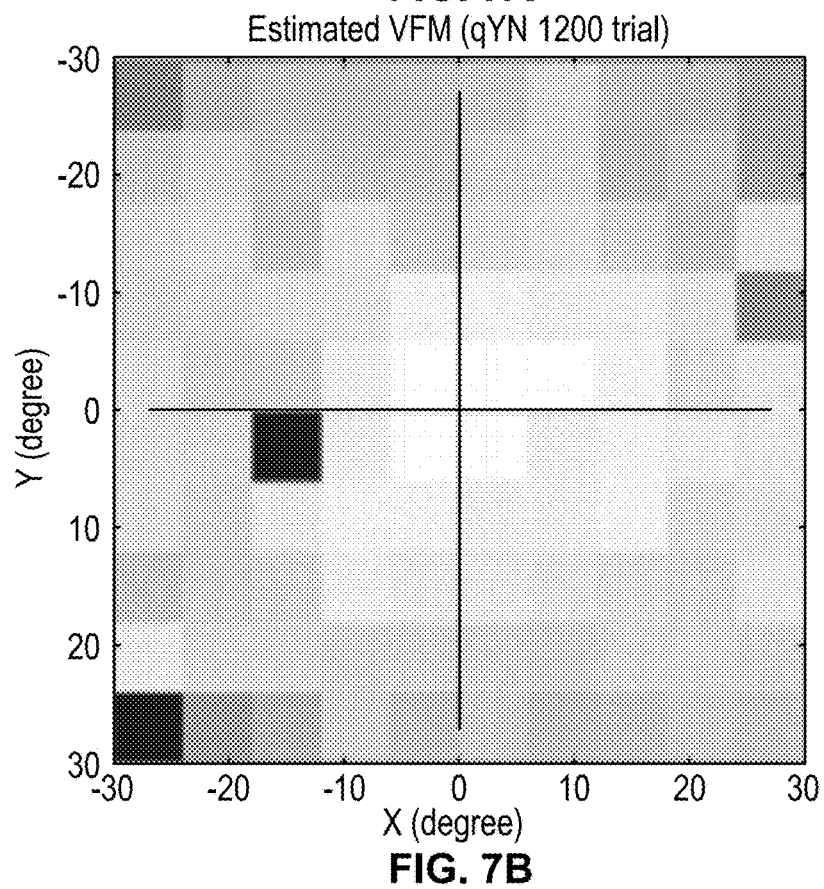
Figure 7C:
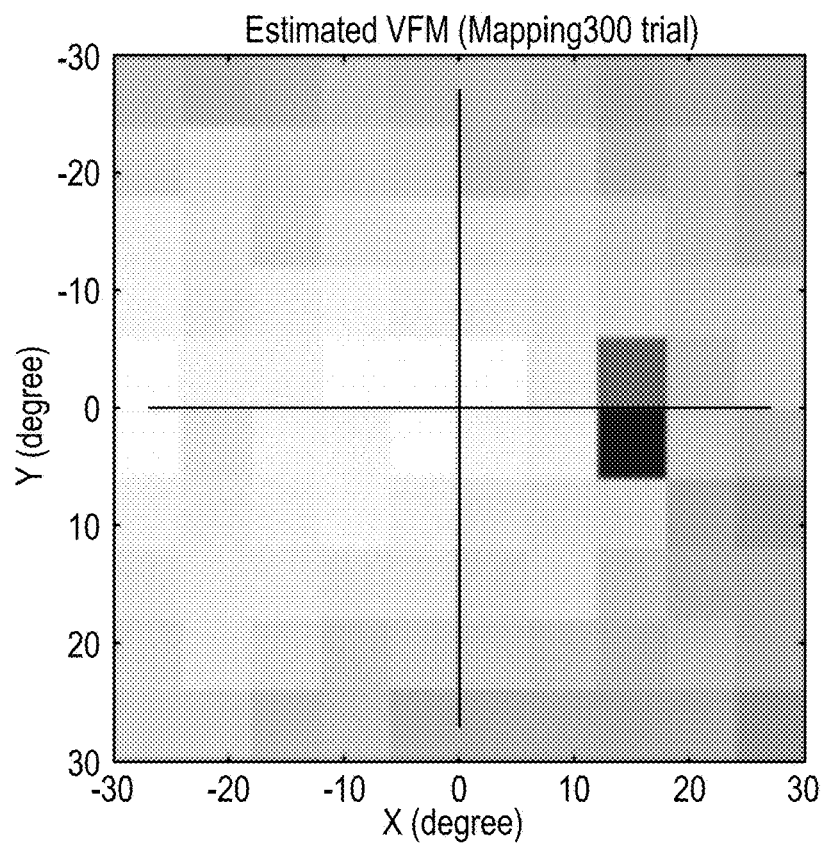
Figure 7D:
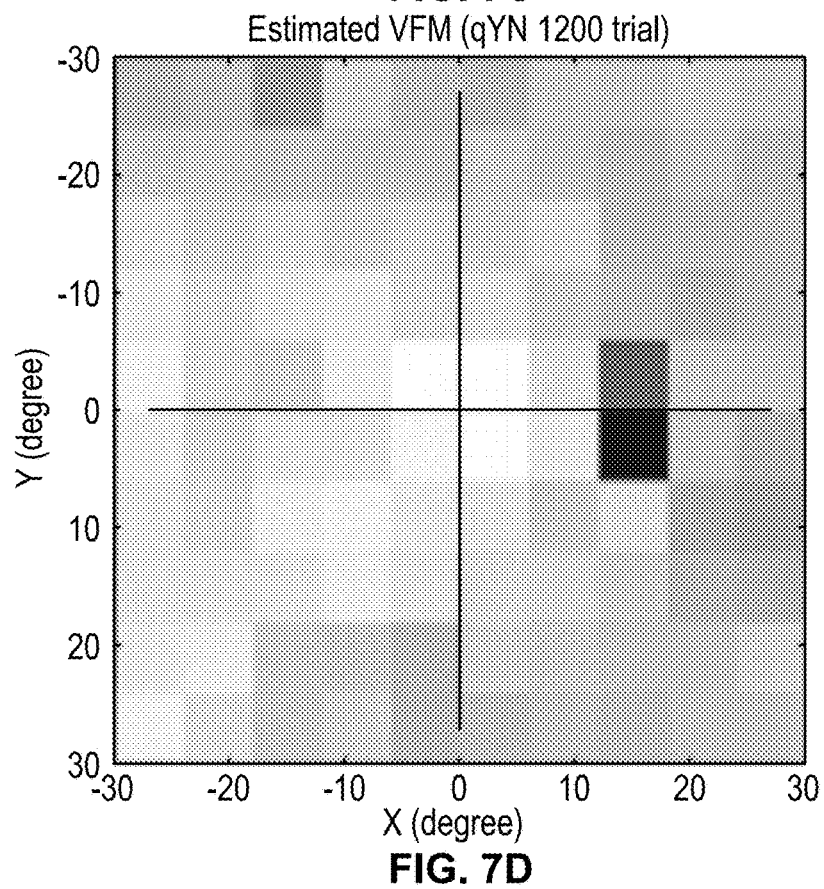
Figure 7E:
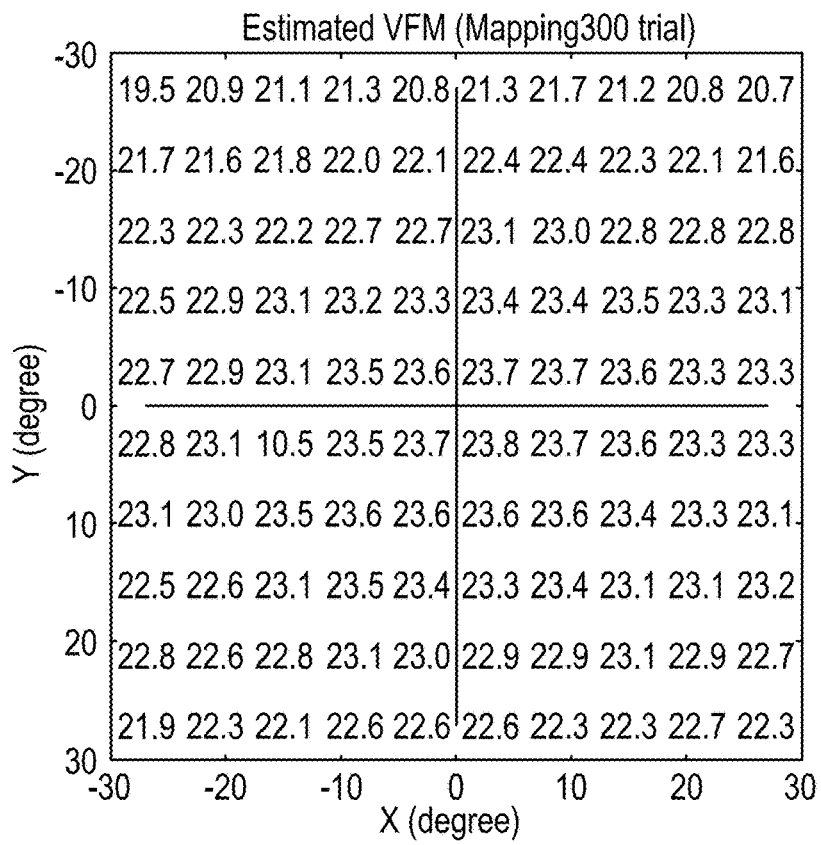
Figure 7F:
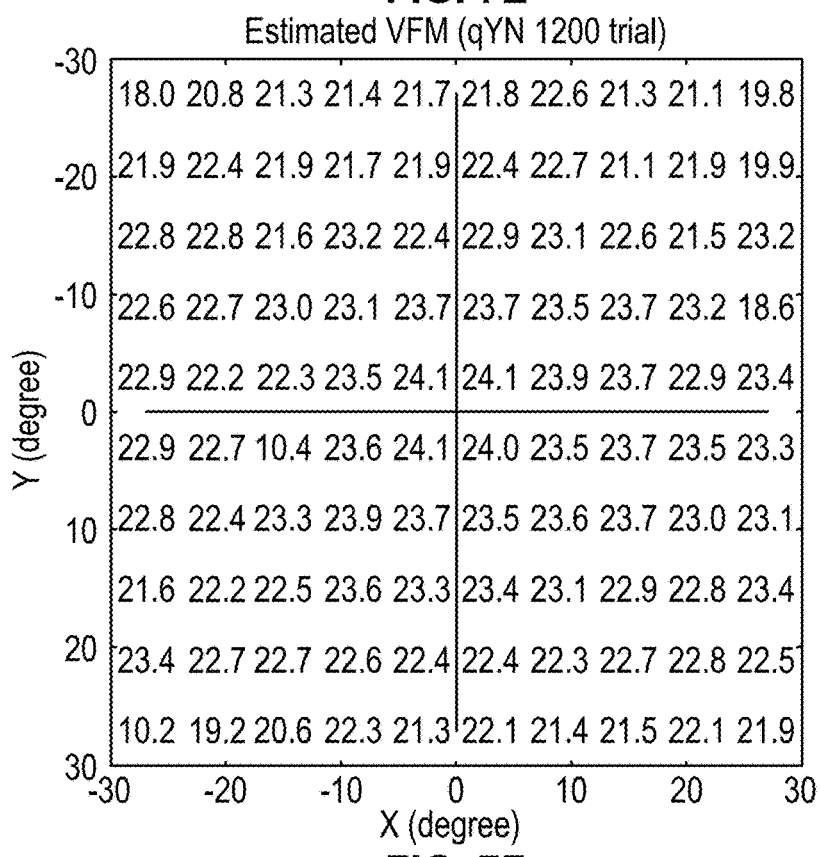
Figure 7G:
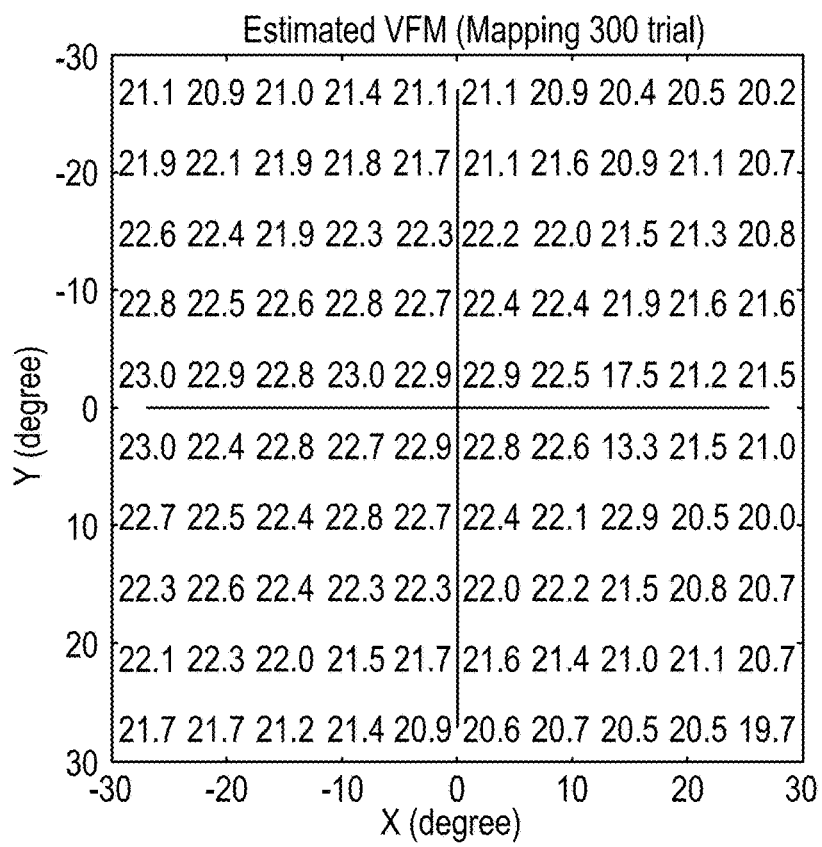
Figure 7H:
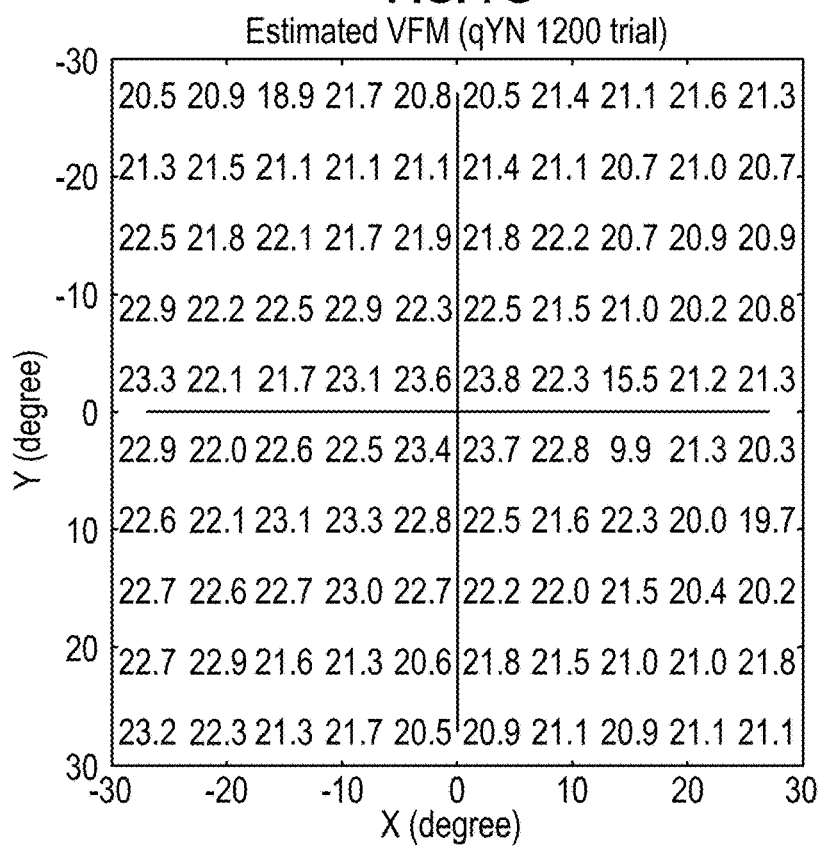
Figure 7I:
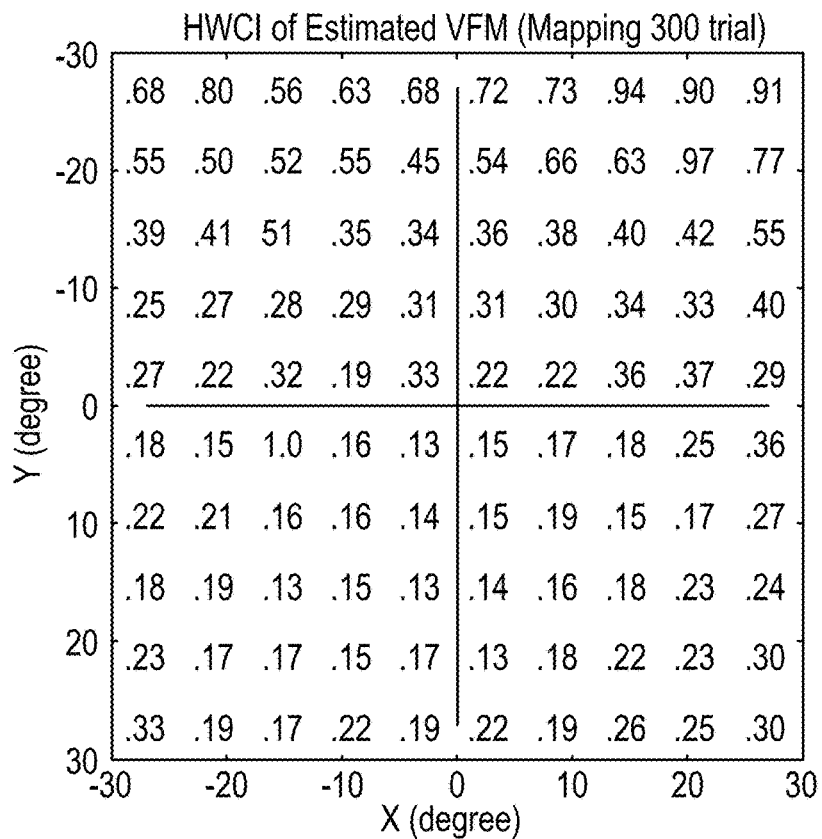
Figure 7J:
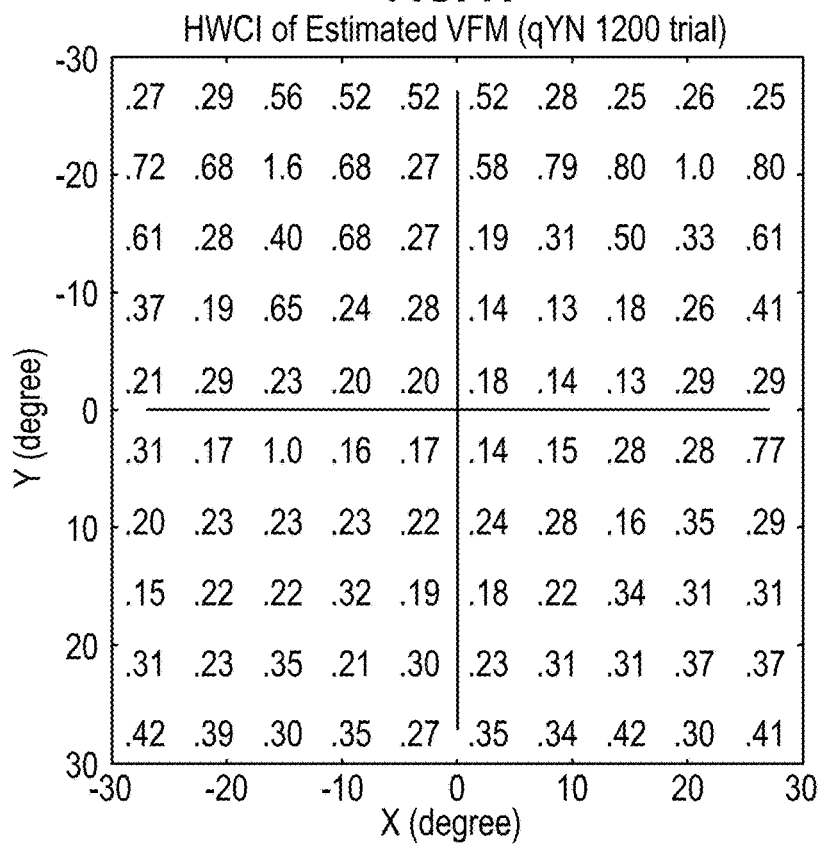
Figure 7K:
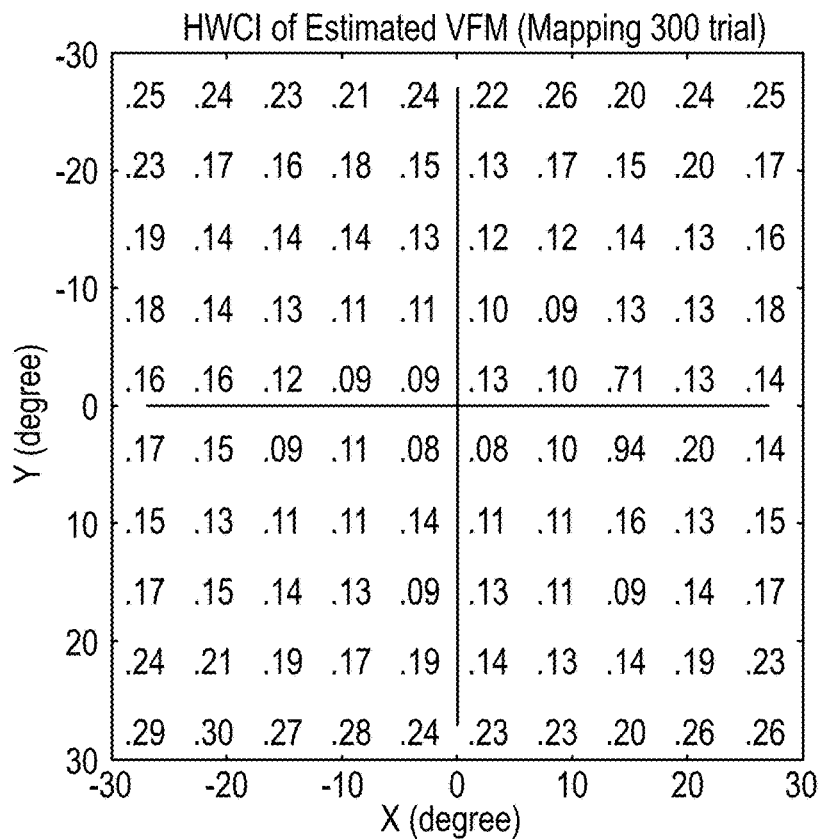
Figure 7L:
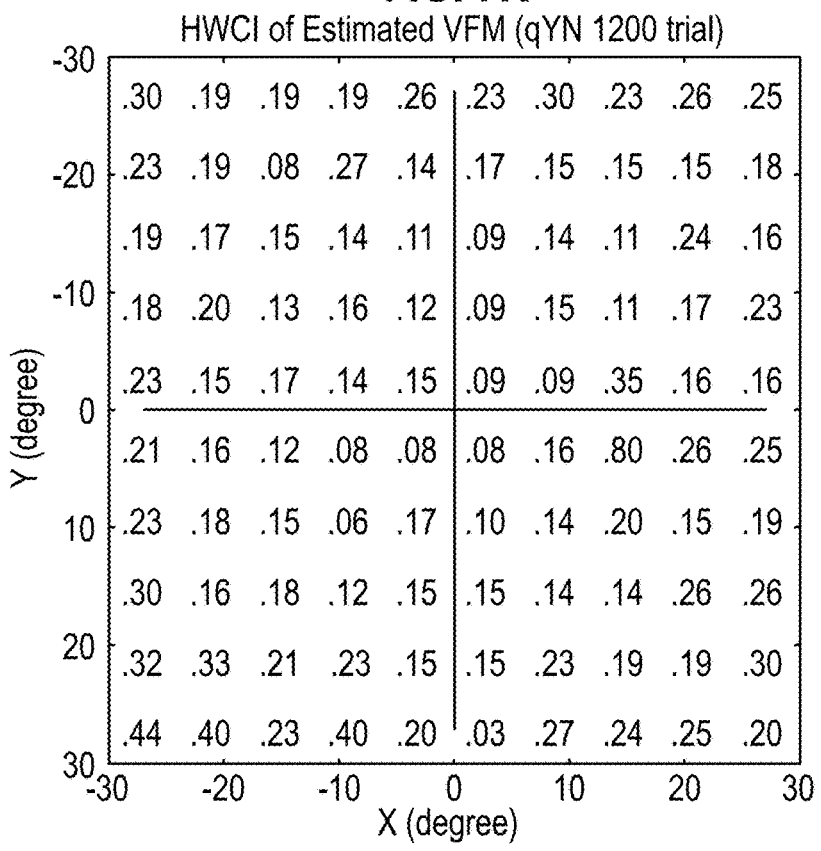
Figure 7M:
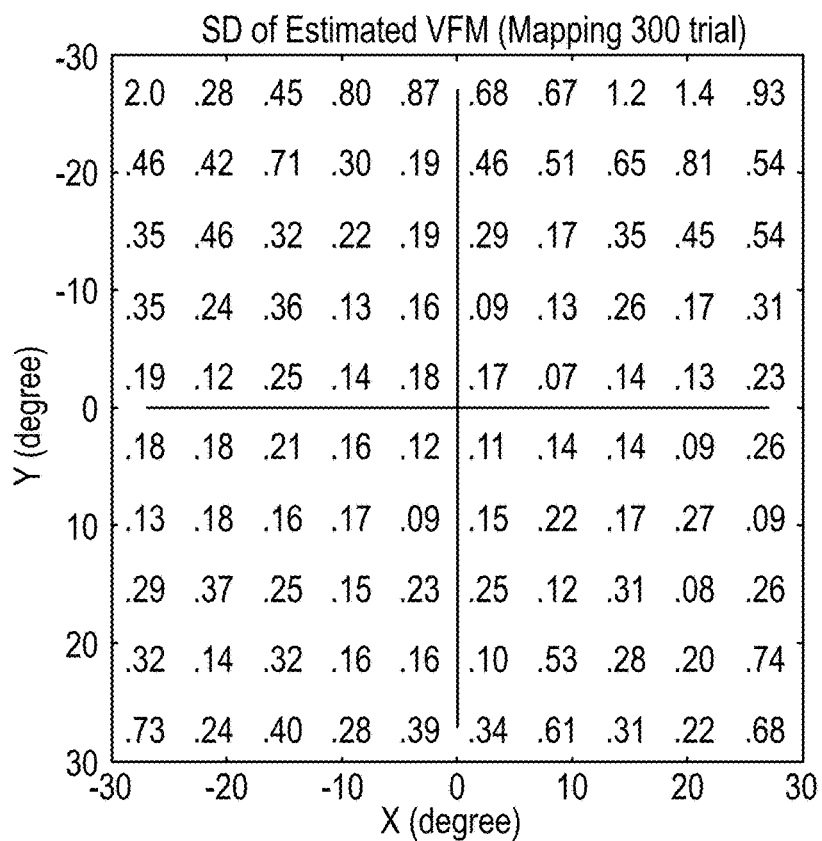
Figure 7N:
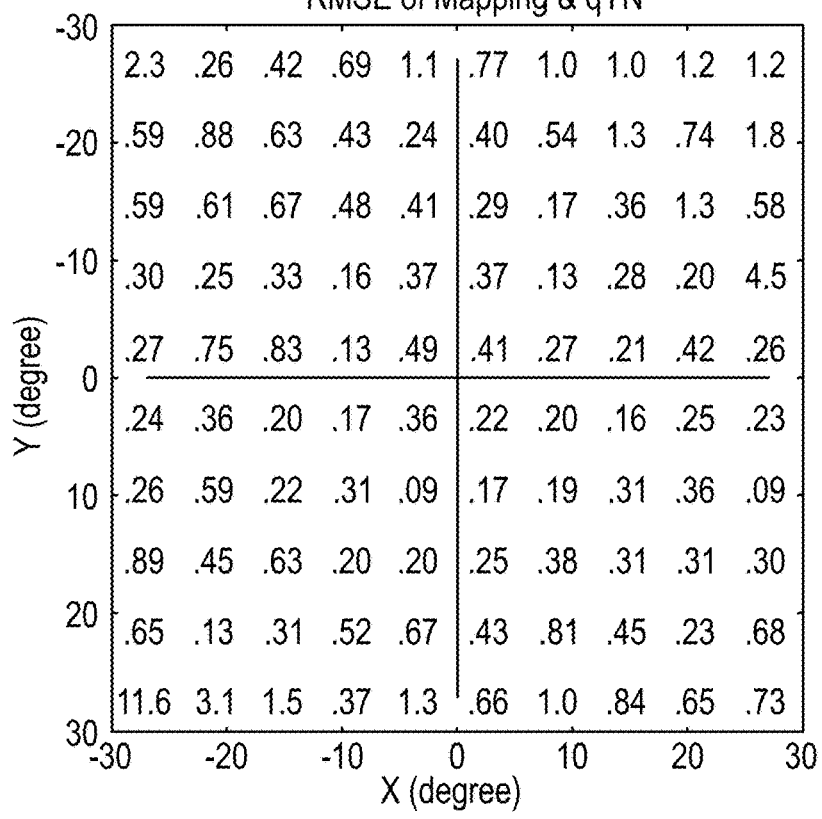
Figure 7O:
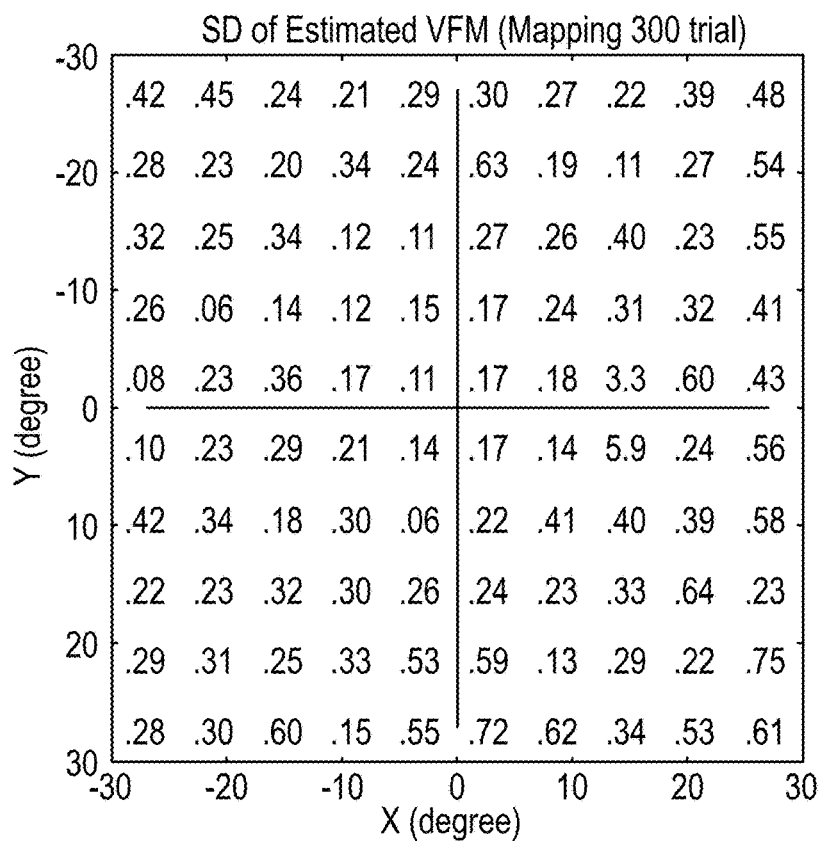
Figure 7P:
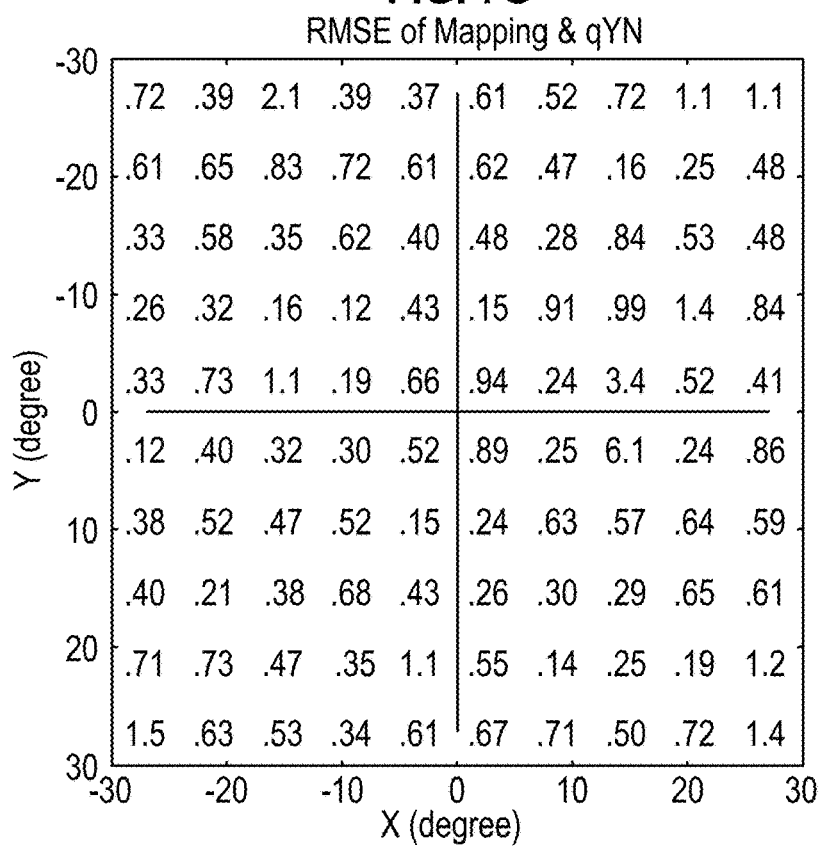
Figure 8A:
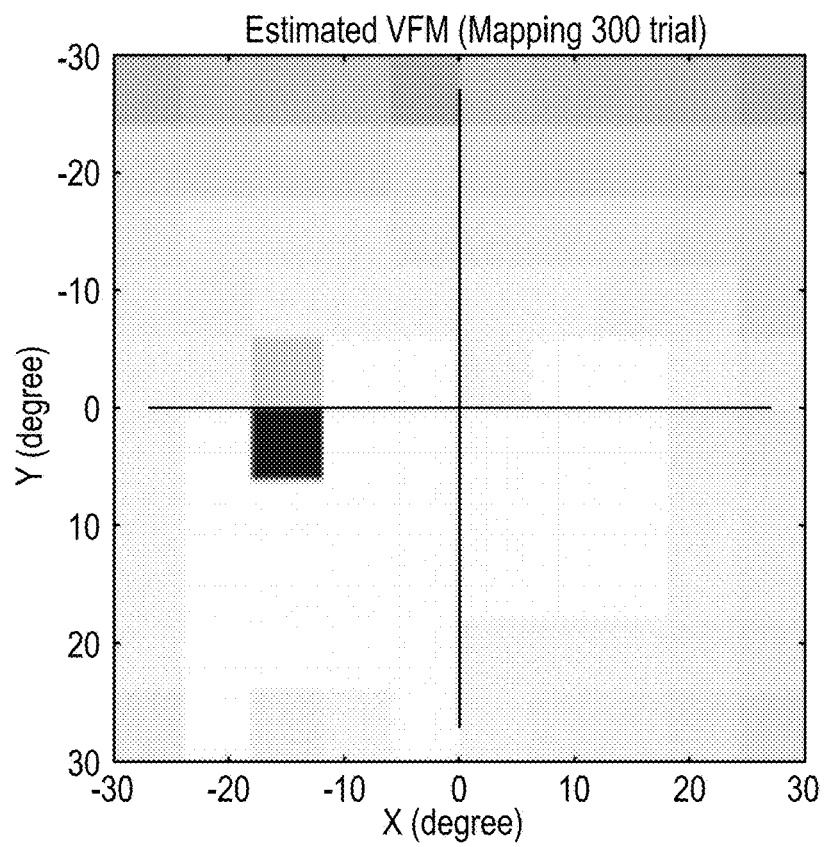
Figure 8B:
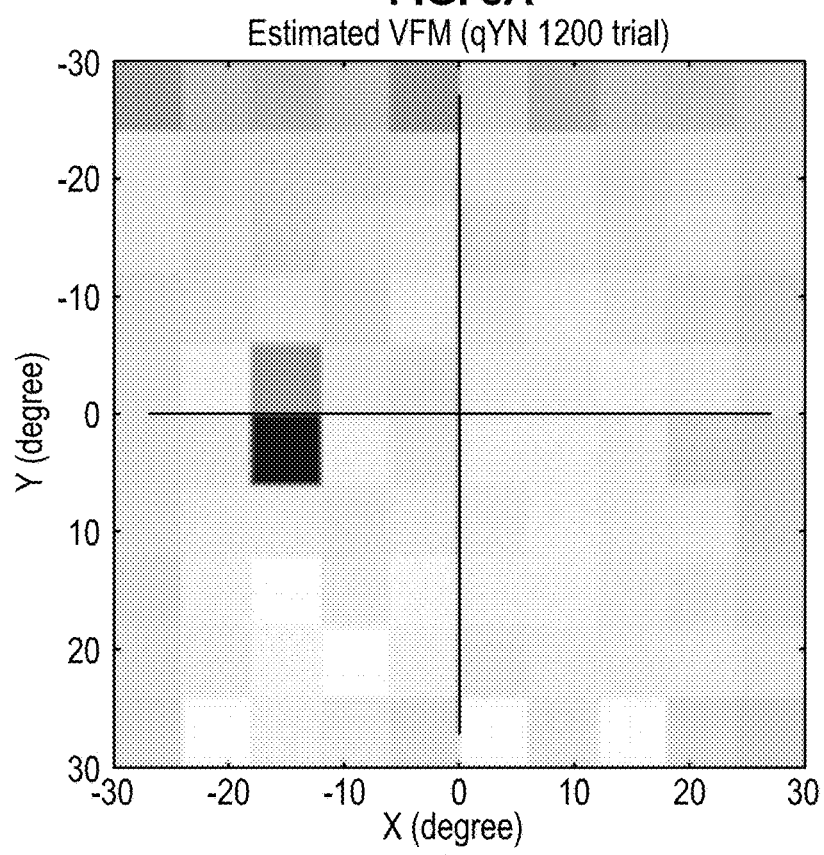
Figure 8C:
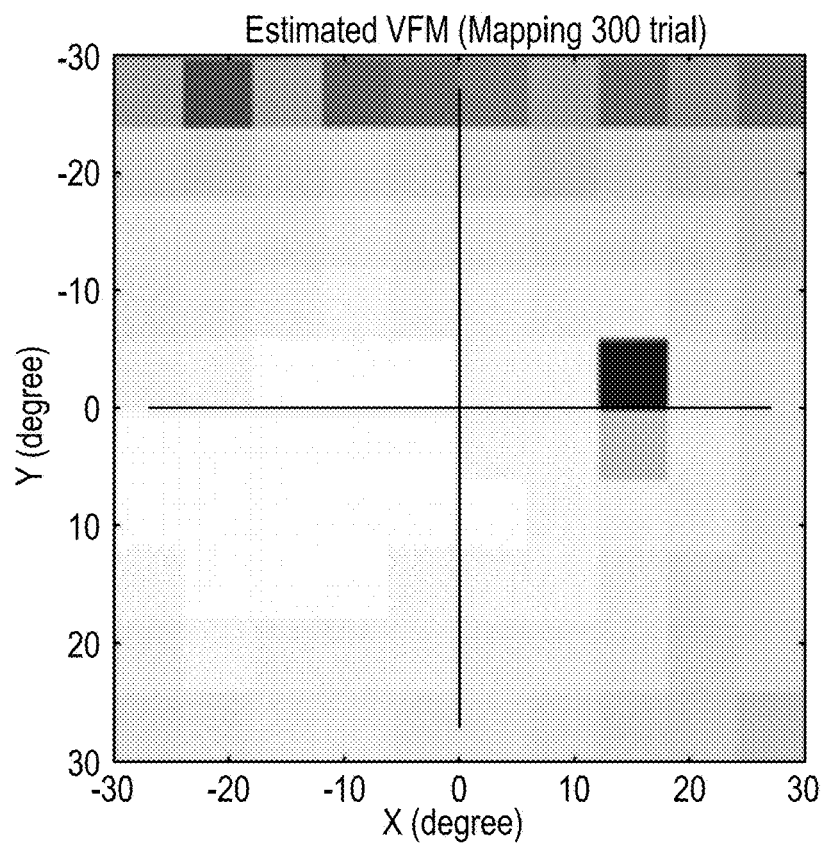
Figure 8D:
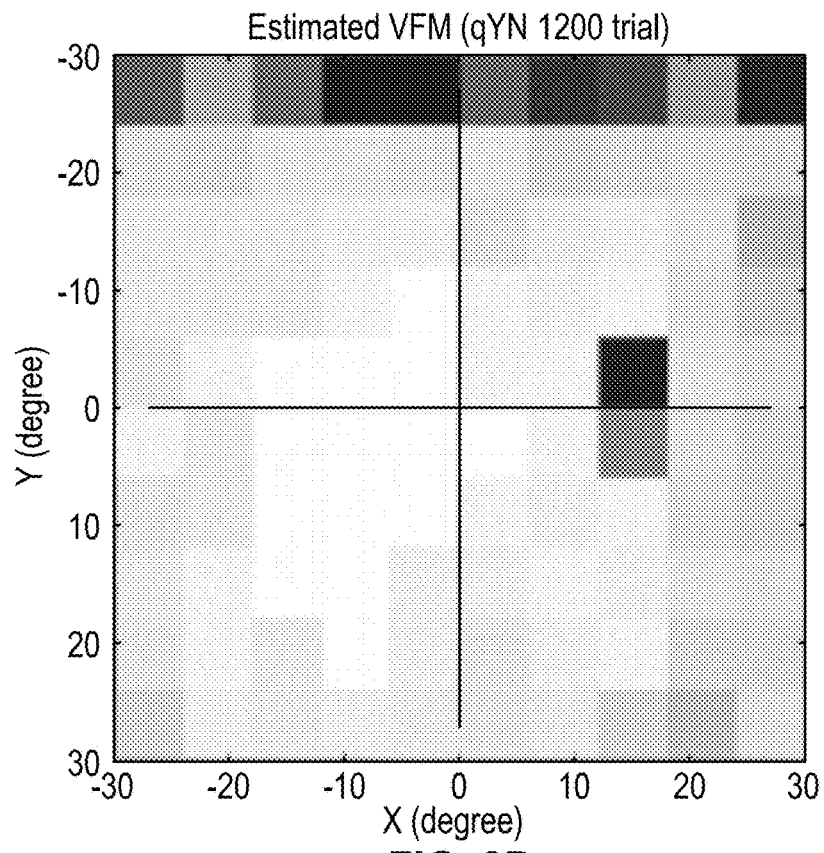
Figure 8E:
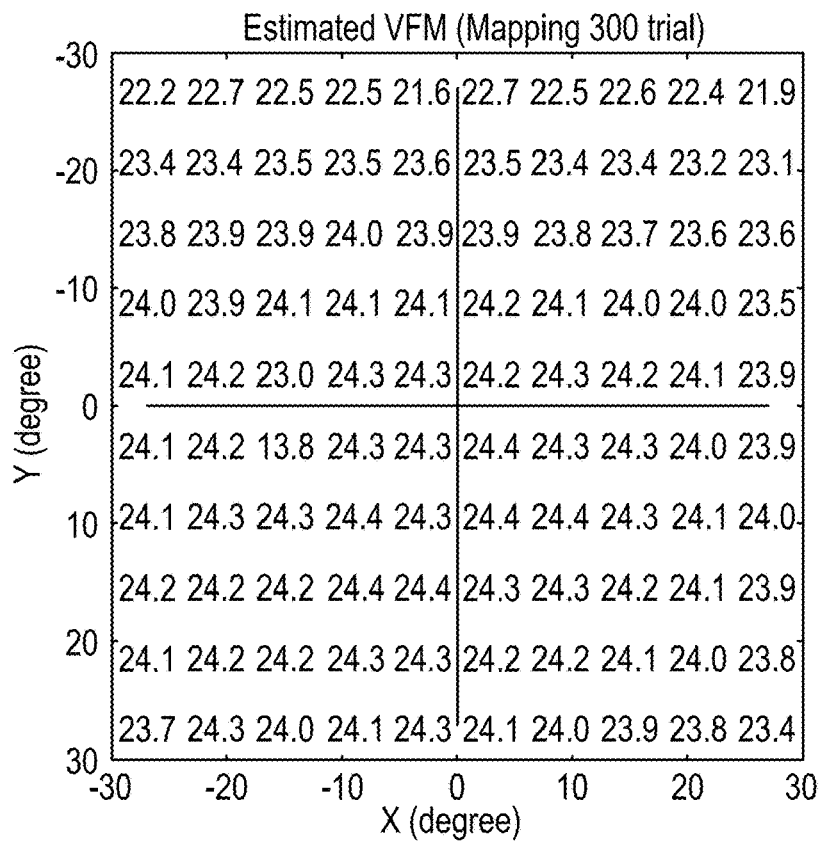
Figure 8F:
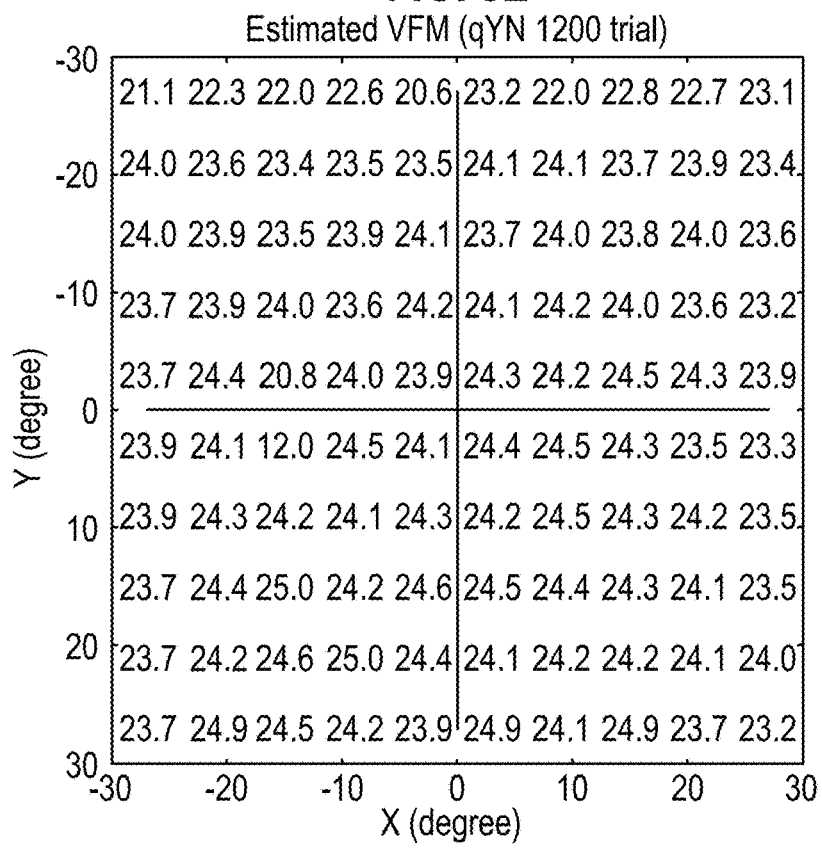
Figure 8G:
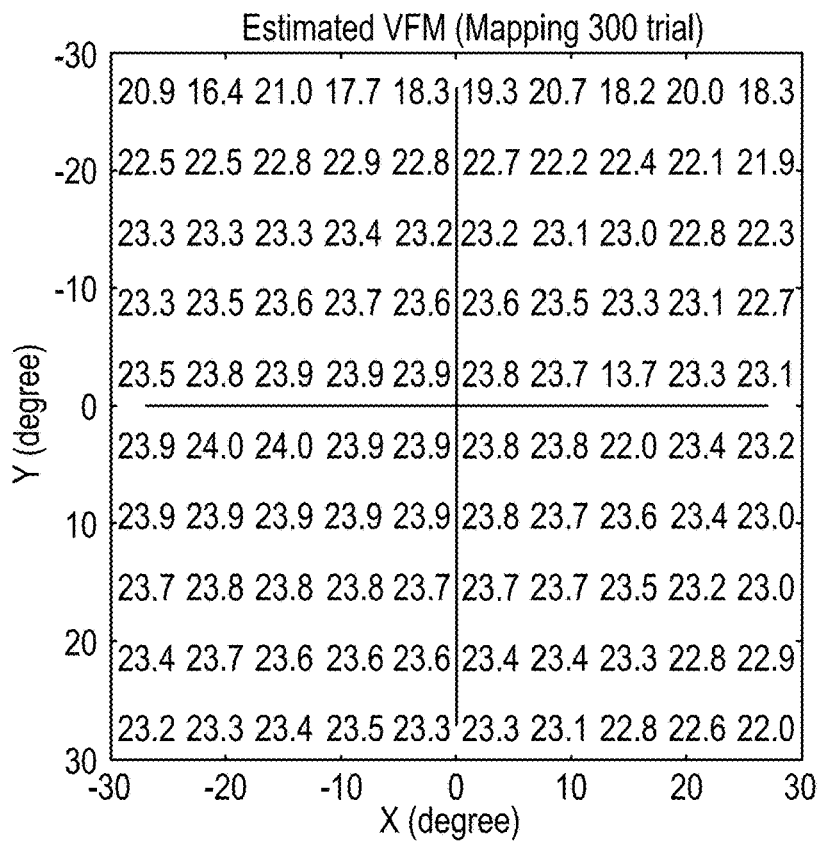
Figure 8H:
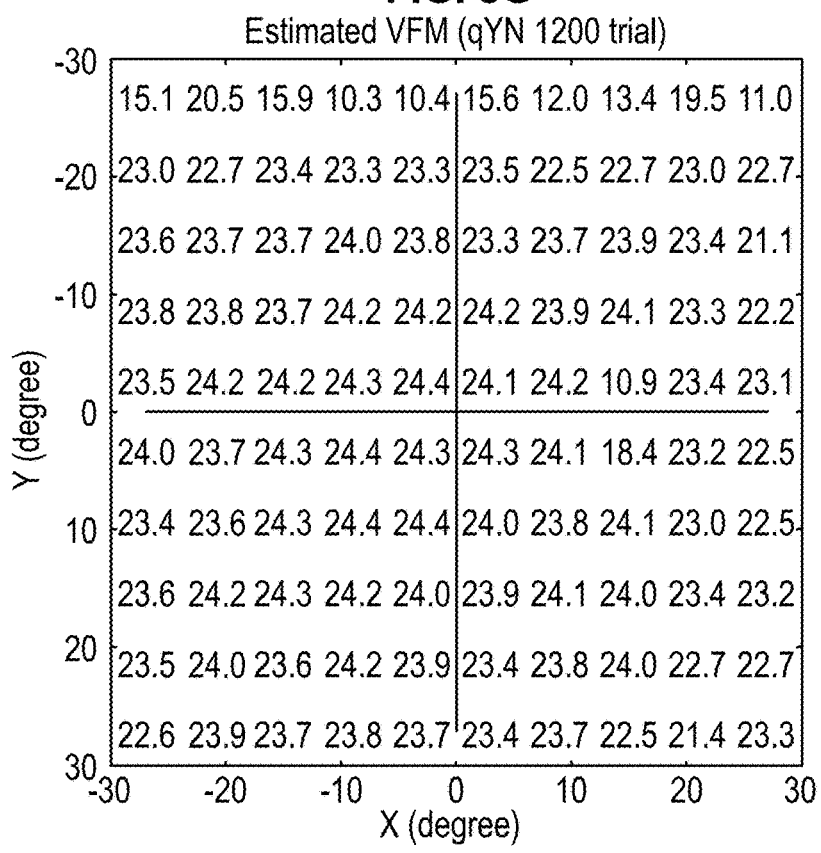
Figure 8I:
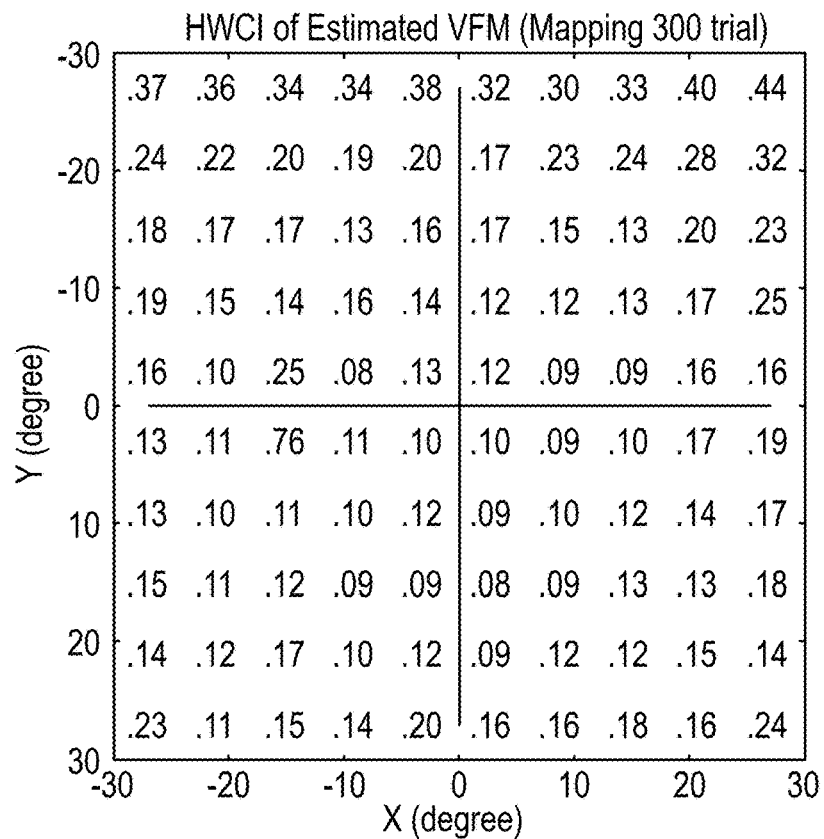
Figure 8J:
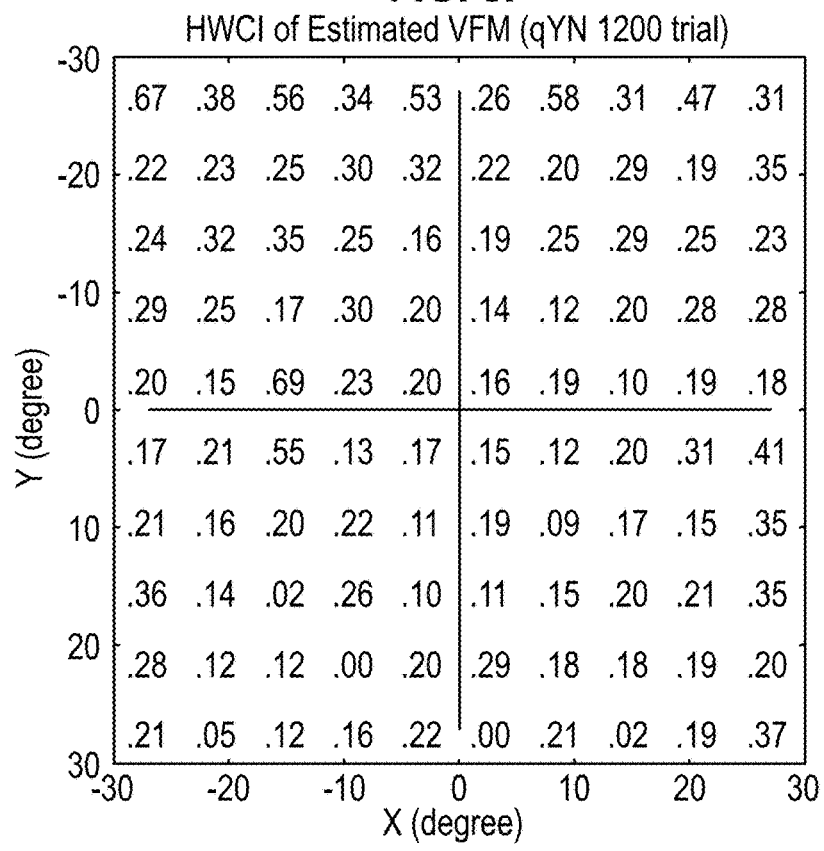
Figure 8K:
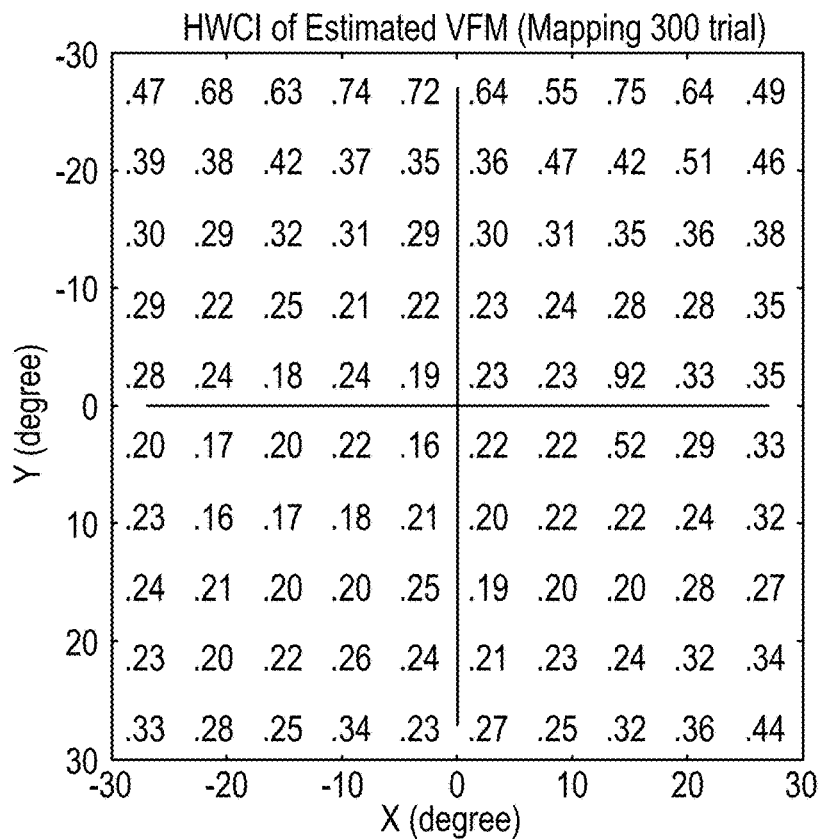
Figure 8L:
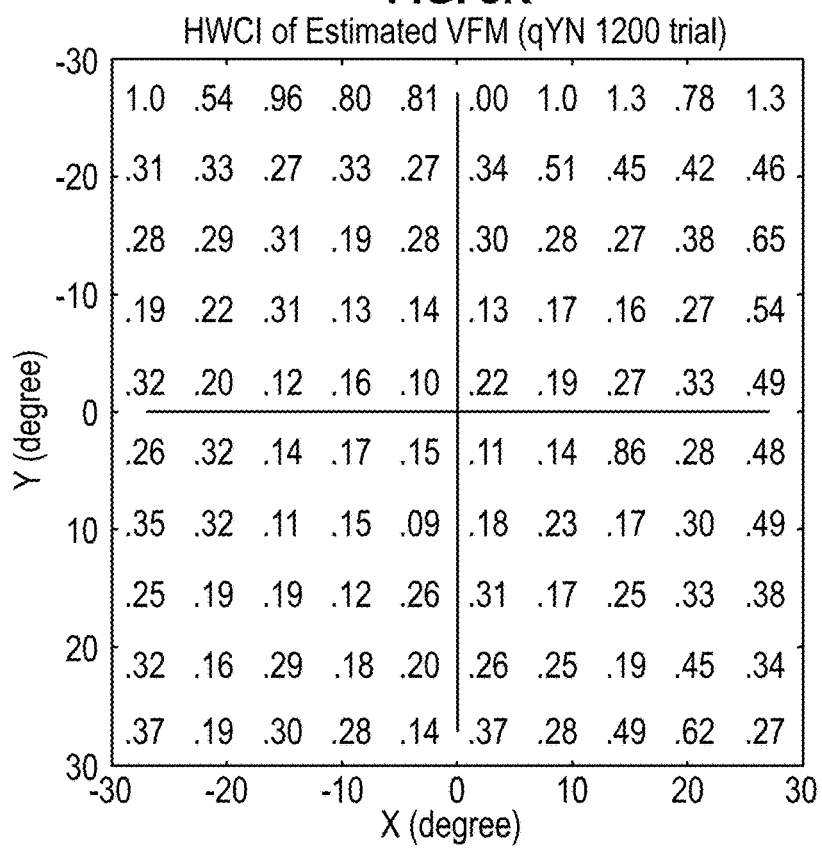
Figure 8M:
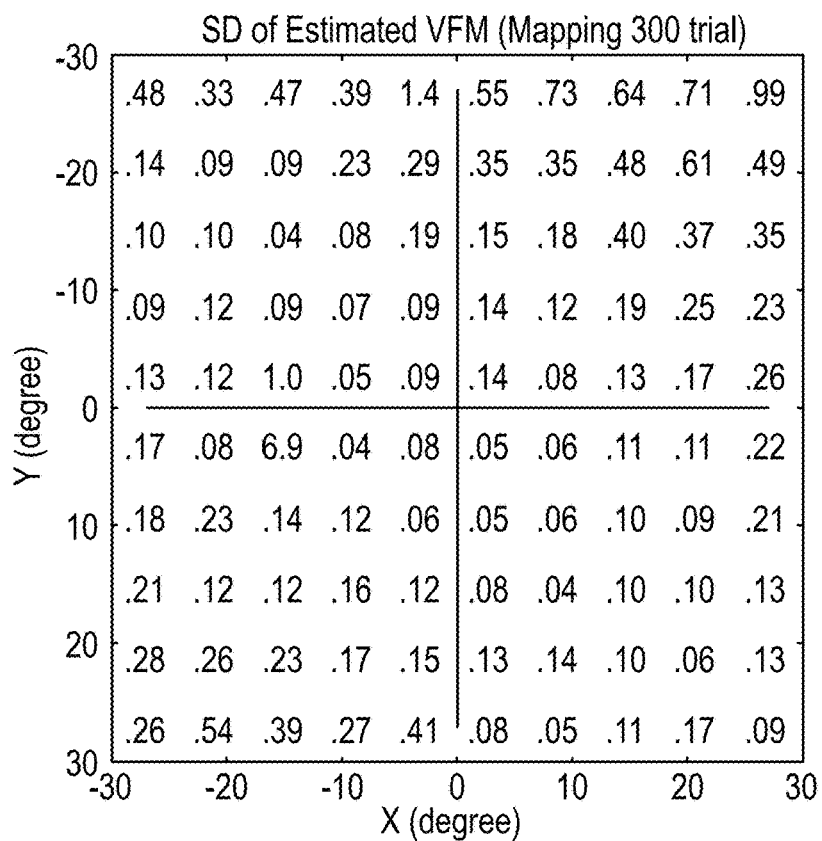
Figure 8N:
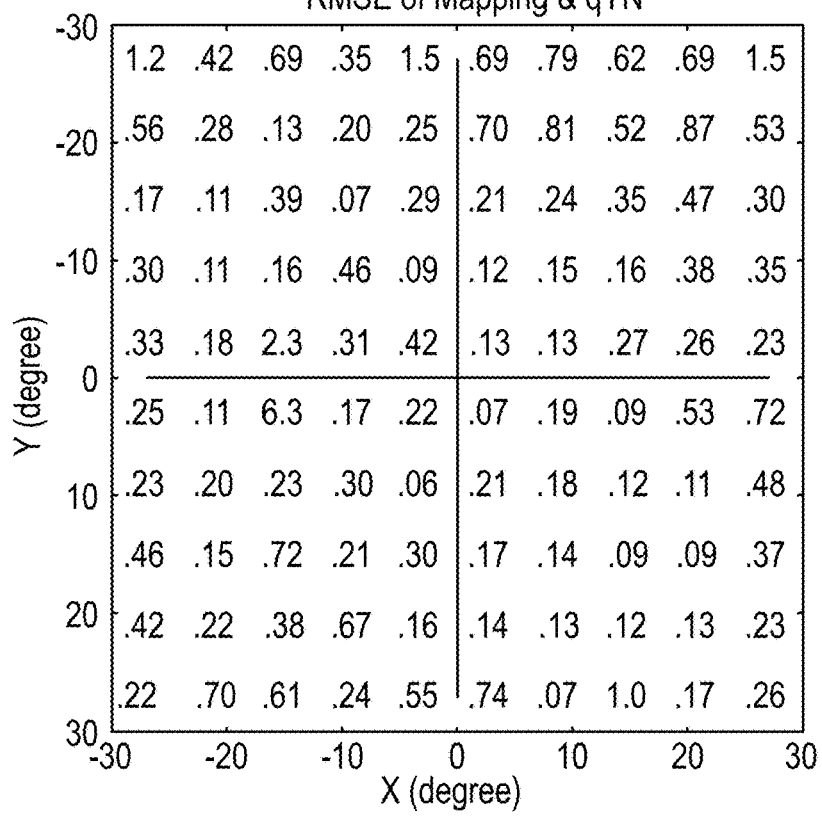
Figure 8O:
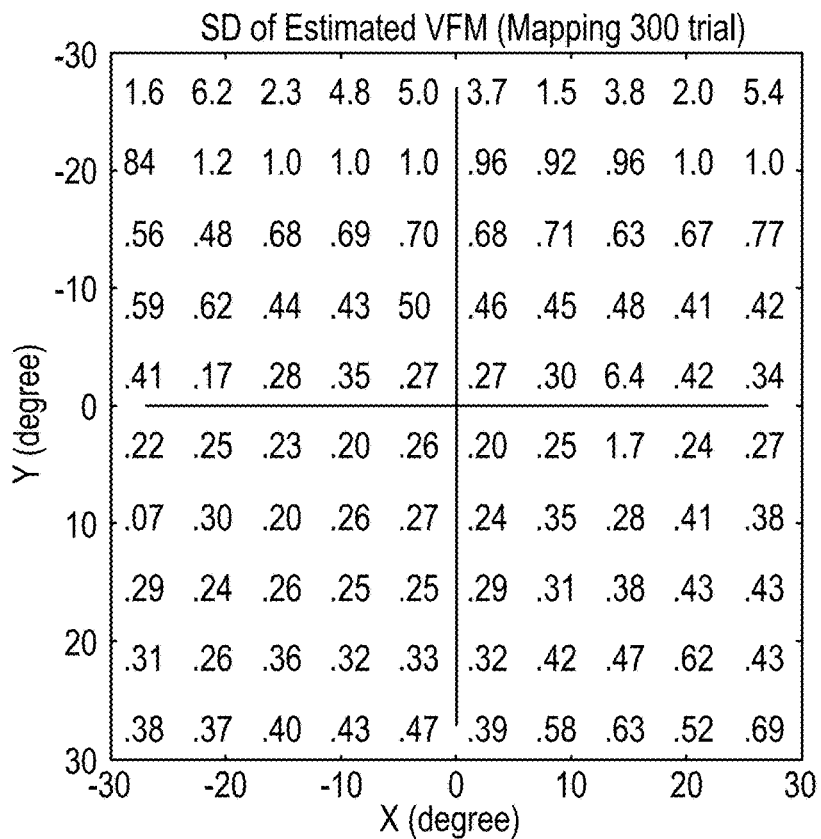
Figure 8P:
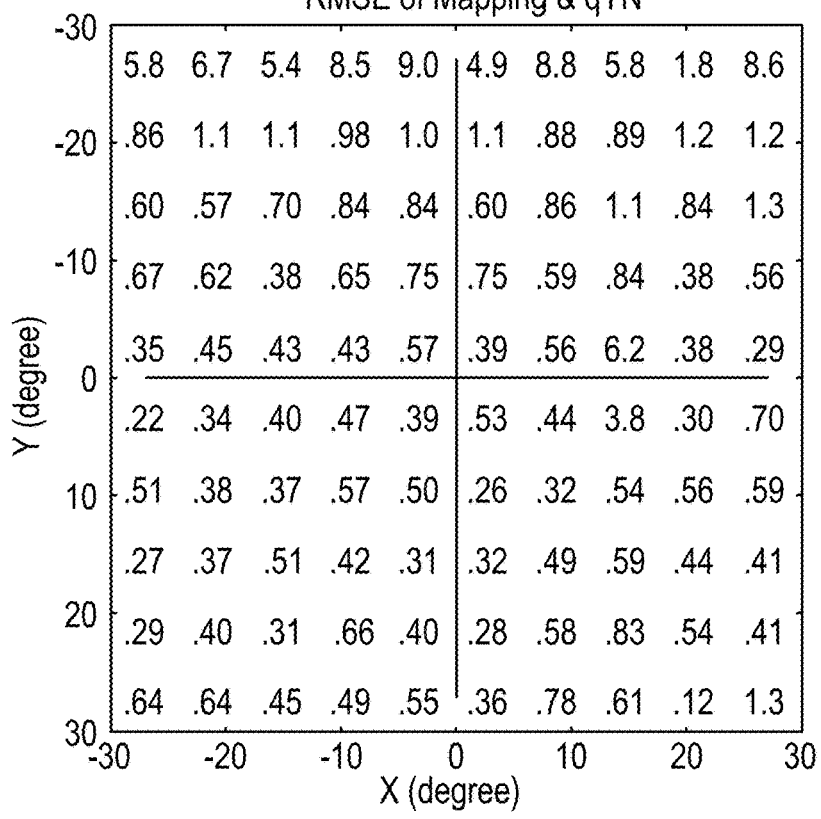
Figure 9A:
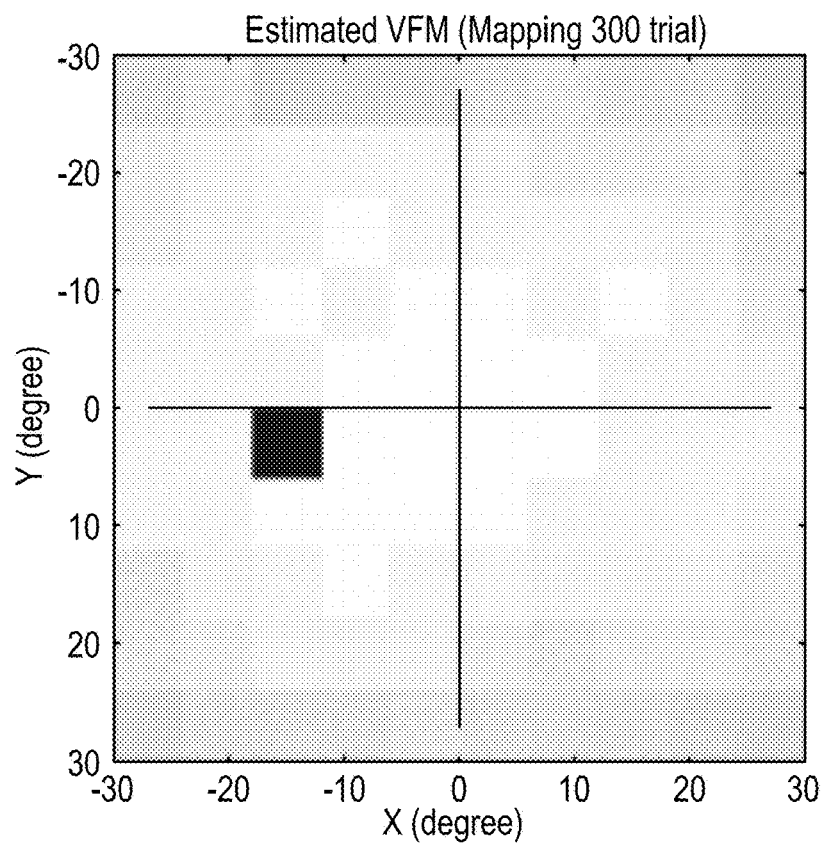
Figure 9B:
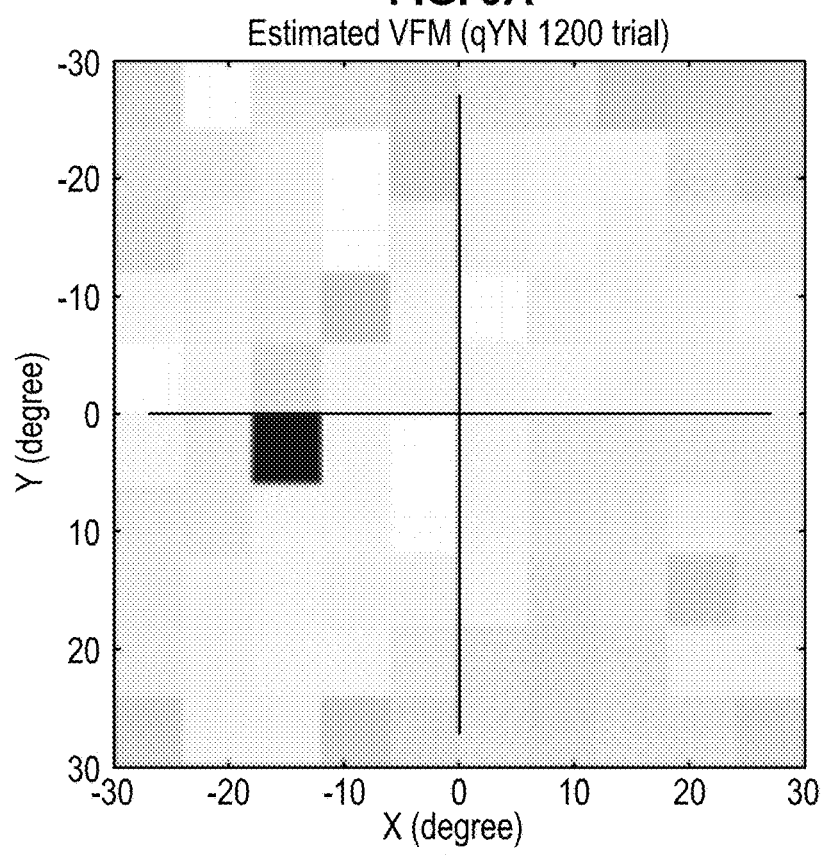
Figure 9C:
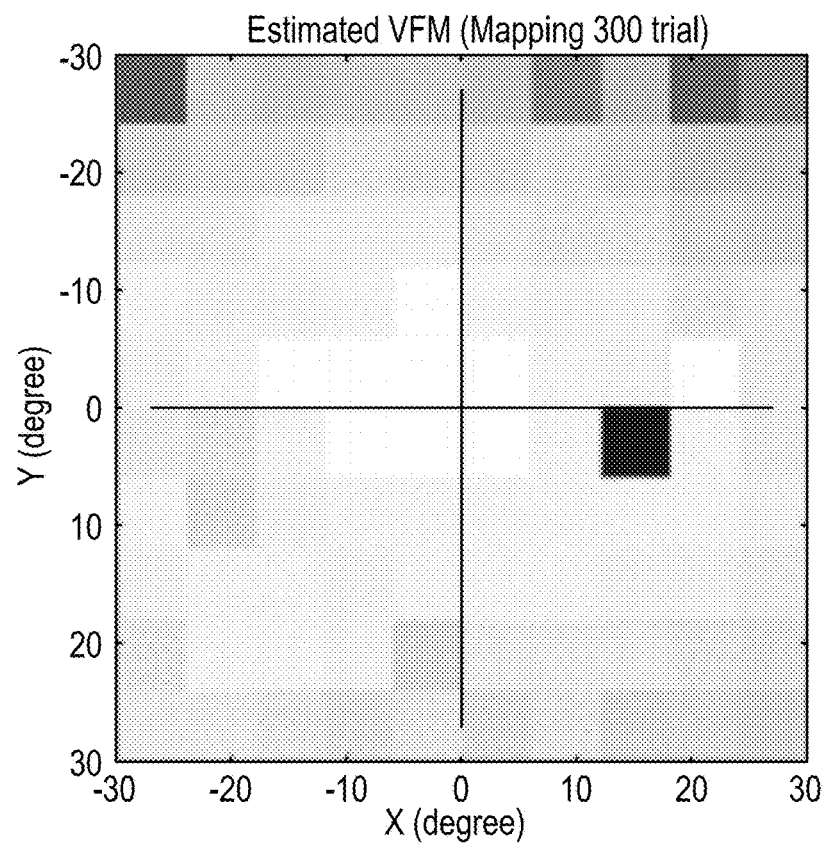
Figure 9D:
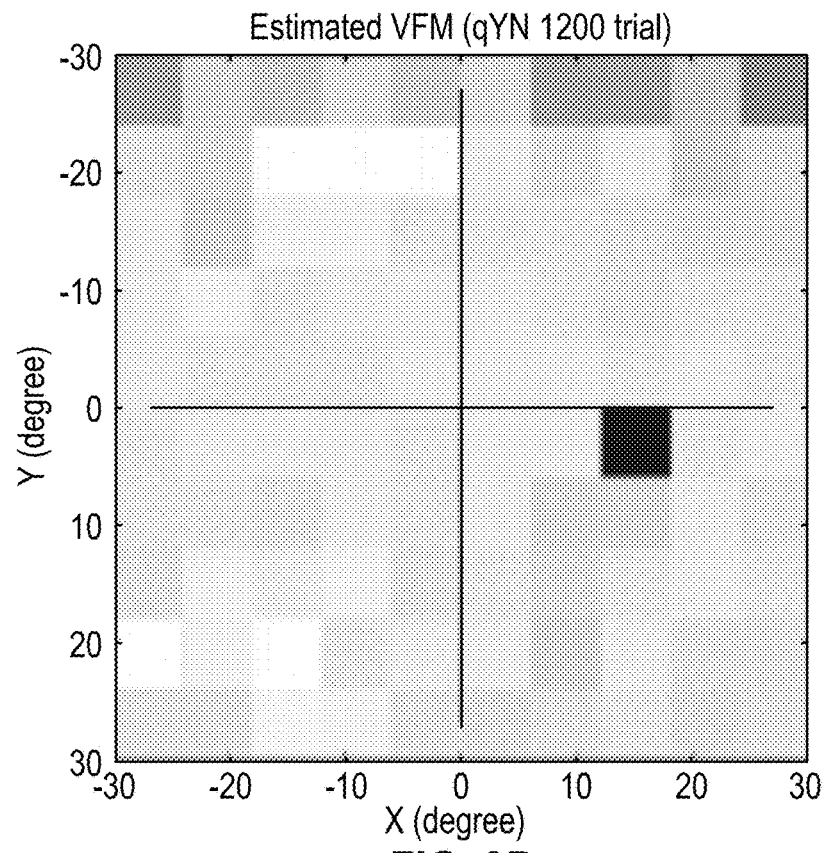
Figure 9E:
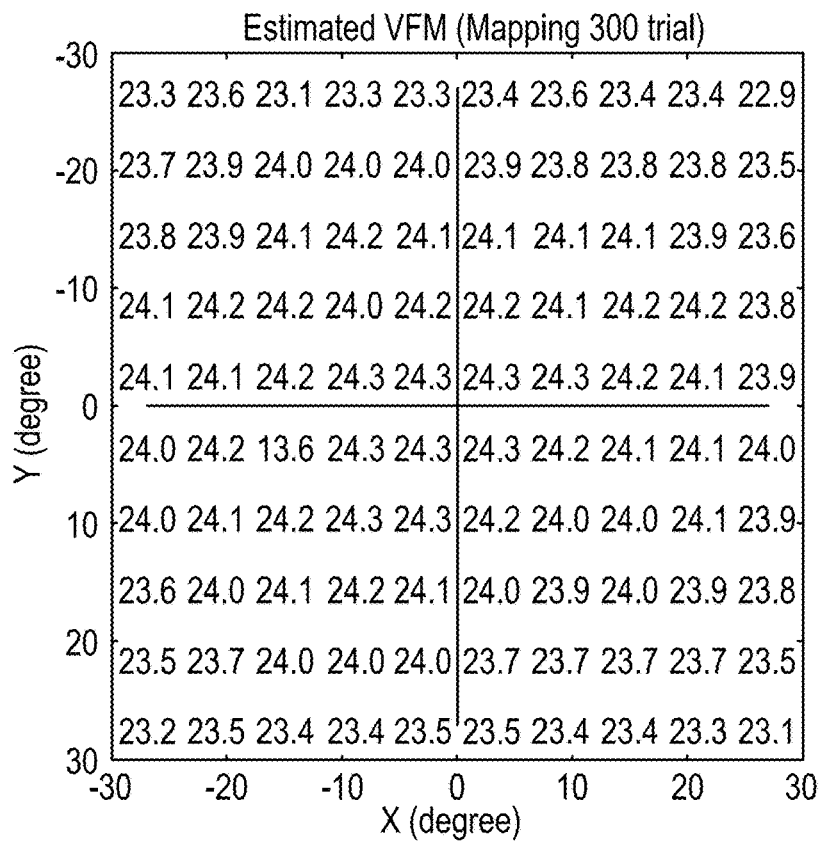
Figure 9F:
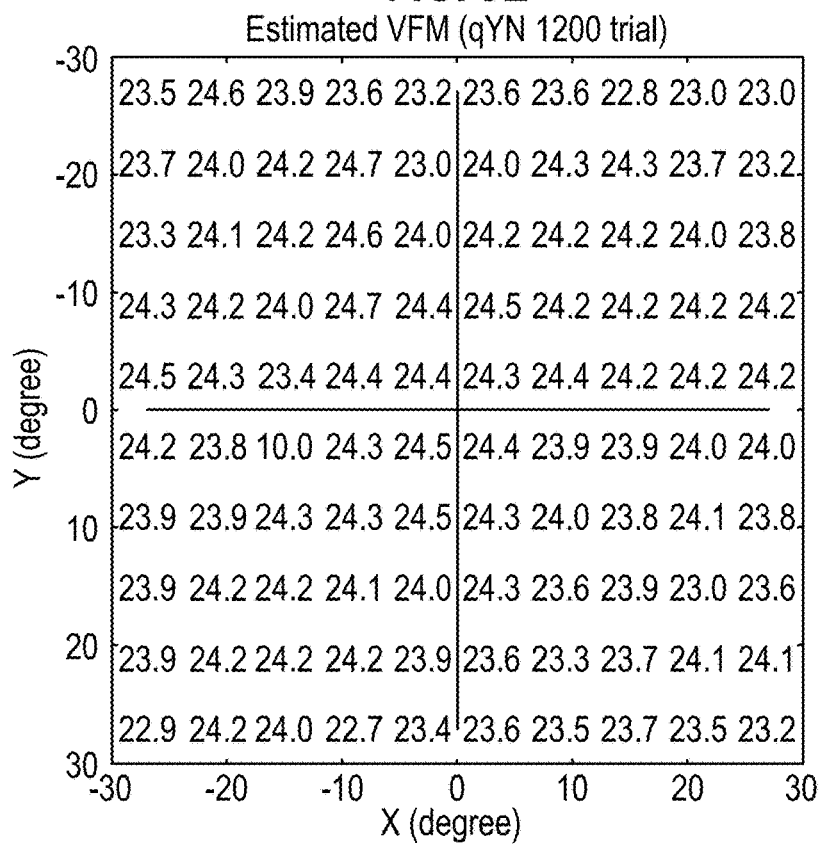
Figure 9G:
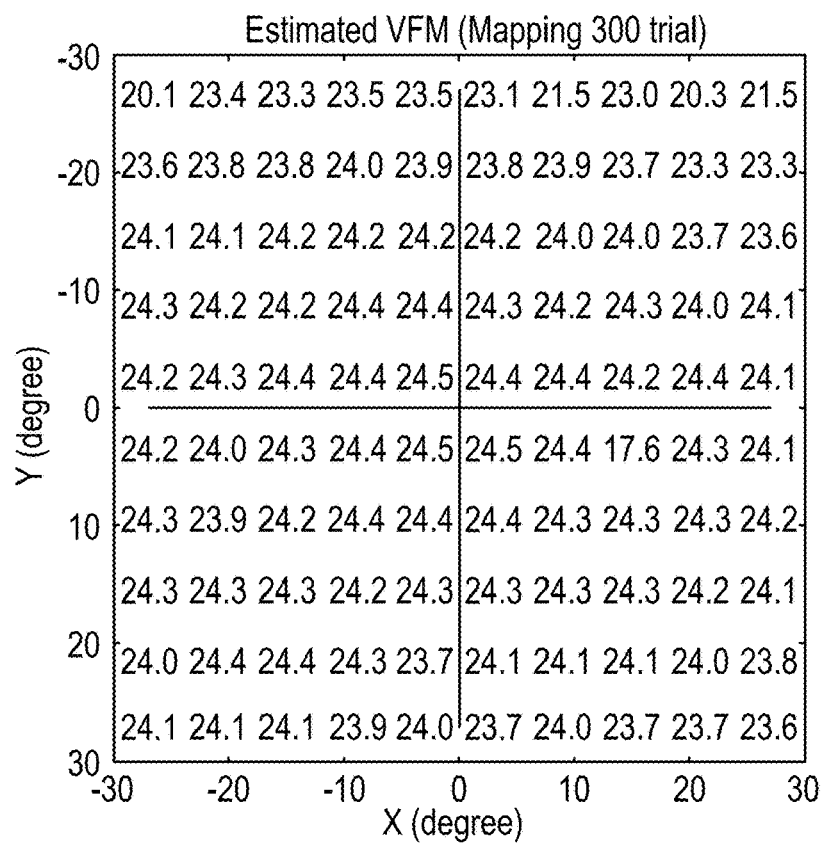
Figure 9H:
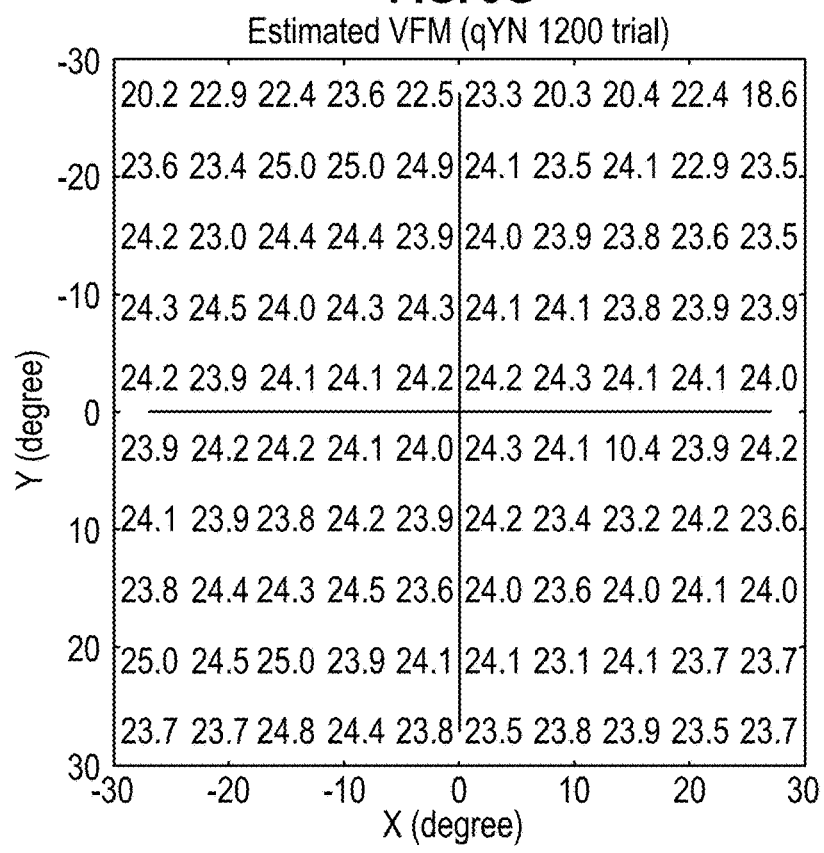
Figure 9I:
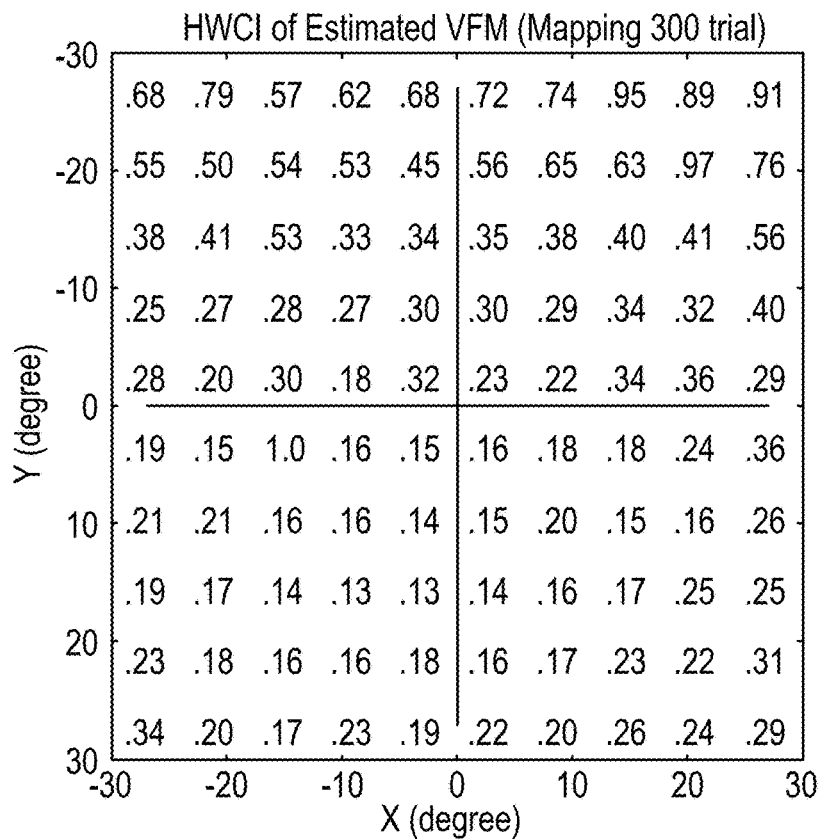
Figure 9J:
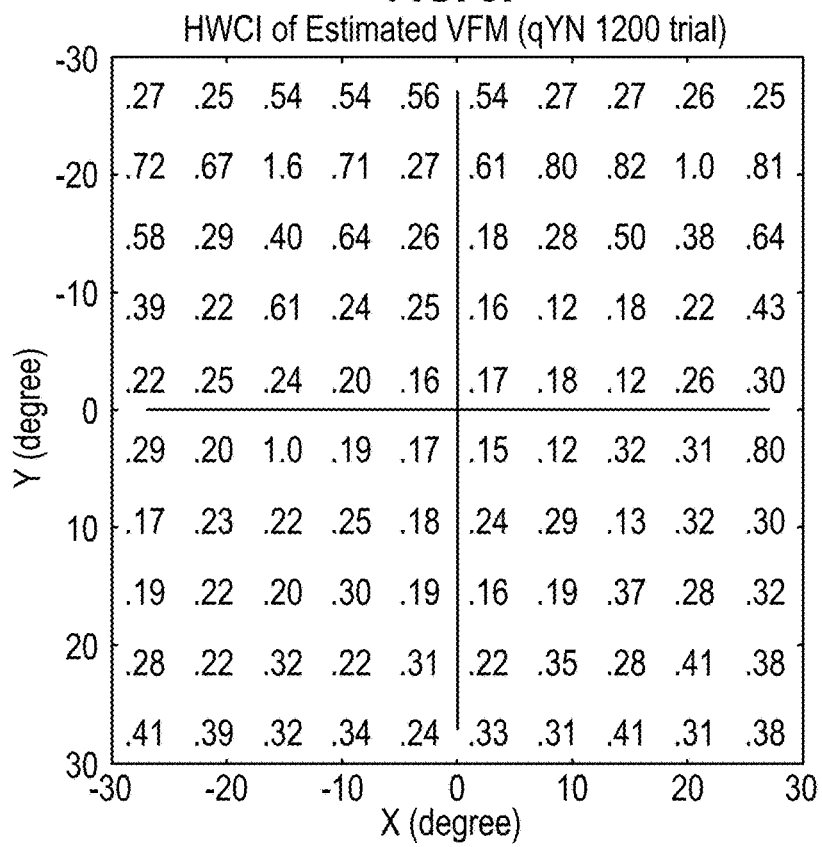
Figure 9K:
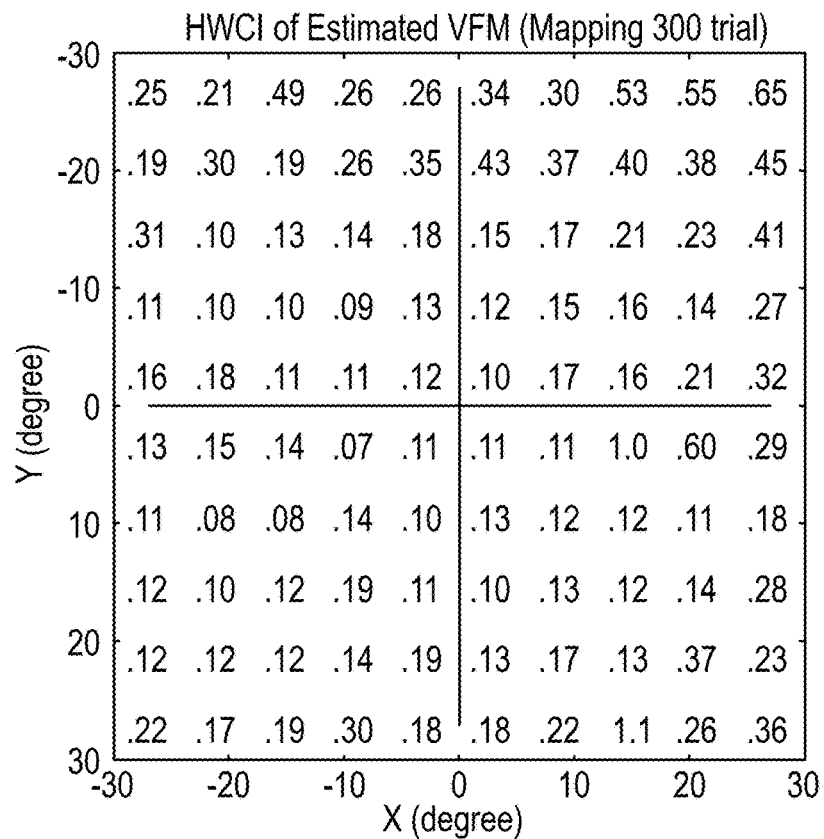
Figure 9L:
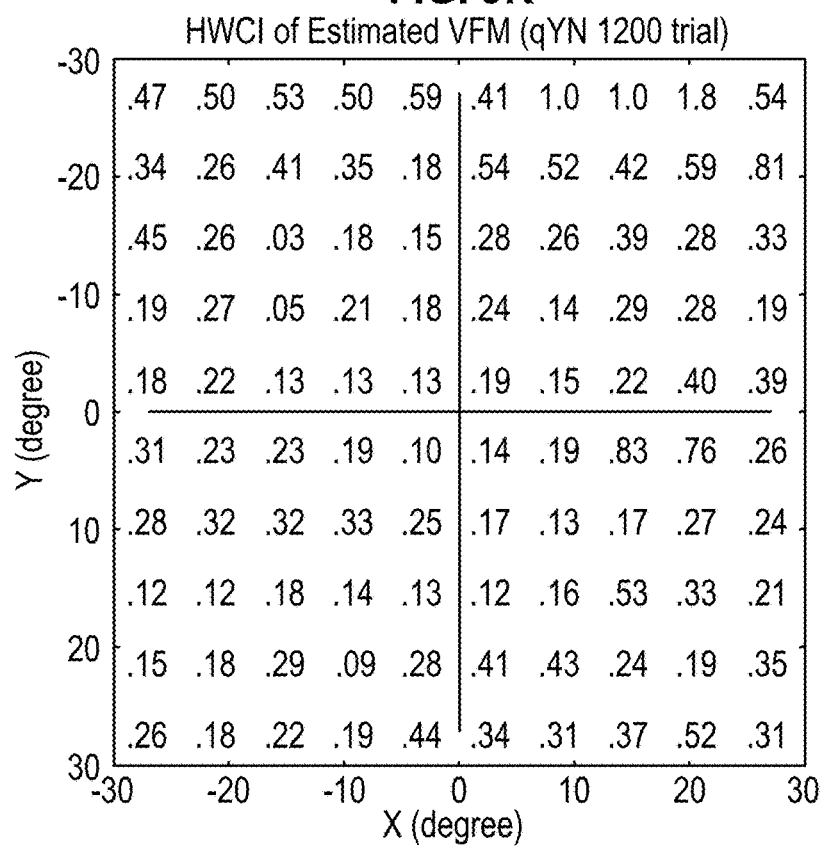
Figure 9M:
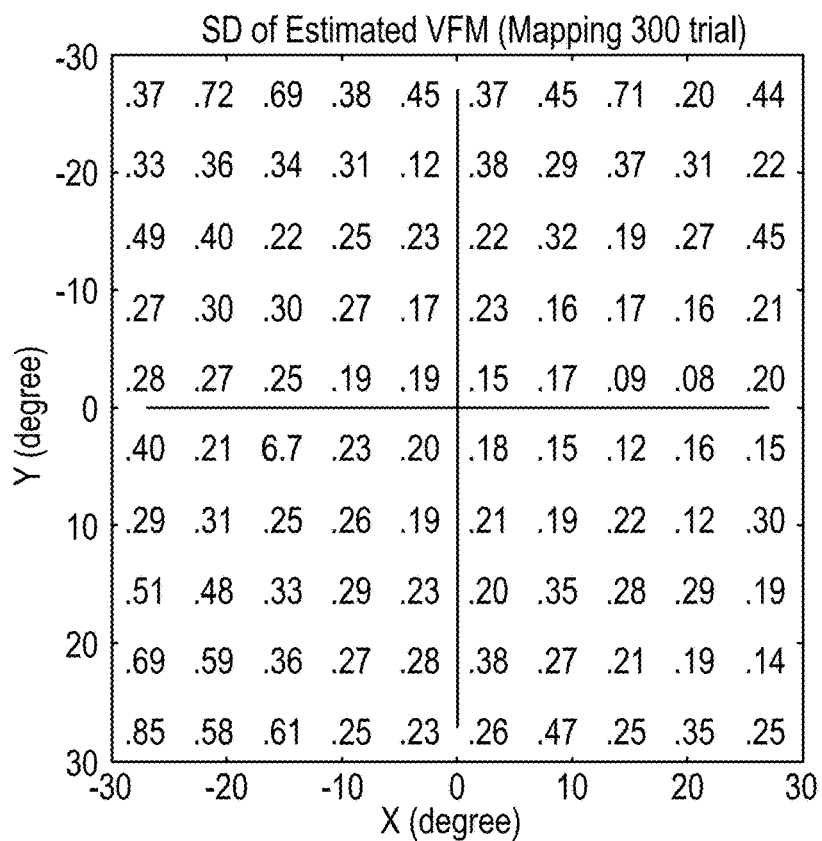
Figure 9N:
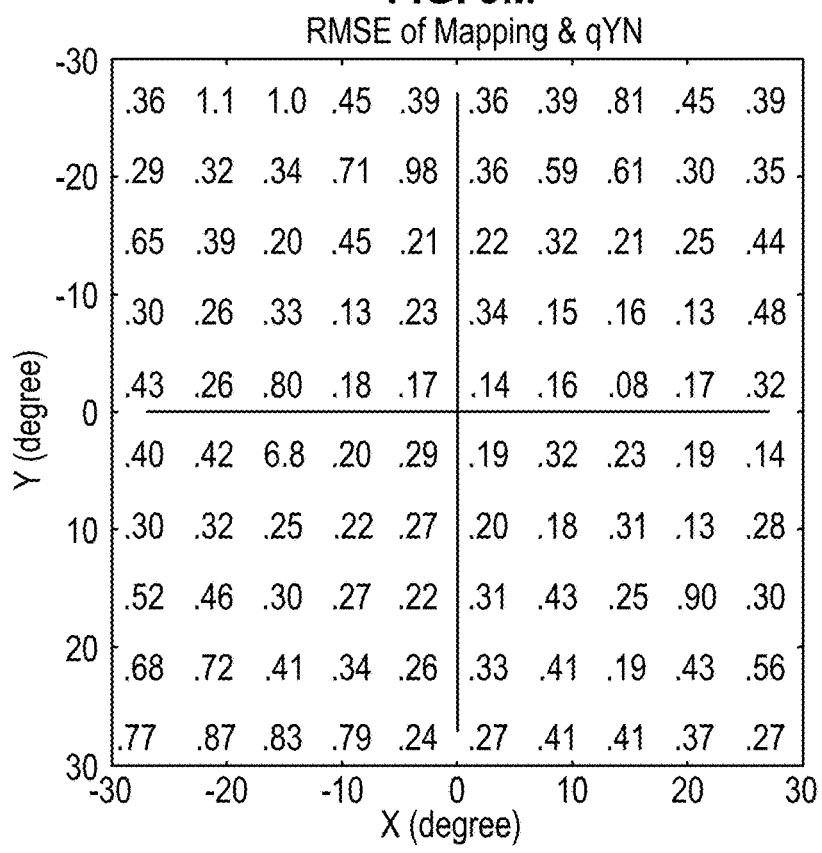
Figure 9O:
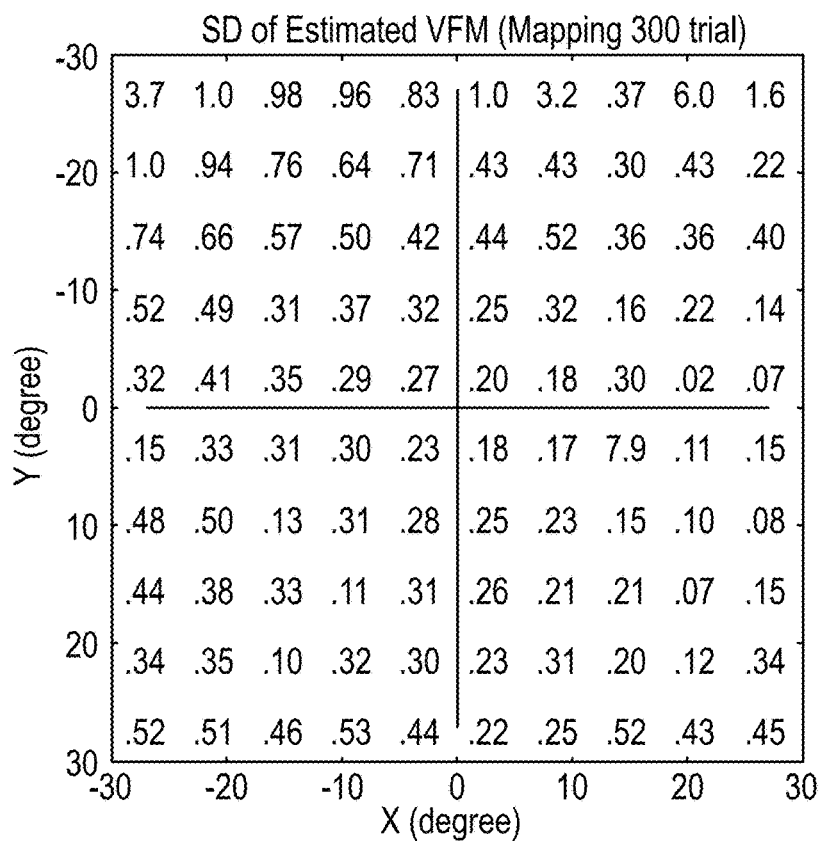
Figure 9P:
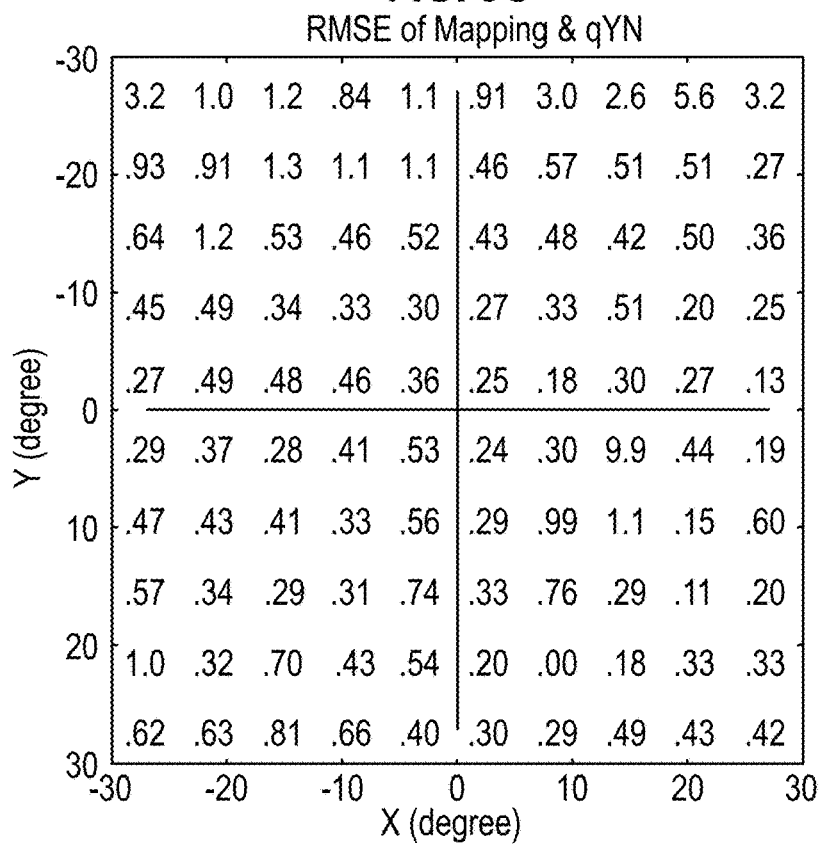
Figure 10A:
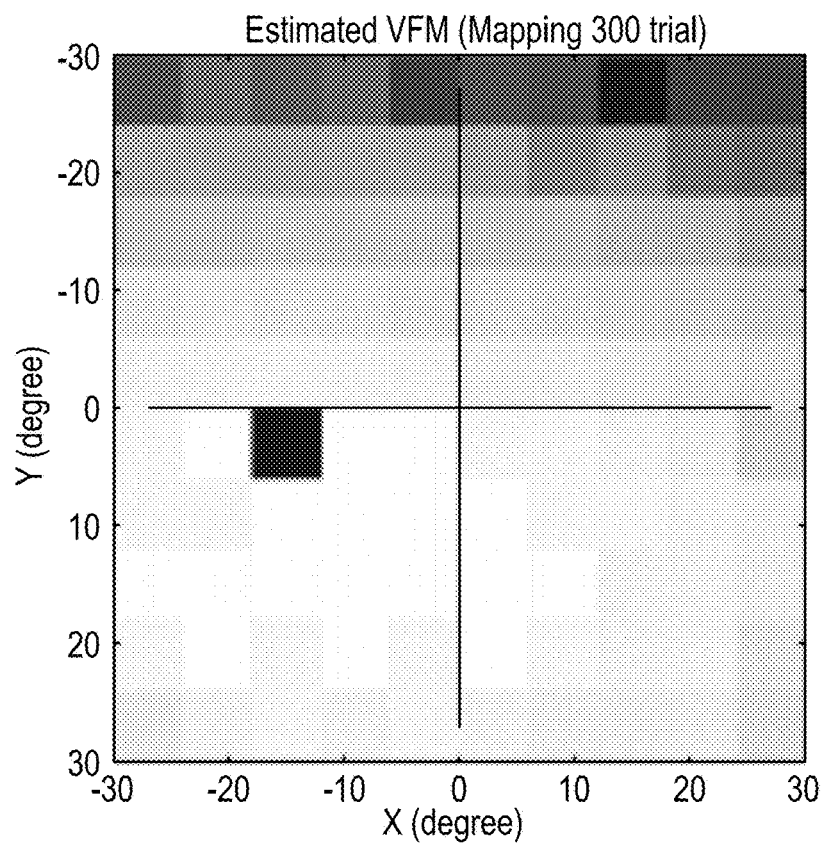
Figure 10B:
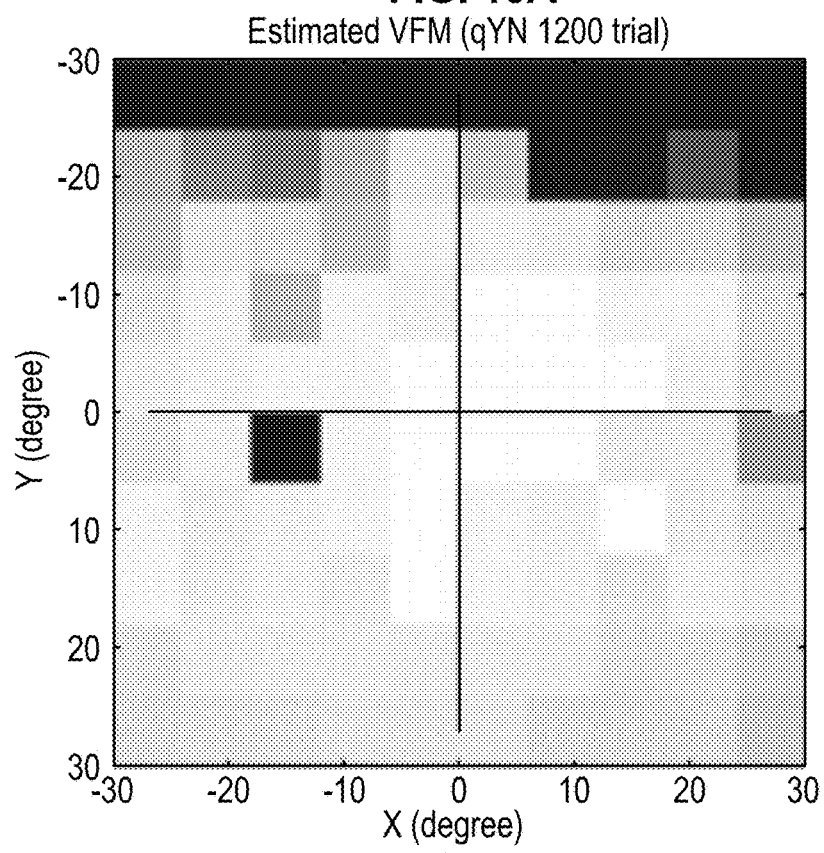
Figure 10C:
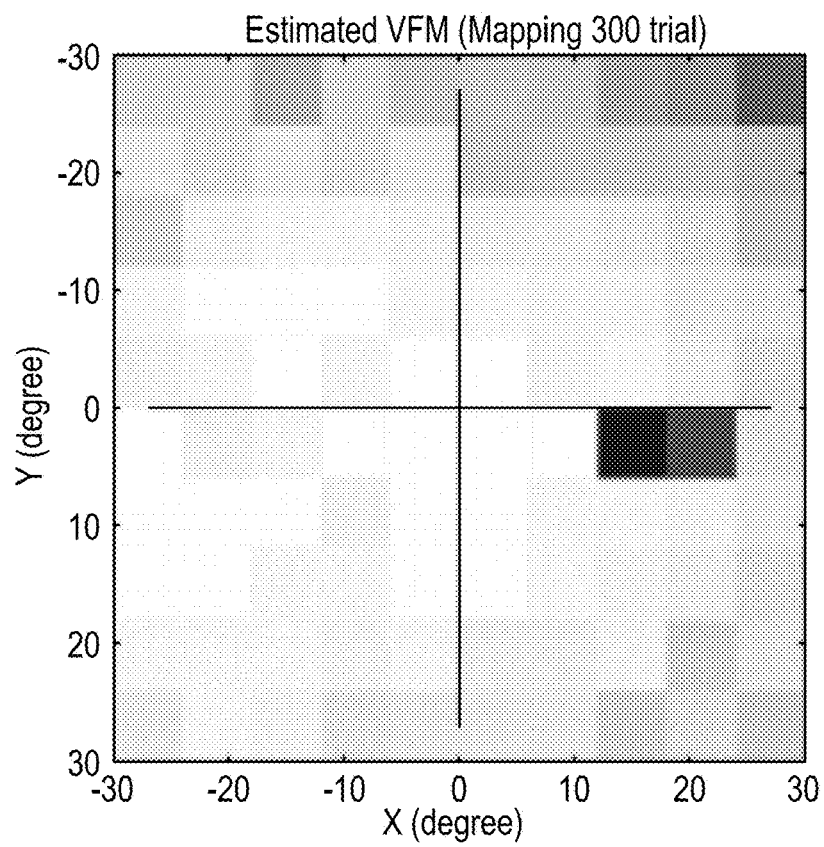
Figure 10D:
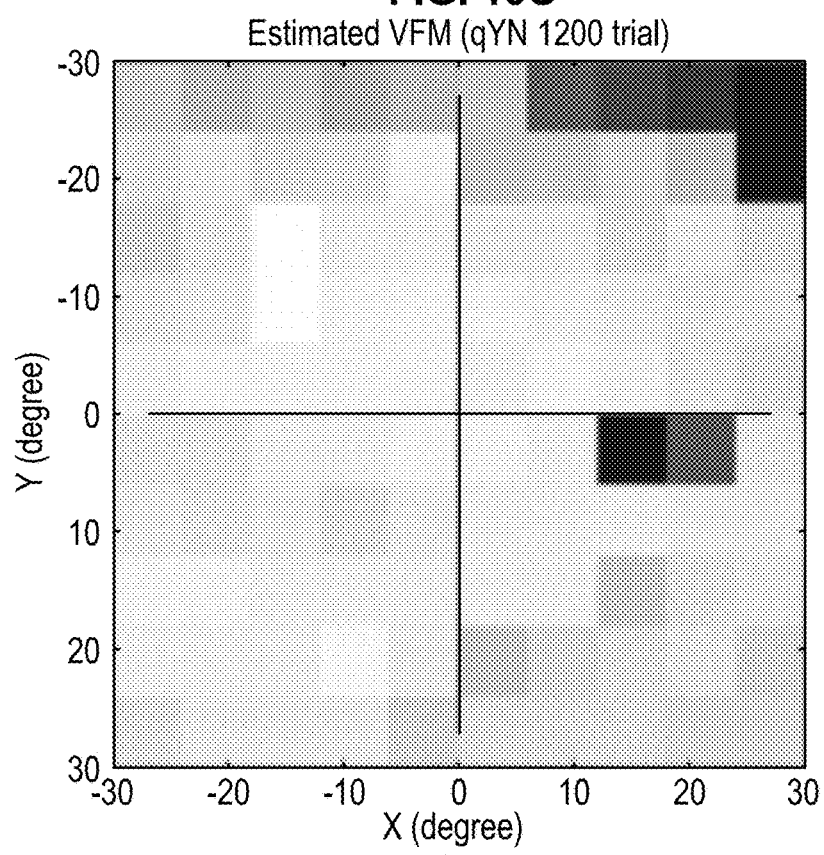
Figure 10E:
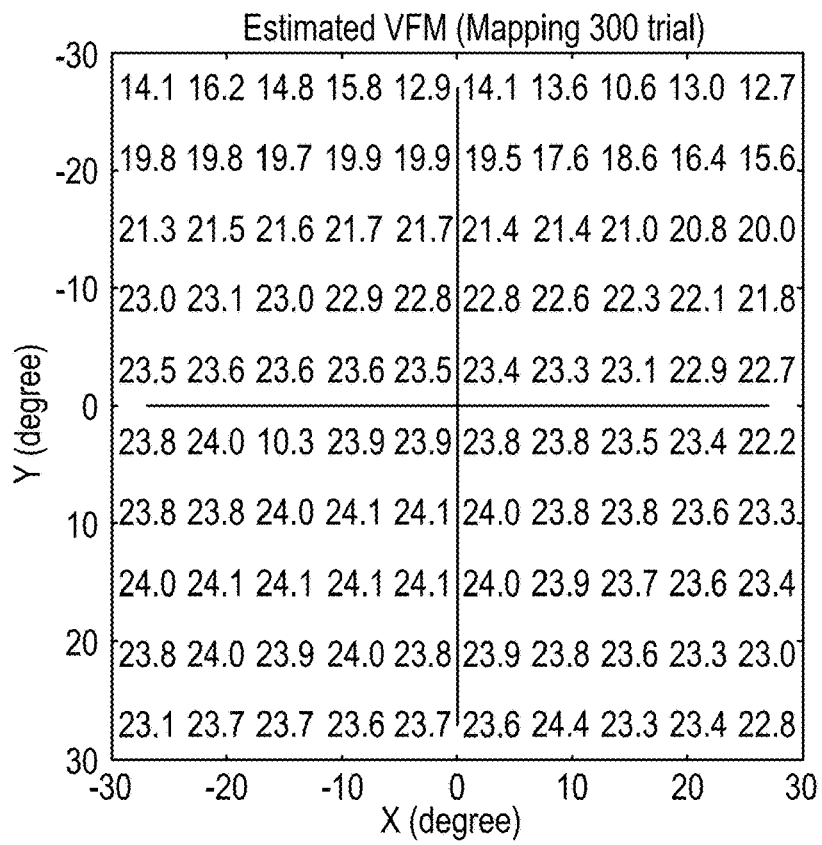
Figure 10F:
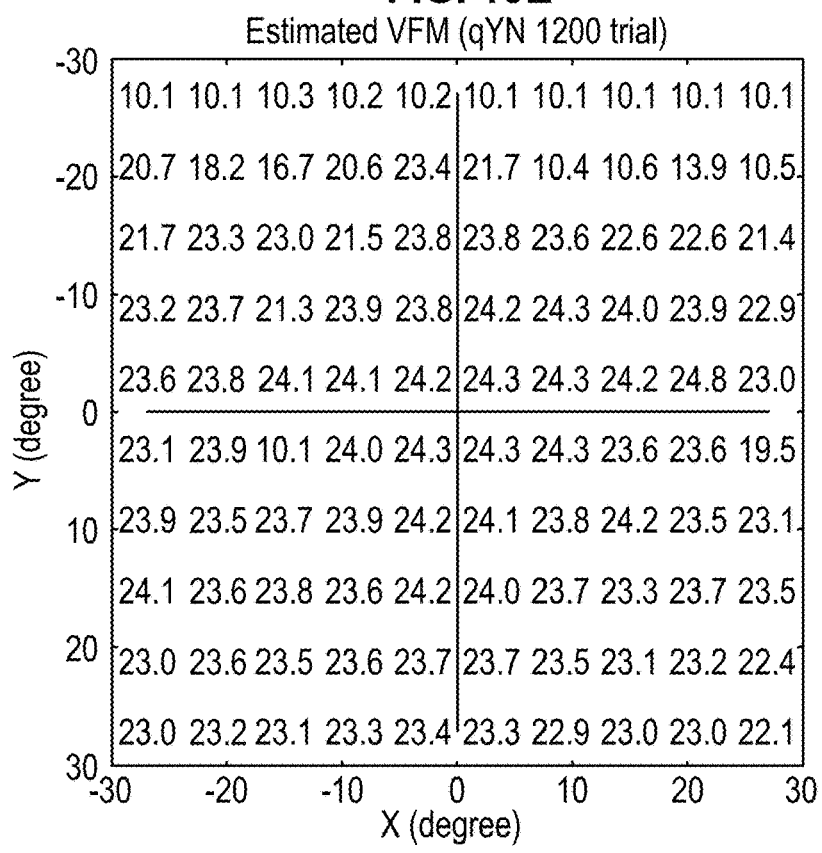
Figure 10G:
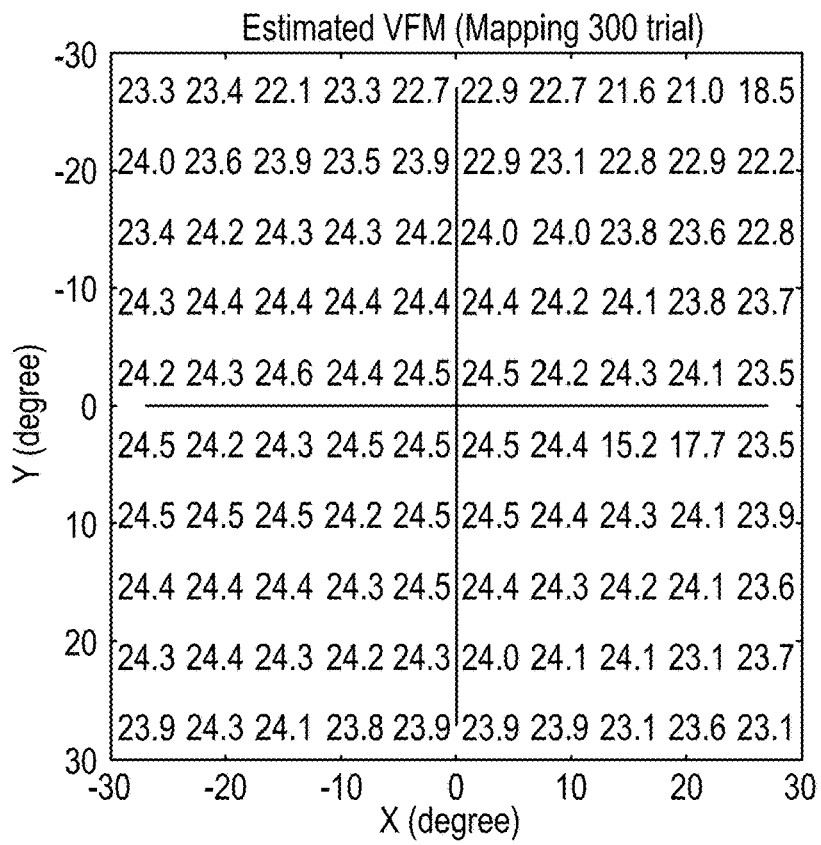
Figure 10H:
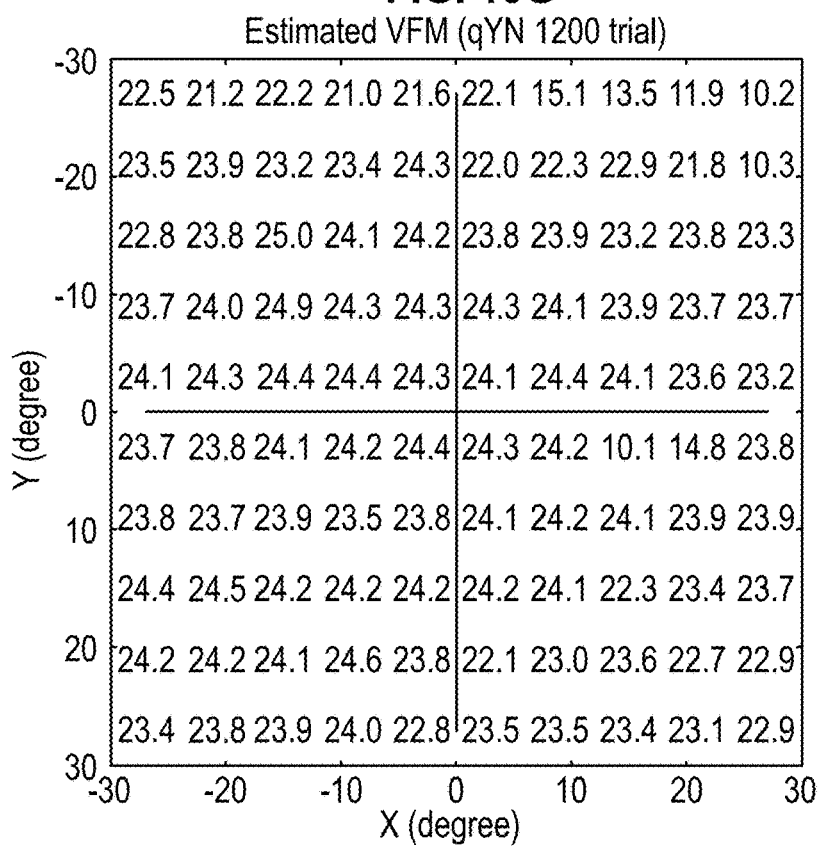
Figure 10I:
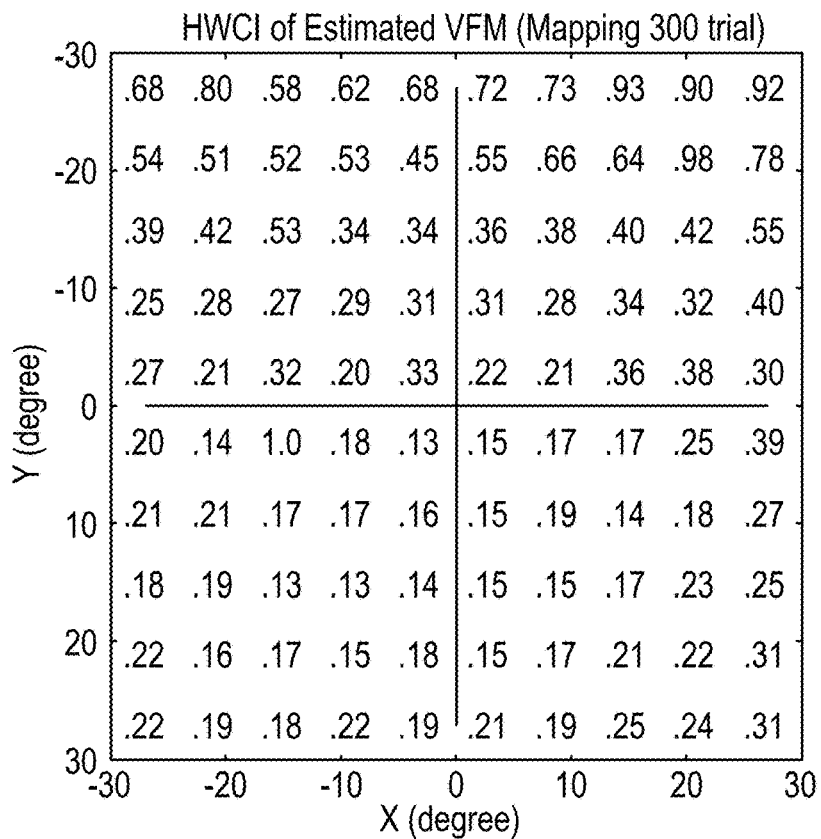
Figure 10J:
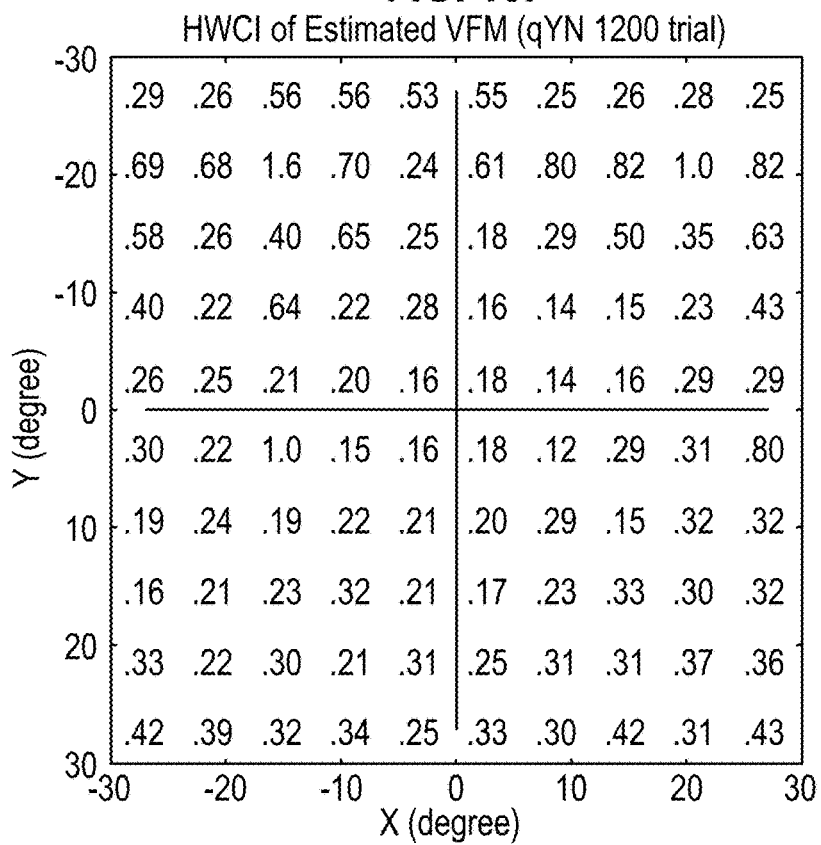
Figure 10K:
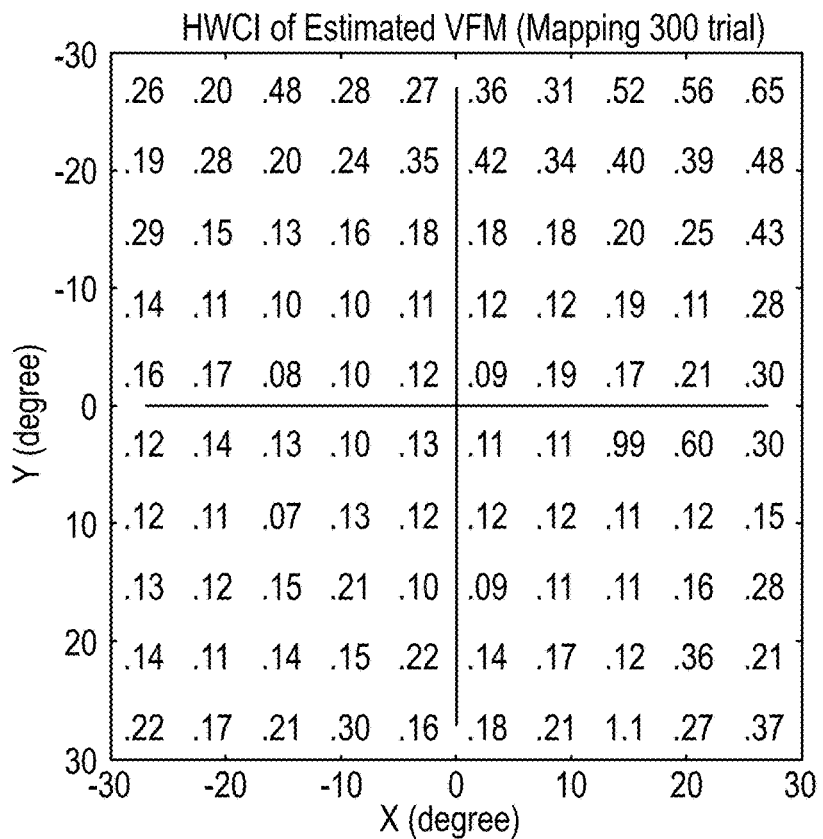
Figure 10L:
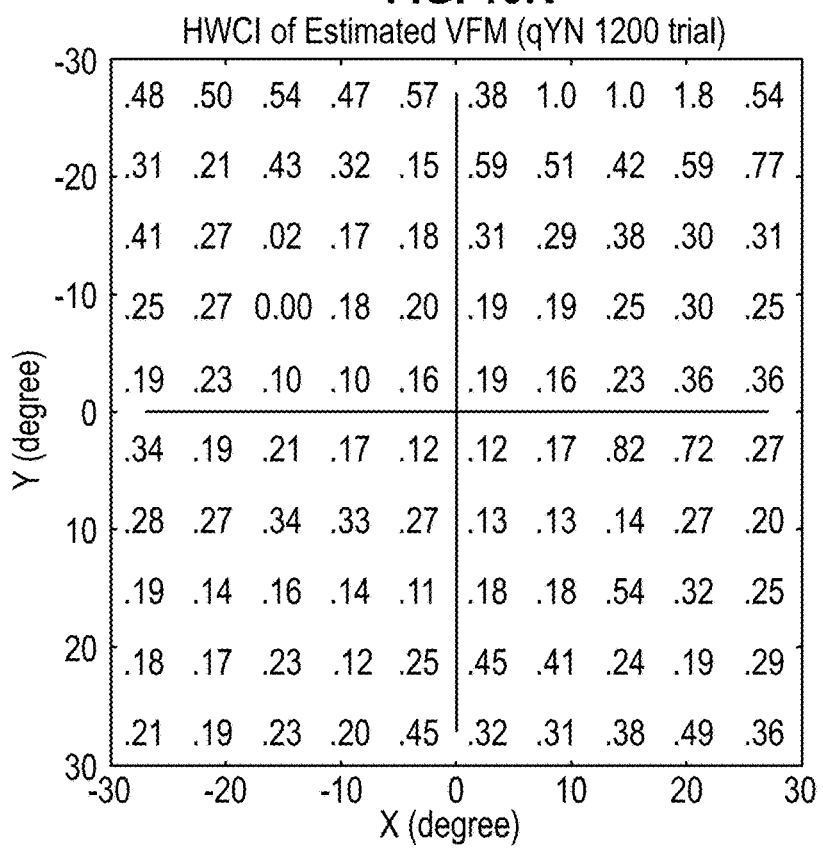
Figure 10M:
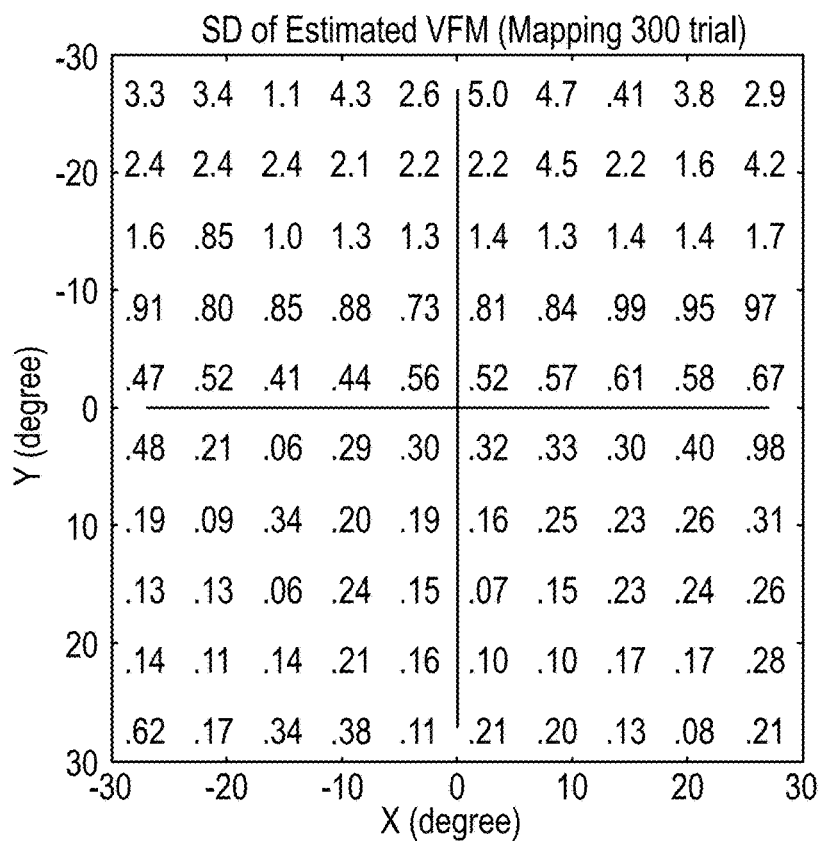
Figure 10N:
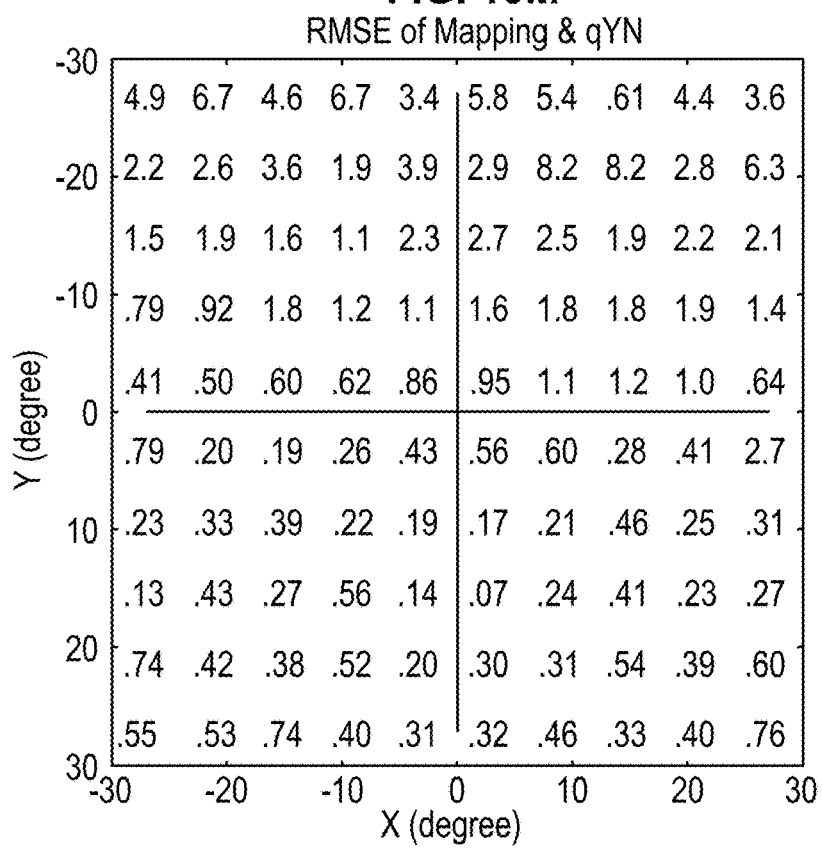
Figure 10O:
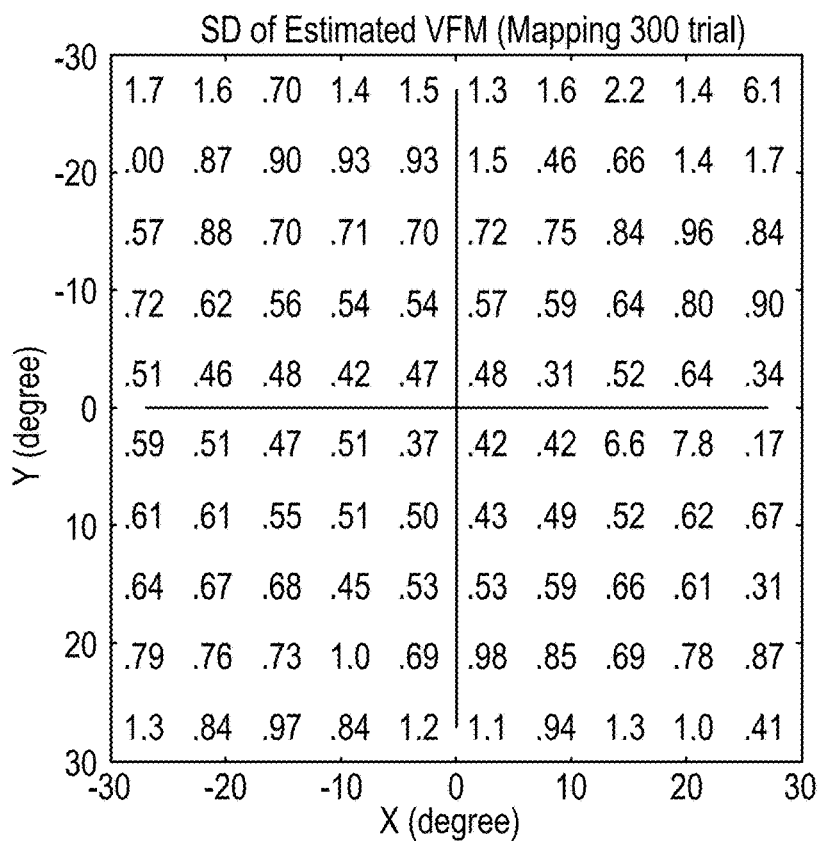
Figure 10P:
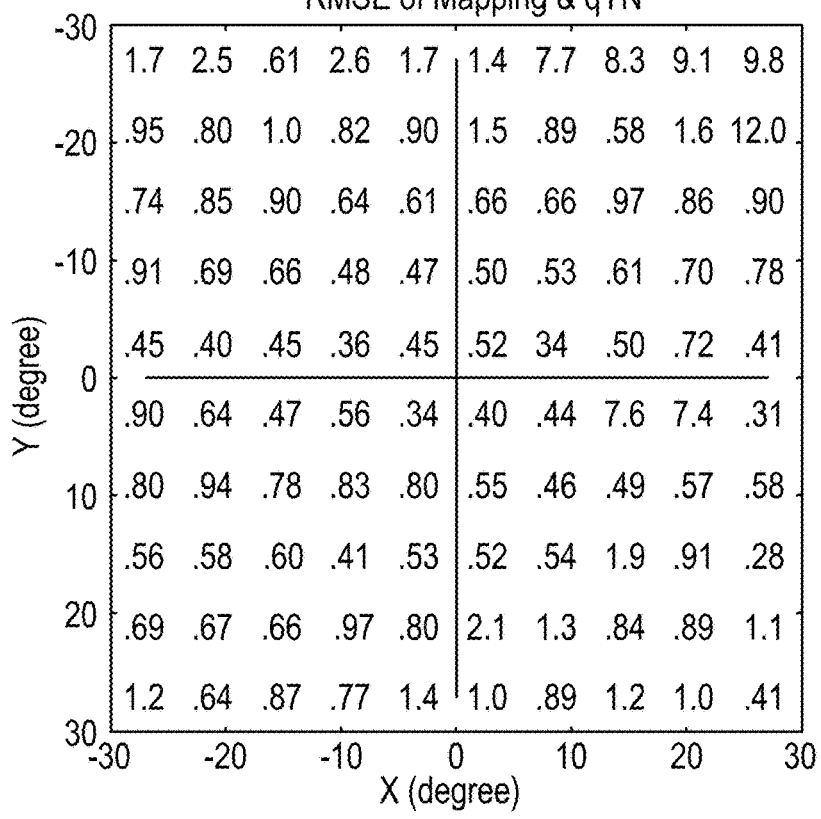
Figure 11A:
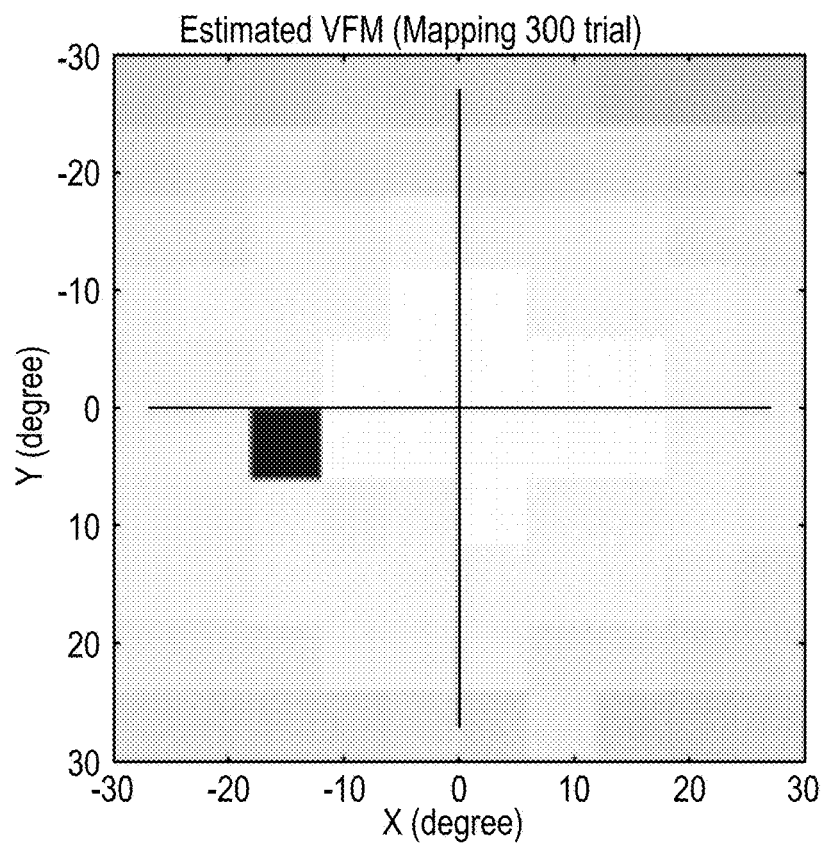
Figure 11B:
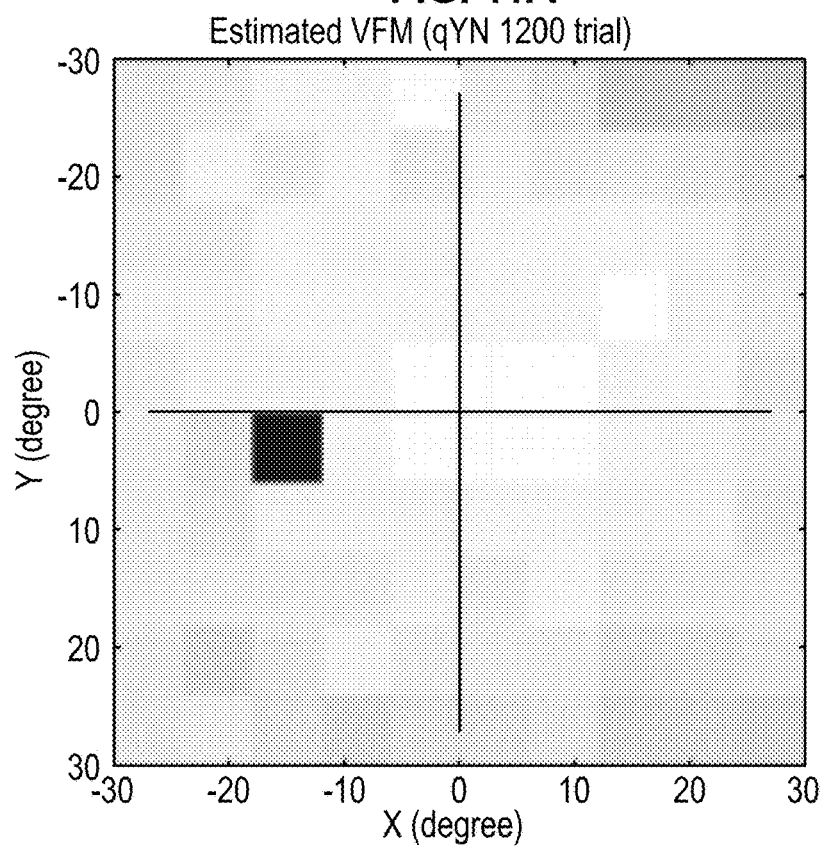
Figure 11C:
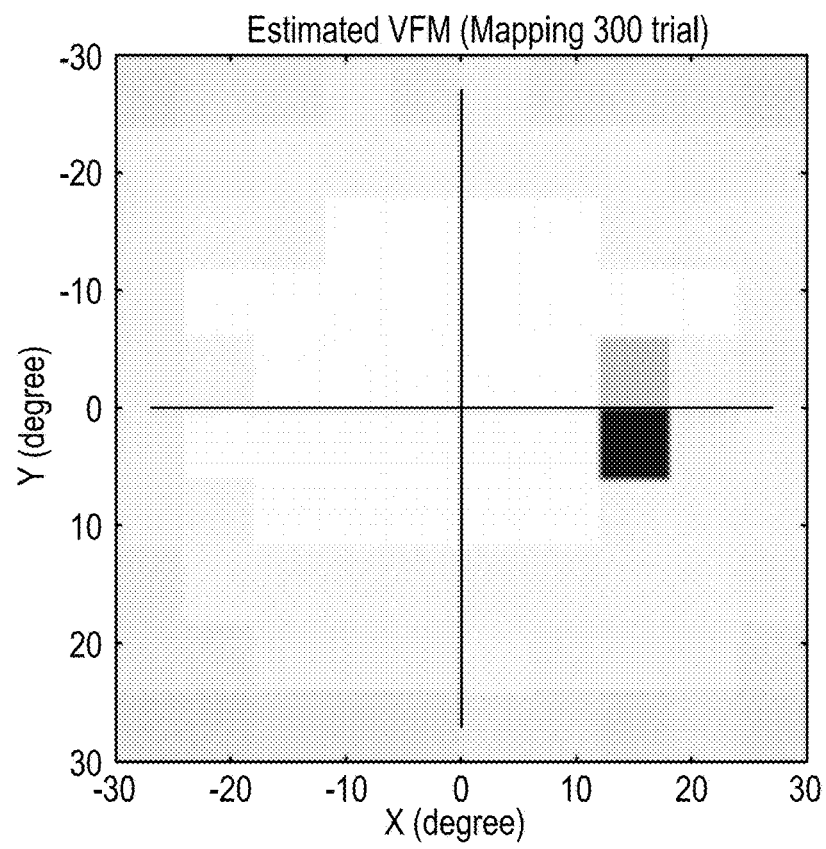
Figure 11D:
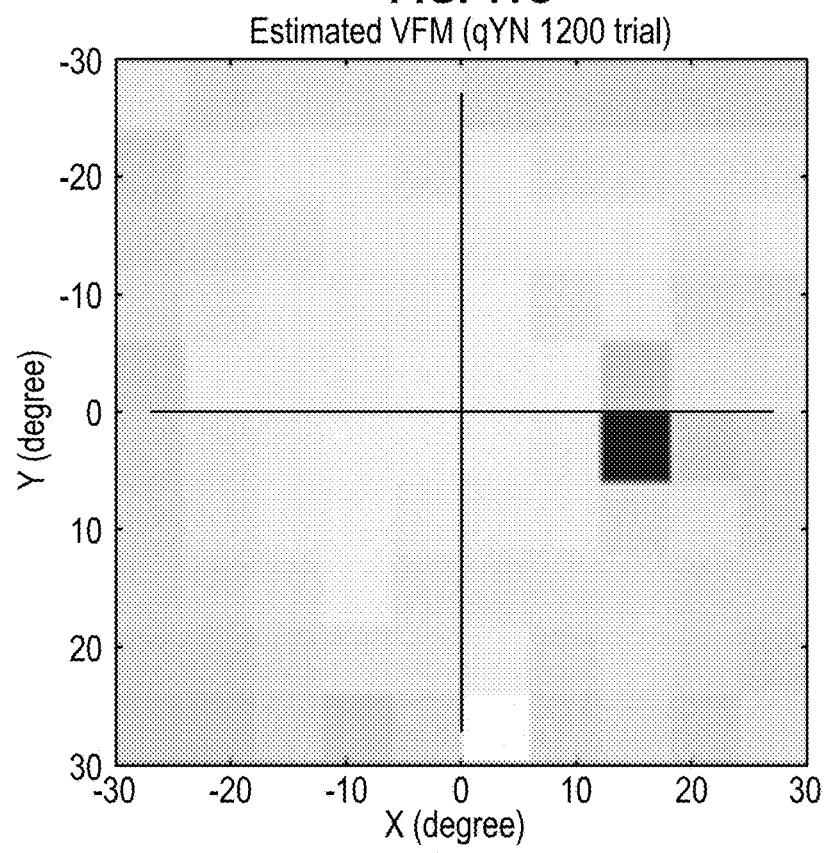
Figure 11E:
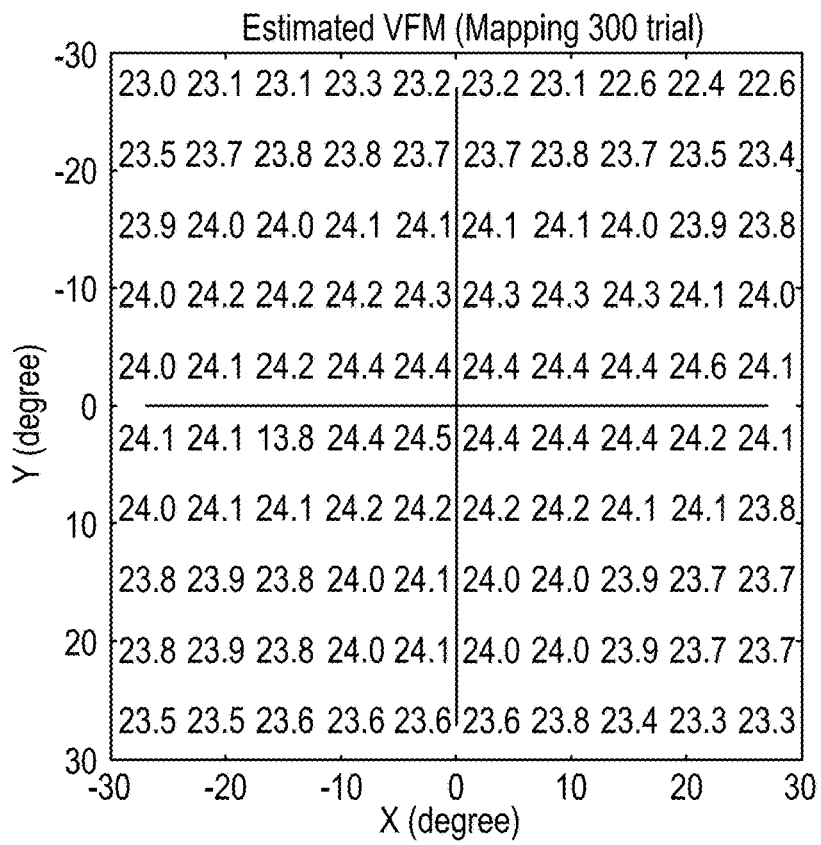
Figure 11F:
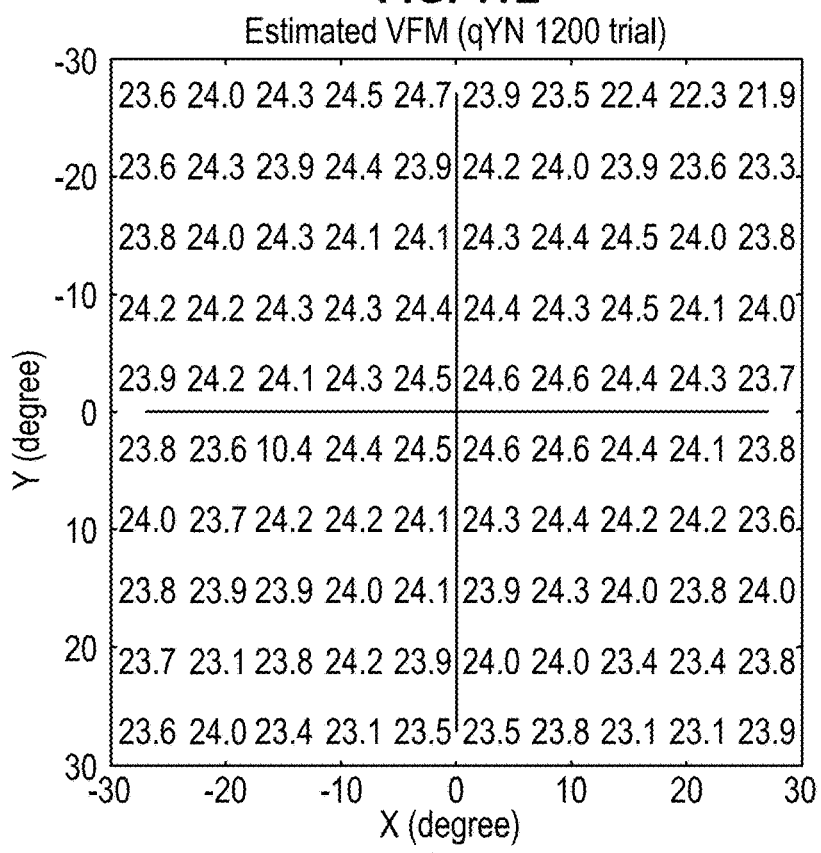
Figure 11G:
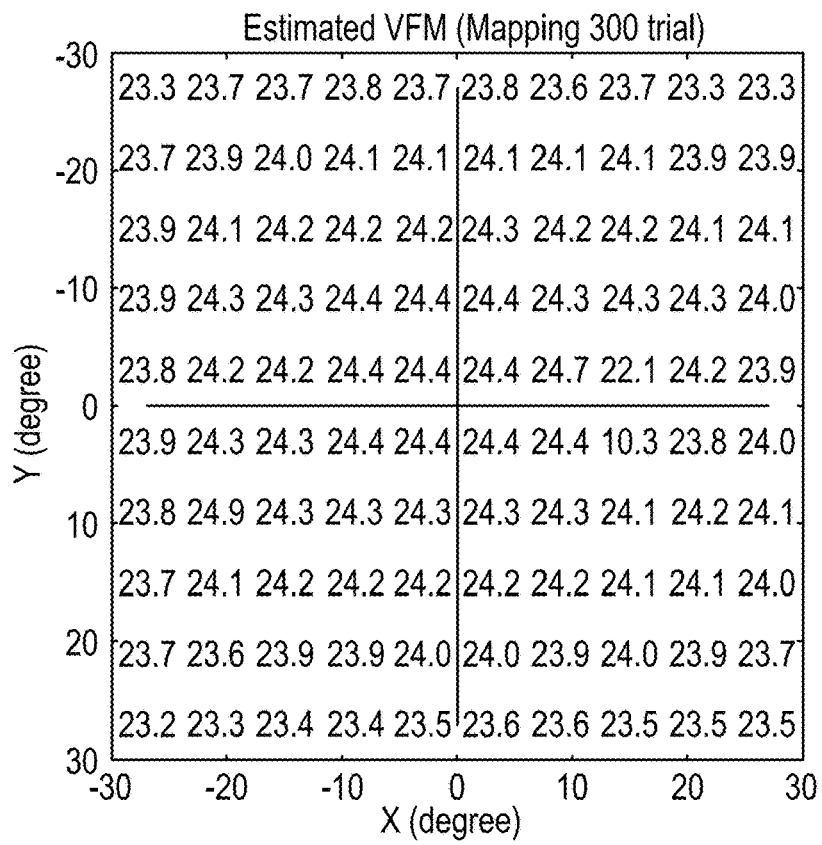
Figure 11H:
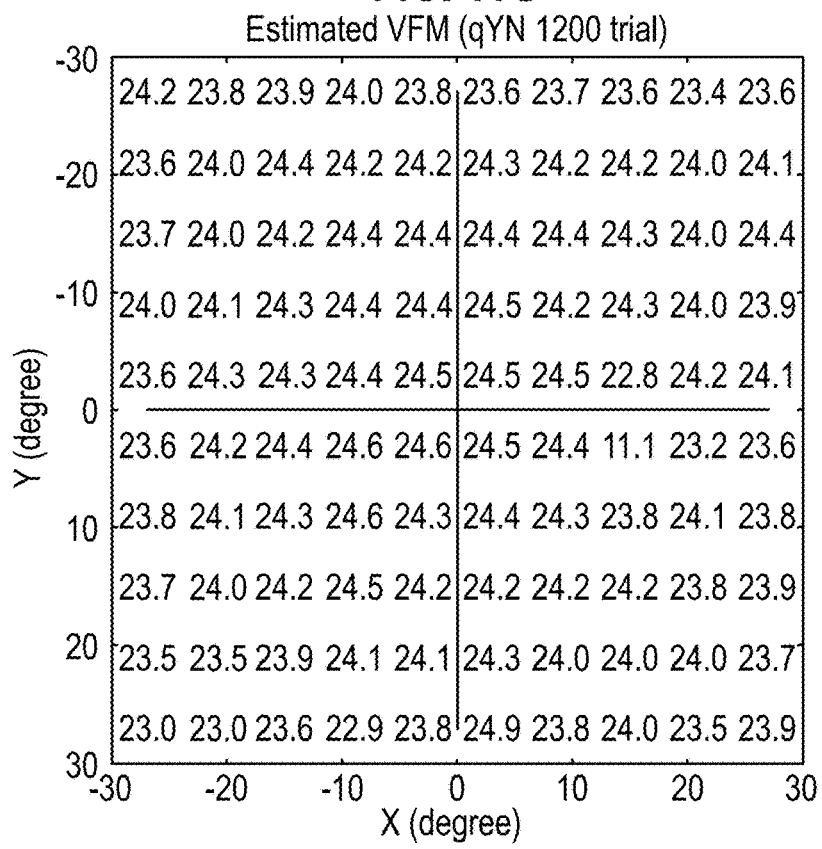
Figure 11I:
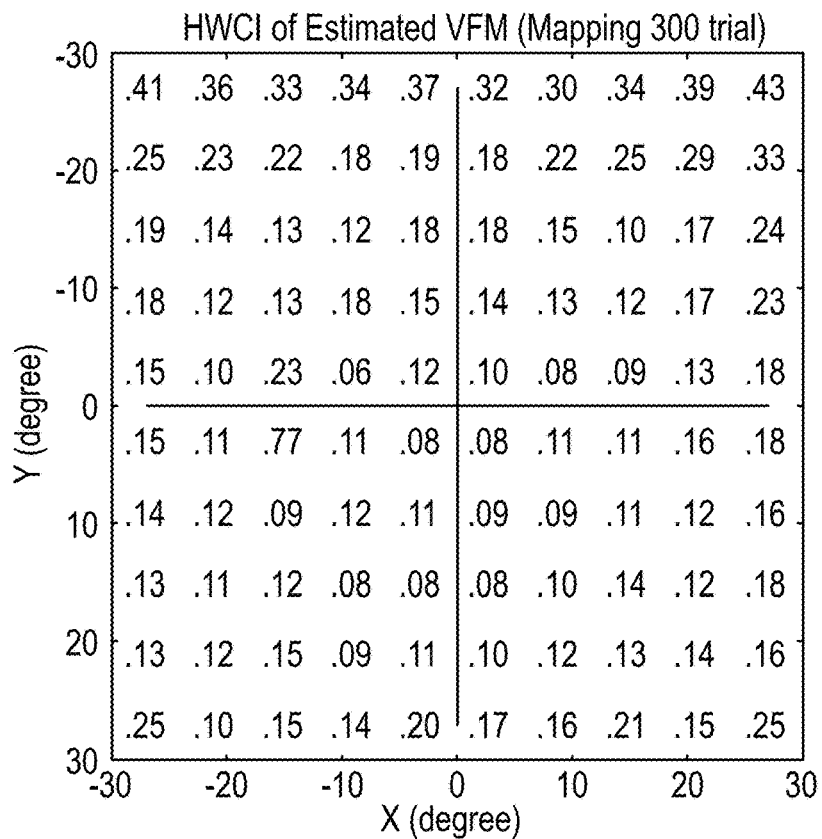
Figure 11J:
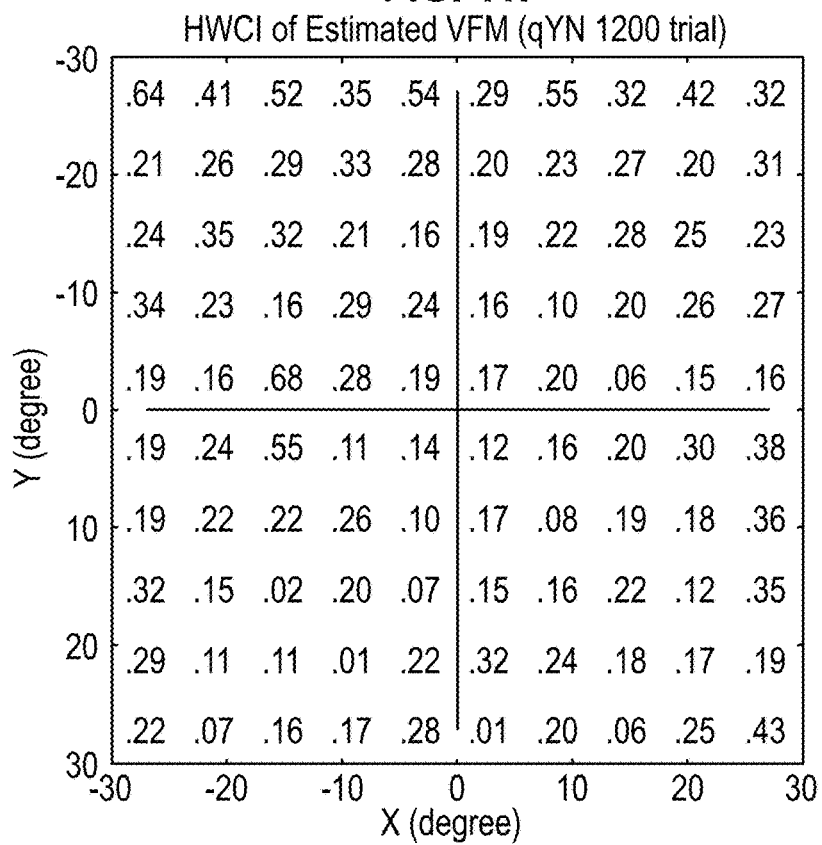
Figure 11K:
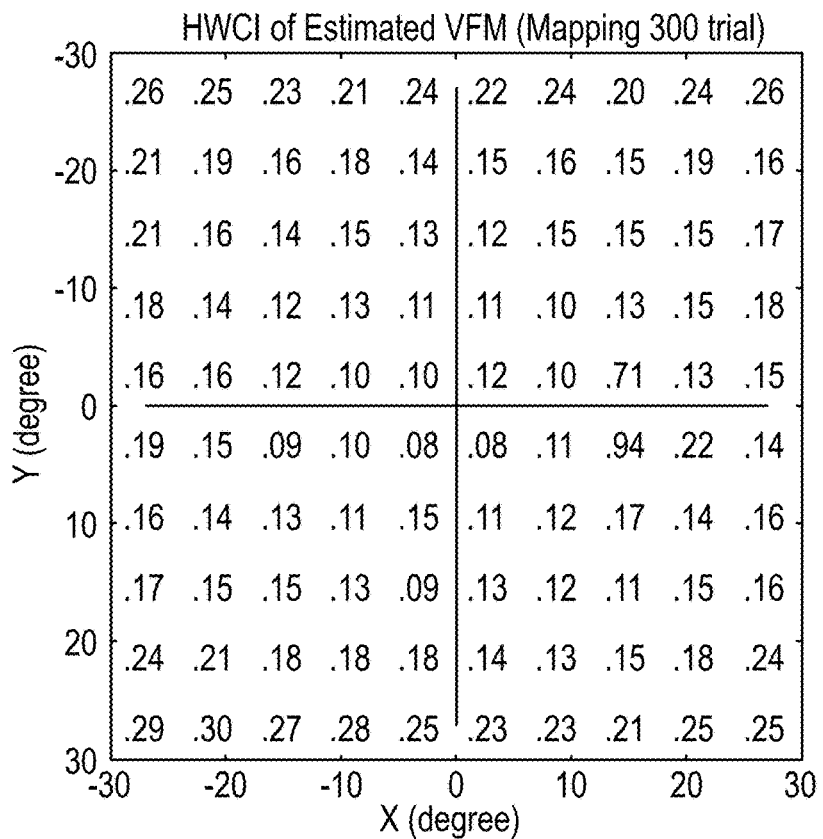
Figure 11L:
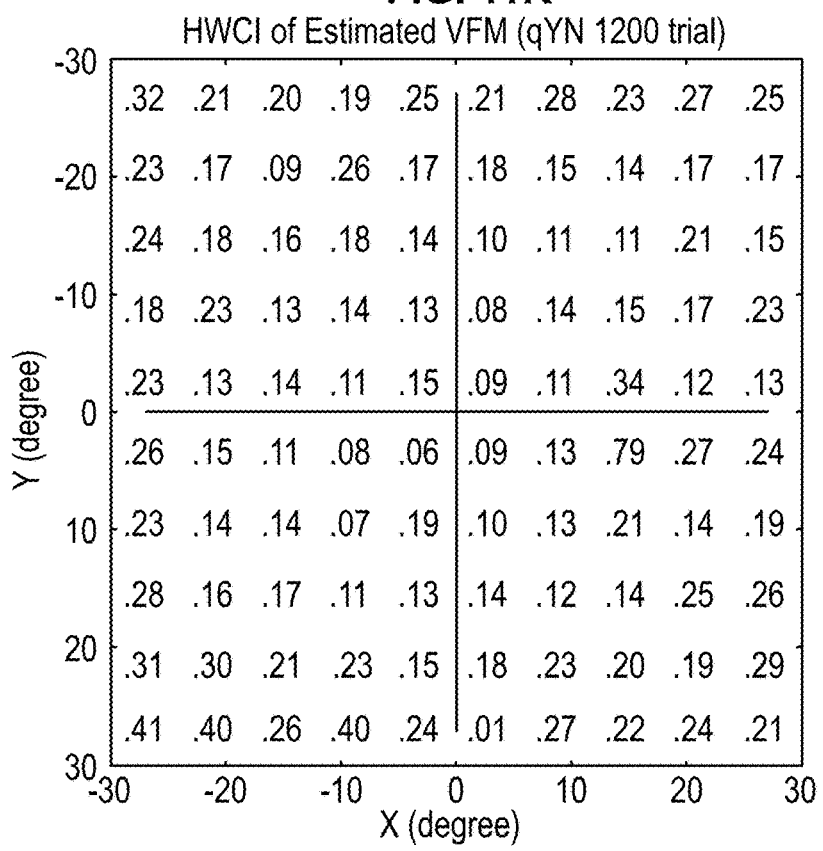
Figure 11M:
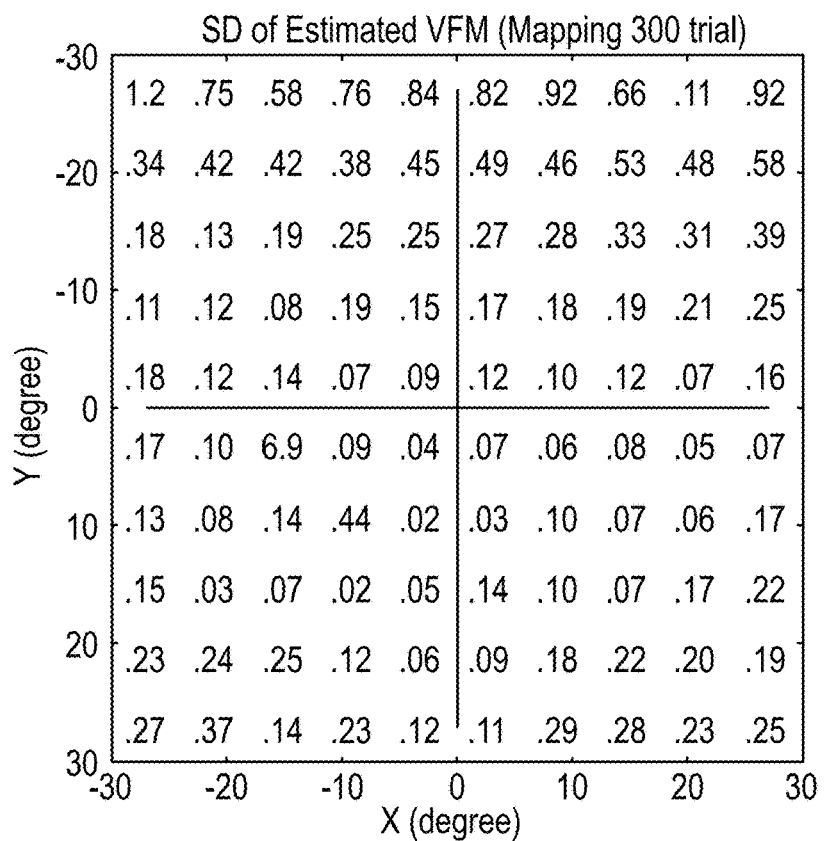
Figure 11N:
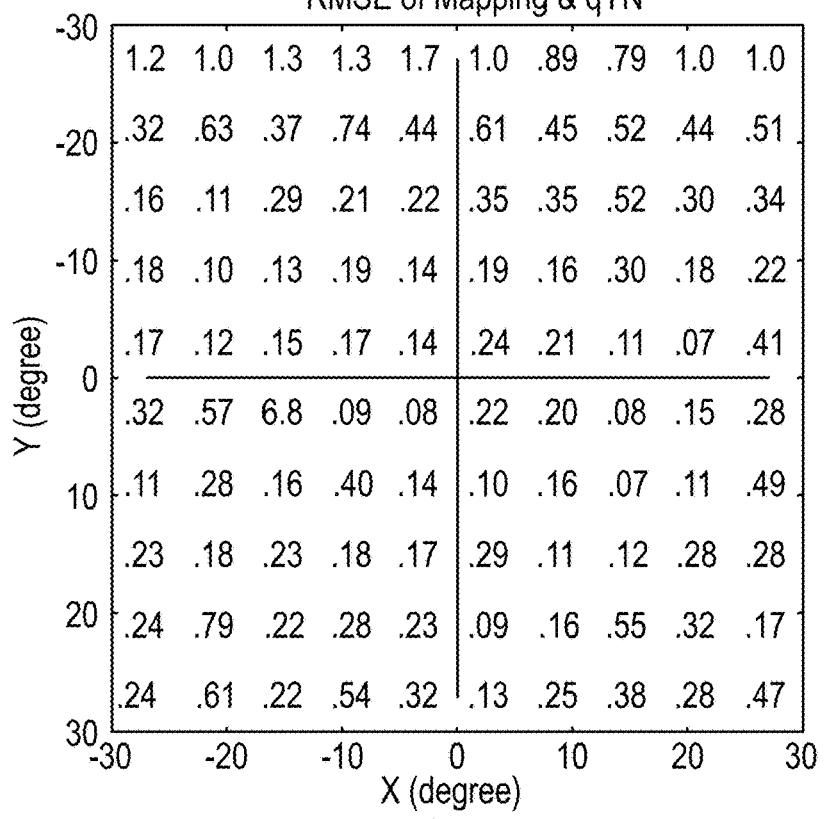
Figure 11O:
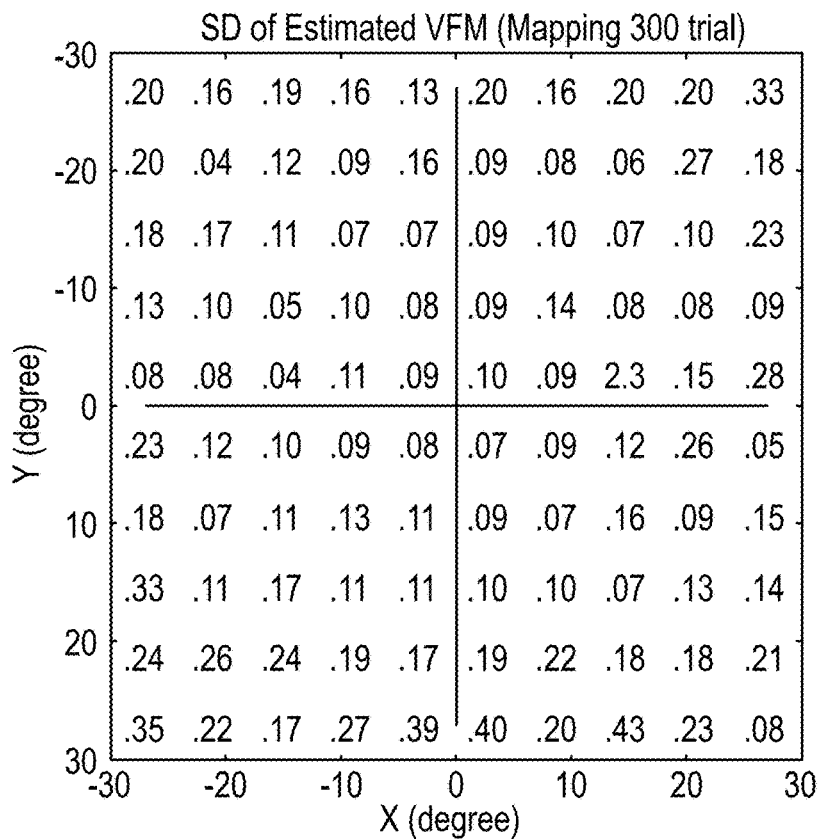
Figure 11P:
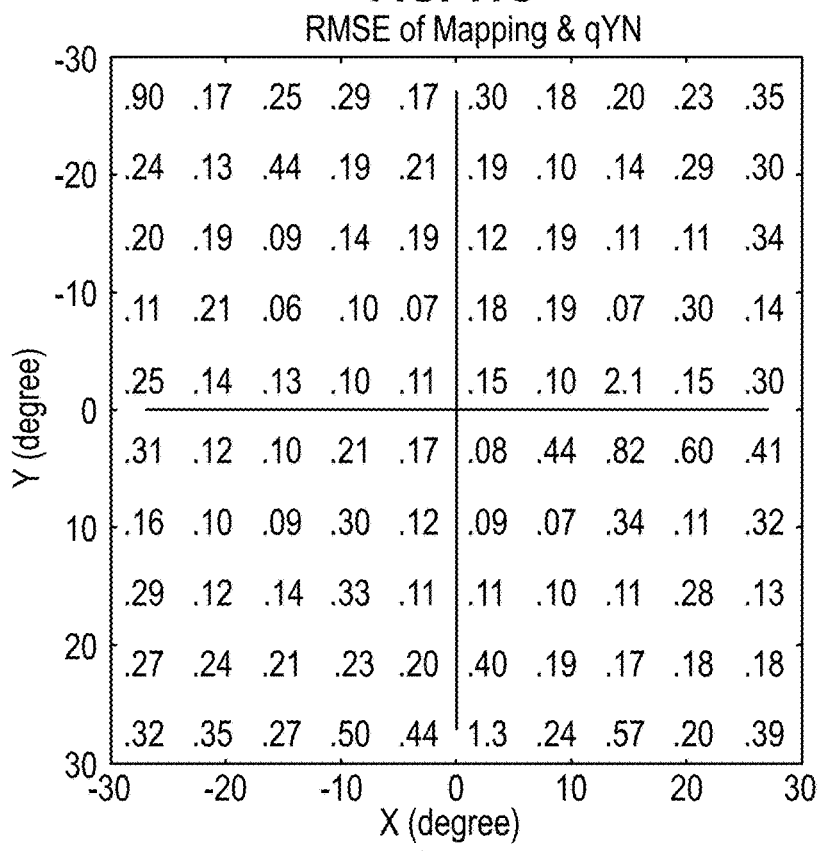

FIG. 5B illustrate an exemplary mean defect, a loss variance, a short-term fluctuation, a corrected loss variance based on simulations of the method described herein and the Bayesian YN method for measuring visual function maps. The mean defect of the estimated sensitivities across all 100 VF locations after the i-th test is calculated as:

$$MD_i = \frac{\sum_k \sum_j (\tau_{ijk} - \tau_k^{true})}{J \times K}, \quad (16)$$

where $\tau_{ijk}$ is the estimated sensitivity at the k-th VF location after i tests obtained in the j-th simulation, and $\tau_k^{true}$ is the true sensitivity at that location. The loss variance is calculated as:

$$LV_i = \frac{\sum_k \sum_j (\tau_{ijk} - \tau_k^{true} - MD_i)^2}{J \times (K-1)}, \quad (17)$$

where $MD_i$ is defined in Equation (16).

The short-term fluctuation is calculated as:

$$SF_i = \sqrt{\frac{\sum_k \sum_j (\tau_{ijk} - \text{mean}(\tau_{ijk})^2}{(J-1) \times K}}, \quad (18)$$

The corrected loss variance is calculated as:

$$CLV_i = LV_i - SF_i^2, \quad (19)$$

where $LV_i$ is defined in Equation (17) and $SF_i$ is defined in Equation (18), In FIGS. 5A-5B, results based on the method described herein are shown as solid lines and results based on the Bayesian YN method are shown as dashed lines.

Psychophysical Evaluation

A performance of the method described herein was evaluated relative to the Bayesian YN method for measuring visual function in a psychophysical evaluation. The psychophysical evaluation was conducted on an Intel Business Machine (IBM) programmable computer (PC) compatible computer running PsychToolbox extensions. A stimulus was displayed on a Samsung 55-in monitor (Model: NU55) with background luminance set to 31.5 absolute. Subjects viewed the stimuli monocularly with natural pupil at a viewing distance of 30 centimeters (cm) in a dimly lit room. The stimulus was a white round dot. The white round dot included a diameter of about 0.43 visual degree and a luminance of about 31.5-950 absolute in a center of a circle. The circle included a diameter of about 8.17 visual degree and luminance that was fixed to about 77.4 apostilb (abs). In each trial, a stimulus and a cue were presented simultaneously for 142 millisecond (ms) in one of the 10×10 possible retina locations evenly distributed in 60×60 visual degree of visual field. A fixation dot was displayed in the center of visual field throughout the whole procedure. The interval-trial-interval was set to 1.2 seconds (s). The subjects were exposed to about 300 trials, including the method described herein and the Bayesian YN method, randomly mixed, in each of four sessions in each eye. As such, these procedures resulted in data from twelve eyes (6 OS, 6 OD) of six normal subjects.

FIGS. 6A-6P, 7A-P, 8A-P, 9A-P, 10A-P and 11A-P illustrate exemplary estimated light sensitivity VFMs for six subjects, respectively, generated by the method described herein and the Bayesian YN method for measuring visual function. For each subject, estimated VFMs are presented in a first row with color-maps and a second row with numerical values. The 68.2% HWCI of VFM estimates are presented in a third row; the standard deviation of the estimates from the method described herein and the mean squared error (RMSE) between the method described herein and the Bayesian YN method are presented in a fourth row. The results obtained from OS and OD are displayed in first and second columns, and third and fourth columns. The results based on the method described herein and the Bayesian YN method are displayed in different columns.

In the psychophysical evaluation, an agreement between the method described herein and the Bayesian YN method was evaluated according to an RMSE of the estimated thresholds across all 100 retina locations, which started at 2.47 dB on a first method described herein trial and decreased to 1.87 dB after 150 tests and to 1.48 dB after 300 tests for all sessions and eyes. The average 68.2% HWCI of the estimated thresholds on 12 eyes across all 100 retina locations decreased from 2.27 dB on the first method described herein trial, decreased to 0.27 dB after 150 tests and 0.25 dB after 300 tests. The average 68.2% HWCI of the estimated thresholds decreased from 2.28 dB on the first Bayesian YN method trial, reaching 1.05 dB after 150 tests, 0.69 dB after 300 tests, 0.29 dB after 1200 tests. The average RMSE of the estimated sensitivities from both the method described herein and Bayesian YN method across all 100 retina locations started at 1.41 dB. It decreased to 0.76 dB and 1.15 dB in the method described herein and Bayesian YN after the first 300 trials, and to 0.15 dB and 0.26 dB in the two methods after 1200 trials.

Figure 12:
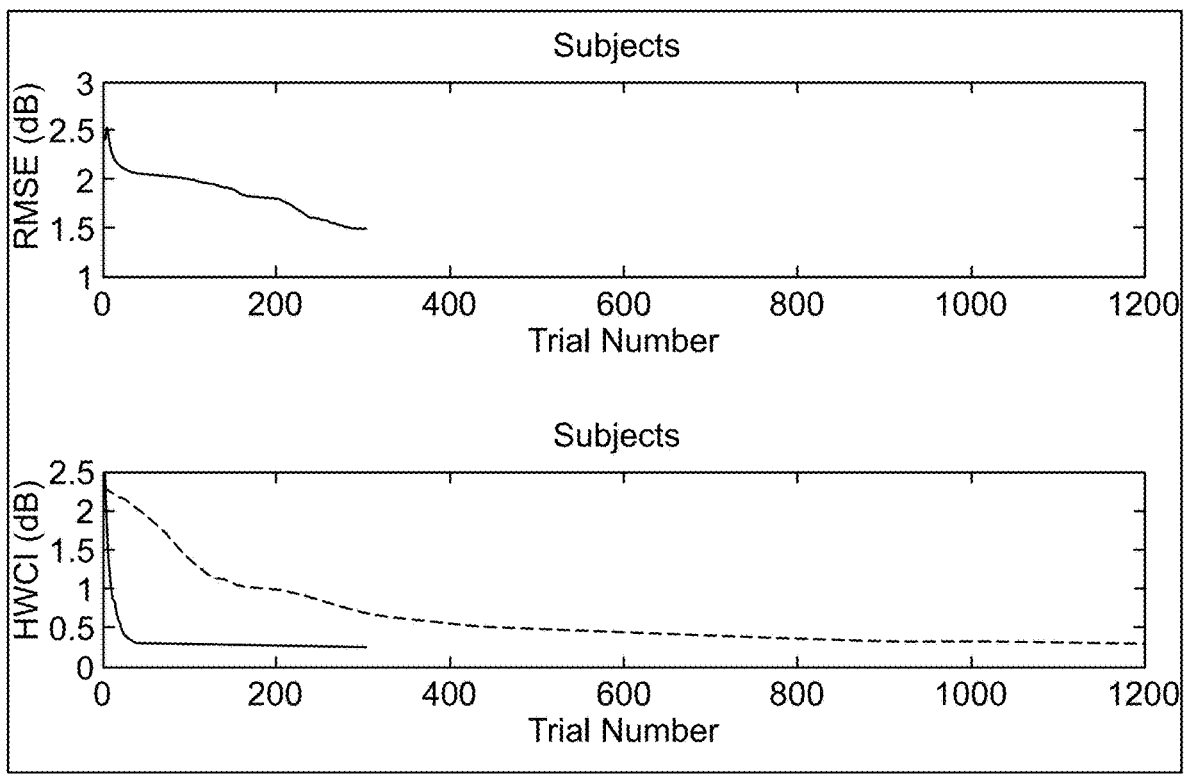
FIG. 12 illustrates an exemplary root mean squared error (RMSE) and a 68.2% HWCI based on a method, for example, as depicted in FIG. 3, and a YN method for measuring visual function maps.

FIG. 12 illustrate an exemplary RMSE and a 68.2% HWCI based on the method described herein, and the Bayesian YN method for measuring visual function. The RMSE and 68.2% HWCI of the psychophysical evaluations for twelve eyes (6 OS, 6 OD) of six subjects. In FIG. 12, example results based on the method described herein are shown as solid lines and results based on the Bayesian YN method are shown as dashed lines.

Figure 13:
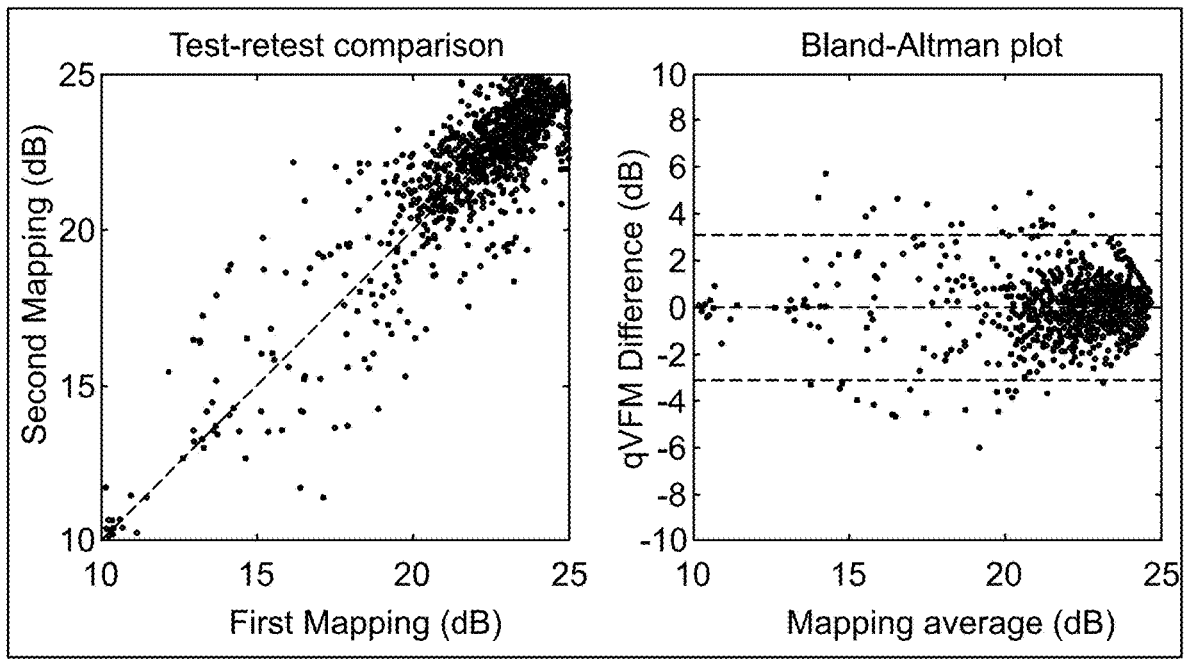
FIG. 13 illustrates plots of example test-retest reliability of a method, for example, as depicted in FIG. 3, for measuring visual function maps.

FIG. 13, illustrates plots of example test-retest reliability of the method described herein assessed through analysis of the 4 method described herein runs completed in 4 sessions. The left plot plots estimated sensitivities of the paired method described herein runs from 1 vs. 2, 4 vs. 3, 3 vs. 2 sessions. The average test-retest correlation for the paired estimation was 90.5% (SD=0.6%). Though test-retest correlations are widely reported as measures of test-retest reliability, they are not the most useful way to characterize method reliability or agreement (Bland & Altman, 1986). The right plot represents a Bland-Altman plot of the difference of the method described herein estimates between 1 and 2, 4 and 3, 3 and 2 sessions against their mean. The mean and standard deviation of test-retest differences were −0.01 and 1.55 dB. These results signify that (1) sensitivity measures do not change systematically over the course of testing sessions, and (2) the precision of test-retest differences within sessions agrees with that estimated RMSE: compare 1.55 dB with 1.38 dB. The repeated runs of the method described herein can show consistent results and exhibit its robustness on this multi-location measurement task.

Implementation Two: Contrast Sensitivity Mapping

Figure 14:
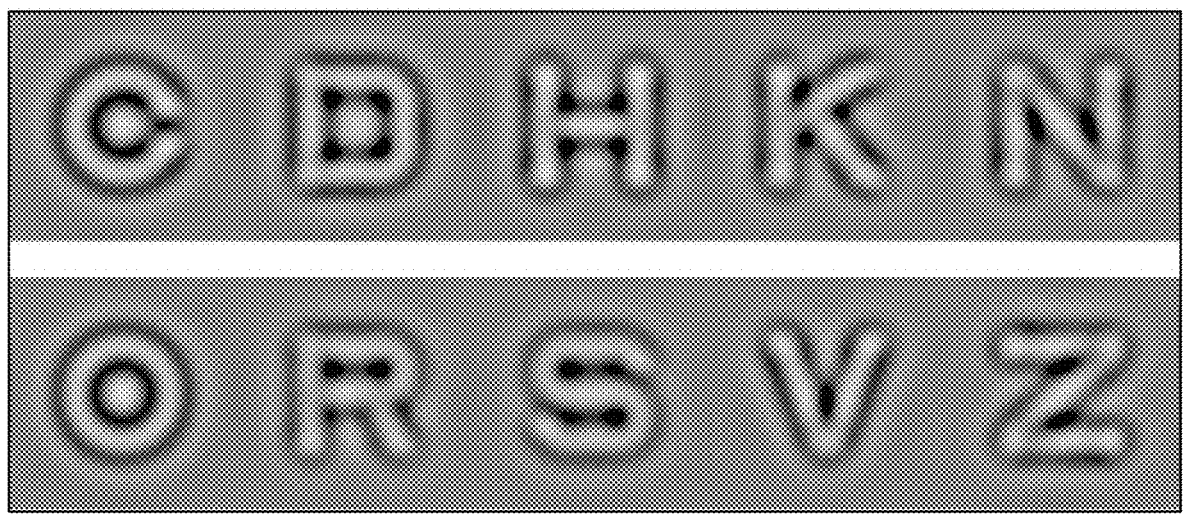
FIG. 14 illustrates example filtered Sloan letters.
Figure 15A:
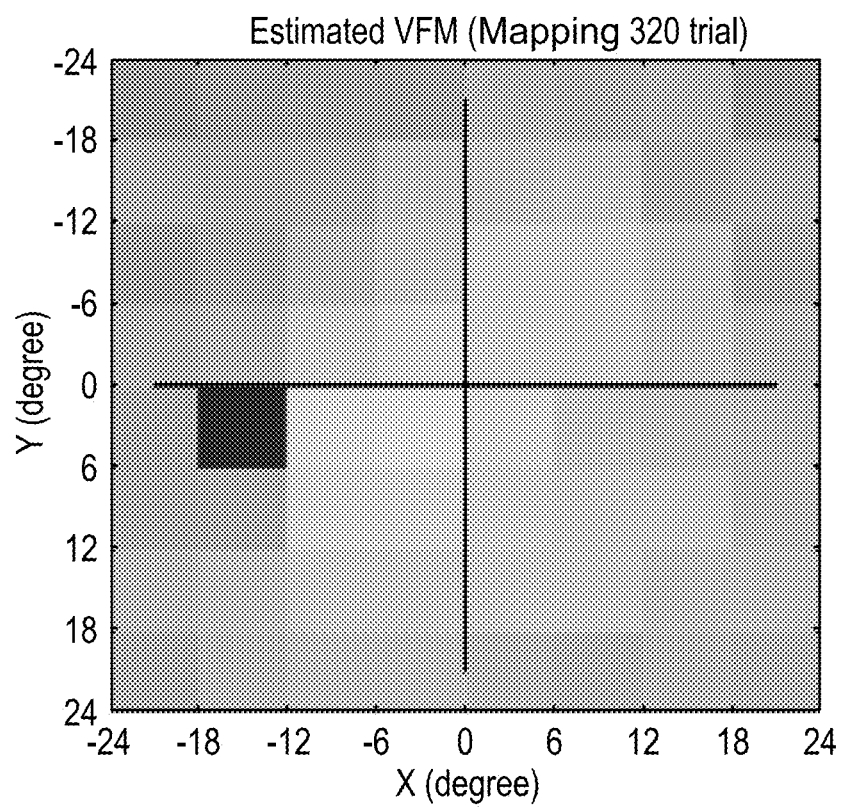
FIGS. 15A-P illustrate exemplary estimated the contrast sensitivity VFMs for subject 1 (8 eyes) generated by a method, for example, as depicted in FIG. 3, and a Bayesian YN method for measuring visual function maps.
Figure 15B:
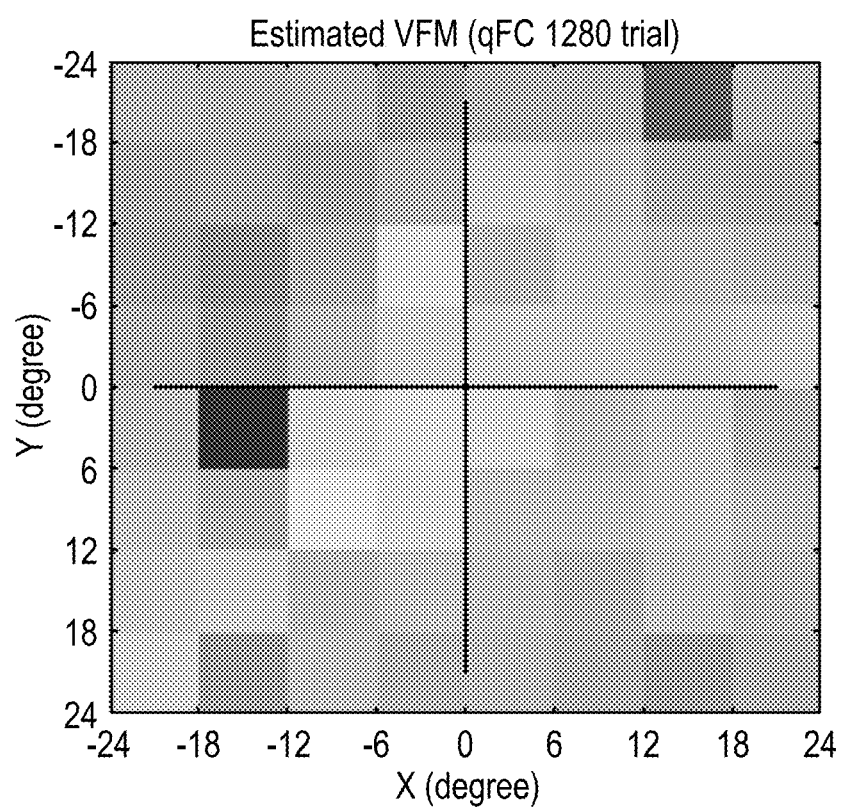
Figure 15C:
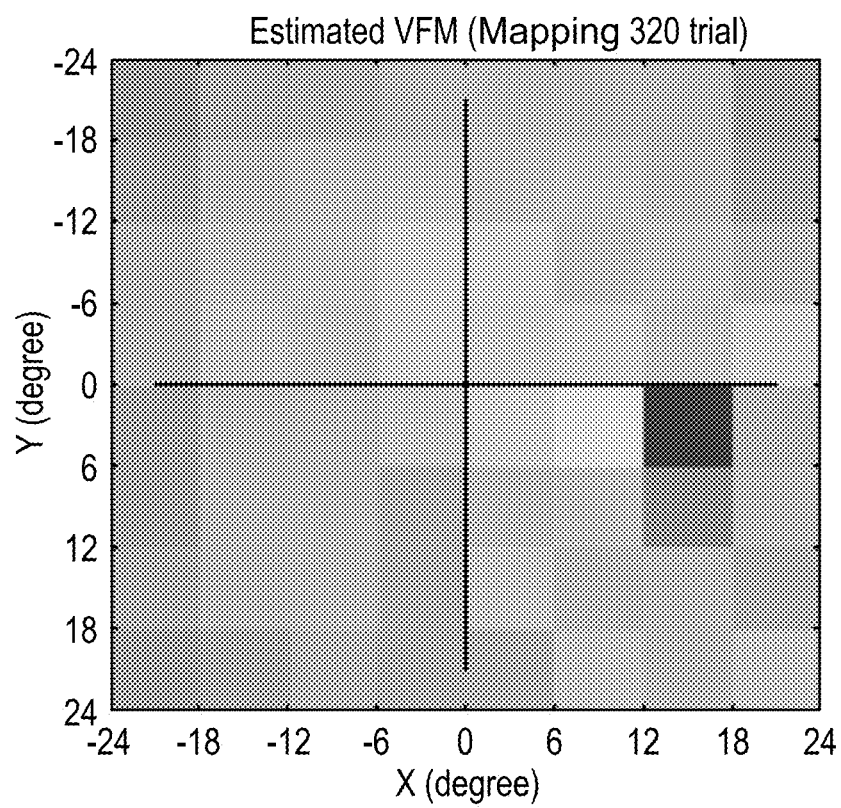
Figure 15D:
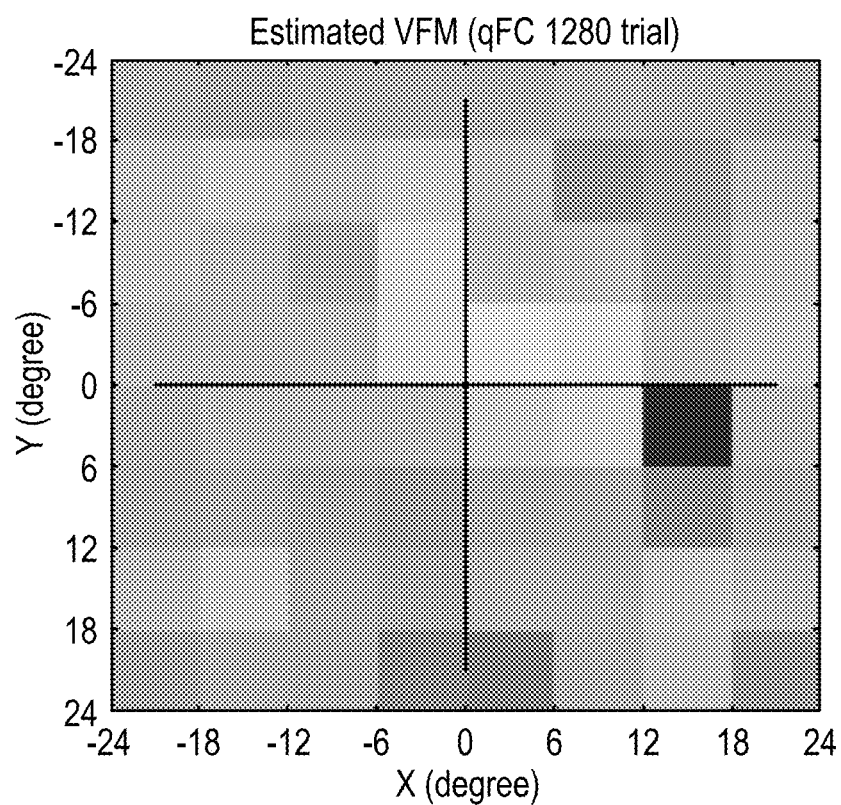
Figure 15E:
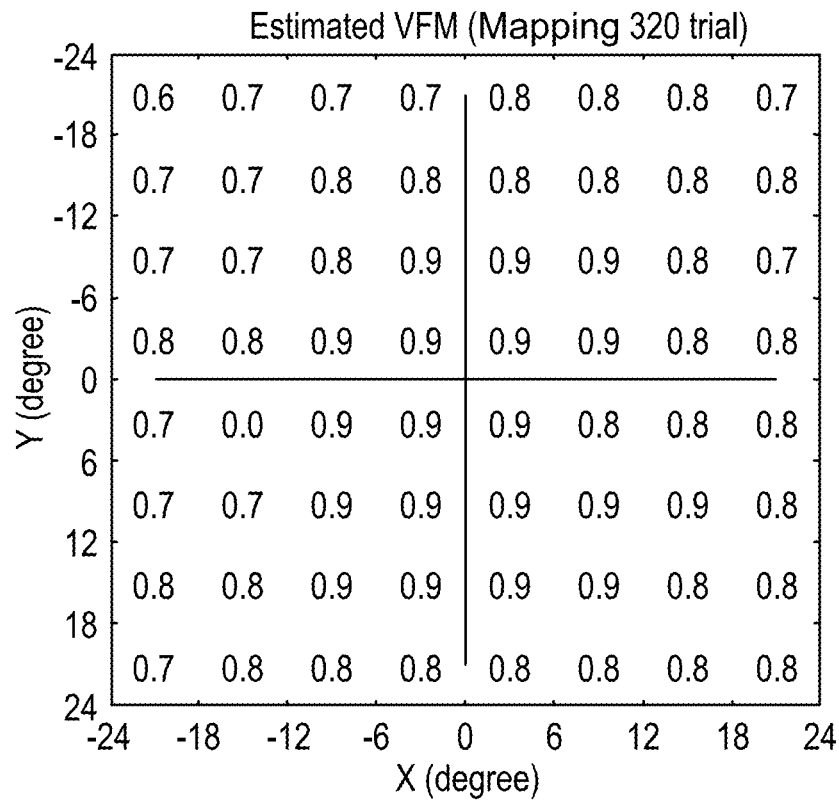
Figure 15F:
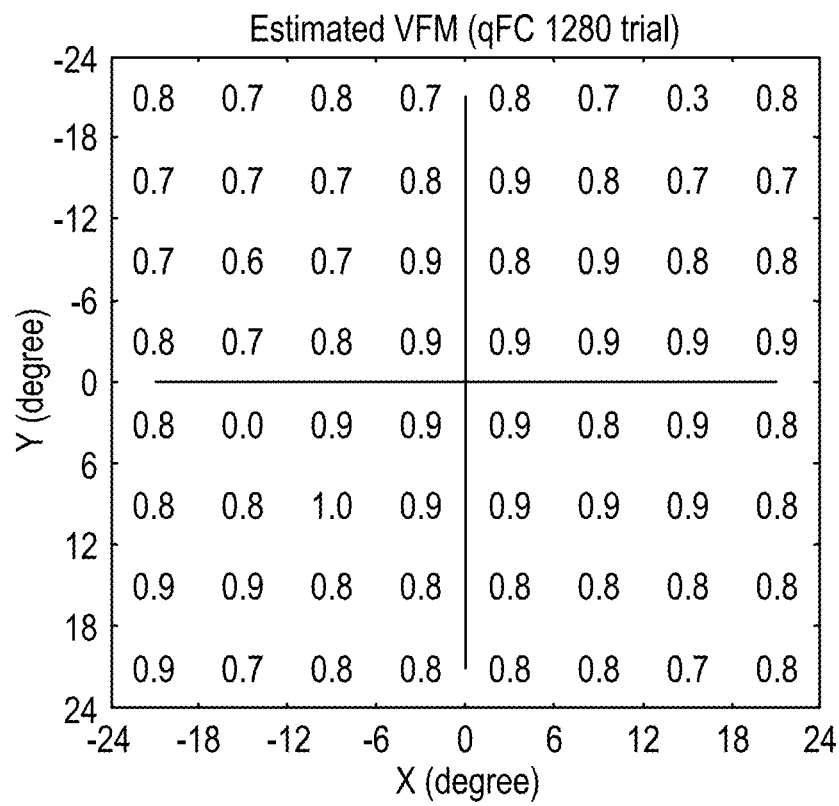
Figure 15G:
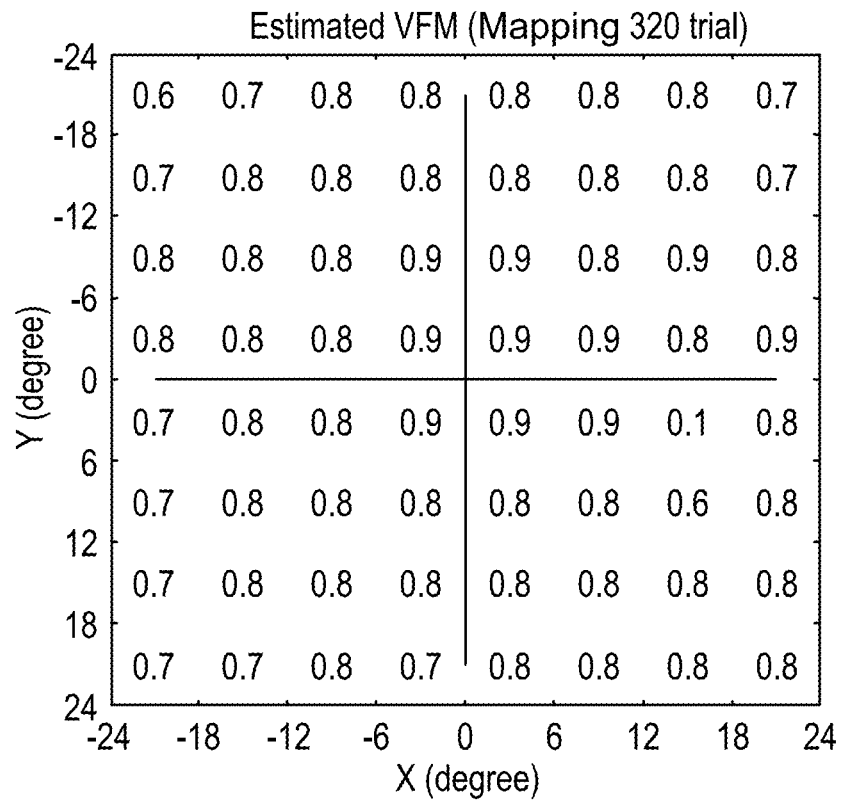
Figure 15H:
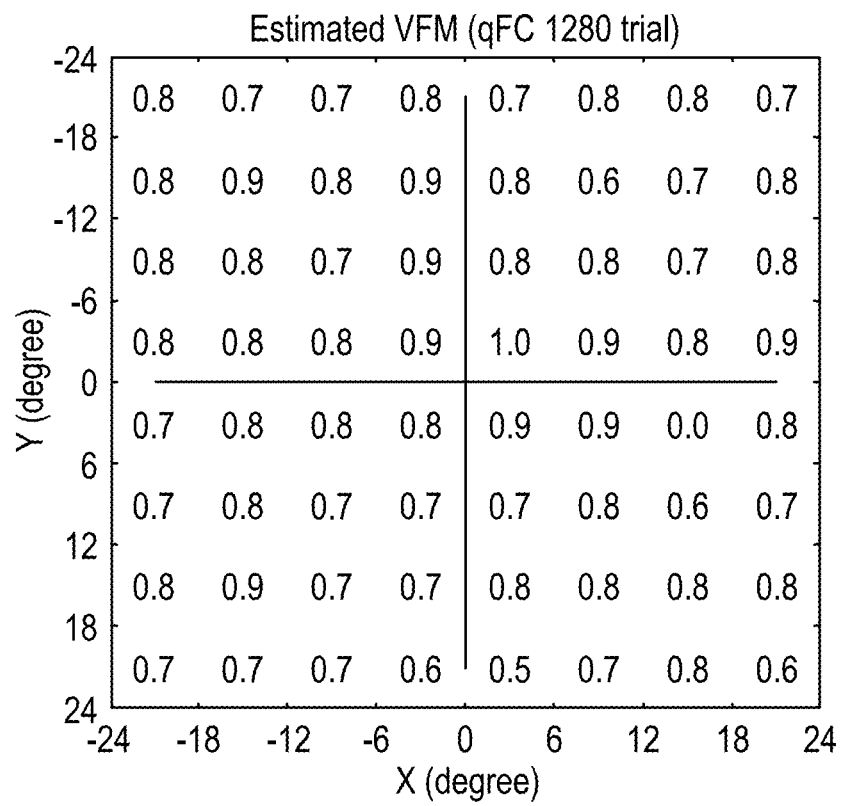
Figure 15I:
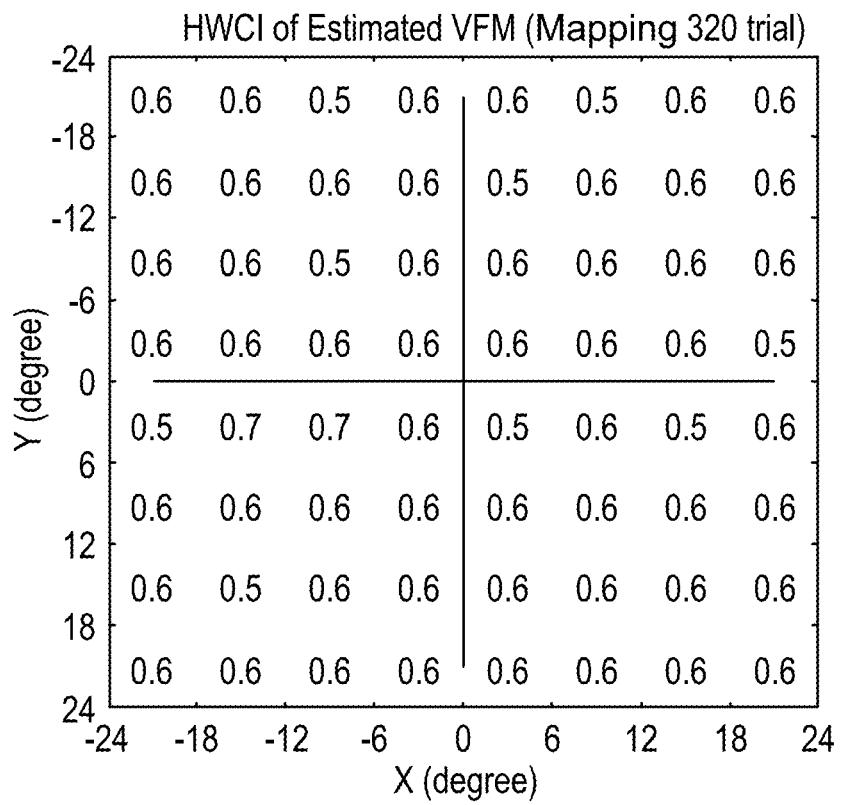
Figure 15J:
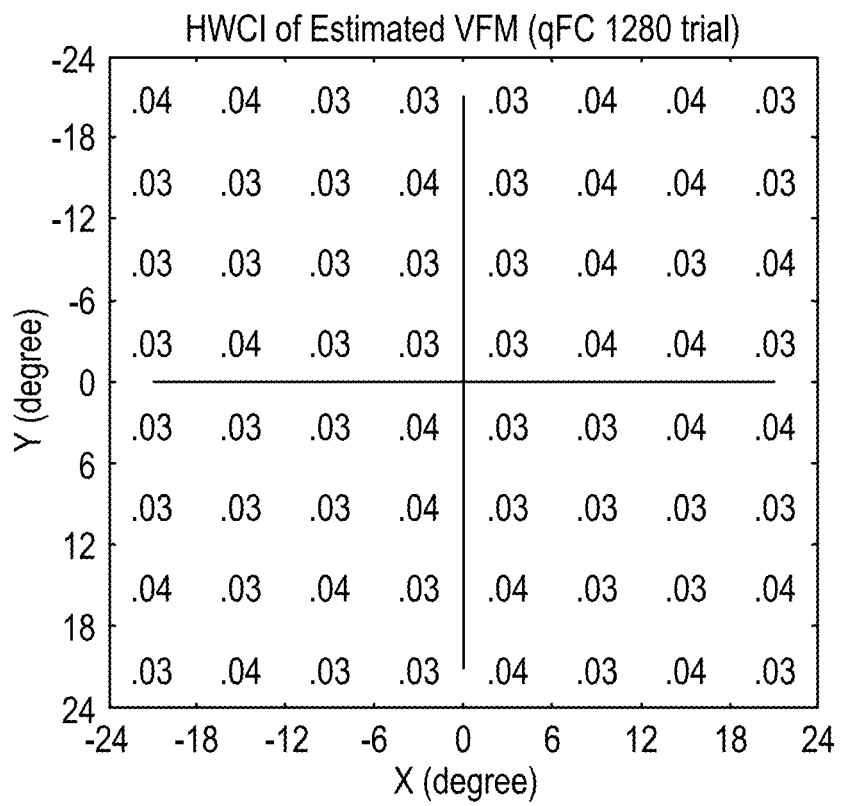
Figure 15K:
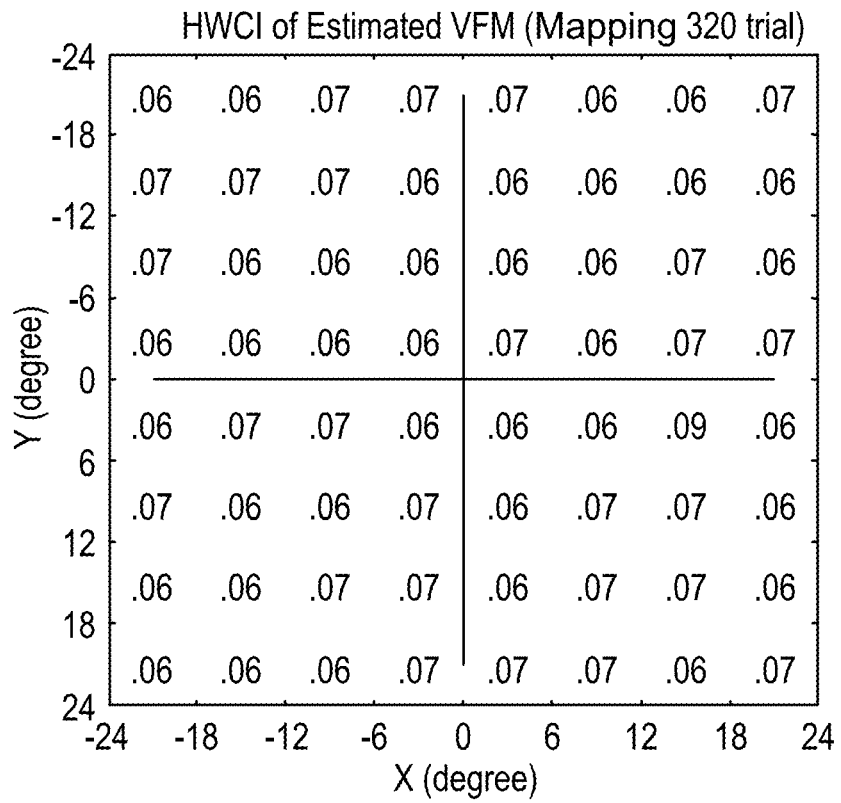
Figure 15L:
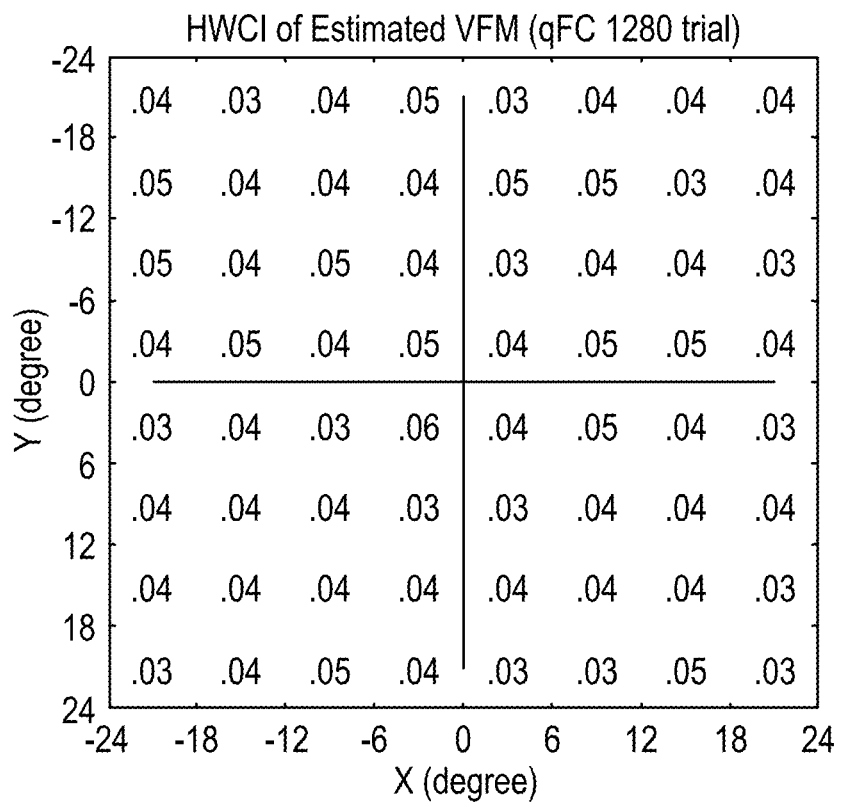
Figure 15M:
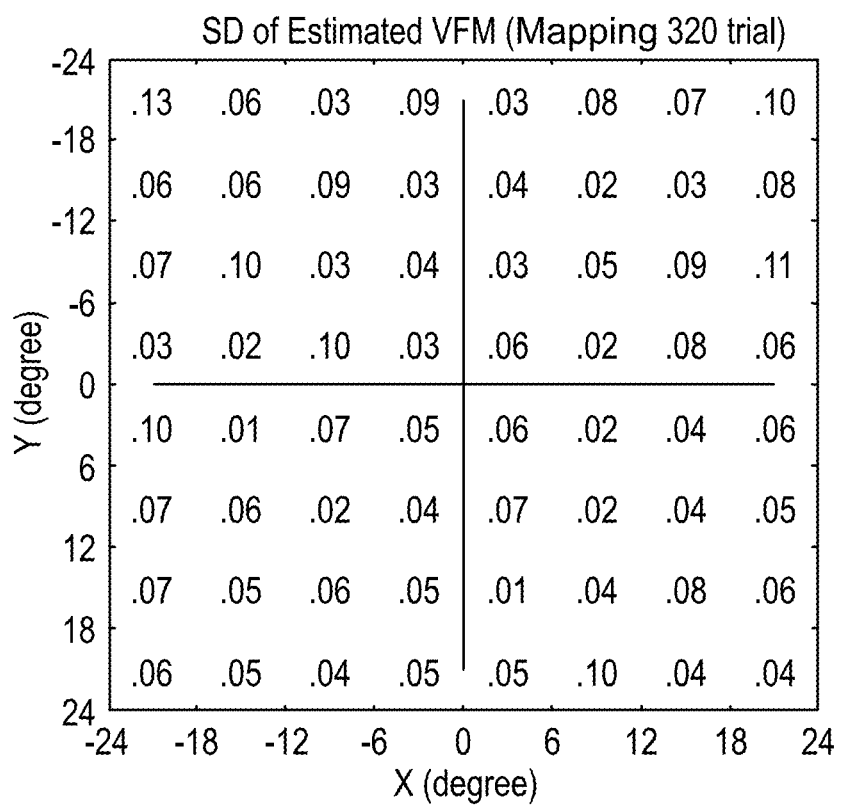
Figure 15N:
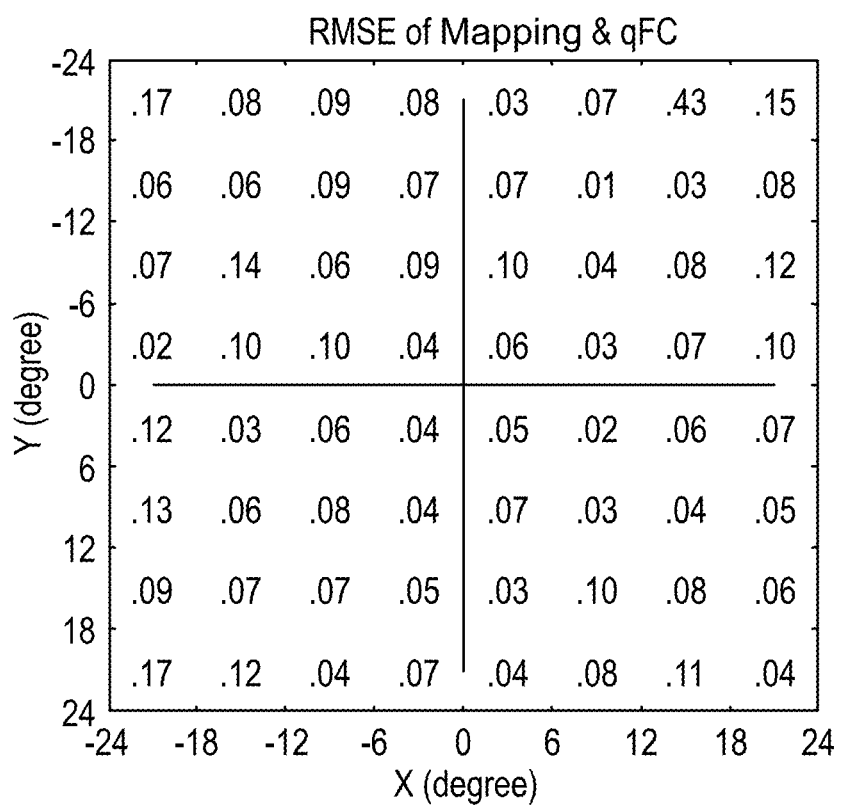
Figure 15O:
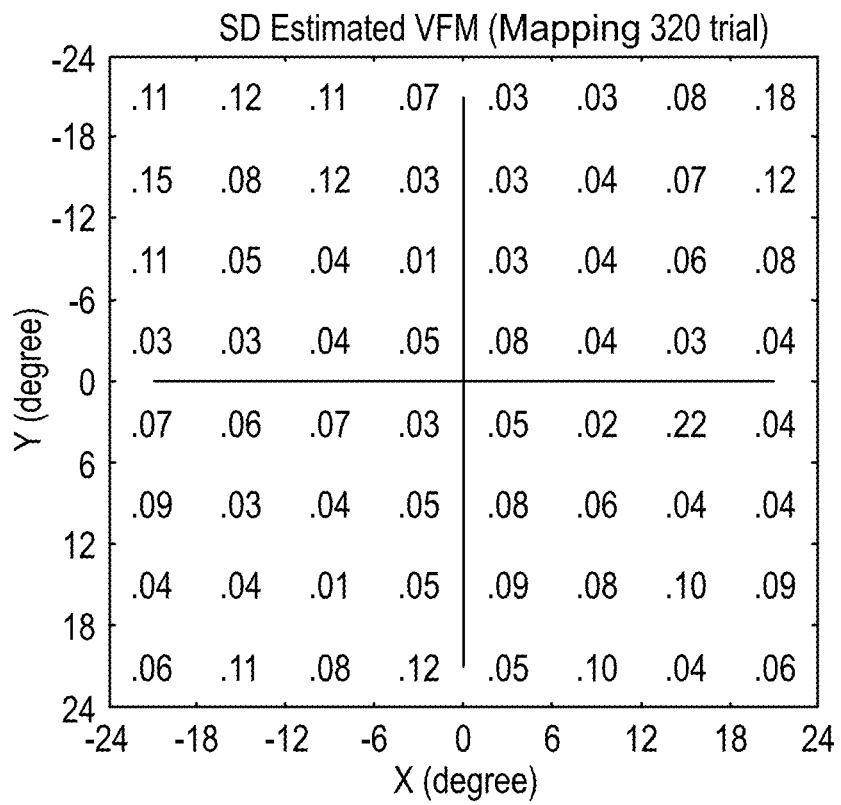
Figure 15P:
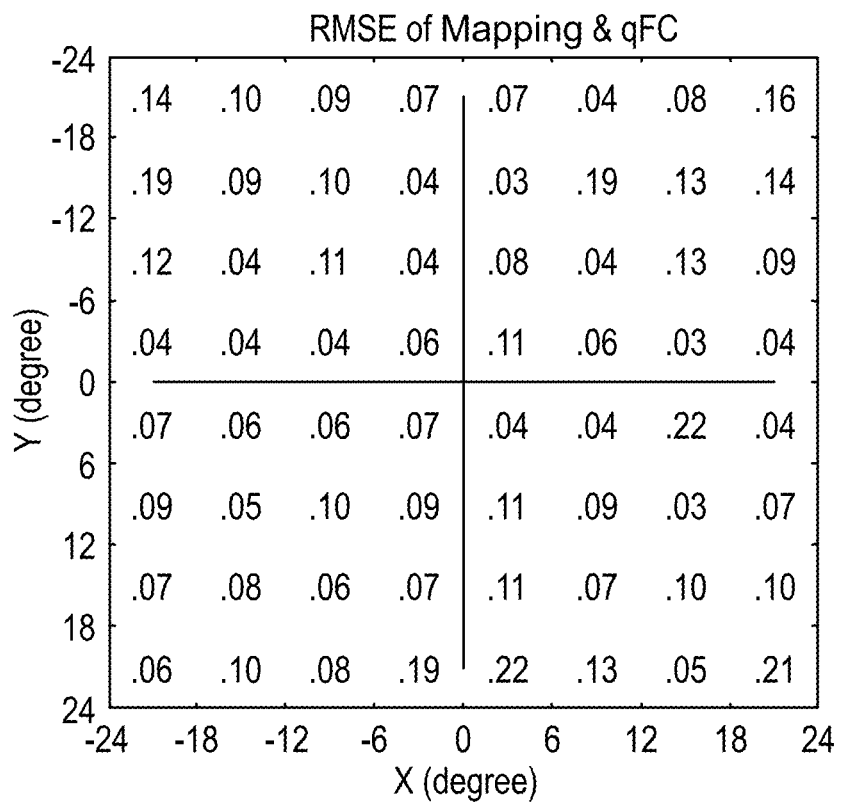
Figure 16A:
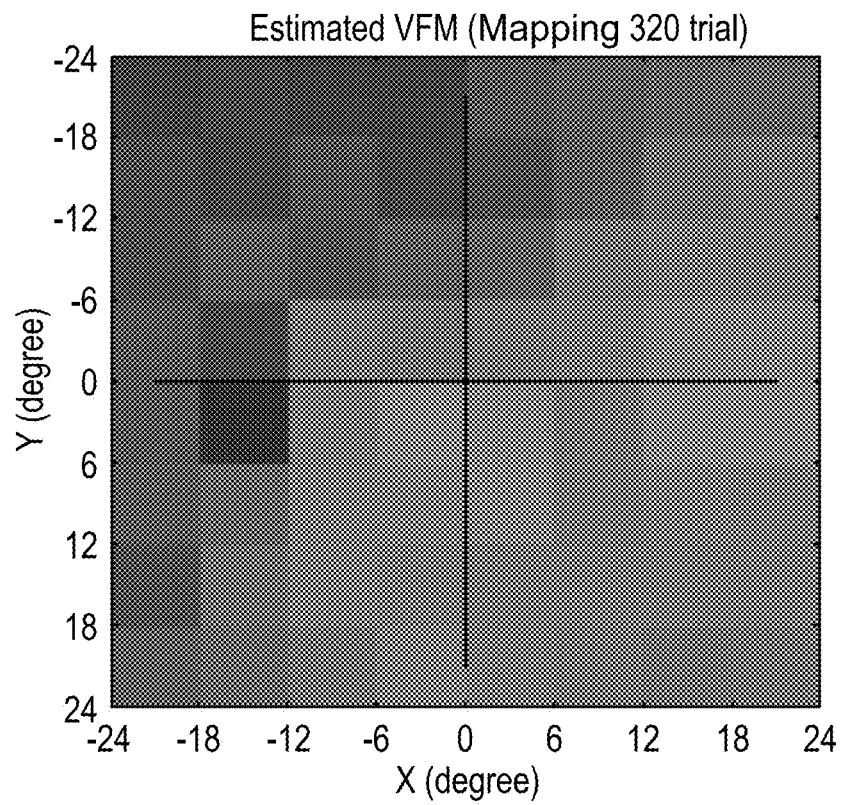
FIGS. 16A-P illustrate exemplary estimated the contrast sensitivity. VFMs for subject 2 (8 eyes) generated by a method, for example, as depicted in FIG. 3, and a Bayesian YN method for measuring visual function maps.
Figure 16B:
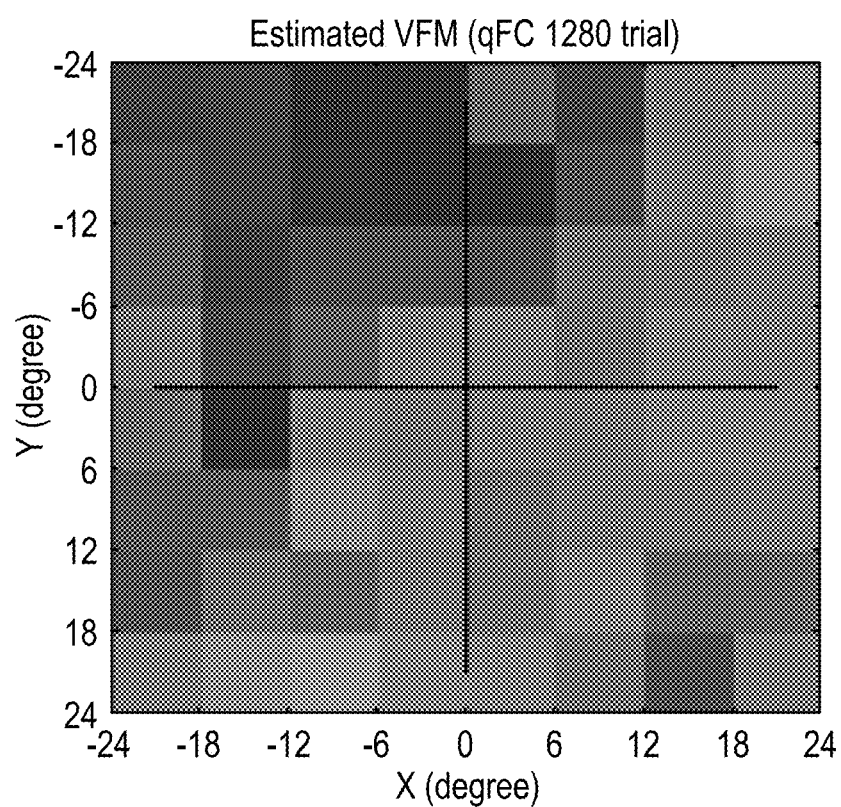
Figure 16C:
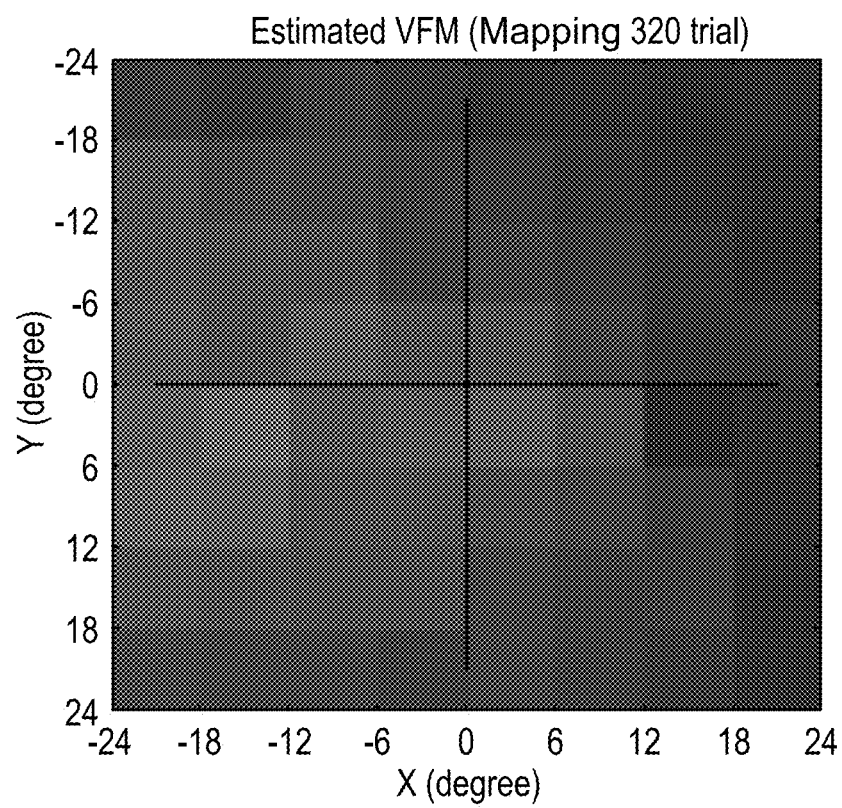
Figure 16D:
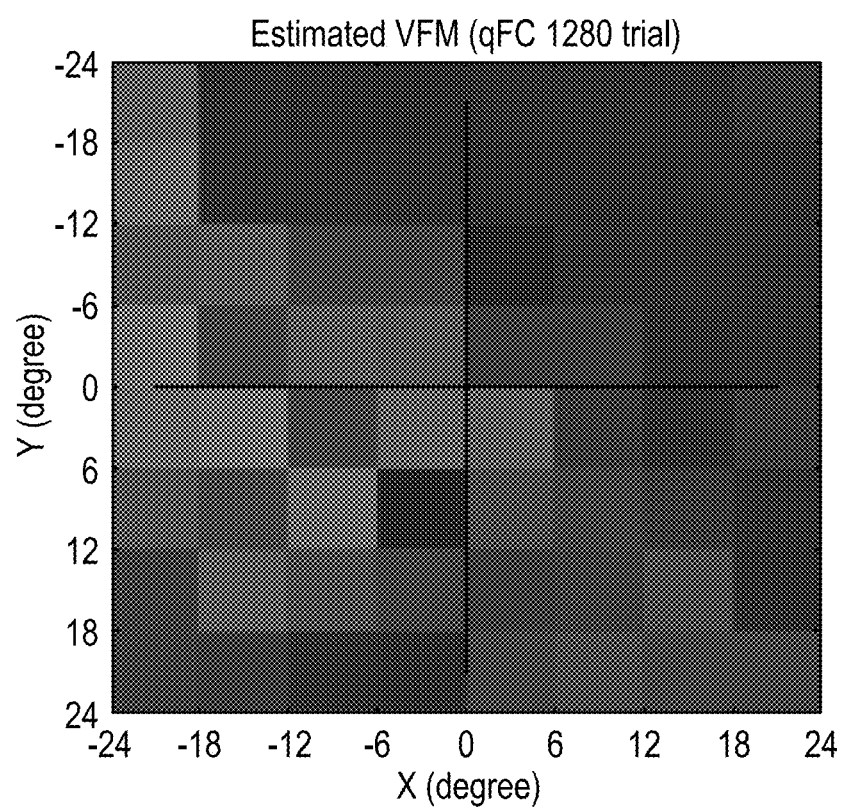
Figure 16E:
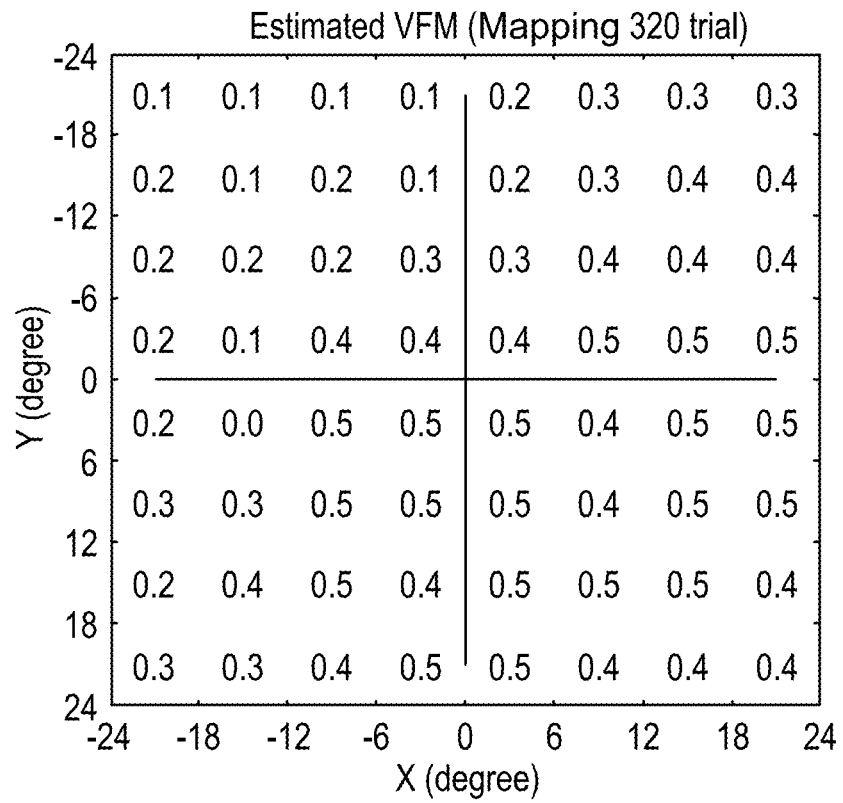
Figure 16F:
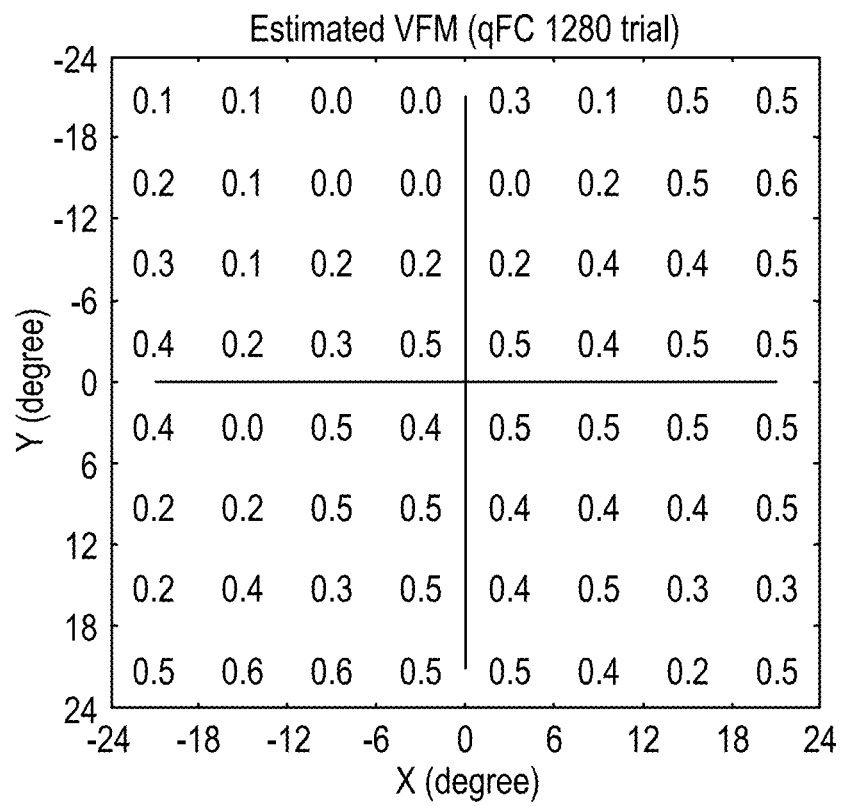
Figure 16G:
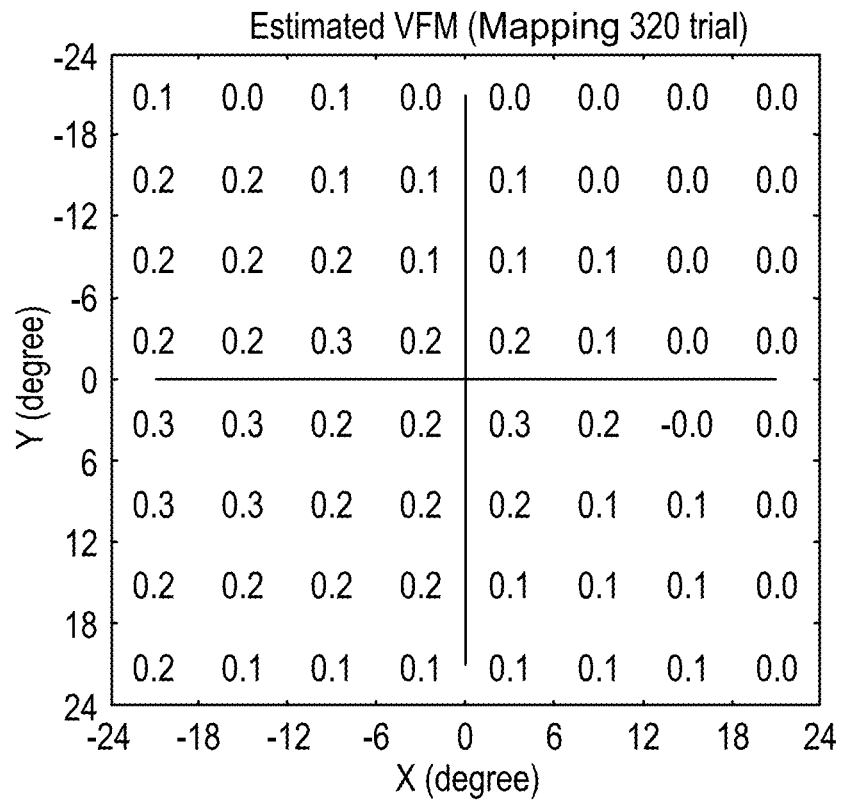
Figure 16H:
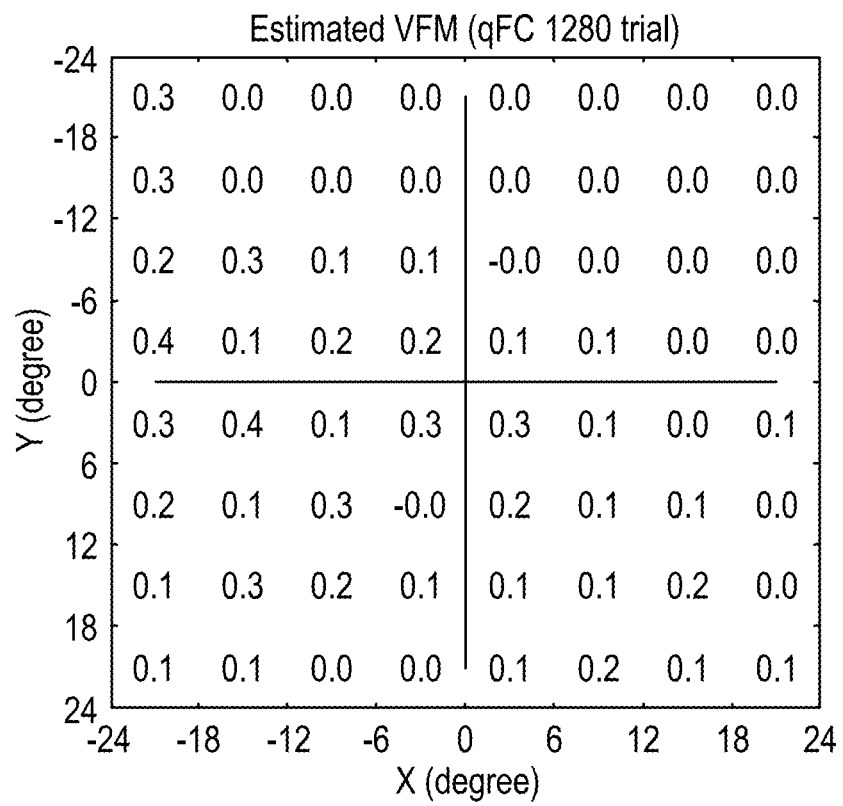
Figure 16I:
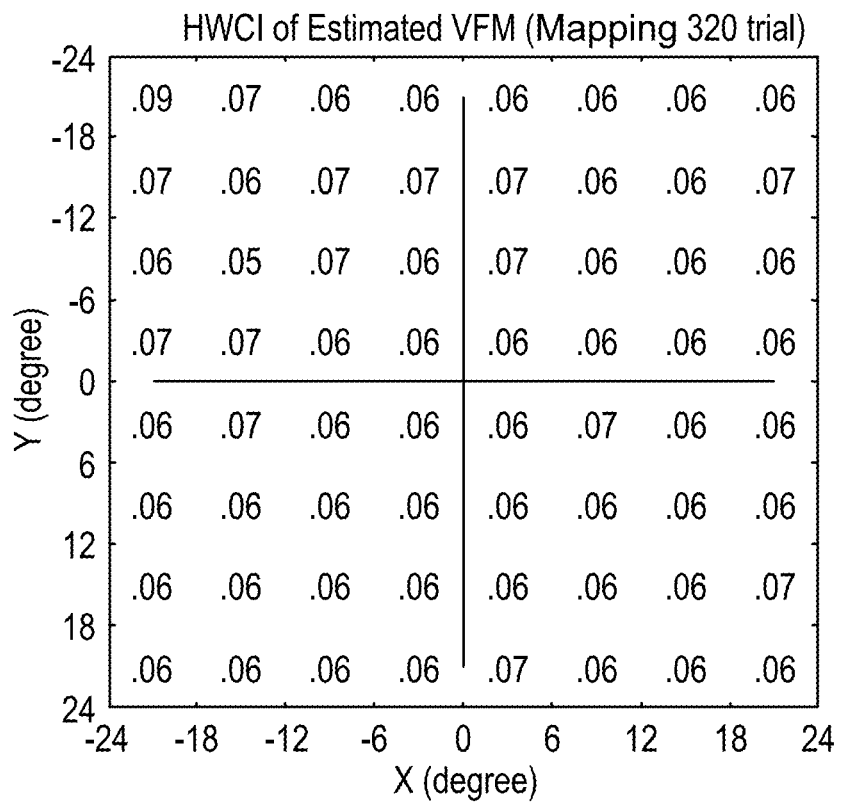
Figure 16J:
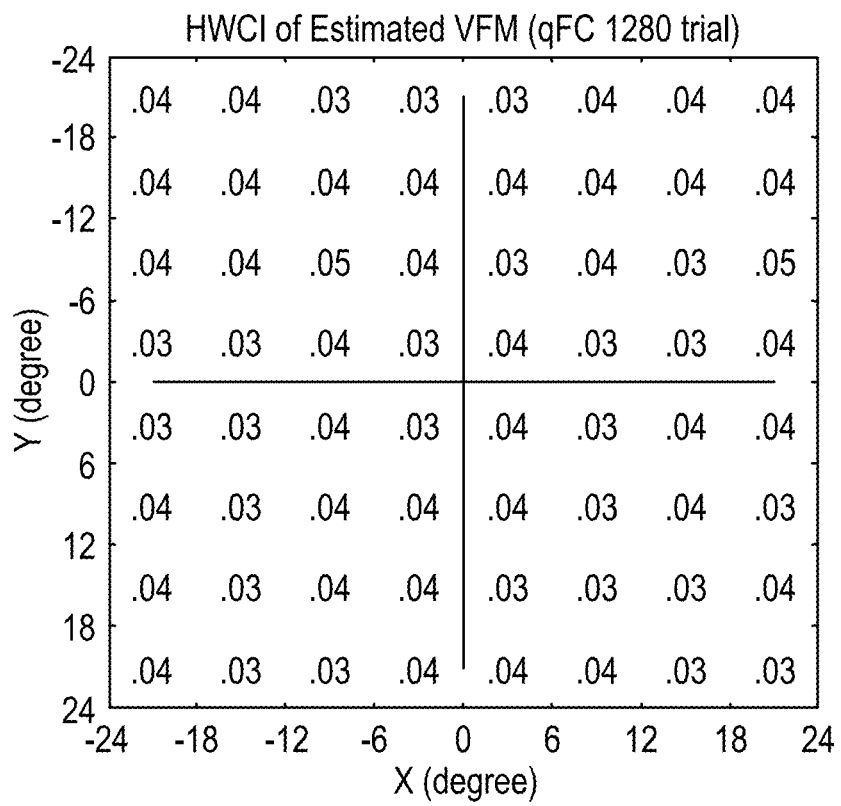
Figure 16K:
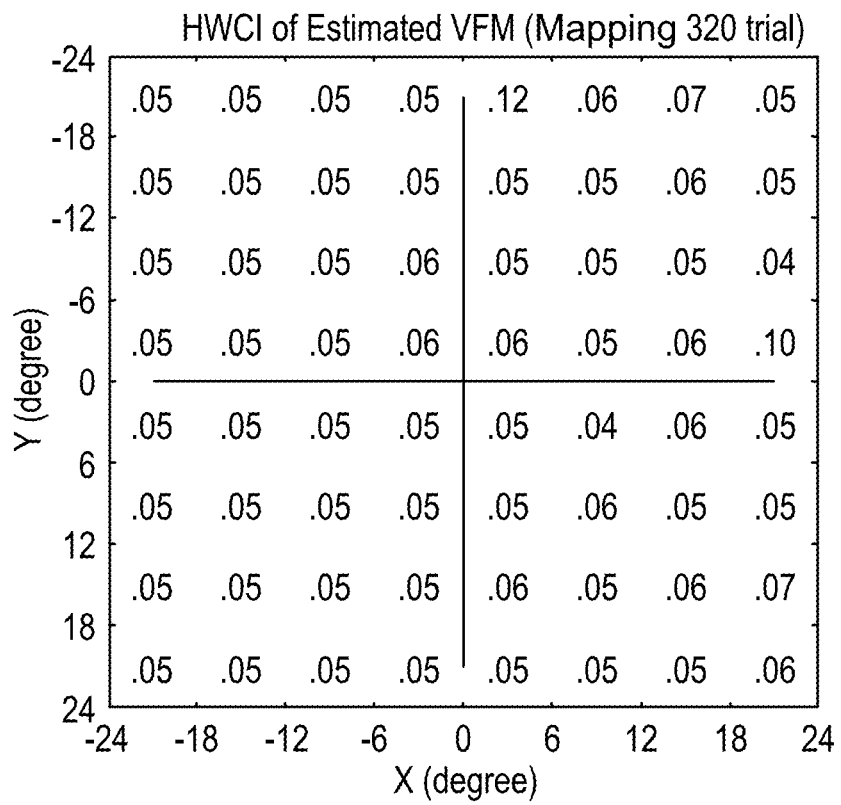
Figure 16L:
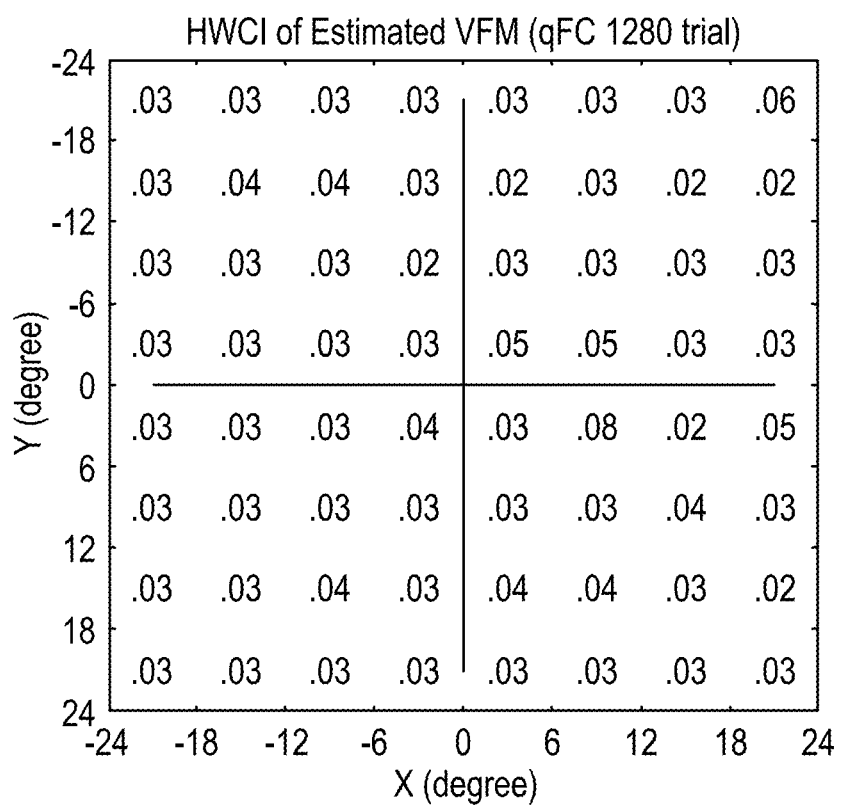
Figure 16M:
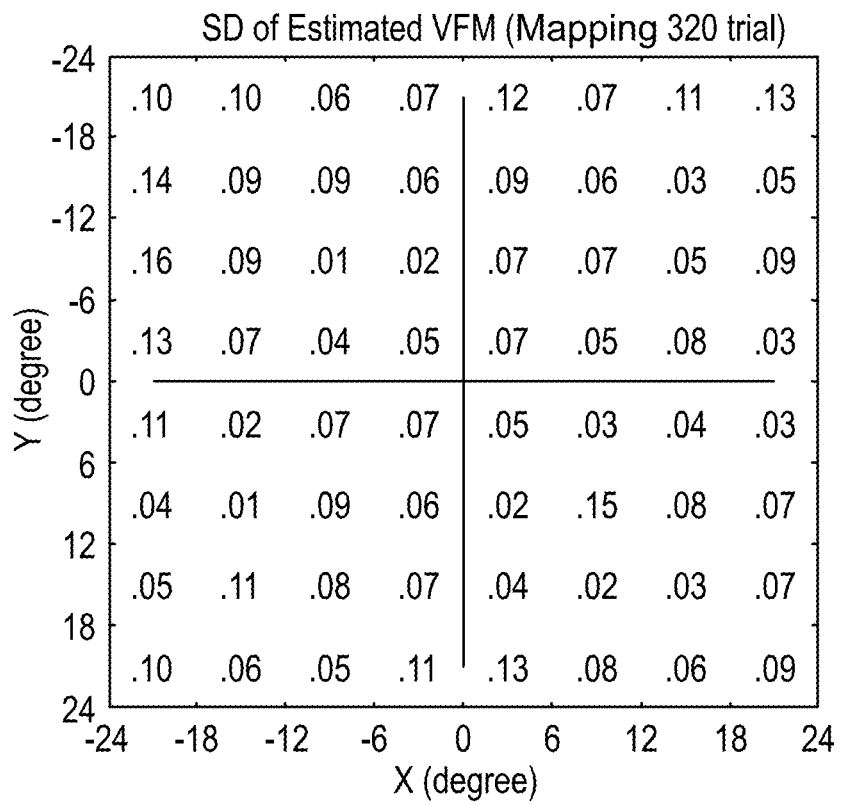
Figure 16N:
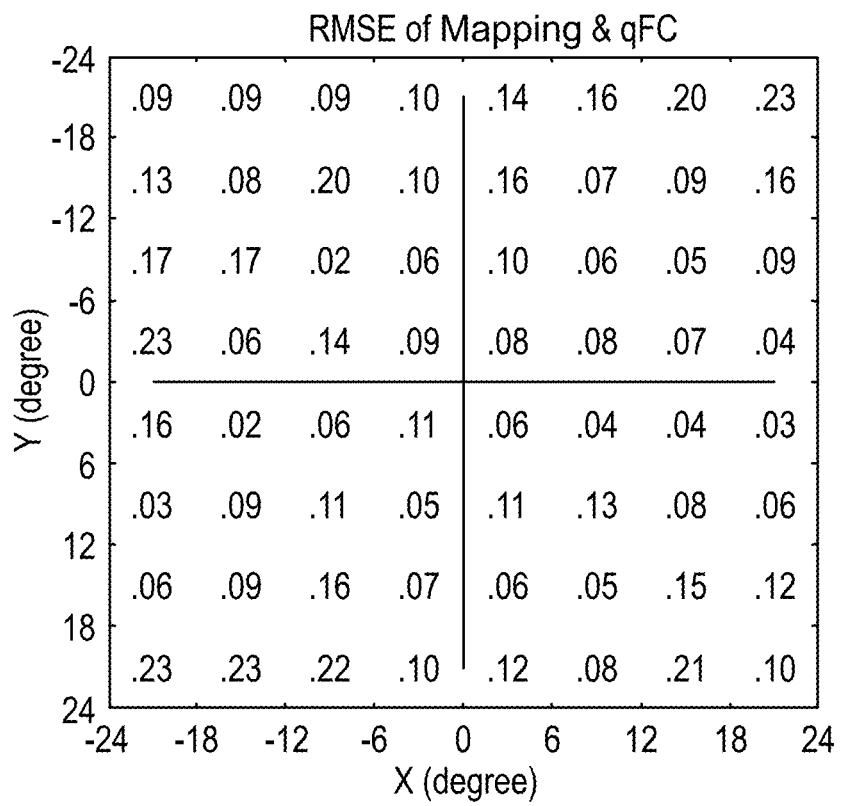
Figure 16O:
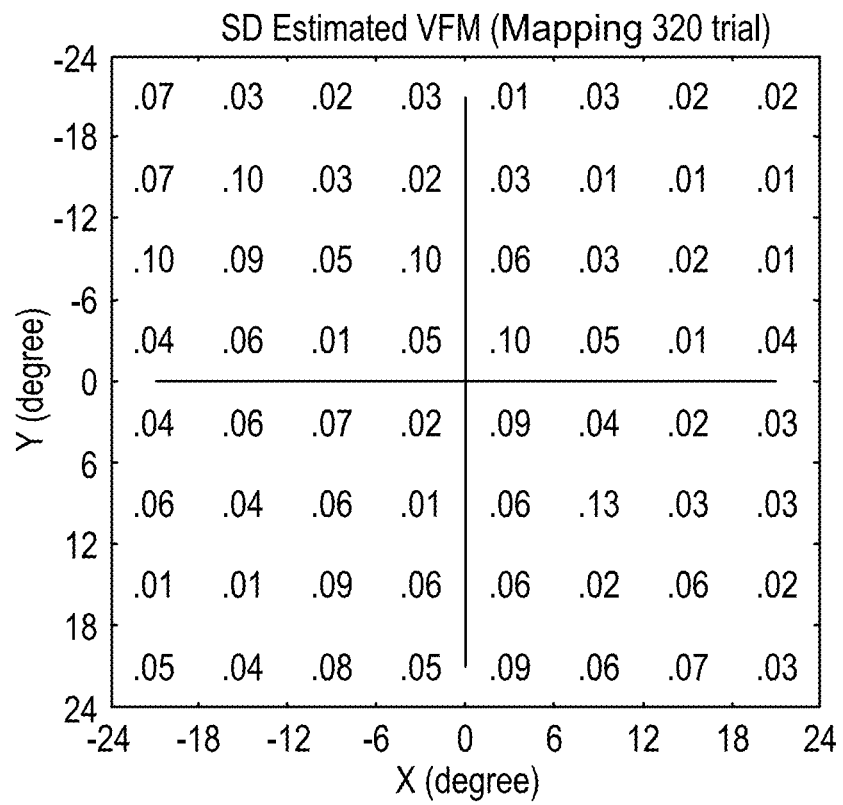
Figure 16P:
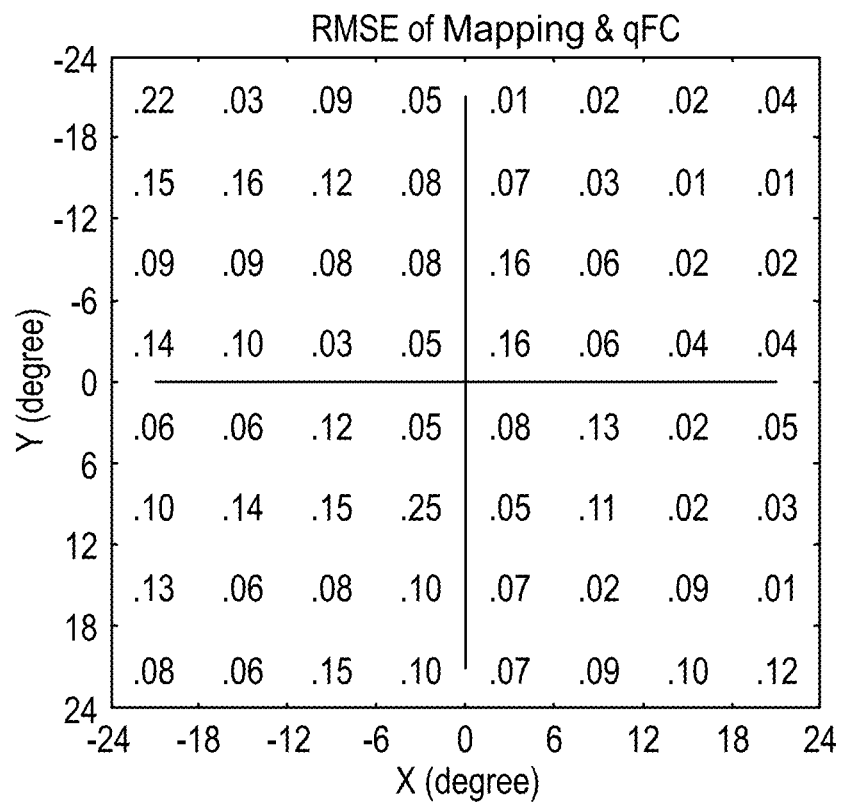
Figure 17A:
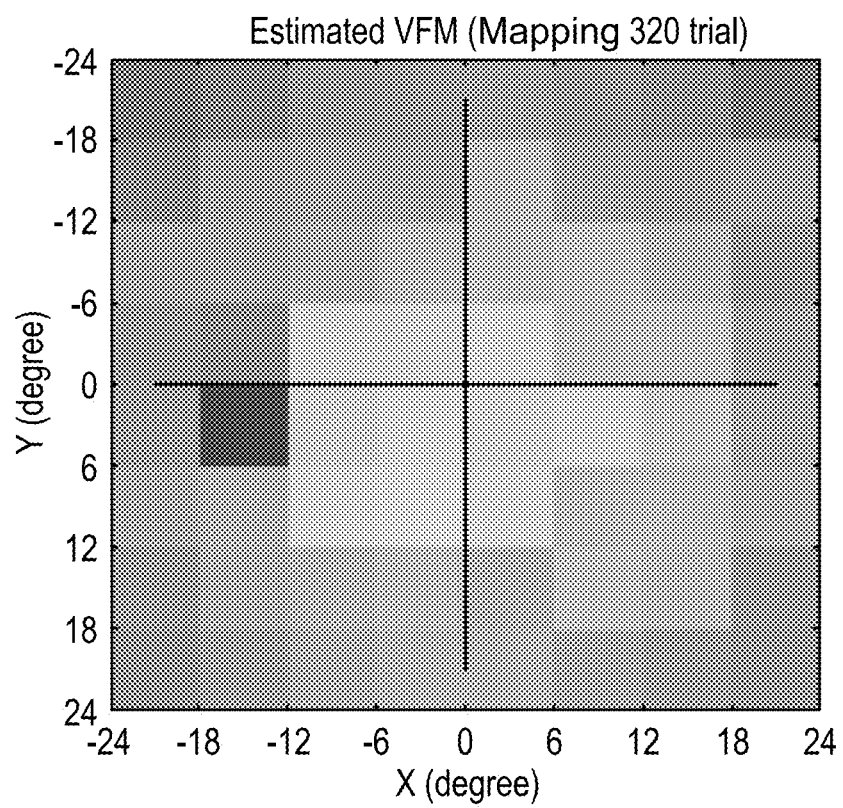
FIGS. 17A-P illustrate exemplary estimated the contrast sensitivity VFMs for subject 3 (8 eyes) generated by a method, for example, as depicted in FIG. 3, and a Bayesian YN method for measuring visual function maps.
Figure 17B:
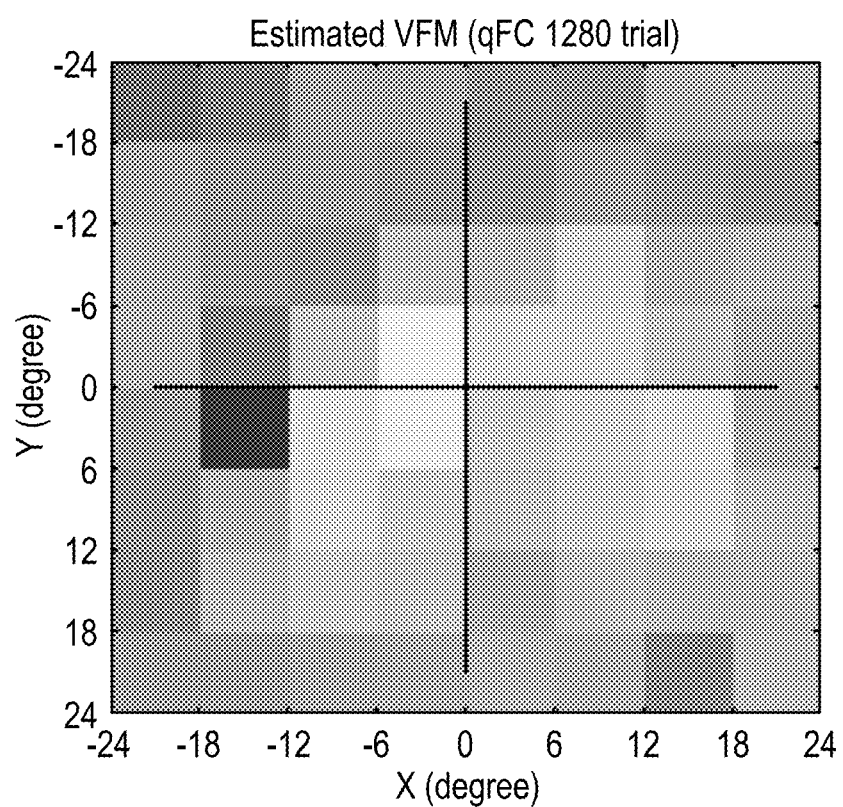
Figure 17C:
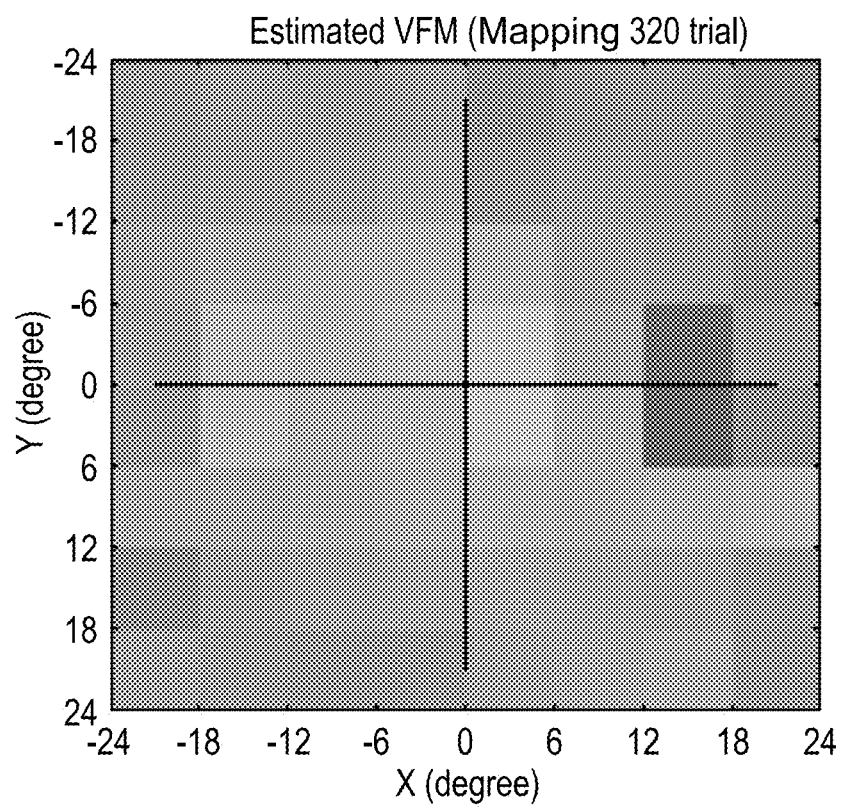
Figure 17D:
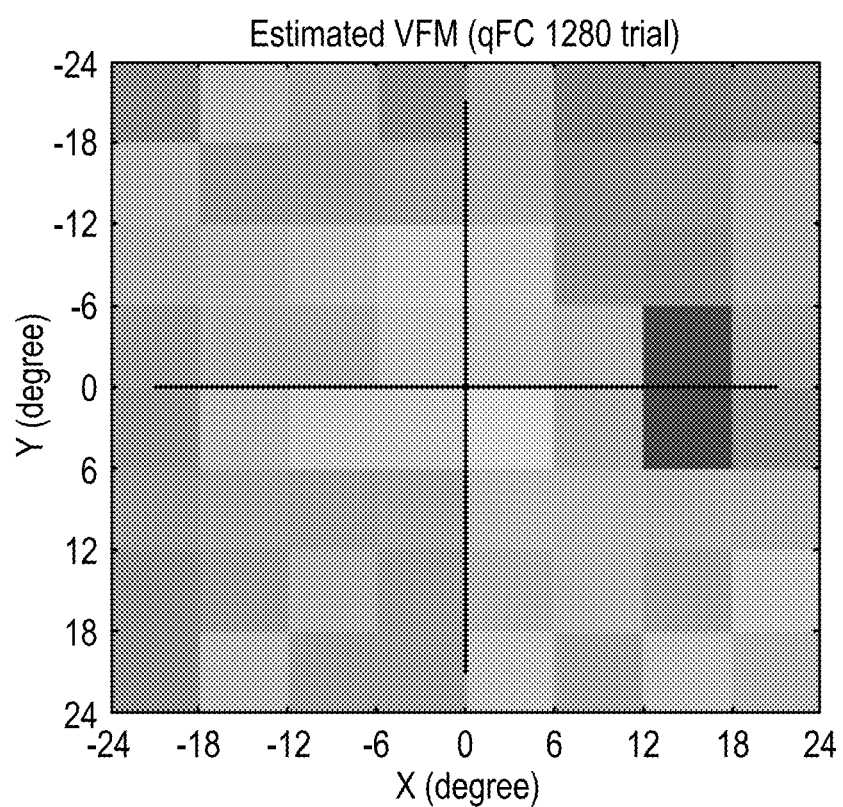
Figure 17E:
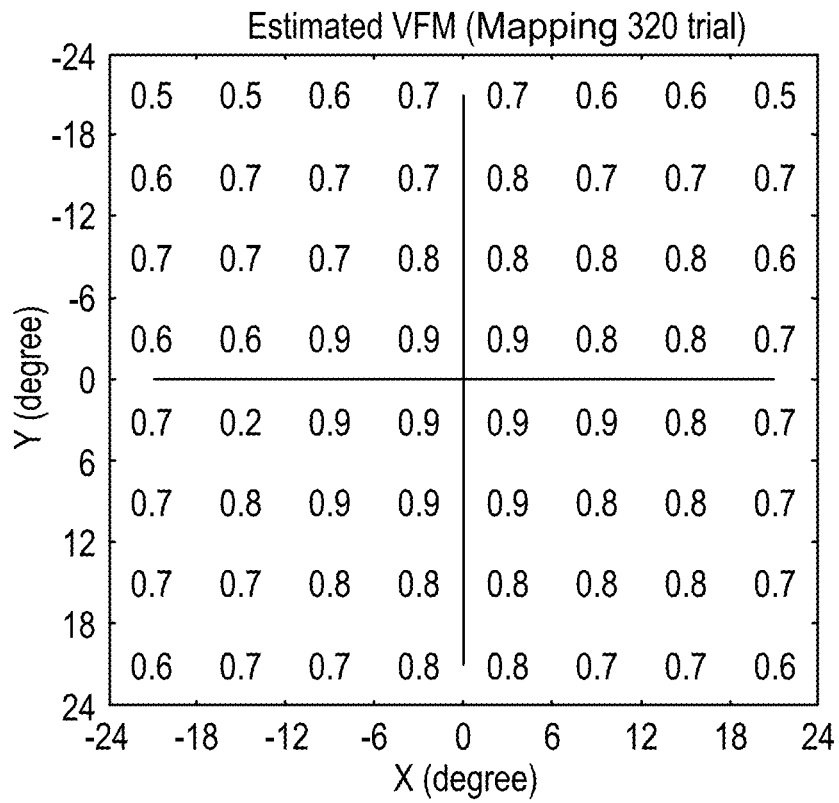
Figure 17F:
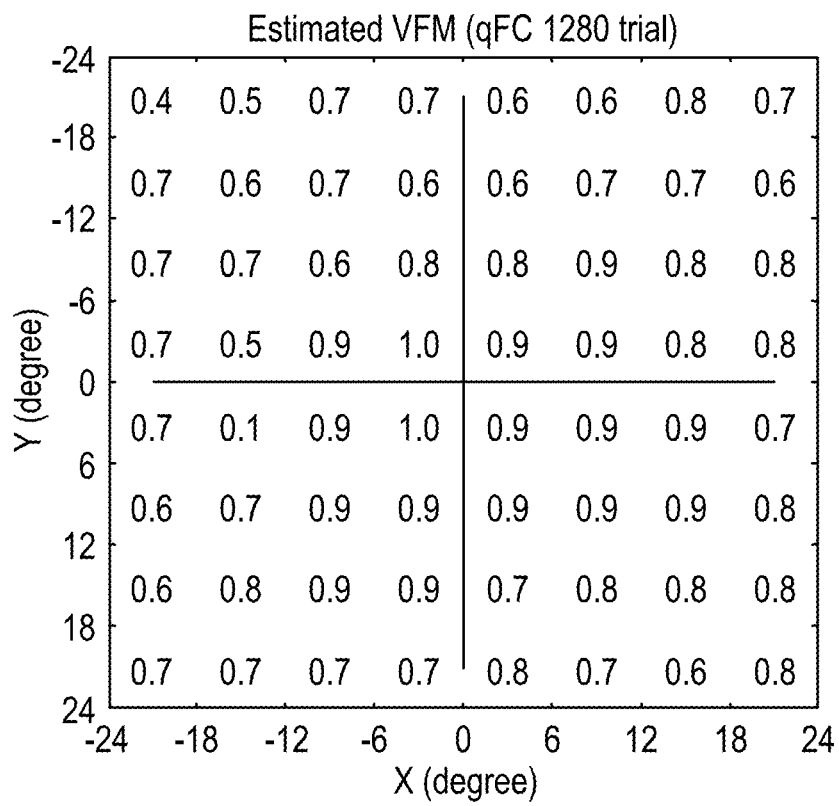
Figure 17G:
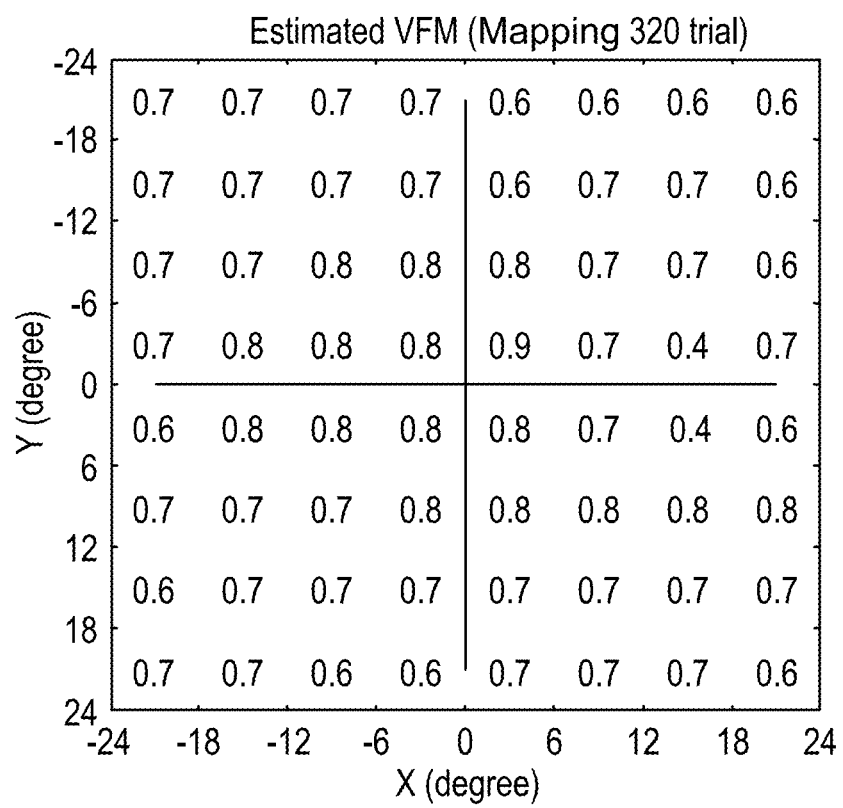
Figure 17H:
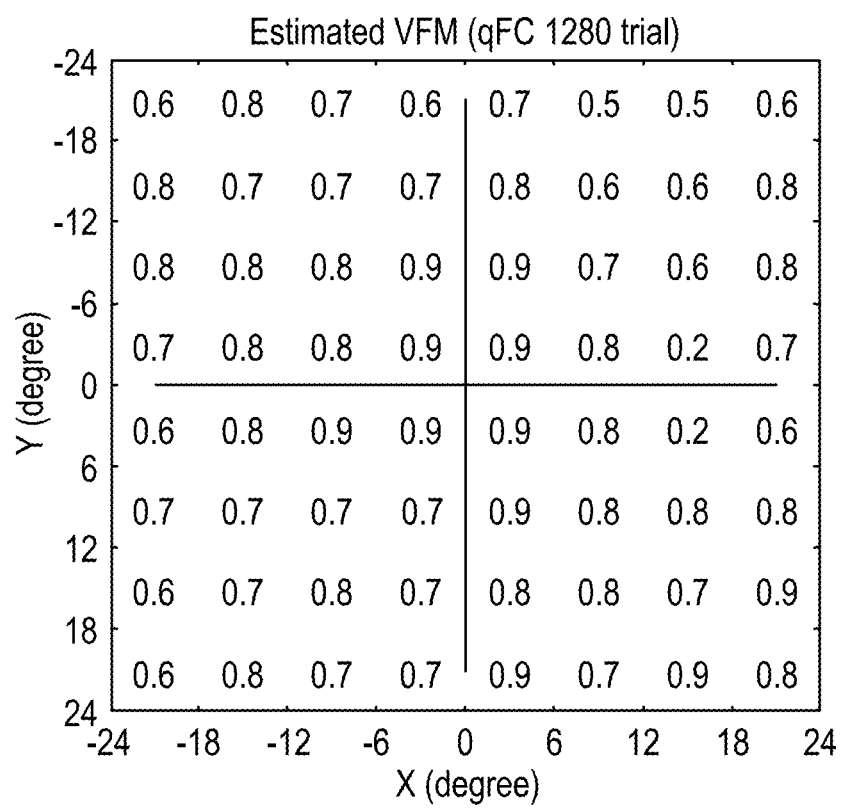
Figure 17I:
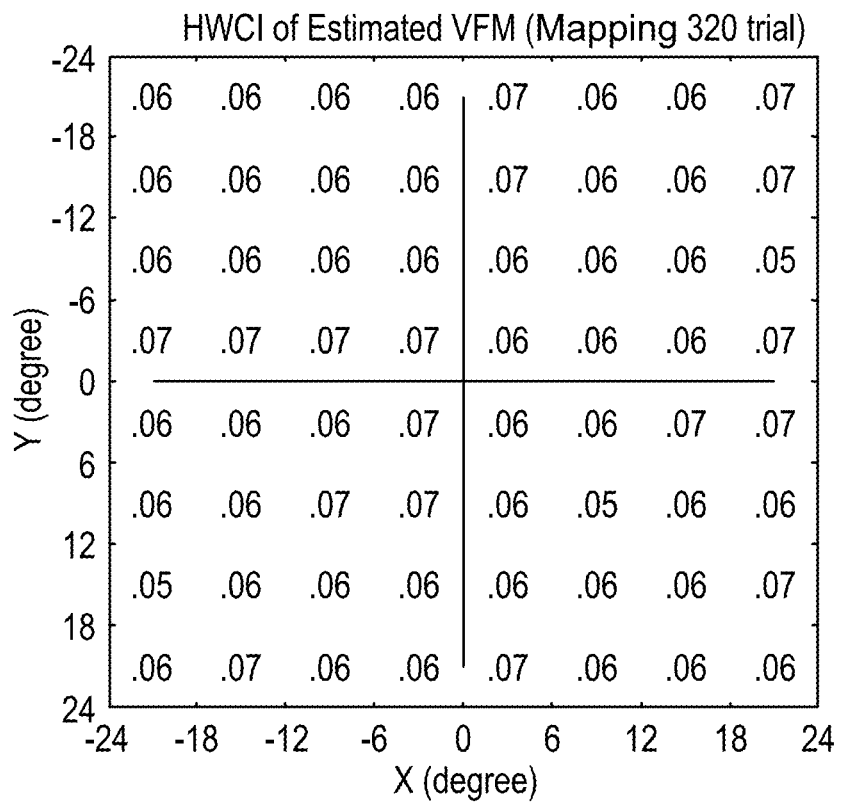
Figure 17J:
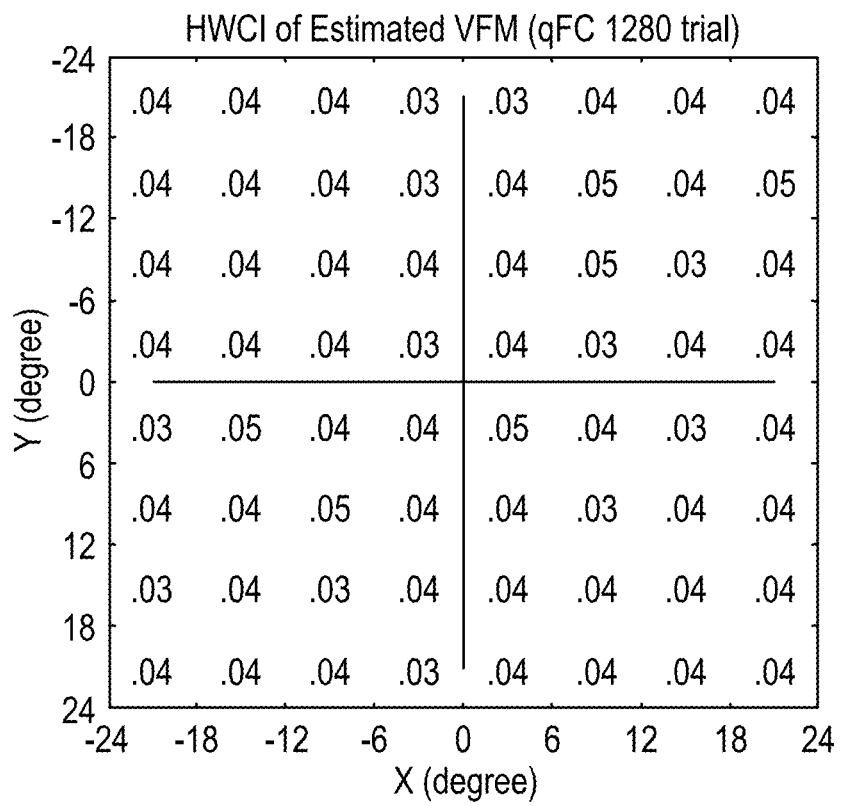
Figure 17K:
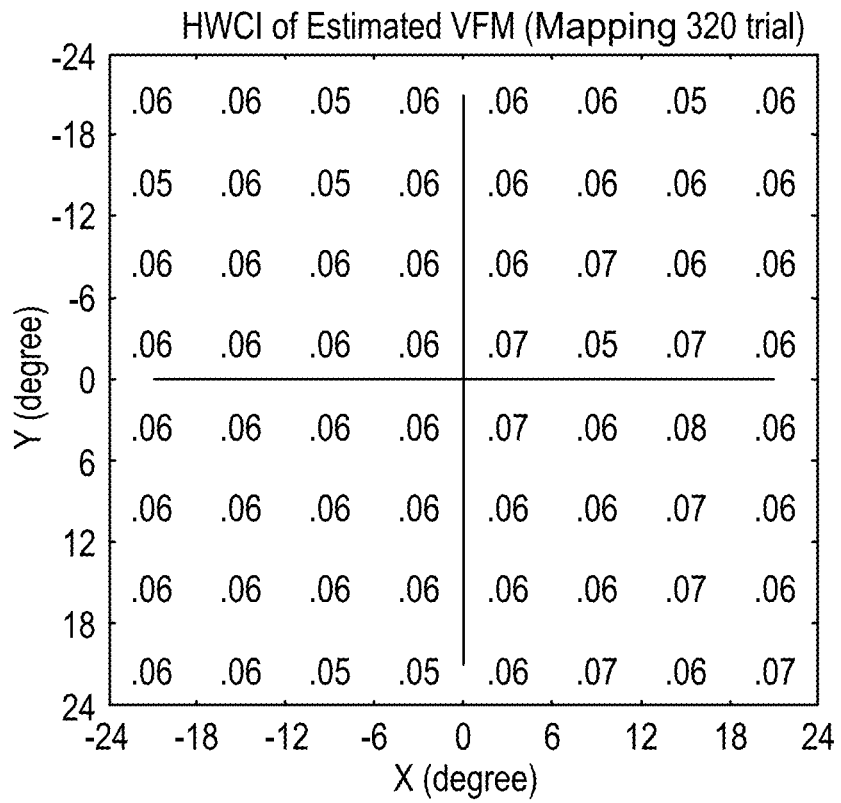
Figure 17L:
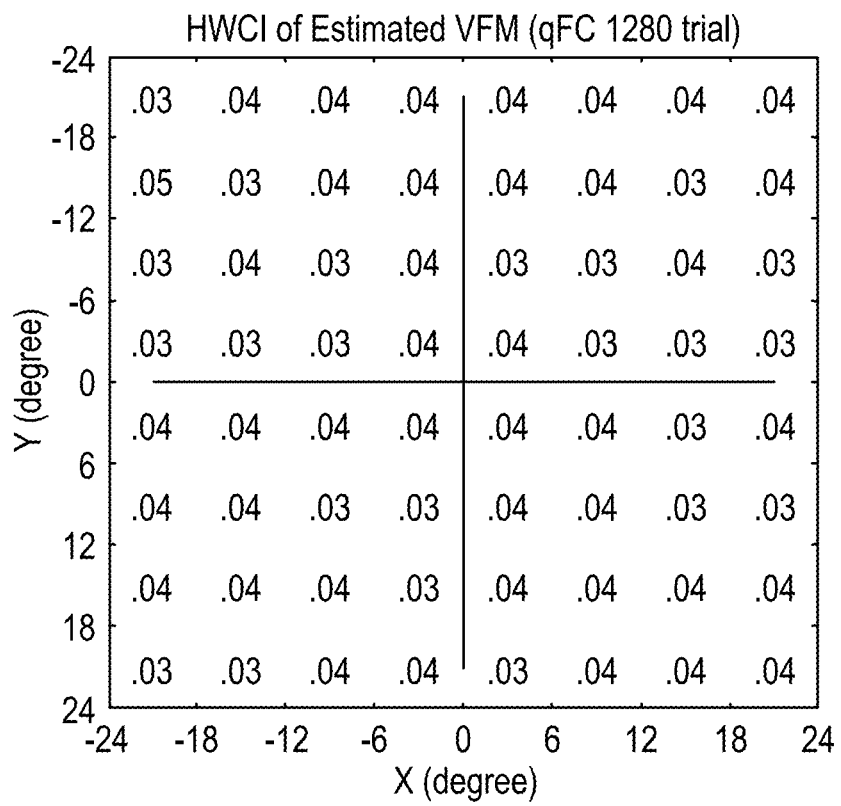
Figure 17M:
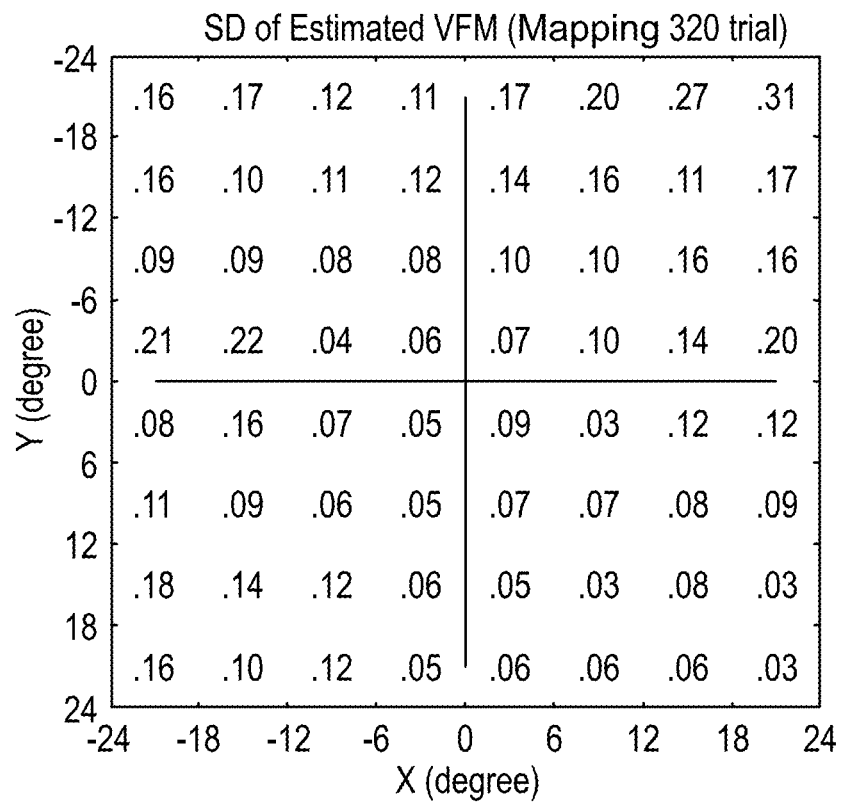
Figure 17N:
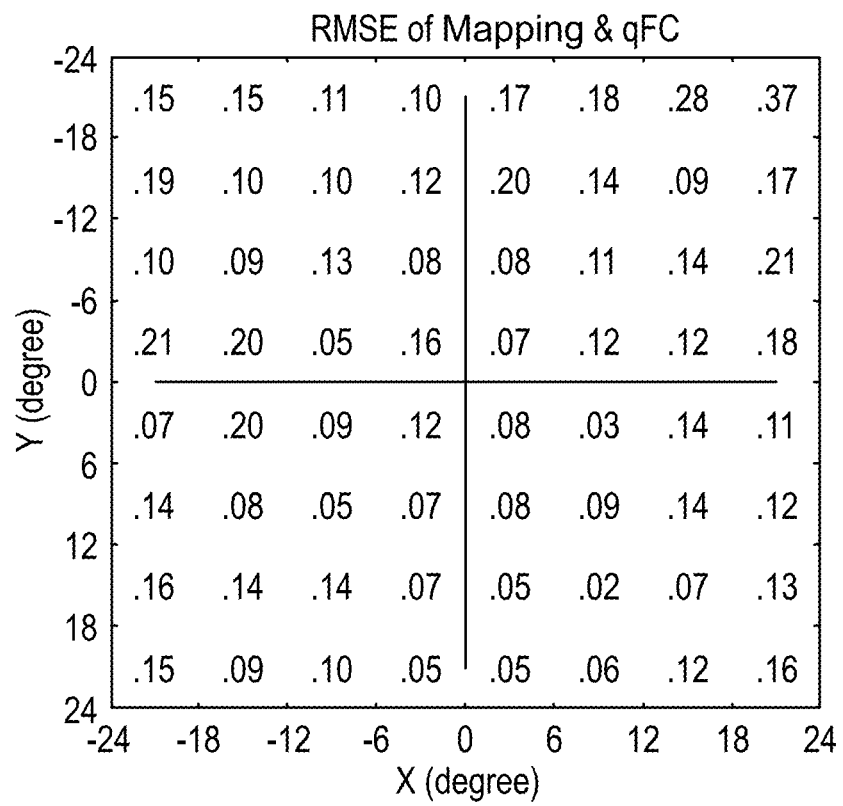
Figure 17O:
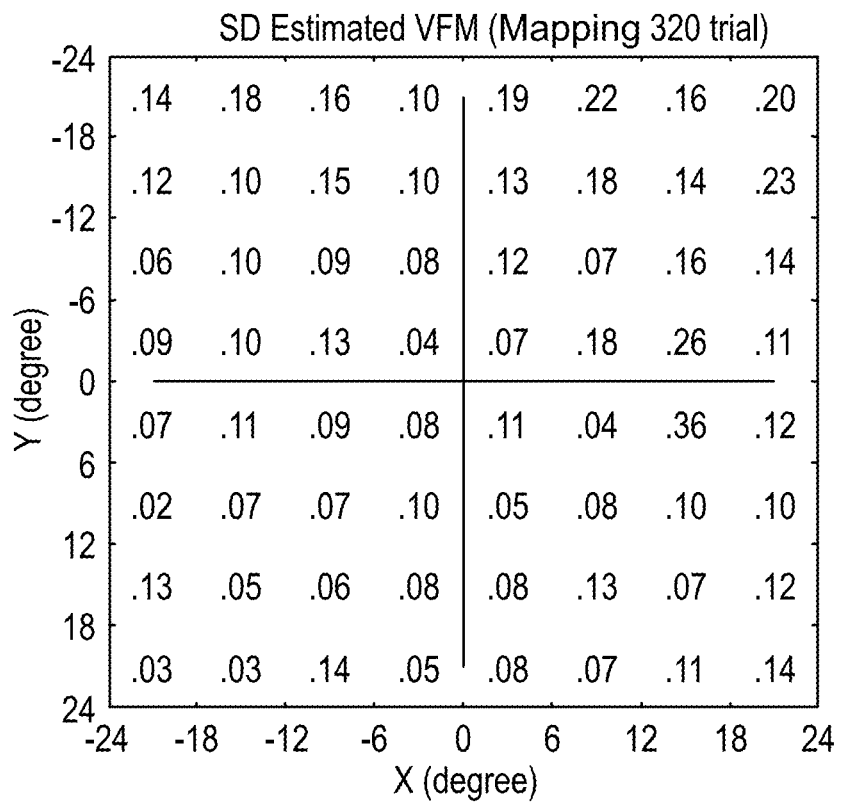
Figure 17P:
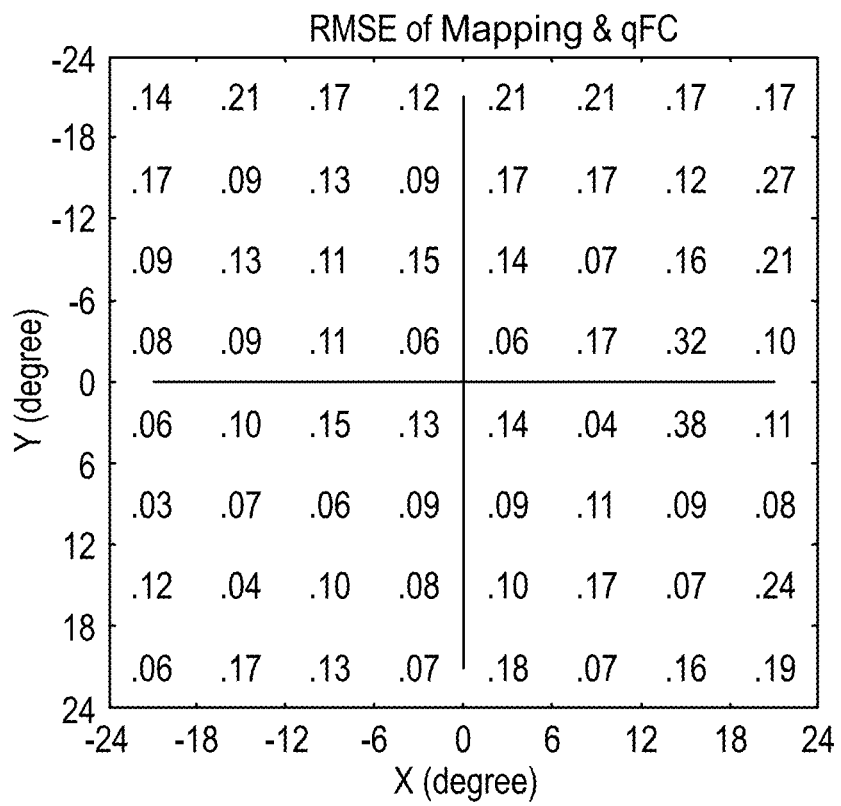
Figure 18A:
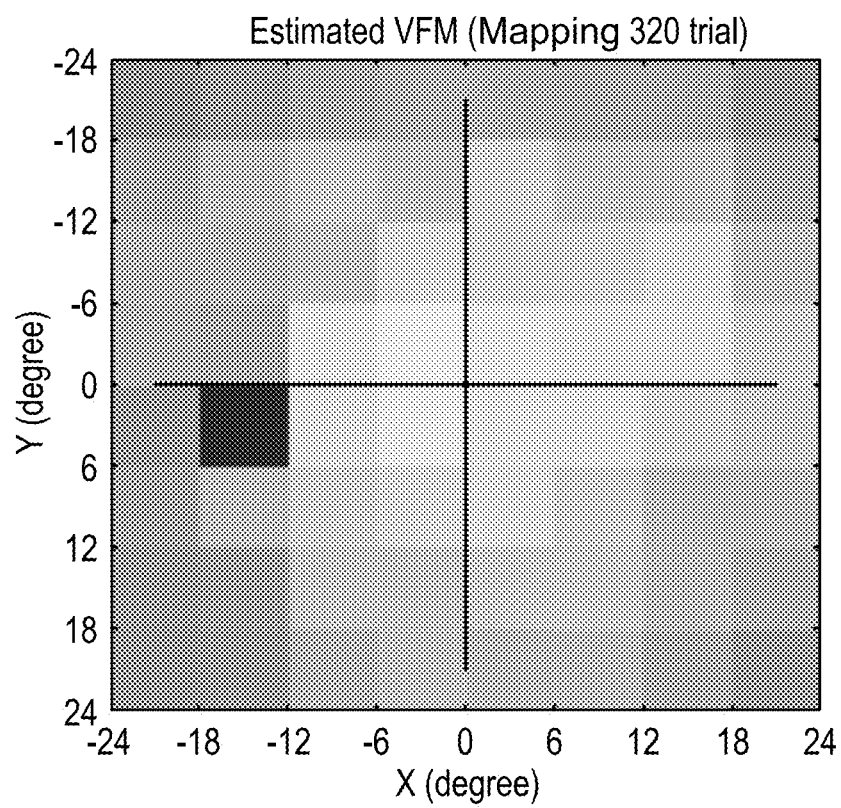
FIGS. 18A-P illustrate exemplary estimated the contrast sensitivity. VFMs for subject 4 (8 eyes) generated by a method, for example, as depicted in FIG. 3, and a Bayesian YN method for measuring visual function maps.
Figure 18B:
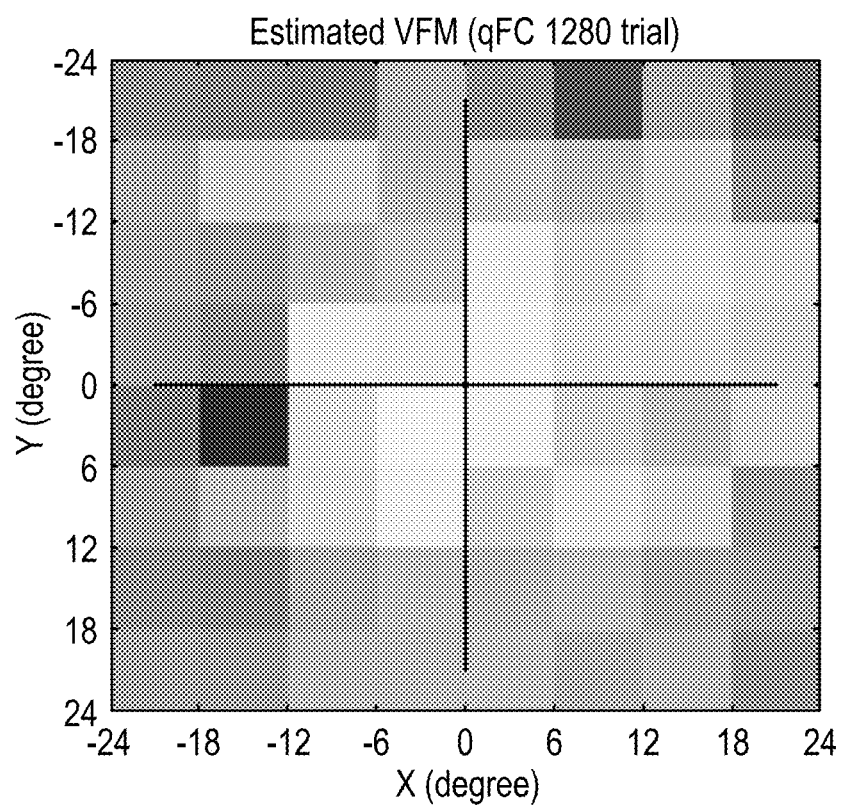
Figure 18C:
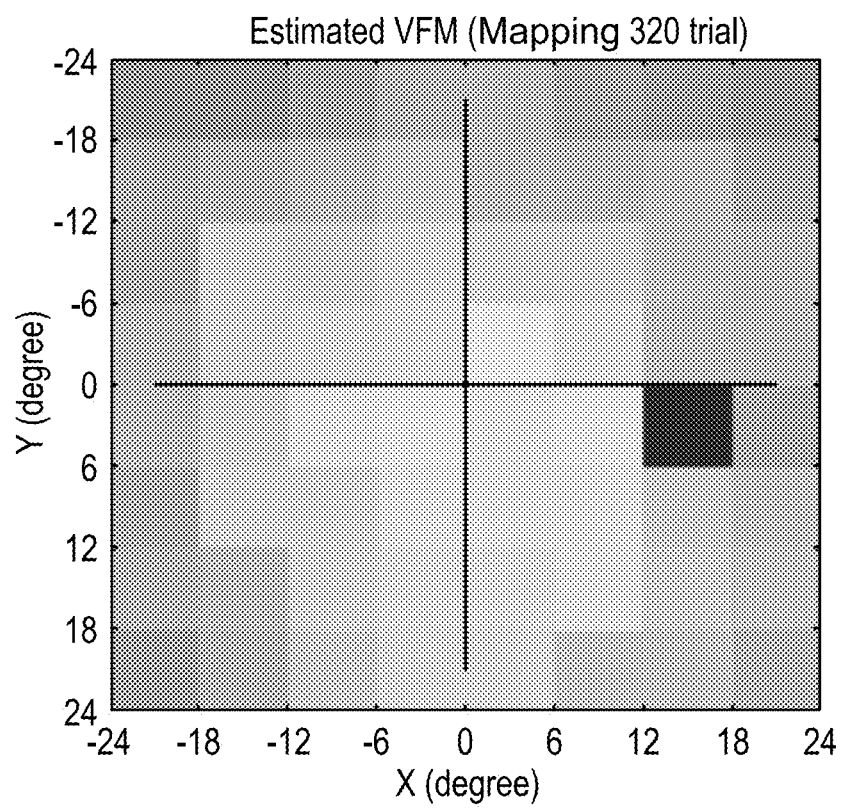
Figure 18D:
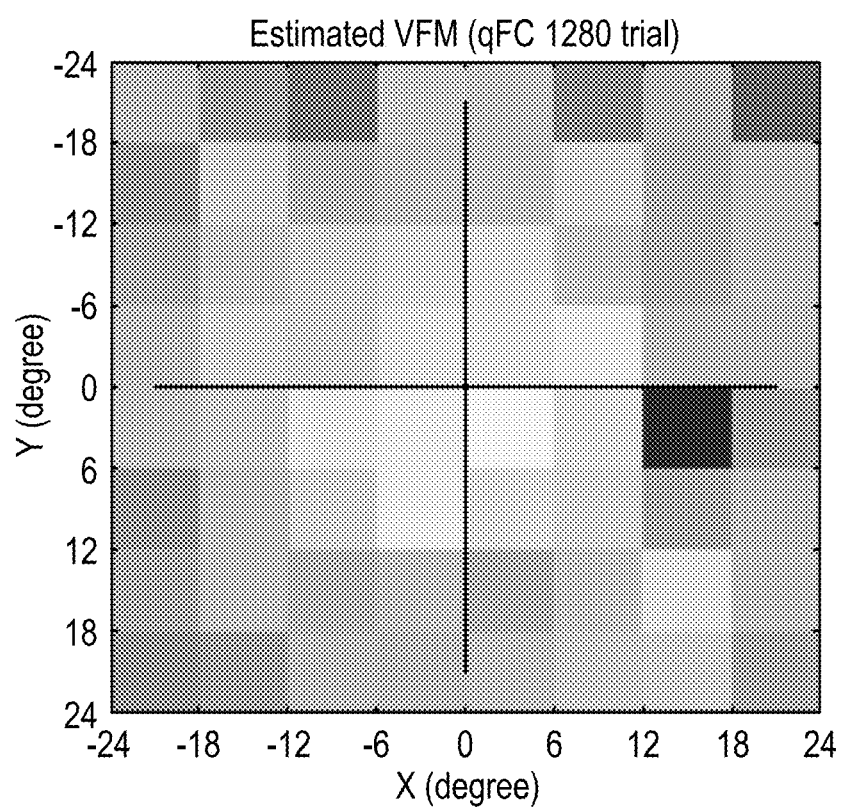
Figure 18E:
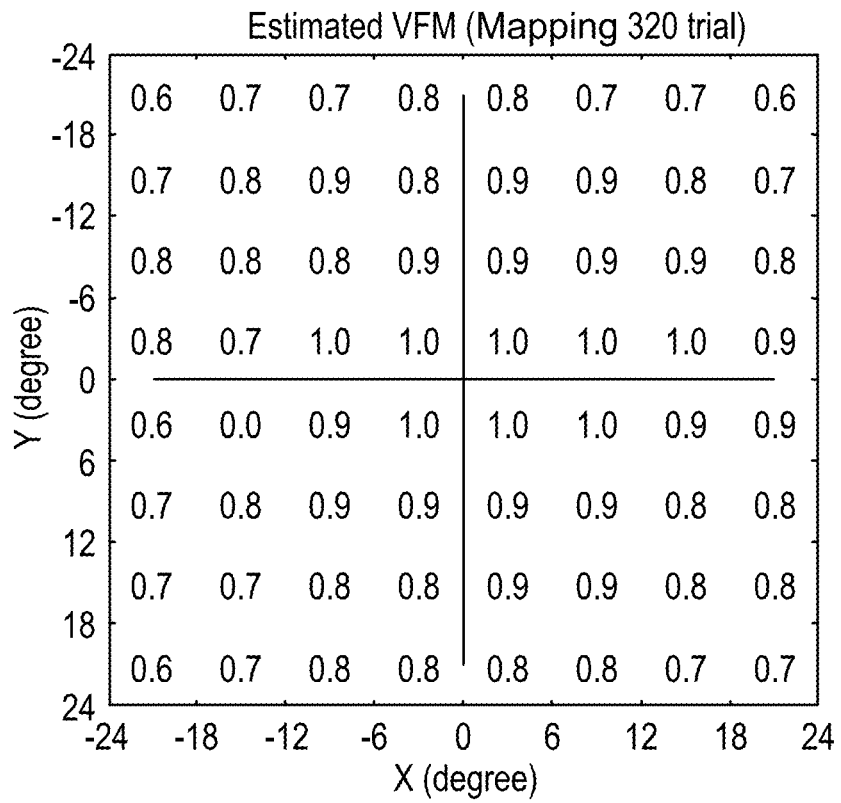
Figure 18F:
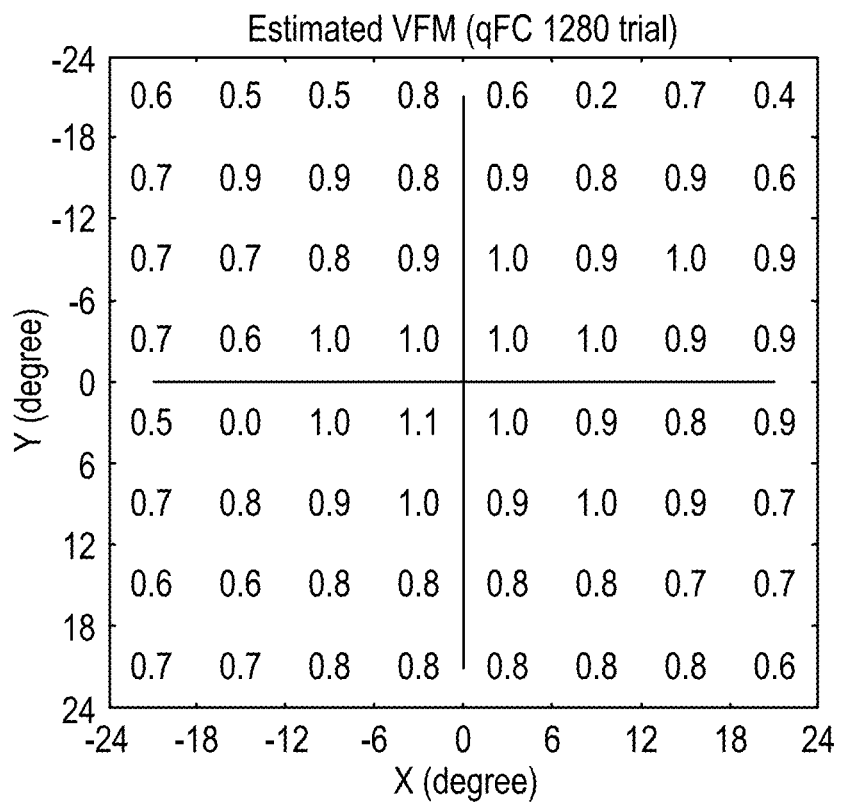
Figure 18G:
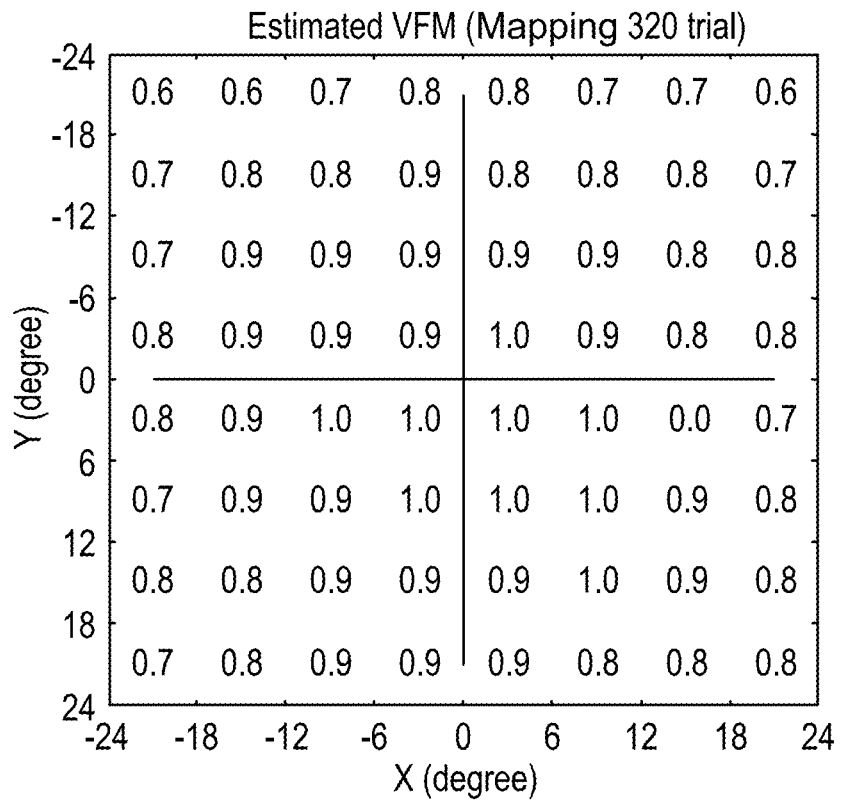
Figure 18H:
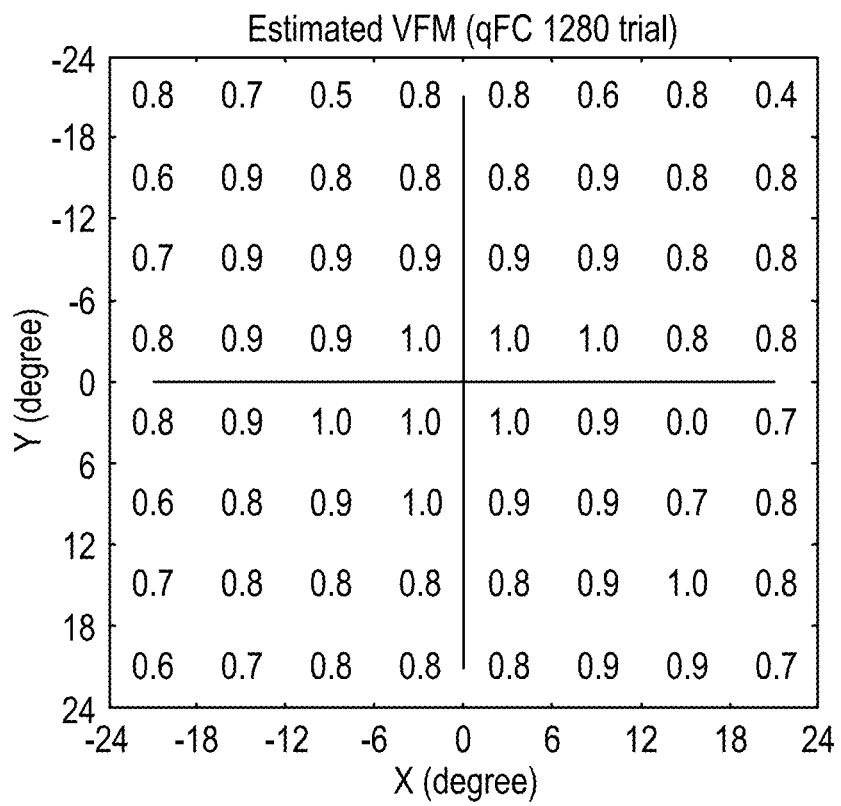
Figure 18I:
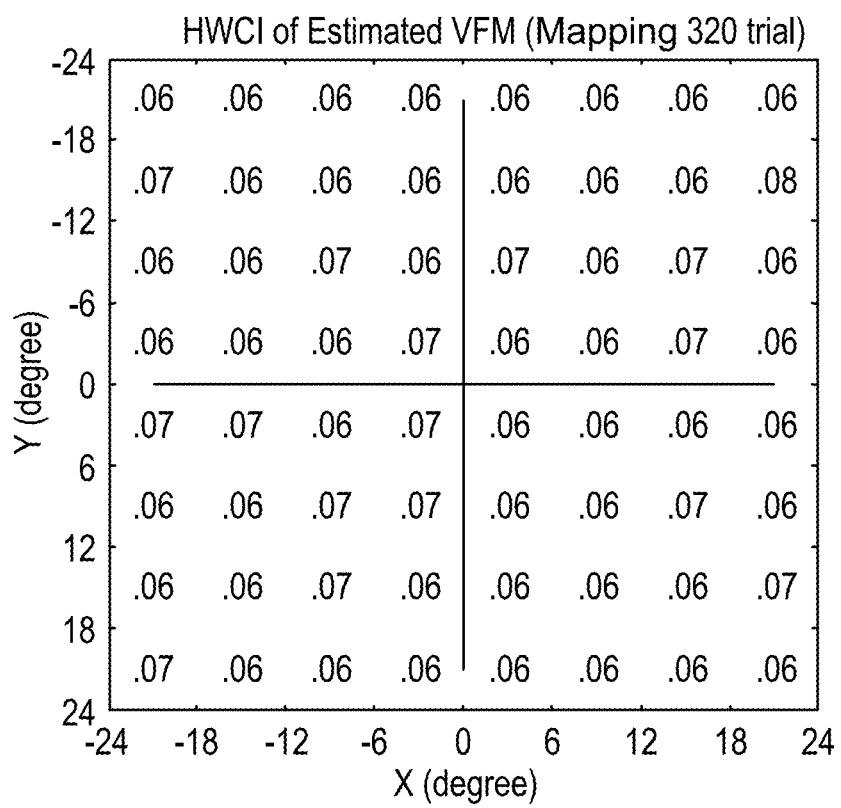
Figure 18J:
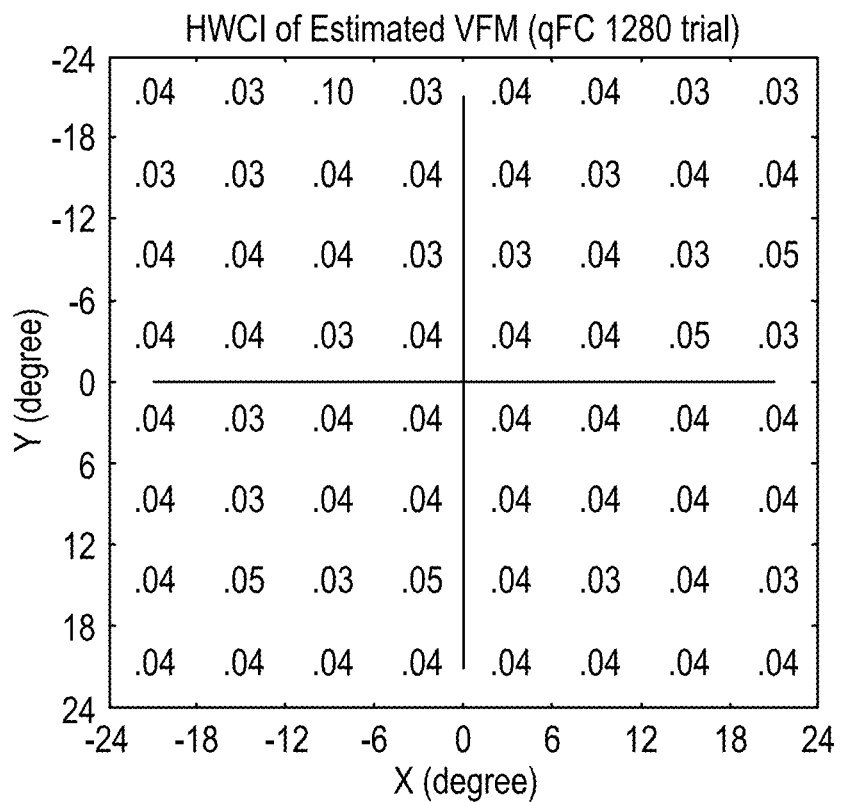
Figure 18K:
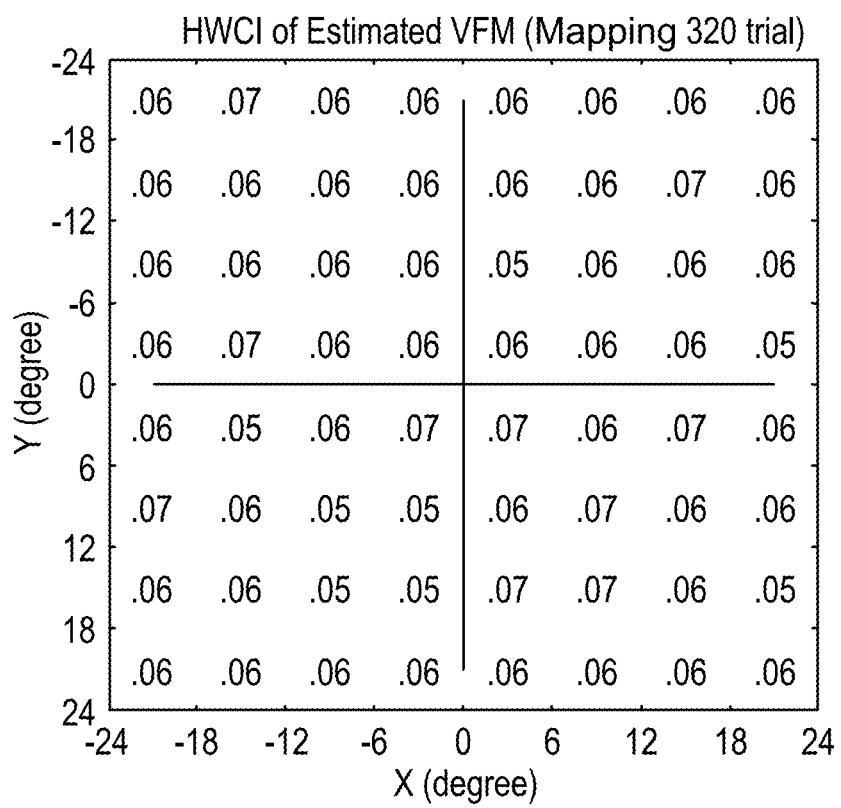
Figure 18L:
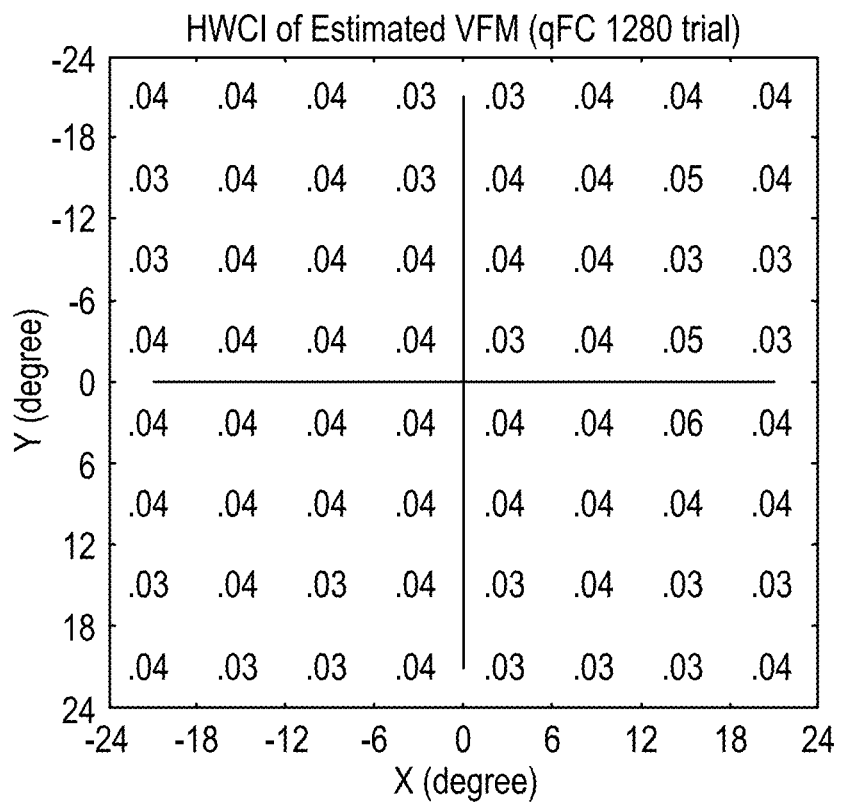
Figure 18M:
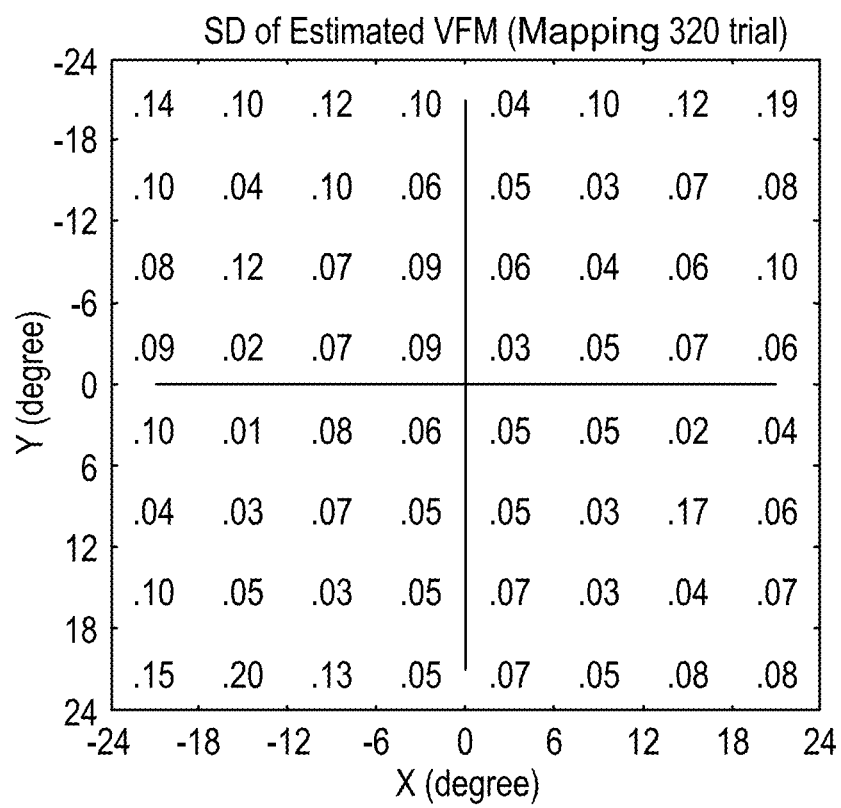
Figure 18N:
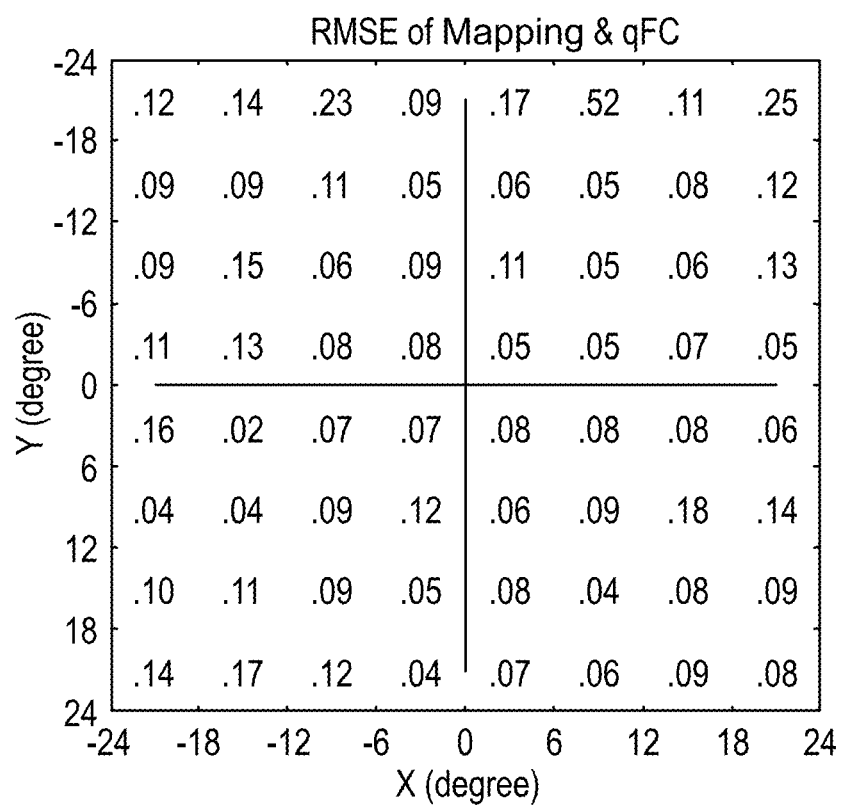
Figure 18O:
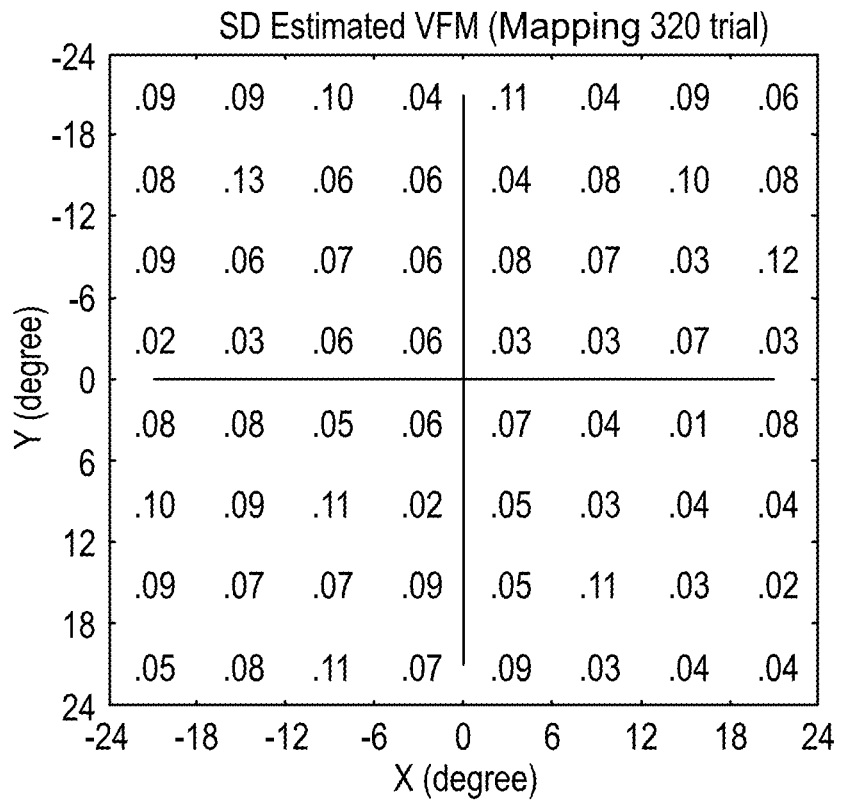
Figure 18P:
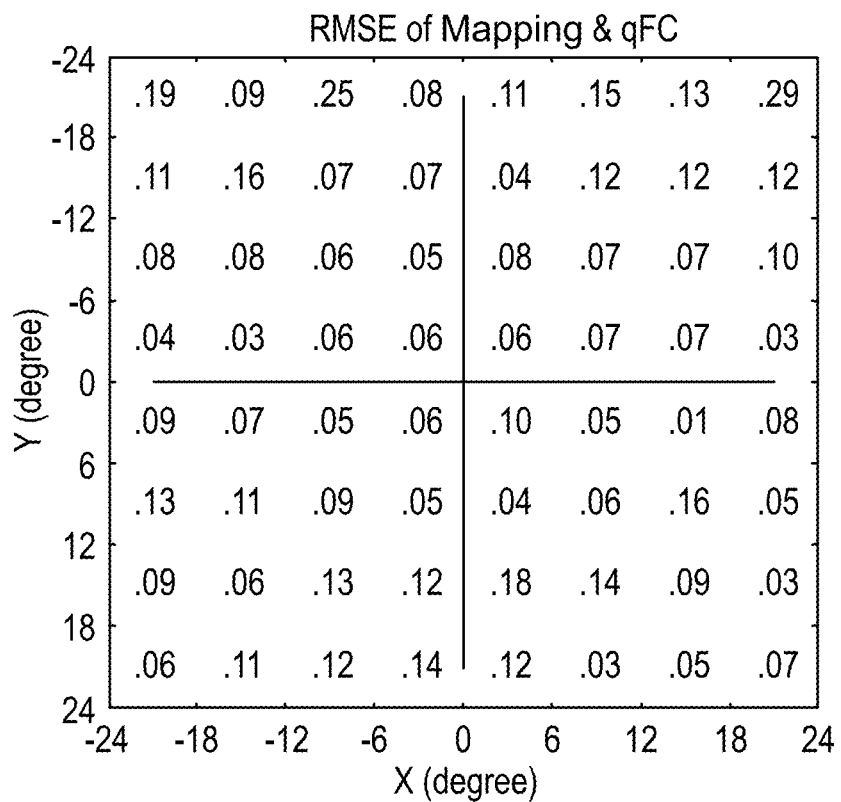

FIG. 14 illustrates example filtered Sloan letters for mapping the contrast sensitivity of the visual field with the method described herein. Current clinical evaluation, which focuses on central vision, could be improved through characterization of residual vision with peripheral testing of visual acuity, contrast sensitivity, color vision, crowding, and reading speed. Assessing more than light sensitivity, a comprehensive visual field map (VFM) of functional vision can be valuable for detecting and managing eye diseases. As discussed above, the method described herein combines a global approach for preliminary assessment of the VFM's shape, and a local approach for assessment at individual retinal locations. The method can be validated in measuring the light sensitivity map. Beginning with FIG. 14, the method can be extended to measure contrast sensitivity across the visual field with an efficient 10 alternative forced-choice (10AFC) task. In both simulations and psychophysics, an example 64 visual field locations are sampled (48×48 deg) and the results from the method described herein were compared with those from a procedure that tests each location independently (Bayesian F C; Lesmes et al., 2015). Subjects identity a single optotype (size: 2.5×2.5 deg), one of 10 Sloan alternatives, filtered with a raised cosine filter and octave bandwidth, e.g., FIG. 14. On each trial, the contrast and location of the stimulus can be adaptively selected. Three eyes can be simulated to compare the accuracy and precision of the estimated contrast sensitivity VFMs measured with 1280 trials of each method. In addition, example data is collected from eight eyes (4 OS, 4 OD) of four normal subjects. Each eye was tested in four sessions, each including an independent 320-trial method described herein assessment and an independent 320-trial Bayesian FC assessment, with the two types of trials randomly mixed.

With example results of simulations, the average biases of the estimated contrast sensitivity from the method described herein and the Bayesian FC method were 0.021 and 0.072 after 320 trials, and 0.0079 and 0.0080 after 1280 trials, respectively (all in log10 units). The average standard deviations (SD) of the estimated contrast sensitivity from the two methods were 0.053 and 0.089 after 320 trials, and 0.031 and 0.049 after 1280 trials, respectively (all in log10 units). The estimated within-run variability (68.2% HWCIs) were comparable to the estimated cross-run variability (SD).

FIGS. 15A-P, 16A-P, 17A-P and 18A-P illustrate example results for psychophysical validation of four subjects (8 eyes), respectively. Psychophysics—the estimated contrast sensitivity VFMs of all 8 tested eyes, from both the method described herein and the Bayesian FC method, are shown, including detailed analysis of data. For each subject, the estimated VFMs are presented in the first row with colormaps and second row with numerical values. The 68.2% HWCIs of the estimated VFM are presented in the third row. The standard deviation of the estimates from the method described herein and the RMSE between the method described herein and the Bayesian FC methods are presented in the fourth row. The results obtained from OS and OD are displayed in the first and second columns, and the third and fourth columns, respectively. The example results from the method described herein and the Bayesian FC method are displayed in different columns.

Figure 19A:
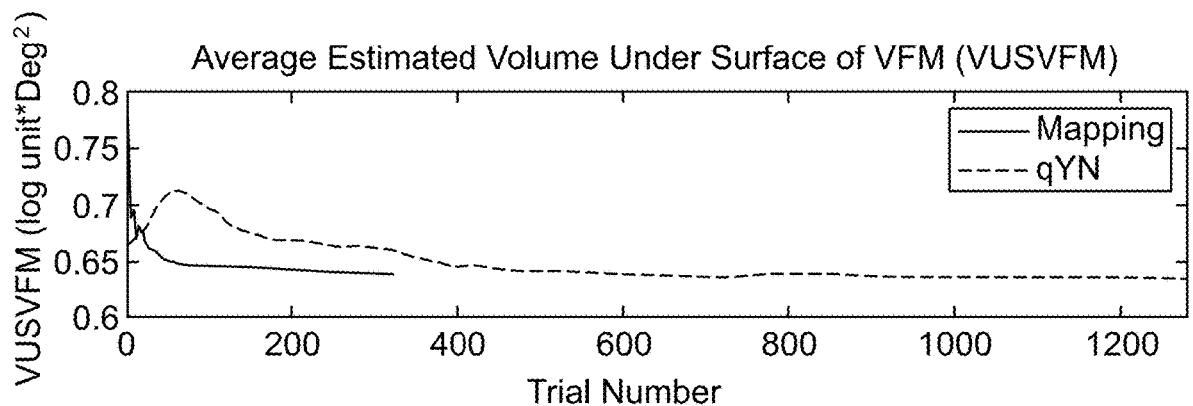
FIG. 19A illustrates an average contrast sensitivity volume under the surface of the VFM (VUSVFM) across 8 eyes.
Figure 19B:
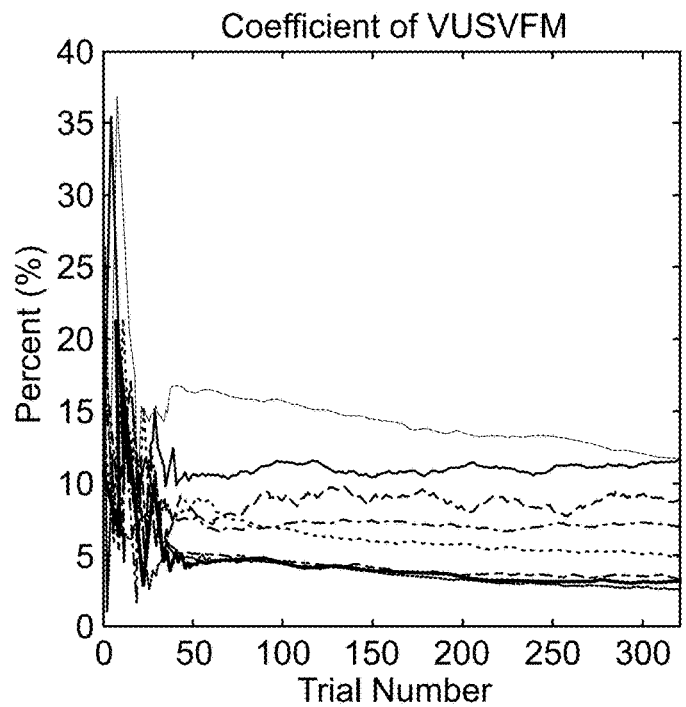
FIG. 19B illustrates an example coefficient of variability of estimated contrast sensitivity VUSVFMs (4 test runs each) as functions of test number for the 8 tested eyes.

To characterize the overall contrast sensitivity with a single summary metric of the entire visual field, the volume under the surface of the contrast sensitivity VFM (VUSVFM) is calculated. FIG. 19A illustrates an average contrast sensitivity VUSVFM across 8 eyes. Results from the method described herein are shown in solid lines and results from the Bayesian FC method are shown in dashed lines. FIG. 19B illustrates an example coefficient of variability of the estimated VUSVFMs (4 runs each) as functions of trial number for the 8 tested eyes. In FIG. 19A the average estimated VUSVFM of 8 eyes is illustrated as a function of trial number for the method described herein and the Bayesian FC method. The estimated VUSVFMs from the two methods were less than 0.1% different alter 320 trials. To demonstrate the convergence of VUSVFM estimates obtained with the method described herein, FIG. 19B presents the coefficient of variation of VUSVFM as a function of trial number for each eye. The coefficient of variation, also known as relative standard deviation, is determined as the ratio of the standard deviation to the mean:

$$cv_i = \frac{\sigma_i}{\mu_i}$$

where $\sigma_i$ is the standard deviation of estimated VUSVFM after the ith trial across 4 runs, and $\mu_i$ is the mean of estimated VUSVFM after the ith trial across 4 runs. A consistent pattern, exhibited in all tested eyes, is a decrease in variability with trial number, from about 20% after 20 trials to about 7% after 320 trials.

FIG. 19A illustrates a graph of an example result of an average 68.2% HWCI of the estimated sensitivities across 64 locations and 8 eyes. FIG. 19B illustrates a graph of RMSE of the estimated sensitivities from the method described herein as a function of trial number, using the estimated sensitivities from 1200 Bayesian FC trials as the "truth". The average HWCIs of the contrast sensitivity from the method described herein and the Bayesian FC method across the visual field decreased from 0.28 log10 units after the first trial to 0.083 log10 units and 0.15 log units after 160 trials, and to 0.061 log10 units and 0.092 log10 units after 320 trials (FIG. 19A). FIG. 19B starts at 0.21 log10 units, decreased to 0.12 log10 units after 160 and to 0.10 log10 units after 320 the method described herein trials.

Figure 20A:
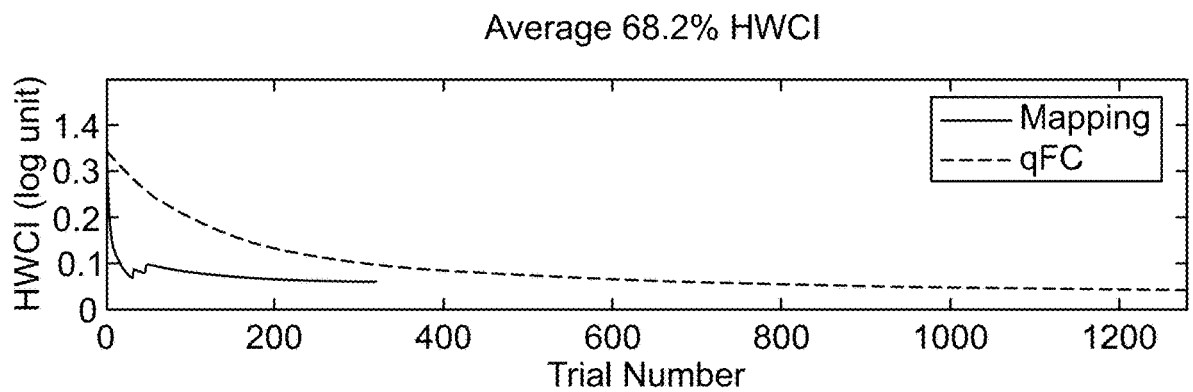
FIG. 20A illustrates a graph of an example result of an average 68.2% HWCI of the estimated contrast sensitivities across 64 locations and 8 eyes.
Figure 20B:
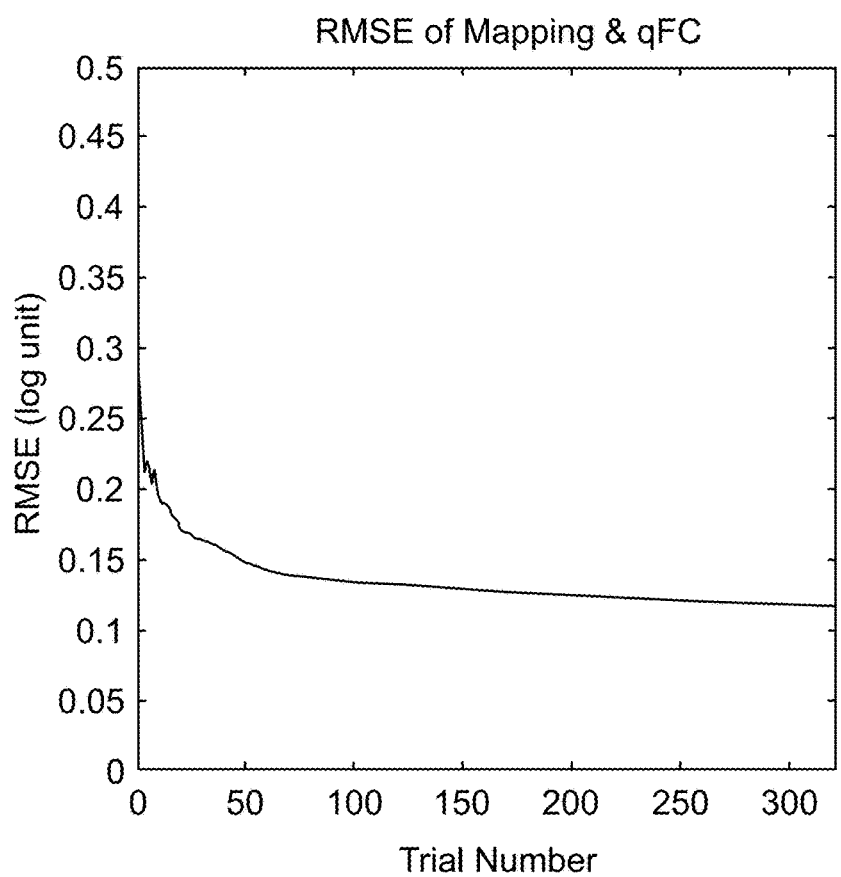
FIG. 20B illustrates a graph of RMSE of the estimated contrast sensitivities based on a method, for example, as depicted in FIG. 3, and a Bayesian Forced-Choice (FC) method for measuring visual function maps.
Figure 21A:
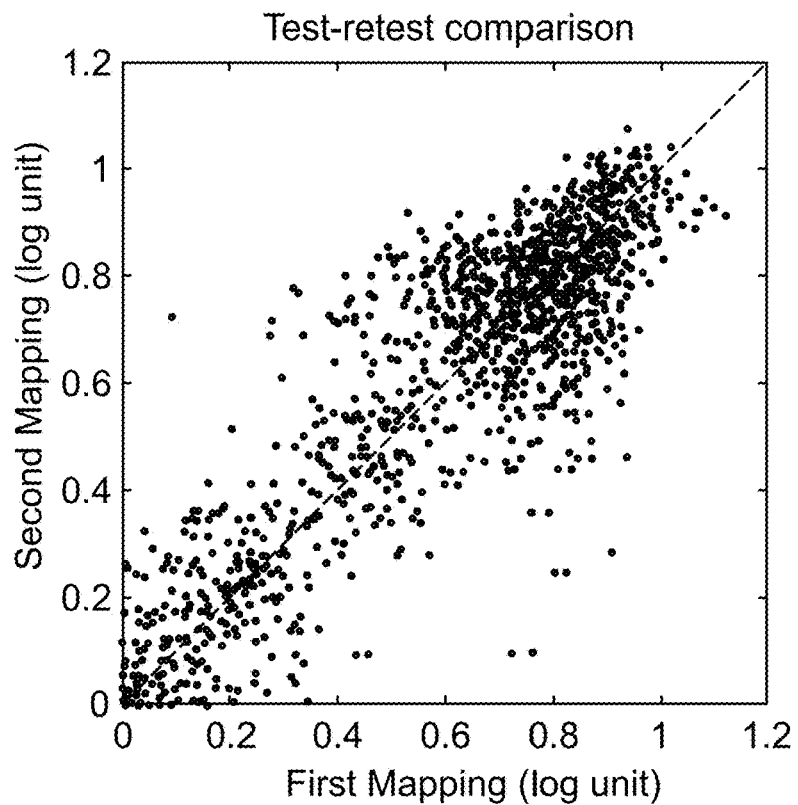
FIG. 21A illustrates example plot results for a test-retest comparison of the estimated contrast sensitivities from a method, for example, as depicted in FIG. 3, for measuring visual function maps.
Figure 21B:
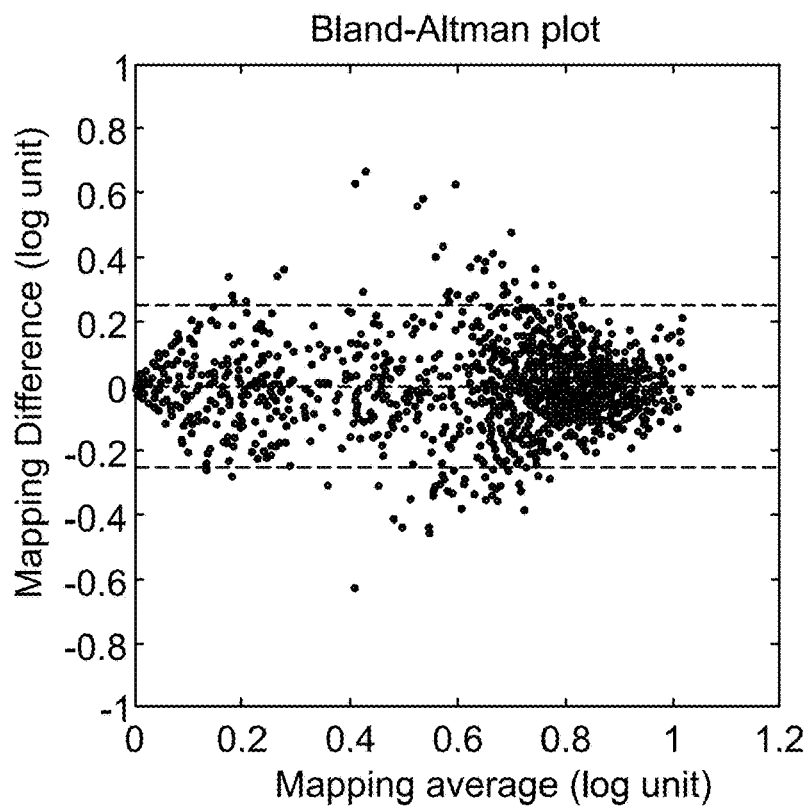
FIG. 21B illustrates an example Bland-Altman plot for estimated contrast sensitivity from a method, for example, as depicted in FIG. 3, for measuring visual function maps.

The test-retest reliability of the method described herein can be assessed through analysis of the 4 the method described herein runs completed in 4 sessions. FIG. 20A illustrates example plot results for a test-retest comparison of the estimated sensitivities from repeated the method described herein runs. FIG. 20B illustrates an example Bland-Altman plot for repeated method described herein runs. In FIG. 21A, a scatter plot plots the estimated sensitivities from the method described herein runs 1 and 2, runs 4 and 3, and runs 3 and 2. The average test-retest correlation was 89.8% (SD=0.5%). FIG. 21B presents a Bland-Altman plot of the difference of the method described herein estimates between runs 1 and 2, runs 4 and 3, and runs 3 and 2 against their mean. The mean and standard deviation of the test-retest difference were −0.0035 and 0.13 log10 units. These results signify that (1) the estimated sensitivity did not change systematically over the course of testing sessions, and (2) the test-retest differences were comparable to the estimated RMSE: 0.13 vs 0.12 log10 units. The repeated runs of the method described herein generated quite consistent results, exhibiting robustness in this multi-location measurement task. The method described herein can provide an accurate, precise, and efficient mapping of contrast sensitivity across the entire visual field. The systems and methods can find potential clinical applications in monitoring vision loss, evaluating therapeutic interventions, and developing effective rehabilitation for low vision.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
   a non-transitory memory to store machine readable instructions and data;
   a processor to access the memory and execute the machine-readable instructions, the machine-readable instructions comprising:
      a global module programmed to generate a visual field map (VFM) model comprising a set of visual function map parameters for all retinal locations of a visual field for a subject, wherein the global module is programmed to update the set of visual function map parameters corresponding to updating a shape of the VFM based on subject response data generated during each administration of a vision test to a subject;
      a switch module programmed to evaluate the performance of the global module and make a determination as to whether to switch to a local module; and upon switching, calculate independent parameters for each retinal location of the visual field based on the set of visual function map parameters in the global module; and
      the local module programmed to update the independent parameters based on the subject response data generated during a subsequent administration of the vision test to the subject to provide an assessment of visual function at each retinal location of the visual field for the subject.

2. The system of claim 1, wherein the global module is programmed to generate a visual function map across all retinal locations in the visual field, wherein each visual function map comprises a corresponding set of parameters.

3. The system of claim 2, wherein the visual function is one of but not limited to light sensitivity, contrast sensitivity, visual acuity, contrast sensitivity function, color sensitivity, stereo vision, temporary frequency sensitivity, motion sensitivity, reading speed, and crowding.

4. The system of claim 2, wherein the global module is programmed to generate a prior probability density function for each combination of the visual function map parameters of each visual function.

5. The system of claim 4, wherein the prior probability density function is one of an uninformative prior, a weakly informative prior, or an informative prior.

6. The system of claim 4, wherein the global module is programmed to update the prior probability density function, for each combination of the visual function map parameters according to a Bayes rule based on the response data to generate a posterior probability density function for each combination of the visual function map parameters.

7. The system of claim 6, wherein the global module is programmed to select a stimulus parameter from a stimulus parameter space to control a subsequent administration of the vision test to the subject based on the updated probability density function for each combination of the visual function map parameters of each visual function.

8. The system of claim 7, wherein the global module is programmed to iteratively update the probability density function for each combination of the visual function map parameters of each visual function based on the subject response data generated during each administration of the vision test to the subject.

9. The system of claim 8, wherein the global module is programmed to select the stimulus parameter from among a plurality of stimulus parameters that optimizes an expected information gain on each combination of the visual function map parameters of each visual function.

10. The system of claim 9, wherein the global module is programmed to select the stimulus parameter based on the posterior probability density function for each combination of the visual function map parameters of each visual function and based on an expected response by the subject according to a given amount of vision tests.

11. The system of claim 4, wherein the global module is programmed to obtain a prior according to one of (i) a structure-based prior, (ii) a prior derived from statistical or machine learning, (iii) a prior derived from a hierarchical adaptive method, and (iv) a prior from a previous visual function map.

12. The system of claim 1, wherein to calculate the independent parameters for each retinal location comprises generating a prior distribution of visual function for each retinal location in the visual field based on the posterior probability distribution for each combination of the visual function map parameters of each visual function generated by the global module.

13. The system of claim 1, wherein the switch module is programmed to evaluate one of a rate of information gain and improvement in information gain by the global module relative to an information criterion.

14. The system of claim 13, wherein the switch module is programmed to generate the prior probability distribution on measures of visual function at each retinal location based on a result of the evaluation.

15. The system of claim 13, wherein to evaluate comprises comparing a total expected information gain (TEI) in a subsequent vision test with an average TEI of a plurality of prior administered vision tests to the subject.

16. The system of claim 1, wherein updating the independent parameters comprises assessing the visual function at each retinal location of the visual field based on an adaptive testing procedure.

17. The system of claim 16, wherein the adaptive testing procedure comprises a Bayesian adaptive procedure.

18. The system of claim 16, wherein the adaptive testing procedure comprises a Bayesian active learning procedure.

19. The system of claim 1, wherein the local module is programmed to evaluate the visual function at each retinal location and an expected information gain across all retinal locations and stimuli parameters in the stimulus space to determine a given stimulus for a subsequent administration of the vision test.

20. The system of claim 19, wherein the local module is programmed to terminate evaluating the visual function at each retinal location of the visual field based on the adaptive procedure according to an evaluation criterion.

21. The system of claim 1, further comprising:

a vision stimulation device configured to administer the vision test to the subject in response to one of the global module and the local module.

22. The system of claim 21, wherein the processor comprises one or more graphics processing unit (GPUs).

23. The system of claim 22, further comprising an eye tracking unit configured to record an eye movement of the subject during the vision test and generate eye movement data characterizing the eye movements of the subject.

24. The system of claim 23, wherein the eye movement data are part of the subject response data.

25. The system of claim 21, further comprising a structural imaging device and a recording device configured to operate in cooperation with the processor.

* * * * *